United States Patent
Stocki et al.

(10) Patent No.: US 11,766,482 B2
(45) Date of Patent: Sep. 26, 2023

(54) IN VIVO METHODS FOR SELECTING PEPTIDES THAT CROSS THE BLOOD BRAIN BARRIER, RELATED COMPOSITIONS AND METHODS OF USE

(71) Applicant: Ossianix, Inc., Philadelphia, PA (US)

(72) Inventors: Pawel Stocki, Royston (GB); Krzysztof Bartlomiej Wicher, Cambridge (GB); Julia Lynn Rutkowski, Bryn Mawr, PA (US); Fabrizio Comper, Stevenage (GB); Mykhaylo Demydchuk, Cambridge (GB); Jaroslaw Michal Szary, Stevenage (GB)

(73) Assignee: Ossianix, Inc., Philadelphia, PA (US)

( * ) Notice: Subject to any disclaimer, the term of this patent is extended or adjusted under 35 U.S.C. 154(b) by 0 days.

(21) Appl. No.: 17/381,775

(22) Filed: Jul. 21, 2021

(65) Prior Publication Data
US 2022/0031857 A1 Feb. 3, 2022

Related U.S. Application Data

(62) Division of application No. 16/323,727, filed as application No. PCT/US2017/045592 on Aug. 4, 2017, now Pat. No. 11,097,010.

(60) Provisional application No. 62/415,631, filed on Nov. 1, 2016, provisional application No. 62/371,727, filed on Aug. 6, 2016.

(51) Int. Cl.
| | |
|---|---|
| *A61K 39/00* | (2006.01) |
| *A61K 47/64* | (2017.01) |
| *G01N 33/68* | (2006.01) |
| *C07K 16/28* | (2006.01) |
| *C07K 16/40* | (2006.01) |
| *C12N 15/10* | (2006.01) |
| *C12N 15/09* | (2006.01) |
| *G01N 33/58* | (2006.01) |
| *A61K 47/56* | (2017.01) |
| *C12N 15/113* | (2010.01) |
| *C40B 30/06* | (2006.01) |
| *C40B 40/10* | (2006.01) |

(52) U.S. Cl.
CPC ............ *A61K 47/64* (2017.08); *A61K 47/56* (2017.08); *C07K 16/2881* (2013.01); *C07K 16/2887* (2013.01); *C07K 16/40* (2013.01); *C12N 15/09* (2013.01); *C12N 15/1037* (2013.01); *C12N 15/113* (2013.01); *G01N 33/58* (2013.01); *G01N 33/68* (2013.01); *A61K 2039/505* (2013.01); *C07K 2317/20* (2013.01); *C07K 2317/31* (2013.01); *C07K 2317/569* (2013.01); *C07K 2317/622* (2013.01); *C07K 2317/64* (2013.01); *C07K 2317/732* (2013.01); *C07K 2317/734* (2013.01); *C07K 2317/94* (2013.01); *C07K 2319/30* (2013.01); *C12N 2320/32* (2013.01); *C40B 30/06* (2013.01); *C40B 40/10* (2013.01)

(58) Field of Classification Search
None
See application file for complete search history.

(56) References Cited

U.S. PATENT DOCUMENTS

| | | |
|---|---|---|
| 2017/0198281 A1 | 7/2017 | Häsler |
| 2017/0348416 A1 | 12/2017 | Häsler |

FOREIGN PATENT DOCUMENTS

| | | |
|---|---|---|
| WO | 2002057445 A1 | 7/2002 |
| WO | 2007036021 A1 | 4/2007 |
| WO | 2010033913 A1 | 3/2010 |
| WO | 2012075037 A1 | 6/2012 |
| WO | 2013177062 A2 | 11/2013 |
| WO | 2014189973 A2 | 11/2014 |
| WO | 2015200883 A2 | 12/2015 |
| WO | 2016070959 A1 | 5/2016 |
| WO | 2016077840 A1 | 5/2016 |
| WO | 2016081643 A1 | 5/2016 |
| WO | 2016094566 A2 | 6/2016 |
| WO | 2016097315 A2 | 6/2016 |
| WO | 2016207240 A1 | 12/2016 |

OTHER PUBLICATIONS

Abbott et al. (2010) "Structure and function of the blood-brain barrier," Neurobiol. Dis. 37:13-25.
Ahmad et al. (2012) "scFv Antibody: Principles and Clinical Application," Clin. Dev. Immunol. 2012: 980250, 15 pages.
Alata et al. (2014) "Brain uptake of a fluorescent vector targeting the transferrin receptor: a novel application of in situ brain perfusion," Mol. Pharm 11: 243-253.
Arap et al. (1998) "Cancer Treatment by Targeted Drug Delivery to Tumor Vasculature in a Mouse Model," Science 279:377-380.
Armour et al. (1999) "Recombinant human IgG molecules lacking Fcγ receptor I binding and monocyte triggering activities," Eur. J. Immunol. 29:2613-2624.
Bien-Ly et al. (2014) "Transferrin receptor (TfR) trafficking determines brain uptake of TfR antibody affinity variants," J. Exp. Med. 211:233-44.

(Continued)

*Primary Examiner* — Thomas S Heard
(74) *Attorney, Agent, or Firm* — KDW FIRM PLLC

(57) ABSTRACT

The present invention relates to the fields of molecular medicine and targeted delivery of therapeutic or diagnostic agents to cells outside the vascular system and into the parenchymal tissue of organs within the body. More specifically, the present invention relates to the methods used to identify membrane receptors or transporters capable of carrying cargo specifically targeted to the parenchymal tissue of the brain and to in vivo enrichment methods for selecting peptides that are transported across the blood-brain barrier ("BBB"), or analogously, across other membrane containing organs or structures, such as liver, spleen, kidney and tumors.

12 Claims, 19 Drawing Sheets
Specification includes a Sequence Listing.

(56) References Cited

OTHER PUBLICATIONS

Boado et al (2009) "Engineering and Expression of a Chimeric Transferrin Receptor Monoclonal Antibody for Blood-Brain Barrier Delivery in the Mouse," Biotechnol. Bioeng. 102:1251-8.
Couch et al. (2013) "Addressing Safety Liabilities of TfR Bispecific Antibodies That Cross the Blood-Brain Barrier," Sci. Transl. Med. 5:183ra57, 12 pages.
Demeule et al. (2014) "Conjugation of a brain-penetrant peptide with neurotensin provides antinociceptive properties," J. Clin. Invest. 124:1199-1213.
Diaz et al. (2002) "Structural analysis, selection, and ontogeny of the shark new antigen receptor (IgNAR): identification of a new locus preferentially expressed in early development," Immunogenetics 54:501-512.
Fennell et al. (2010) "Dissection of the IgNAR V Domain: Molecular Scanning and Orthologue Database Mining Define Novel IgNAR Hallmarks and Affinity Maturation Mechanisms," J. Mol. Biol. 400:155-170.
Friden et al. (1996) "Characterization, Receptor Mapping and Blood-Brain Barrier Transcytosis of Antibodies to the Human Transferrin Receptor," J. Pharm Exp. Ther. 278:1491-1498.
Häsler et al. (2015) "Species cross-reactive single domain antibodies (VNARs) to the transferrin receptor 1 (TfR-1) that cross the BBB", Poster presentation at Cold Spring Harbor Laboratory Blood Brain Barrier meeting, Dec. 10-13, 2014.
Helguera et al. (2012) "An Antibody Recognizing the Apical Domain of Human Transferrin Receptor 1 Efficiently Inhibits the Entry of All New World Hemorrhagic Fever Arena Viruses," J. Virol. 86:4024-4028.
Jones et al. (2007) "Blood-Brain Barrier Transport of Therapeutics via Receptor-Mediation," Pharm. Res. 24:1759-71.
Jones et al. (2014) "Identifying Blood-Brain Barrier Selective Single-Chain Antibody Fragments," Biotechnopl. J. 9:664-674.
Lee et al. (2000) "Targeting Rat Anti-Mouse Transferrin Receptor Monoclonal Antibodies through Blood-Brain Barrier in Mouse," J. Pharm. Exp. Ther. 292:1048-1052.
Li et al. (2015) "In vivo phage display screen for peptide sequences that cross the blood-cerebrospinal-fluid barrier," Amino Acids 47:401-405.
Moos et al. (2002) "Restricted transport of anti-transferrin receptor antibody (OX26) through the blood±brain barrier in the rat," J. Neurochem. 79:119-129.
Nałęcz (2017) "Solute Carriers in the Blood-Brain Barrier: Safety in Abundance," Neurochem. Res. 42:795-809; published online Aug. 9, 2016.
Pardridge (2002) "Drug and gene targeting to the brain with molecular Trojan horses," Nat. Rev. Drug Discov. 1:131-9.
Pardridge (2012a) "Drug transport across the blood-brain barrier," J. Cereb. Blood Flow Metab. 32:1959-72.
Pardridge et al. (2012) "Reengineering Biopharmaceuticals for Targeted Delivery Across the Blood-Brain Barrier," Methods Enzymol. 503:269-92.
Pardridge (2015) "Blood-brain barrier drug delivery of IgG fusion proteins with a transferrin receptor monoclonal antibody," Expert Opin. Drug Deliv. 12:207-222.
Pasqualini et al. (1996) "Organ targeting in vivo using phage display peptide libraries," Nature 380:364-366.
Poul et al. (2000) "Selection of Tumor-Specific Internalizing Human Antibodies from Phage Libraries," J. Mol. Biol. 301:1149-61.
Regina et al. (2014) "ANG4043, a Novel Brain-Penetrant Peptide-mAb Conjugate, Is Efficacious against HER2-Positive Intracranial Tumors in Mice," Mol. Canc. Ther. 14:129-140.
Sade et al. (2010) "A Human Blood-Brain Barrier Transcytosis Assay Reveals Antibody Transcytosis Influenced by pH-Dependent Receptor Binding," PLoS ONE 9(4): e96340.
Triguero et al. (1990) "Capillary Depletion Method for Quantification of Blood-Brain Barrier Transport of Circulating Peptides and Plasma Proteins," J. Neurochem. 54:1882-8.
Tuma et al. {2003) "Transcytosis: Crossing Cellular Barriers," Physiol. Rev. 83:871-932.
Yu et al. (2011) "Boosting Brain Uptake of a Therapeutic Antibody by Reducing its Affinity for a Transcytosis Target," Sci. Transl. Med., vol. 3(84) 84ra44, 8 pages.
Yu et al. (2014) "Therapeutic bispecific antibodies cross the blood-brain barrier in nonhuman primates," Sci. Transl. Med. vol. 6(261) 261ra154, 10 pages.
Zielonka et al. (2014) "Structural insights and biomedical potential of IgNAR scaffolds from sharks", mAbs, vol. 7, pp. 15-25.
Guixer, B., et al., "Chemically synthesized peptide libraries as a new source of BBB shuttles. Use of mass spectrometry for peptide identification", Journal of Peptide Science 22:577-591 (2016).
Iezzi, M.E., et al., "Single-Domain Antibodies and the Promise of Modular Targeting in Cancer Imaging and Treatment", Frontiers in Immunology (273):1-11 (2018).
Shao, C-Y, et al., "Rapid isolation of IgNAR variable single-domain antibody fragments from a shark synthetic library", Molecular Immunology 44:656-665 (2007).
Stanimirovic, D., et al., "Engineering and Pharmacology of Blood-Brain Barrier-Permeable Bispecific Antibodies", Advances in Pharmacology, vol. 71, Chapter Ten pp. 301-335 (2014).
Van Rooy, I., et al., "Identification of Peptide Ligands for Targeting to the Blood-Brain Barrier" Pharmaceutical Research 27(4):673-682 (2010).

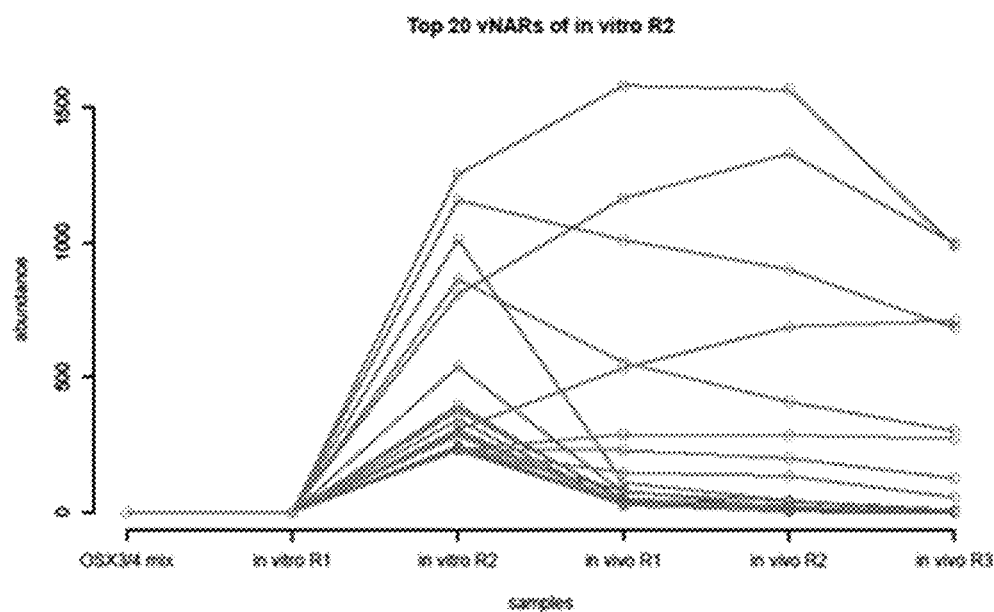
FIG. 9
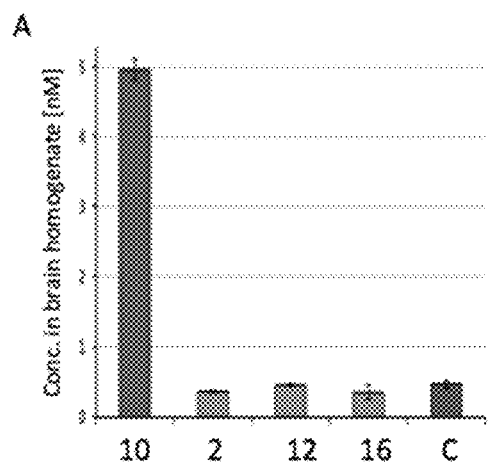 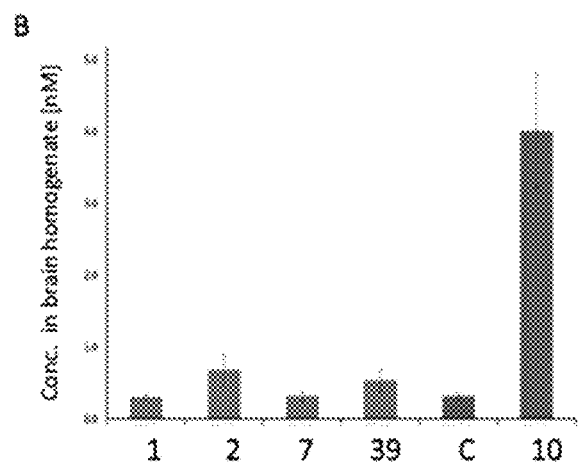
FIG. 10A                FIG. 10B

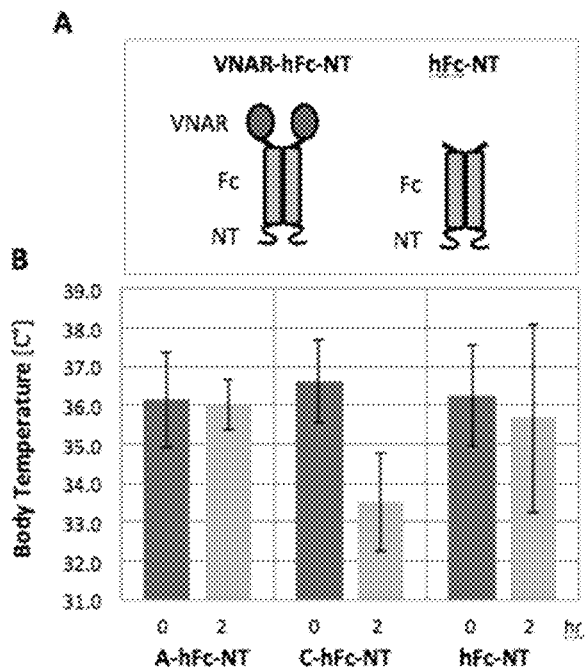
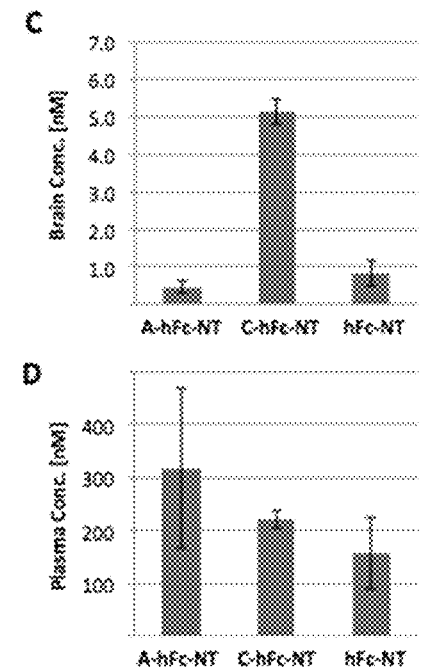
FIG. 26A  FIG. 26B  FIG. 26C  FIG. 26D
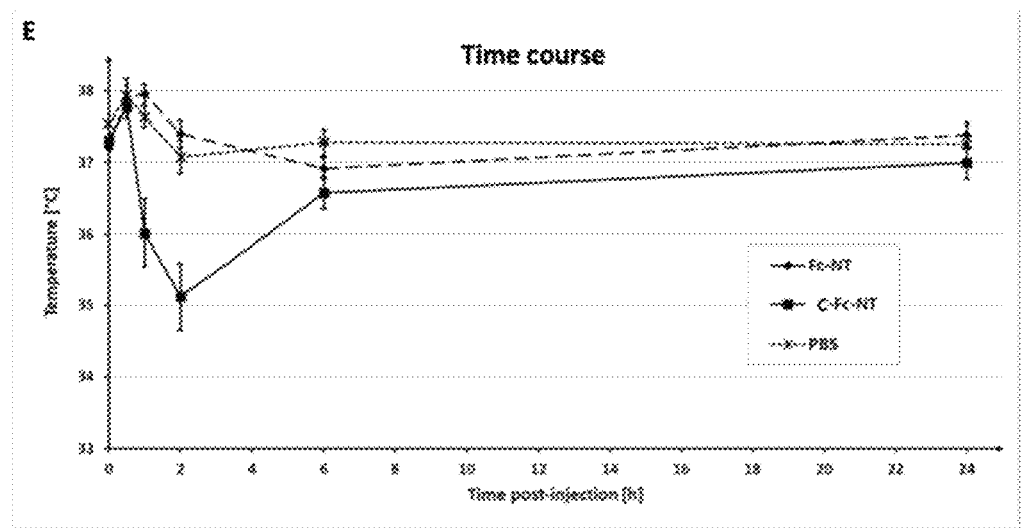
FIG. 26E

SEQUENCE LISTING

<160> NUMBER OF SEQ ID NOS: 262

<210> SEQ ID NO 1
<211> LENGTH: 111
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 1

Ala Arg Val Asp Gln Thr Pro Gln Thr Ile Thr Lys Glu Thr Gly Glu
1               5                   10                  15

Ser Leu Thr Ile Asn Cys Val Leu Arg Asp Asn Asn Cys Ala Leu Ser
            20                  25                  30

Thr Thr Tyr Trp Tyr Arg Lys Lys Ser Gly Ser Thr Asn Glu Glu Asn
        35                  40                  45

Ile Ser Lys Gly Gly Arg Tyr Val Glu Thr Val Asn Ser Gly Ser Lys
    50                  55                  60

Ser Phe Ser Leu Lys Ile Asn Asp Leu Thr Val Glu Asp Ser Gly Thr
65                  70                  75                  80

Tyr Arg Cys Asn Val Arg Asp Val Gln Ala Cys Gly Asn Asp Trp Val
                85                  90                  95

Trp Leu Asp Val Tyr Gly Gly Gly Thr Val Val Thr Val Asn Ala
            100                 105                 110

<210> SEQ ID NO 2
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ala Arg Val Asp Gln Thr Pro Gln Thr Ile Thr Lys Glu Thr Gly Glu
1               5                   10                  15

Ser Leu Thr Ile Asn Cys Val Leu Arg Asp Asn Asn Cys Ala Leu Ser
            20                  25                  30

Thr Thr Tyr Trp Tyr Arg Lys Lys Ser Gly Ser Thr Asn Glu Glu Asn
        35                  40                  45

Ile Ser Lys Gly Gly Arg Tyr Val Glu Thr Val Asn Ser Gly Ser Lys
    50                  55                  60

Ser Phe Ser Leu Lys Ile Asn Asp Leu Thr Val Glu Asp Ser Gly Thr
65                  70                  75                  80

Tyr Arg Cys Asn Val Phe Gly Val Asp Asn Gly Trp Trp Cys Asp Val
                85                  90                  95

Tyr Gly Gly Gly Thr Val Val Thr Val Asn Ala
            100                 105

<210> SEQ ID NO 3
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Ala Arg Val Asp Gln Thr Pro Gln Thr Ile Thr Lys Glu Thr Gly Glu
1               5                   10                  15

Ser Leu Thr Ile Asn Cys Val Leu Arg Asp Asn Asn Cys Ala Leu Ser
            20                  25                  30

Thr Thr Tyr Trp Tyr Arg Lys Lys Ser Gly Ser Thr Asn Glu Glu Asn
        35                  40                  45

```
Ile Ser Lys Gly Gly Arg Tyr Val Glu Thr Val Asn Ser Gly Ser Lys
            50                  55                  60

Ser Phe Ser Leu Lys Ile Asn Asp Leu Thr Val Glu Asp Ser Gly Thr
 65                  70                  75                  80

Tyr Arg Cys Asn Val Thr Gly Tyr Phe Arg Ser Thr Cys Leu Trp Arg
                 85                  90                  95

Asp Val Tyr Gly Gly Gly Thr Ala Val Thr Val Asn Ala
            100                 105
```

<210> SEQ ID NO 4
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Ala Arg Val Asp Gln Thr Pro Gln Thr Ile Thr Lys Glu Thr Gly Glu
 1               5                  10                  15

Ser Leu Thr Ile Asn Cys Val Leu Arg Asp Ser Asn Cys Ala Leu Ser
                20                  25                  30

Ser Thr Tyr Trp Tyr Arg Lys Lys Ser Gly Ser Thr Asn Glu Glu Asn
            35                  40                  45

Ile Ser Lys Gly Gly Arg Tyr Val Glu Thr Val Asn Ser Gly Ser Lys
            50                  55                  60

Ser Phe Ser Leu Lys Ile Asn Asp Leu Thr Val Glu Asp Ser Gly Thr
 65                  70                  75                  80

Tyr Arg Cys Asn Val Gln Phe Thr Ala Ala Leu Trp Cys Glu Ala Val
                 85                  90                  95

Leu Asp Val Tyr Gly Gly Thr Val Val Thr Val Asn Ala
            100                 105                 110
```

<210> SEQ ID NO 5
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Ala Arg Val Asp Gln Thr Pro Gln Thr Ile Thr Lys Glu Thr Gly Glu
 1               5                  10                  15

Ser Leu Thr Ile Asn Cys Val Leu Arg Asp Ser Asn Cys Ala Leu Ser
                20                  25                  30

Ser Thr Tyr Trp Tyr Arg Lys Lys Ser Gly Ser Thr Asn Glu Glu Asn
            35                  40                  45

Ile Ser Lys Gly Gly Arg Tyr Val Glu Thr Val Asn Ser Gly Ser Lys
            50                  55                  60

Ser Phe Ser Leu Lys Ile Asn Asp Leu Thr Val Glu Asp Ser Gly Thr
 65                  70                  75                  80

Tyr Arg Cys Asn Val Gln Lys Gly Gln His Leu Gln Cys His Val Ala
                 85                  90                  95

Val Gln Asp Val Tyr Gly Gly Gly Thr Ala Val Thr Val Asn Ala
            100                 105                 110
```

<210> SEQ ID NO 6

```
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Asp Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Gln Trp Trp Leu Arg Cys Gly Tyr Phe Lys Asp
                85                  90                  95

Val Tyr Gly Gly Gly Thr Val Val Thr Val Asn Ala
            100                 105

<210> SEQ ID NO 7
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Glu Leu Ser
            20                  25                  30

Ser Thr Tyr Trp Tyr Arg Lys Lys Ser Gly Ser Thr Asn Glu Ala Arg
        35                  40                  45

Ile Ser Lys Gly Gly Arg Tyr Val Glu Thr Val Asn Ser Gly Ser Lys
    50                  55                  60

Ser Phe Ser Leu Lys Ile Asn Asp Leu Thr Val Glu Asp Ser Gly Thr
65                  70                  75                  80

Tyr Arg Cys Asn Val Leu Thr Thr Asp Ser Tyr Asp Leu Gly Asp Val
                85                  90                  95

Tyr Gly Asp Gly Thr Val Val Thr Val Asn Ala
            100                 105

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Glu Leu Ser
            20                  25                  30
```

```
Ser Thr Tyr Trp Tyr Arg Lys Lys Ser Gly Ser Thr Asn Glu Ala Arg
        35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Gln Tyr Phe Leu Cys His Phe Val Gly Asp Val
                85                  90                  95

Tyr Gly Asp Gly Thr Ala Val Thr Val Asn Ala
           100                 105
```

```
<210> SEQ ID NO 9
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ala Arg Val Asp Gln Thr Pro Gln Thr Ile Thr Lys Glu Thr Gly Glu
 1               5                  10                  15

Ser Leu Thr Ile Asn Cys Val Leu Arg Asp Ser Asn Cys Ala Leu Pro
                20                  25                  30

Ser Thr Tyr Trp Tyr Arg Lys Lys Ser Gly Ser Thr Asn Glu Ala Arg
        35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Ile Asp Ala Arg Tyr Arg Leu Ser Ala Ser Ala Val Leu Tyr Gln Ser
                85                  90                  95

Tyr Val Asp Val Tyr Gly Gly Gly Thr Ala Val Thr Val Asn Ala
           100                 105                 110
```

```
<210> SEQ ID NO 10
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ala Arg Val Asp Gln Thr Pro Gln Thr Ile Thr Lys Glu Thr Gly Glu
 1               5                  10                  15

Ser Leu Thr Ile Asn Cys Val Leu Arg Asp Ser Asn Cys Ala Leu Ser
                20                  25                  30

Ser Thr Tyr Trp Tyr Arg Lys Lys Ser Gly Ser Thr Asn Glu Glu Asn
        35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Val Gln Tyr Pro Ser Tyr Asn Asn Tyr Phe Trp
                85                  90                  95

Cys Asp Val Tyr Gly Asp Gly Thr Ala Val Thr Val Asn Ala
           100                 105                 110
```

```
<210> SEQ ID NO 11
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr His Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
50                  55                  60

Ser Phe Ser Leu Arg Ile Asn Asp Leu Thr Val Glu Asp Ser Gly Thr
65                  70                  75                  80

Tyr Arg Cys Lys Val Leu Asn Phe Phe Thr His Thr Cys Val Gln Val
                85                  90                  95

Gln Lys Tyr Asp Val Tyr Gly Gly Gly Thr Ala Val Thr Val Asn Ala
            100                 105                 110

<210> SEQ ID NO 12
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Ile Cys Ala Leu Ser
            20                  25                  30

Ser Thr His Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
50                  55                  60

Ser Phe Ser Leu Arg Ile Asn Asp Leu Thr Val Glu Asp Ser Gly Thr
65                  70                  75                  80

Tyr Arg Cys Lys Val Val Arg Ser Gly Val Gly Pro Cys Trp Ala Asp
                85                  90                  95

Val Tyr Gly Gly Gly Thr Ala Val Thr Val Asn Ala
            100                 105

<210> SEQ ID NO 13
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ala Arg Val Asp Gln Thr Pro Gln Thr Ile Thr Lys Glu Thr Gly Glu
1               5                   10                  15
```

```
Ser Leu Thr Ile Asn Cys Val Leu Arg Asp Ser Asn Cys Ala Leu Pro
            20                  25                  30

Ser Thr Tyr Arg Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
50                      55                  60

Ser Phe Ser Leu Arg Ile Asn Asp Leu Thr Val Glu Asp Ser Gly Thr
65                  70                  75                  80

Tyr Arg Cys Lys Val Thr Met Val Arg Gly Arg Gly Cys Tyr Gln Pro
                85                  90                  95

Ala Arg Gly Gln Asp Val Tyr Gly Gly Gly Thr Ala Val Thr Val Asn
            100                 105                 110

Ala

<210> SEQ ID NO 14
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
50                      55                  60

Ser Phe Ser Leu Arg Ile Asn Asp Leu Thr Val Glu Asp Ser Gly Thr
65                  70                  75                  80

Tyr Arg Cys Lys Val Thr Phe Ser Ala Phe Glu Tyr Cys Tyr Val Phe
                85                  90                  95

Lys Val Gln Cys Asp Val Tyr Gly Asp Gly Thr Ala Val Thr Val Asn
            100                 105                 110

Ala

<210> SEQ ID NO 15
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Cys Lys Lys Ser Gly Ser Thr Asn Glu Glu Ser
        35                  40                  45

Ile Ser Lys Gly Gly Arg Tyr Val Glu Thr Val Asn Ser Gly Ser Lys
50                      55                  60
```

Ser Phe Ser Leu Arg Ile Asn Asp Leu Thr Val Lys Asp Ser Gly Thr
65                  70                  75                  80

Tyr Arg Cys Lys Val His Val Arg Ala Gln Ser Leu Cys Cys Gln Cys
                85                  90                  95

Trp Tyr Gly Asp Val Tyr Gly Asp Gly Thr Ala Val Thr Val Asn Ala
            100                 105                 110

<210> SEQ ID NO 16
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
                20                  25                  30

Ser Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
50                  55                  60

Ser Phe Ser Leu Arg Ile Asn Asp Leu Thr Val Lys Asp Ser Gly Thr
65                  70                  75                  80

Tyr Arg Cys Lys Val Asp Leu Pro Arg Tyr Leu Cys Phe Ser Gln Tyr
                85                  90                  95

Gly Arg Trp Tyr Asp Val Tyr Gly Asp Gly Thr Ala Val Thr Val Asn
            100                 105                 110

Ala

<210> SEQ ID NO 17
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
                20                  25                  30

Ser Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
50                  55                  60

Ser Phe Ser Leu Arg Ile Asn Asp Leu Thr Val Lys Asp Ser Gly Thr
65                  70                  75                  80

Tyr Arg Cys Asn Val Ala Arg His Trp Thr Gln Ser Cys Ala Tyr His
                85                  90                  95

Arg Asp Val Tyr Gly Gly Thr Ala Val Thr Val Asn Ala
            100                 105                 110

<210> SEQ ID NO 18
<211> LENGTH: 111

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Lys Asp Ser Gly Thr
65                  70                  75                  80

Tyr Arg Cys Asn Val Gln His Ile Phe Gln His Asn Cys Tyr Trp Phe
                85                  90                  95

Leu Tyr Asp Val Tyr Gly Gly Gly Thr Ala Val Thr Val Asn Ala
            100                 105                 110

<210> SEQ ID NO 19
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Gly Trp Ser Thr Gln Tyr Tyr Cys Val Leu Pro
                85                  90                  95

Asp Val Tyr Gly Gly Gly Thr Ala Val Thr Val Asn Ala
            100                 105

<210> SEQ ID NO 20
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

```
Ser Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Tyr Thr Ser Tyr Cys Ser Val Ala Asp Val
                85                  90                  95

Tyr Gly Gly Gly Thr Ala Val Thr Val Asn Ala
                100                 105

<210> SEQ ID NO 21
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val Leu Thr Ser Gln Ser Gln Gly Gly Cys Val Arg
                85                  90                  95

Val Leu Tyr Ser Asp Val Tyr Gly Asp Gly Thr Ala Val Thr Val Asn
                100                 105                 110

Ala

<210> SEQ ID NO 22
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Asp Ser Thr Asn Glu Glu Ser
            35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val His Ser Phe Asn Met Asp Val Cys Ala Glu Phe
                85                  90                  95
```

Gln Tyr Ser Asp Val Tyr Gly Asp Gly Thr Ala Val Thr Val Asn Ala
            100                 105                 110

<210> SEQ ID NO 23
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Asn Leu Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Ile Asn Phe Phe Ala Met Glu Cys Glu Tyr Gln
                85                  90                  95

Val Gly Asp Val Tyr Gly Asp Gly Thr Ala Val Thr Val Asn Ala
            100                 105                 110

<210> SEQ ID NO 24
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Asn Leu Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Lys Asp Ser Gly Thr
65                  70                  75                  80

Tyr Arg Cys Asn Val Leu Val Ser Met Phe Cys Gln Leu Ala Gln Asp
                85                  90                  95

Val Tyr Gly Asp Gly Thr Ala Val Thr Val Asn Ala
            100                 105

<210> SEQ ID NO 25
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Asn Leu Tyr Trp Tyr Arg Lys Lys Ser Gly Ser Thr Asn Glu Glu Ser
        35                  40                  45

Ile Ser Leu Gly Gly Arg Tyr Val Glu Thr Val Asn Ser Gly Ser Lys
50                  55                  60

Ser Phe Ser Leu Arg Ile Asn Asp Leu Thr Val Glu Asp Ser Gly Thr
65                  70                  75                  80

Tyr Arg Cys Asn Val Cys Leu Leu Gln Leu Ala Gly Tyr Asp Ser Pro
                85                  90                  95

Tyr Asp Val Tyr Gly Gly Gly Thr Ala Val Thr Val Asn Ala
            100                 105                 110

<210> SEQ ID NO 26
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Asn Leu Tyr Trp Tyr Arg Lys Lys Ser Gly Ser Thr Asn Glu Glu Asn
        35                  40                  45

Ile Ser Lys Gly Gly Arg Tyr Val Glu Thr Val Asn Ser Gly Ser Lys
50                  55                  60

Ser Phe Ser Leu Arg Ile Asn Asp Leu Thr Val Glu Asp Ser Gly Thr
65                  70                  75                  80

Tyr Arg Cys Asn Val Asp Val Thr Arg Cys Thr Gln Ser Gln Asp Val
                85                  90                  95

Tyr Gly Gly Gly Thr Ala Val Thr Val Asn Ala
            100                 105

<210> SEQ ID NO 27
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Ala Arg Val Asp Gln Thr Pro Gln Thr Val Thr Lys Glu Thr Gly Glu
1               5                   10                  15

Ser Leu Thr Ile Asn Cys Val Leu Arg Asp Ser Asn Cys Ala Leu Ser
            20                  25                  30

Asn Leu Tyr Trp Tyr Arg Lys Lys Ser Gly Ser Thr Asn Glu Glu Ser
        35                  40                  45

Ile Ser Leu Gly Gly Arg Tyr Val Glu Thr Val Asn Ser Gly Ser Lys
50                  55                  60

Ser Phe Ser Leu Arg Ile Asn Asp Leu Thr Val Glu Asp Ser Gly Thr
65                  70                  75                  80

Tyr Arg Cys Asn Val Lys His Tyr Val Cys Met Gln Ser Lys Asp Val
                85                  90                  95

Tyr Gly Gly Gly Thr Val Val Thr Val Asn Ala
            100                 105

<210> SEQ ID NO 28
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
                20                  25                  30

Asn Leu Tyr Trp Tyr Arg Lys Lys Ser Gly Ser Thr Asn Glu Glu Ser
            35                  40                  45

Ile Ser Leu Gly Gly Arg Tyr Val Glu Thr Val Asn Ser Gly Ser Lys
50                  55                  60

Ser Phe Ser Leu Arg Ile Asn Asp Leu Thr Val Lys Asp Ser Gly Thr
65                  70                  75                  80

Tyr Arg Cys Asn Val Phe Ser Phe Ser Cys Gln Leu Leu Phe Asp Val
                85                  90                  95

Tyr Gly Gly Gly Thr Ala Val Thr Val Asn Ala
            100                 105

<210> SEQ ID NO 29
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
                20                  25                  30

Asn Leu Tyr Trp Tyr Arg Lys Lys Ser Gly Ser Thr Asn Glu Glu Ser
            35                  40                  45

Ile Ser Leu Gly Gly Arg Tyr Val Glu Thr Val Asn Ser Gly Ser Lys
50                  55                  60

Ser Phe Ser Leu Arg Ile Asn Asp Leu Thr Val Glu Asp Ser Gly Thr
65                  70                  75                  80

Tyr Arg Cys Lys Val Ser Thr Ser Val Pro Arg His Tyr Asp Asn Cys
                85                  90                  95

Arg Gln Arg Arg His Asp Val Tyr Gly Gly Gly Thr Ala Val Thr Val
            100                 105                 110

Asn Ala

<210> SEQ ID NO 30
<211> LENGTH: 110
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 30

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Asn Leu Tyr Trp Tyr Arg Lys Lys Ser Gly Ser Thr Asn Glu Glu Ser
        35                  40                  45

Ile Ser Leu Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Cys Gln Trp Leu Gln Trp Tyr Gly Gly Glu Met
                85                  90                  95

Glu Asp Val Tyr Gly Gly Gly Thr Ala Val Thr Val Asn Ala
            100                 105                 110

<210> SEQ ID NO 31
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Asp Leu Ser
            20                  25                  30

Arg Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Lys Ile Asn Asp Leu Thr Val Glu Asp Ser Gly Thr
65                  70                  75                  80

Tyr Arg Cys Asn Val Phe Leu Trp Asn Asn Tyr Asn Pro Met Asp Val
                85                  90                  95

Tyr Gly Gly Gly Thr Ala Val Thr Val Asn Ala
            100                 105

<210> SEQ ID NO 32
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Asn Leu Tyr Trp Tyr Arg Lys Lys Ser Gly Ser Arg Asn Glu Glu Ser
        35                  40                  45

```
Ile Ser Lys Gly Gly Arg Tyr Val Glu Thr Val Asn Ser Gly Ser Lys
        50                  55                  60

Ser Phe Ser Leu Lys Ile Asn Asp Leu Thr Val Glu Asp Ser Gly Thr
65                  70                  75                  80

Tyr Arg Cys Lys Val Phe Gly Met Arg Thr His Cys Gln Trp Val Ile
                85                  90                  95

Tyr Arg Ile Thr Asp Val Tyr Gly Gly Gly Thr Ala Val Thr Val Asn
                100                 105                 110

Ala

<210> SEQ ID NO 33
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Asp Leu Ser
                20                  25                  30

Arg Thr Tyr Trp Tyr Arg Lys Lys Gln Gly Ser Thr Asn Glu Glu Ser
                35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

Tyr Arg Cys Asn Val Ala Leu Tyr His Phe Thr Gly Cys Ser Arg Val
                85                  90                  95

Gln Asp Val Tyr Gly Gly Gly Thr Val Val Thr Val Asn Ala
                100                 105                 110

<210> SEQ ID NO 34
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Asp Leu Ser
                20                  25                  30

Arg Thr Tyr Trp Tyr Arg Lys Lys Ser Gly Ser Thr Asn Glu Glu Ser
                35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Val Val Glu Asp Ser Gly Thr
65                  70                  75                  80

Tyr Arg Cys Asn Val Ala Val Phe Thr Arg Cys His Asn Gln Gln Asp
                85                  90                  95

Val Tyr Gly Gly Gly Thr Ala Val Thr Val Asn Ala
                100                 105
```

<210> SEQ ID NO 35
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Asp Leu Ser
            20                  25                  30

Arg Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Thr Trp Leu Asp Cys His Gln Cys Gly Ala Ser
                85                  90                  95

Asp Val Tyr Gly Gly Gly Thr Val Thr Val Asn Ala
            100                 105

<210> SEQ ID NO 36
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Asp Leu Ser
            20                  25                  30

Arg Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Val Val Glu Asp Ser Gly Thr
65                  70                  75                  80

Tyr Arg Cys Asn Val His Ser Val Ser Cys Ile Gln Arg Leu Asp Val
                85                  90                  95

Tyr Gly Gly Gly Thr Val Thr Val Asn Ala
            100                 105

<210> SEQ ID NO 37
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Ala Arg Val Asp Gln Thr Pro Gln Thr Ile Thr Lys Glu Thr Gly Glu
1               5                   10                  15

```
Ser Leu Thr Ile Asn Cys Val Leu Arg Asp Ser Asn Cys Ala Leu Ser
                20                  25                  30

Ser Thr Leu Trp Tyr Arg Thr Lys Ser Gly Ser Arg Asn Glu Glu Ser
            35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Lys Asp Ser Gly Thr
 65                  70                  75                  80

Tyr Arg Cys Asn Val Gln Gln Gly Val Val Ala Thr Cys Thr Ser Lys
                85                  90                  95

Arg Cys Asp Val Tyr Gly Gly Thr Ala Val Thr Val Asn Ala
                100                 105                 110

<210> SEQ ID NO 38
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Ala Arg Val Asp Gln Thr Pro Gln Thr Ile Thr Lys Glu Thr Gly Glu
1               5                   10                  15

Ser Leu Thr Ile Asn Cys Val Leu Arg Asp Asn Asn Cys Ala Leu Ser
                20                  25                  30

Ser Thr Leu Trp Tyr Arg Thr Lys Ser Gly Ser Arg Asn Glu Glu Ser
            35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Lys Val Trp Gln Asp Ser Leu Ser Gln Pro Cys Glu Ser
                85                  90                  95

Gly Cys Leu Asp Val Tyr Gly Gly Thr Ala Val Thr Val Asn Ala
                100                 105                 110

<210> SEQ ID NO 39
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
                20                  25                  30

Ser Thr Leu Trp Tyr Arg Thr Lys Ser Gly Ser Arg Asn Glu Glu Ser
            35                  40                  45

Ile Ser Lys Gly Gly Arg Tyr Val Glu Thr Val Asn Ser Gly Ser Lys
 50                  55                  60

Ser Phe Ser Leu Lys Ile Asn Asp Leu Thr Val Glu Asp Ser Gly Thr
 65                  70                  75                  80

Tyr Arg Cys Asn Val Gln Gly Met Val Tyr Asp Gly Ser Ser Phe Trp
                85                  90                  95
```

```
Trp Cys Asp Val Tyr Gly Asp Ser Thr Ala Val Thr Val Asn Ala
            100                 105                 110
```

<210> SEQ ID NO 40
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Leu Trp Tyr Arg Thr Lys Ser Gly Ser Arg Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Gln Phe Ser Tyr Asn Cys Asn Phe Trp Lys Asp
                85                  90                  95

Val Tyr Gly Gly Gly Thr Asp Val Thr Val Asn Ala
            100                 105
```

<210> SEQ ID NO 41
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Leu Trp Tyr Arg Thr Lys Ser Gly Ser Arg Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Lys Ile Asn Asp Leu Thr Val Glu Asp Ser Gly Thr
65                  70                  75                  80

Tyr Arg Cys Lys Val Cys Arg Gln Cys Cys Val Ala Thr Cys Asp Asp
                85                  90                  95

Leu Ser Leu Leu Cys Asp Val Tyr Gly Asp Gly Thr Ala Val Thr Val
            100                 105                 110

Asn Ala
```

<210> SEQ ID NO 42
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
            20                  25                  30

Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
65                  70                  75                  80

Tyr Arg Cys Gly Val Cys Glu Met Gln Leu Ile Ala Val Asp Ser Cys
                85                  90                  95

Asp His Thr Leu Asp Asp Gly Leu Cys Gly Gly Val Tyr Ala Ala Cys
            100                 105                 110

Gly Asp Gly Thr Ala Val Thr Val Asn Ala
            115                 120

<210> SEQ ID NO 43
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
            20                  25                  30

Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
65                  70                  75                  80

Tyr Arg Cys Gly Val Tyr Gly Gly Thr His Gln Gly Leu Cys Gly Cys
                85                  90                  95

Asp Trp Gln Leu Arg Phe Ser Leu Cys Gly Asp Gly Arg Ala Ala Cys
            100                 105                 110

Gly Asp Gly Thr Ala Val Thr Val Asn Ala
            115                 120

<210> SEQ ID NO 44
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
            20                  25                  30

```
Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
65                  70                  75                  80

Tyr Arg Cys Gly Val Cys Gln Cys Trp Ser Ala Asn Val Trp Val Asp
                85                  90                  95

Cys Asp Met Thr Ser Thr Ser Ile Arg Met Arg Asp Gly Ser Arg Ser
            100                 105                 110

Asn Ala Arg Ala Ala Cys Gly Asp Gly Thr Ala Val Thr Val Asn Ala
        115                 120                 125
```

<210> SEQ ID NO 45
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

```
Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
                20                  25                  30

Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
65                  70                  75                  80

Tyr Arg Cys Gly Val Cys Glu Ser Ser Phe Cys Ser Leu Pro Tyr Asp
                85                  90                  95

Cys Asp Ser Ser Ser Ala Gly Ser Val Ile Gln Pro Phe Gly His Ile
            100                 105                 110

Val Ser Leu Ala Ala Cys Gly Asp Gly Thr Ala Val Thr Val Asn Ala
        115                 120                 125
```

<210> SEQ ID NO 46
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

```
Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
                20                  25                  30

Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
65                  70                  75                  80
```

```
Tyr Arg Cys Gly Val Cys Ser Asp Tyr Gly Leu Gln Thr Thr Gly Gln
                85                  90                  95

Gln Ala Ala Cys Gly Asp Gly Thr Ala Val Thr Val Asn Ala
            100                 105                 110

<210> SEQ ID NO 47
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
                20                  25                  30

Ser Thr Cys Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Gly Gly Thr
65                  70                  75                  80

Tyr Arg Cys Gly Ala Ala Ile Gln Gly Phe Trp Ala Gly Arg Cys Asp
                85                  90                  95

Asn Leu Pro Gly Lys Cys Val Met Gln Val Ser Asn Ala Ala Ala Cys
            100                 105                 110

Gly Asp Gly Thr Ala Val Thr Val Asn Ala
        115                 120

<210> SEQ ID NO 48
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Glu Leu Gly
                20                  25                  30

Ser Thr Cys Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Gly Gly Thr
65                  70                  75                  80

Tyr Arg Cys Gly Ala Ser Leu Gln Cys Gly Asn Cys Glu Leu Cys Asp
                85                  90                  95

Arg Glu Gln Leu Gln Cys Gly Gln Arg Gly Gln Leu Ala Ala Cys
            100                 105                 110

Gly Asp Gly Thr Ala Val Thr Val Asn Ala
        115                 120

<210> SEQ ID NO 49
```

```
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Glu Leu Gly
            20                  25                  30

Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
65                  70                  75                  80

Tyr Arg Cys Gly Val Ile Ser Gln Tyr Lys Ser Tyr Thr Leu Trp Cys
                85                  90                  95

Asp Ala Leu Tyr Arg Ser Leu Gly Cys Glu Cys Ala Arg Ala Ala Cys
            100                 105                 110

Gly Asp Gly Thr Ala Val Thr Val Asn Ala
            115                 120

<210> SEQ ID NO 50
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
            20                  25                  30

Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
65                  70                  75                  80

Tyr Arg Cys Gly Val Met Asn Asn Val Ser Gln Thr Trp Val Arg Cys
                85                  90                  95

Asp Ser Gln Val Met Ser Gln Gln Cys Val Gln Gln Ser Ala Ala Cys
            100                 105                 110

Gly Asp Gly Thr Ala Val Thr Val Asn Ala
            115                 120

<210> SEQ ID NO 51
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 51

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
            20                  25                  30

Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Ile Gln Tyr Leu Tyr Leu Gly Ser Tyr Phe Ala
                85                  90                  95

Cys Asp Val Tyr Gly Gly Gly Thr Val Val Thr Val Asn Ala
            100                 105                 110

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Asp Val Gln Ala Cys Gly Asn Asp Trp Val Trp Leu Asp Val
1               5                   10                  15

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Phe Gly Val Asp Asn Gly Trp Trp Cys Asp Val
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Thr Gly Tyr Phe Arg Ser Thr Cys Leu Trp Arg Asp Val
1               5                   10

<210> SEQ ID NO 55
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gln Phe Thr Ala Ala Leu Trp Cys Glu Ala Val Leu Asp Val
1               5                   10

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gln Lys Gly Gln His Leu Gln Cys His Val Ala Val Gln Asp Val
1               5                   10                  15

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gln Trp Trp Leu Arg Cys Gly Tyr Phe Lys Asp Val
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Leu Thr Thr Asp Ser Tyr Asp Leu Gly Asp Val
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gln Tyr Phe Leu Cys His Phe Val Gly Asp Val
1               5                   10

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Arg Leu Ser Ala Ser Ala Val Leu Tyr Gln Ser Tyr Val Asp Val
1               5                   10                  15

<210> SEQ ID NO 61
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 61

Val Gln Tyr Pro Ser Tyr Asn Asn Tyr Phe Trp Cys Asp Val
1               5                   10

<210> SEQ ID NO 62
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Leu Asn Phe Phe Thr His Thr Cys Val Gln Val Gln Lys Tyr Asp Val
1               5                   10                  15

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Val Arg Ser Gly Val Gly Pro Cys Trp Ala Asp Val
1               5                   10

<210> SEQ ID NO 64
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Thr Met Val Arg Gly Arg Gly Cys Tyr Gln Pro Ala Arg Gly Gln Asp
1               5                   10                  15

Val

<210> SEQ ID NO 65
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Thr Phe Ser Ala Phe Glu Tyr Cys Tyr Val Phe Lys Val Gln Cys Asp
1               5                   10                  15

Val

<210> SEQ ID NO 66
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

His Val Arg Ala Gln Ser Leu Cys Cys Gln Cys Trp Tyr Gly Asp Val
1               5                   10                  15
```

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Asp Leu Pro Arg Tyr Leu Cys Phe Ser Gln Tyr Gly Arg Trp Tyr Asp
1               5                   10                  15

Val

<210> SEQ ID NO 68
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ala Arg His Trp Thr Gln Ser Cys Ala Tyr His Arg Asp Val
1               5                   10

<210> SEQ ID NO 69
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gln His Ile Phe Gln His Asn Cys Tyr Trp Phe Leu Tyr Asp Val
1               5                   10                  15

<210> SEQ ID NO 70
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Trp Ser Thr Gln Tyr Tyr Cys Val Leu Pro Asp Val
1               5                   10

<210> SEQ ID NO 71
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Tyr Thr Ser Tyr Cys Cys Ser Val Ala Asp Val
1               5                   10

<210> SEQ ID NO 72
<211> LENGTH: 17
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 72

Leu Thr Ser Gln Ser Gln Gly Gly Cys Val Arg Val Leu Tyr Ser Asp
1               5                   10                  15

Val

<210> SEQ ID NO 73
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

His Ser Phe Asn Met Asp Val Cys Ala Glu Phe Gln Tyr Ser Asp Val
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ile Asn Phe Phe Ala Met Glu Cys Glu Tyr Gln Val Gly Asp Val
1               5                   10                  15

<210> SEQ ID NO 75
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Leu Val Ser Met Phe Cys Gln Leu Ala Gln Asp Val
1               5                   10

<210> SEQ ID NO 76
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Cys Leu Leu Gln Leu Ala Gly Tyr Asp Ser Pro Tyr Asp Val
1               5                   10

<210> SEQ ID NO 77
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Asp Val Thr Arg Cys Thr Gln Ser Gln Asp Val
1               5                   10
```

<210> SEQ ID NO 78
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Lys His Tyr Val Cys Met Gln Ser Lys Asp Val
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Phe Ser Phe Ser Cys Gln Leu Leu Phe Asp Val
1               5                   10

<210> SEQ ID NO 80
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ser Thr Ser Val Pro Arg His Tyr Asp Asn Cys Arg Gln Arg Arg His
1               5                   10                  15

Asp Val

<210> SEQ ID NO 81
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Cys Gln Trp Leu Gln Trp Tyr Gly Gly Glu Met Glu Asp Val
1               5                   10

<210> SEQ ID NO 82
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Phe Leu Trp Asn Asn Tyr Asn Pro Met Asp Val
1               5                   10

<210> SEQ ID NO 83
<211> LENGTH: 17
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 83

Phe Gly Met Arg Thr His Cys Gln Trp Val Ile Tyr Arg Ile Thr Asp
1               5                   10                  15

Val

<210> SEQ ID NO 84
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ala Leu Tyr His Phe Thr Gly Cys Ser Arg Val Gln Asp Val
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ala Val Phe Thr Arg Cys His Asn Gln Gln Asp Val
1               5                   10

<210> SEQ ID NO 86
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Thr Trp Leu Asp Cys His Gln Cys Gly Ala Ser Asp Val
1               5                   10

<210> SEQ ID NO 87
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

His Ser Val Ser Cys Ile Gln Arg Leu Asp Val
1               5                   10

<210> SEQ ID NO 88
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gln Gln Gly Val Val Ala Thr Cys Thr Ser Lys Arg Cys Asp Val
1               5                   10                  15
```

<210> SEQ ID NO 89
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Trp Gln Asp Ser Leu Ser Gln Pro Cys Glu Ser Gly Cys Leu Asp Val
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gln Gly Met Val Tyr Asp Gly Ser Ser Phe Trp Trp Cys Asp Val
1               5                   10                  15

<210> SEQ ID NO 91
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gln Phe Ser Tyr Asn Cys Asn Phe Trp Lys Asp Val
1               5                   10

<210> SEQ ID NO 92
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gln Cys Cys Val Ala Thr Cys Asp Asp Leu Ser Leu Leu Cys Asp Val
1               5                   10                  15

<210> SEQ ID NO 93
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Cys Glu Met Gln Leu Ile Ala Val Asp Ser Cys Asp His Thr Leu Asp
1               5                   10                  15

Asp Gly Leu Cys Gly Gly Val
            20

<210> SEQ ID NO 94
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Tyr Gly Gly Thr His Gln Gly Leu Cys Gly Cys Asp Trp Gln Leu Arg
1               5                   10                  15

Phe Ser Leu Cys Gly Asp Gly
            20

<210> SEQ ID NO 95
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Cys Gln Cys Trp Ser Ala Asn Val Trp Val Asp Cys Asp Met Thr Ser
1               5                   10                  15

Thr Ser Ile Arg Met Arg Asp Gly Ser Arg Ser Asn Ala
            20                  25

<210> SEQ ID NO 96
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Cys Glu Ser Ser Phe Cys Ser Leu Pro Tyr Asp Cys Asp Ser Ser Ser
1               5                   10                  15

Ala Gly Ser Val Ile Gln Pro Phe Gly His Ile Val Ser
            20                  25

<210> SEQ ID NO 97
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Cys Ser Asp Tyr Gly Leu Gln Thr Thr Gly Gln
1               5                   10

<210> SEQ ID NO 98
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ala Ile Gln Gly Phe Trp Ala Gly Arg Cys Asp Asn Leu Pro Gly Lys
1               5                   10                  15

Cys Val Met Gln Val Ser Asn
            20

<210> SEQ ID NO 99

```
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ser Leu Gln Cys Gly Asn Cys Glu Leu Cys Asp Arg Glu Gln Leu Gln
1               5                   10                  15

Cys Gly Gly Gln Arg Gly Gln
            20

<210> SEQ ID NO 100
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ile Ser Gln Tyr Lys Ser Tyr Thr Leu Trp Cys Asp Ala Leu Tyr Arg
1               5                   10                  15

Ser Leu Gly Cys Glu Cys Ala
            20

<210> SEQ ID NO 101
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Met Asn Asn Val Ser Gln Thr Trp Val Arg Cys Asp Ser Gln Val Met
1               5                   10                  15

Ser Gln Gln Cys Val Gln Gln
            20

<210> SEQ ID NO 102
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ile Gln Tyr Leu Tyr Leu Gly Ser Tyr Phe Ala Cys Asp Val
1               5                   10

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Asp Asn Asn Cys Ala Leu Ser
1               5

<210> SEQ ID NO 104
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Asp Ser Asn Cys Ala Leu Ser
1               5

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Asp Ser Asn Cys Glu Leu Ser
1               5

<210> SEQ ID NO 106
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Asp Ser Asn Cys Ala Leu Pro
1               5

<210> SEQ ID NO 107
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Asp Ser Ile Cys Ala Leu Ser
1               5

<210> SEQ ID NO 108
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Asp Ser Asn Cys Asp Leu Ser
1               5

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 109

Asp Ala Ser Tyr Ala Leu Gly
1               5

<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Asp Ala Ser Tyr Glu Leu Gly
1               5

<210> SEQ ID NO 111
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111
gccagggtgg accagacccc ccagaccatc accaaggaga ccggcgagag cctgaccatc      60
aactgcgtgc tgagggacaa caactgcgcc ctgagcacca cctactggta caggaagaag     120
agcggcagca ccaacgagga gaacatcagc aagggcggca ggtacgtgga gaccgtgaac     180
agcggcagca agagcttcag cctgaagatc aacgacctga ccgtggagga cagcggcacc     240
tacaggtgca acgtgaggga cgtgcaggcc tgcggcaacg actgggtgtg gctggacgtg     300
tacggcggcg gcaccgtggt gaccgtgaac                                      330

<210> SEQ ID NO 112
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 112
gccagggtgg accagacccc ccagaccatc accaaggaga ccggcgagag cctgaccatc      60
aactgcgtgc tgagggacaa caactgcgcc ctgagcacca cctactggta caggaagaag     120
agcggcagca ccaacgagga gaacatcagc aagggcggca ggtacgtgga gaccgtgaac     180
agcggcagca agagcttcag cctgaagatc aacgacctga ccgtggagga cagcggcacc     240
tacaggtgca acgtgttcgg cgtggacaac ggctggtggt gcgacgtgta cggcggcggc     300
accgtggtga ccgtgaac                                                   318

<210> SEQ ID NO 113
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113

```
gccagggtgg accagacccc ccagaccatc accaaggaga ccggcgagag cctgaccatc        60
aactgcgtgc tgagggacaa caactgcgcc ctgagcacca cctactggta caggaagaag       120
agcggcagca ccaacgagga gaacatcagc aagggcggca ggtacgtgga gaccgtgaac       180
agcggcagca agagcttcag cctgaagatc aacgacctga ccgtggagga cagcggcacc       240
tacaggtgca acgtgaccgg ctacttcagg agcacctgcc tgtggaggga cgtgtacggc       300
ggcggcaccg ccgtgaccgt gaac                                              324
```

<210> SEQ ID NO 114
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114

```
gccagggtgg accagacccc ccagaccatc accaaggaga ccggcgagag cctgaccatc        60
aactgcgtgc tgagggacag caactgcgcc ctgagcagca cctactggta caggaagaag       120
agcggcagca ccaacgagga gaacatcagc aagggcggca ggtacgtgga gaccgtgaac       180
agcggcagca agagcttcag cctgaagatc aacgacctga ccgtggagga cagcggcacc       240
tacaggtgca acgtgcagtt caccgccgcc ctgtggtgcg aggccgtgct ggacgtgtac       300
ggcggcggca ccgtggtgac cgtgaac                                           327
```

<210> SEQ ID NO 115
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115

```
gccagggtgg accagacccc ccagaccatc accaaggaga ccggcgagag cctgaccatc        60
aactgcgtgc tgagggacag caactgcgcc ctgagcagca cctactggta caggaagaag       120
agcggcagca ccaacgagga gaacatcagc aagggcggca ggtacgtgga gaccgtgaac       180
agcggcagca agagcttcag cctgaagatc aacgacctga ccgtggagga cagcggcacc       240
tacaggtgca acgtgcagaa gggccagcac ctgcagtgcc acgtggccgt gcaggacgtg       300
tacggcggcg gcaccgccgt gaccgtgaac                                        330
```

<210> SEQ ID NO 116
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 116

```
gccagggtgg accagacccc ccagaccatc accaaggaga ccggcgagag cctgaccatc        60
aactgcgtgc tgagggacag caactgcgcc ctgagcagca cctactggta caggaagaag       120
agcgacagca ccaacgagga gagcatcagc aagggcggca ggtacgtgga gaccgtgaac       180
agcggcagca agagcttcag cctgaggatc aacgacctga ccgtggagga cagcggcacc       240
```

<210> SEQ ID NO 117
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117

```
gccagggtgg accagacccc ccagaccatc accaaggaga ccggcgagag cctgaccatc      60
aactgcgtgc tgagggacag caactgcgag ctgagcagca cctactggta caggaagaag     120
agcggcagca ccaacgaggc caggatcagc aagggcggca ggtacgtgga gaccgtgaac     180
agcggcagca agagcttcag cctgaagatc aacgacctga ccgtggagga cagcggcacc     240
tacaggtgca acgtgctgac caccgacagc tacgacctgg cgacgtgta cggcgacggc      300
accgtggtga ccgtgaac                                                    318
```

<210> SEQ ID NO 118
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 118

```
gccagggtgg accagacccc ccagaccatc accaaggaga ccggcgagag cctgaccatc      60
aactgcgtgc tgagggacag caactgcgag ctgagcagca cctactggta caggaagaag     120
agcggcagca ccaacgaggc caggatcagc aagggcggca ggtacgtgga gaccgtgaac     180
agcggcagca agagcttcag cctgaggatc aacgacctga ccgtggagga cagcggcacc     240
tacaggtgca acgtgcagta cttcctgtgc cacttcgtgg cgacgtgta cggcgacggc      300
accgccgtga ccgtgaac                                                    318
```

<210> SEQ ID NO 119
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 119

```
gccagggtgg accagacccc ccagaccatc accaaggaga ccggcgagag cctgaccatc      60
aactgcgtgc tgagggacag caactgcgcc ctgcccagca cctactggta caggaagaag     120
agcggcagca ccaacgaggc caggatcagc aagggcggca ggtacgtgga gaccgtgaac     180
agcggcagca agagcttcag cctgaggatc aacgacctga ccgtggagga cagcggcacc     240
atcgacgcca ggtacaggct gagcgccagc gccgtgctgt accagagcta cgtggacgtg     300
tacggcggcg gcaccgccgt gaccgtgaac                                       330
```

<210> SEQ ID NO 120
<211> LENGTH: 327
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 120
gccagggtgg accagacccc ccagaccatc accaaggaga ccggcgagag cctgaccatc      60
aactgcgtgc tgagggacag caactgcgcc ctgagcagca cctactggta caggaagaag     120
agcggcagca ccaacgagga gaacatcagc aagggcggca ggtacgtgga ccgtgaac       180 agcggcagca agagcttcag cctgaggatc aacgacctga ccgtggagga cagcggcacc    240
tacaggtgca acgtggtgca gtaccccagc tacaacaact acttctggtg cgacgtgtac    300
ggcgacggca ccgccgtgac cgtgaac                                         327

<210> SEQ ID NO 121
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121
gccagggtgg accagacccc ccagaccatc accaaggaga ccggcgagag cctgaccatc      60
aactgcgtgc tgagggacag caactgcgcc ctgcccagca cccactggta caggaagaag    120
agcggcagca ccaacgagga gagcatcagc aagggcggca ggtacgtgga ccgtgaac       180 agcggcagca agagcttcag cctgaggatc aacgacctga ccgtggagga cagcggcacc    240
tacaggtgca aggtgctgaa cttcttcacc cacacctgcg tgcaggtgca gaagtacgac    300
gtgtacggcg gcggcaccgc cgtgaccgtg aac                                  333

<210> SEQ ID NO 122
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122
gccagggtgg accagacccc ccagaccatc accaaggaga ccggcgagag cctgaccatc      60
aactgcgtgc tgagggacag catctgcgcc ctgagcagca cccactggta caggaagaag    120
agcggcagca ccaacgagga gagcatcagc aagggcggca ggtacgtgga ccgtgaac       180 agcggcagca agagcttcag cctgaggatc aacgacctga ccgtggagga cagcggcacc    240
tacaggtgca aggtggtgag gagcggcgtg ggccctgct gggccgacgt gtacggcggc      300
ggcaccgccg tgaccgtgaa c                                               321

<210> SEQ ID NO 123
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 123
gccagggtgg accagacccc ccagaccatc accaaggaga ccggcgagag cctgaccatc      60
aactgcgtgc tgagggacag caactgcgcc ctgcccagca cctacaggta caggaagaag    120
```

```
agcggcagca ccaacgagga gagcatcagc aagggcggca ggtacgtgga gaccgtgaac    180
agcggcagca agagcttcag cctgaggatc aacgacctga ccgtggagga cagcggcacc    240
tacaggtgca aggtgaccat ggtgagggc aggggctgct accagcccgc caggggccag    300
gacgtgtacg gcggcggcac cgccgtgacc gtgaac                              336

<210> SEQ ID NO 124
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124
gccagggtgg accagacccc ccagaccatc accaaggaga ccggcgagag cctgaccatc    60
aactgcgtgc tgagggacag caactgcgcc ctgcccagca cctactggta caggaagaag    120
agcggcagca ccaacgagga gagcatcagc aagggcggca ggtacgtgga gaccgtgaac    180
agcggcagca agagcttcag cctgaggatc aacgacctga ccgtggagga cagcggcacc    240
tacaggtgca aggtgacctt cagcgccttc gagtactgct acgtgttcaa ggtgcagtgc    300
gacgtgtacg gcgacggcac cgccgtgacc gtgaac                              336

<210> SEQ ID NO 125
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125
gccagggtgg accagacccc ccagaccatc accaaggaga ccggcgagag cctgaccatc    60
aactgcgtgc tgagggacag caactgcgcc ctgcccagca cctactggta ctgcaagaag    120
agcggcagca ccaacgagga gagcatcagc aagggcggca ggtacgtgga gaccgtgaac    180
agcggcagca agagcttcag cctgaggatc aacgacctga ccgtgaagga cagcggcacc    240
tacaggtgca aggtgcacgt gagggcccag agcctgtgct gccagtgctg gtacggcgac    300
gtgtacggcg acggcaccgc cgtgaccgtg aac                                 333

<210> SEQ ID NO 126
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 126
gccagggtgg accagacccc ccagaccatc accaaggaga ccggcgagag cctgaccatc    60
aactgcgtgc tgagggacag caactgcgcc ctgcccagca cctactggta caggaagaag    120
agcggcagca ccaacgagga gagcatcagc aagggcggca ggtacgtgga gaccgtgaac    180
agcggcagca agagcttcag cctgaggatc aacgacctga ccgtgaagga cagcggcacc    240
tacaggtgca aggtggacct gcccaggtac ctgtgcttca gccagtacgg caggtggtac    300
gacgtgtacg gcgacggcac cgccgtgacc gtgaac                              336

<210> SEQ ID NO 127
```

<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 127
gccagggtgg accagacccc ccagaccatc accaaggaga ccggcgagag cctgaccatc    60
aactgcgtgc tgagggacag caactgcgcc ctgcccagca cctactggta caggaagaag   120
agcggcagca ccaacgagga gagcatcagc aagggcggca ggtacgtgga ccgtgaac    180 agcggcagca agagcttcag cctgaggatc aacgacctga ccgtgaagga cagcggcacc   240
tacaggtgca acgtggccag gcactggacc cagagctgcg cctaccacag ggacgtgtac   300
ggcggcggca ccgccgtgac cgtgaac                                       327

<210> SEQ ID NO 128
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 128
gccagggtgg accagacccc ccagaccatc accaaggaga ccggcgagag cctgaccatc    60
aactgcgtgc tgagggacag caactgcgcc ctgcccagca cctactggta caggaagaag   120
agcggcagca ccaacgagga gagcatcagc aagggcggca ggtacgtgga ccgtgaac    180 agcggcagca agagcttcag cctgaggatc aacgacctga ccgtgaagga cagcggcacc   240
tacaggtgca acgtgcagca catcttccag cacaactgct actggttcct gtacgacgtg   300
tacggcggcg gcaccgccgt gaccgtgaac                                    330

<210> SEQ ID NO 129
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 129
gccagggtgg accagacccc ccagaccatc accaaggaga ccggcgagag cctgaccatc    60
aactgcgtgc tgagggacag caactgcgcc ctgcccagca cctactggta caggaagaag   120
agcggcagca ccaacgagga gagcatcagc aagggcggca ggtacgtgga ccgtgaac    180 agcggcagca agagcttcag cctgaggatc aacgacctga ccgtggagga cagcggcacc   240
tacaggtgca acgtgggctg gagcacccag tactactgcg tgctgcccga cgtgtacggc   300
ggcggcaccg ccgtgaccgt gaac                                          324

<210> SEQ ID NO 130
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 130

```
gccagggtgg accagacccc ccagaccatc accaaggaga ccggcgagag cctgaccatc      60
aactgcgtgc tgagggacag caactgcgcc ctgcccagca cctactggta caggaagaag     120
agcggcagca ccaacgagga gagcatcagc aagggcggca ggtacgtgga gaccgtgaac     180
agcggcagca agagcttcag cctgaggatc aacgacctga ccgtggagga cagcggcacc     240
tacaggtgca acgtgtacac cagctactgc tgcagcgtgg ccgacgtgta cggcggcggc     300
accgccgtga ccgtgaac                                                   318
```

<210> SEQ ID NO 131
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 131

```
gccagggtgg accagacccc ccagaccatc accaaggaga ccggcgagag cctgaccatc      60
aactgcgtgc tgagggacag caactgcgcc ctgagcagca cctactggta caggaagaag     120
agcggcagca ccaacgagga gagcatcagc aagggcggca ggtacgtgga gaccgtgaac     180
agcggcagca agagcttcag cctgaggatc aacgacctga ccgtggagga cagcggcacc     240
tacaggtgca aggtgctgac cagccagagc cagggcggct gcgtgagggt gctgtacagc     300
gacgtgtacg gcgacggcac cgccgtgacc gtgaac                               336
```

<210> SEQ ID NO 132
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 132

```
gccagggtgg accagacccc ccagaccatc accaaggaga ccggcgagag cctgaccatc      60
aactgcgtgc tgagggacag caactgcgcc ctgagcagca cctactggta caggaagaag     120
agcgacagca ccaacgagga gagcatcagc aagggcggca ggtacgtgga gaccgtgaac     180
agcggcagca agagcttcag cctgaggatc aacgacctga ccgtggagga cagcggcacc     240
tacaggtgca aggtgcacag cttcaacatg gacgtgtgcg ccgagttcca gtacagcgac     300
gtgtacggcg acggcaccgc cgtgaccgtg aac                                  333
```

<210> SEQ ID NO 133
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 133

```
gccagggtgg accagacccc ccagaccatc accaaggaga ccggcgagag cctgaccatc      60
aactgcgtgc tgagggacag caactgcgcc ctgagcaacc tgtactggta caggaagaag     120
agcggcagca ccaacgagga gagcatcagc aagggcggca ggtacgtgga gaccgtgaac     180
agcggcagca agagcttcag cctgaggatc aacgacctga ccgtggagga cagcggcacc     240
```

```
tacaggtgca acgtgatcaa cttcttcgcc atggagtgcg agtaccaggt gggcgacgtg        300
tacggcgacg gcaccgccgt gaccgtgaac                                         330

<210> SEQ ID NO 134
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 134
gccagggtgg accagacccc ccagaccatc accaaggaga ccggcgagag cctgaccatc        60
aactgcgtgc tgagggacag caactgcgcc ctgagcaacc tgtactggta caggaagaag       120
agcggcagca ccaacgagga gagcatcagc aagggcggca ggtacgtgga gaccgtgaac       180
agcggcagca agagcttcag cctgaggatc aacgacctga ccgtgaagga cagcggcacc       240
tacaggtgca acgtgctggt gagcatgttc tgccagctgg cccaggacgt gtacggcgac       300
ggcaccgccg tgaccgtgaa c                                                 321

<210> SEQ ID NO 135
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 135
gccagggtgg accagacccc ccagaccatc accaaggaga ccggcgagag cctgaccatc        60
aactgcgtgc tgagggacag caactgcgcc ctgagcaacc tgtactggta caggaagaag       120
agcggcagca ccaacgagga gagcatcagc ctgggcggca ggtacgtgga gaccgtgaac       180
agcggcagca agagcttcag cctgaggatc aacgacctga ccgtggagga cagcggcacc       240
tacaggtgca acgtgtgcct gctgcagctg gccggctacg acagcccta cgacgtgtac        300 ggcggcggca ccgccgtgac cgtgaac                                           327

<210> SEQ ID NO 136
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 136
gccagggtgg accagacccc ccagaccatc accaaggaga ccggcgagag cctgaccatc        60
aactgcgtgc tgagggacag caactgcgcc ctgagcaacc tgtactggta caggaagaag       120
agcggcagca ccaacgagga gaacatcagc aagggcggca ggtacgtgga gaccgtgaac       180
agcggcagca agagcttcag cctgaggatc aacgacctga ccgtggagga cagcggcacc       240
tacaggtgca acgtggacgt gaccaggtgc acccagagcc aggacgtgta cggcggcggc       300
accgccgtga ccgtgaac                                                     318

<210> SEQ ID NO 137
<211> LENGTH: 318
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 137
gccagggtgg accagacccc ccagaccgtg accaaggaga ccggcgagag cctgaccatc     60
aactgcgtgc tgagggacag caactgcgcc ctgagcaacc tgtactggta caggaagaag    120
agcggcagca ccaacgagga gagcatcagc ctgggcggca ggtacgtgga gaccgtgaac    180
agcggcagca agagcttcag cctgaggatc aacgacctga ccgtggagga cagcggcacc    240
tacaggtgca acgtgaagca ctacgtgtgc atgcagagca aggacgtgta cggcggcggc    300
accgtggtga ccgtgaac                                                  318

<210> SEQ ID NO 138
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 138
gccagggtgg accagacccc ccagaccatc accaaggaga ccggcgagag cctgaccatc     60
aactgcgtgc tgagggacag caactgcgcc ctgagcaacc tgtactggta caggaagaag    120
agcggcagca ccaacgagga gagcatcagc ctgggcggca ggtacgtgga gaccgtgaac    180
agcggcagca agagcttcag cctgaggatc aacgacctga ccgtgaagga cagcggcacc    240
tacaggtgca acgtgttcag cttcagctgc cagctgctgt tcgacgtgta cggcggcggc    300
accgccgtga ccgtgaac                                                  318

<210> SEQ ID NO 139
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 139
gccagggtgg accagacccc ccagaccatc accaaggaga ccggcgagag cctgaccatc     60
aactgcgtgc tgagggacag caactgcgcc ctgagcaacc tgtactggta caggaagaag    120
agcggcagca ccaacgagga gagcatcagc ctgggcggca ggtacgtgga gaccgtgaac    180
agcggcagca agagcttcag cctgaggatc aacgacctga ccgtggagga cagcggcacc    240
tacaggtgca aggtgagcac cagcgtgccc aggcactacg acaactgcag gcagaggagg    300
cacgacgtgt acggcggcgg caccgccgtg accgtgaac                           339

<210> SEQ ID NO 140
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 140
gccagggtgg accagacccc ccagaccatc accaaggaga ccggcgagag cctgaccatc     60
aactgcgtgc tgagggacag caactgcgcc ctgagcaacc tgtactggta caggaagaag    120

```
agcggcagca ccaacgagga gagcatcagc ctgggcggca ggtacgtgga gaccgtgaac        180
agcggcagca agagcttcag cctgaggatc aacgacctga ccgtggagga cagcggcacc        240
tacaggtgca acgtgtgcca gtggctgcag tggtacggcg gcgagatgga ggacgtgtac        300
ggcggcggca ccgccgtgac cgtgaac                                            327
```

<210> SEQ ID NO 141
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 141

```
gccagggtgg accagacccc ccagaccatc accaaggaga ccggcgagag cctgaccatc        60
aactgcgtgc tgagggacag caactgcgac ctgagcagga cctactggta caggaagaag       120
agcggcagca ccaacgagga gagcatcagc aagggcggca ggtacgtgga gaccgtgaac       180
agcggcagca agagcttcag cctgaagatc aacgacctga ccgtggagga cagcggcacc       240
tacaggtgca acgtgttcct gtggaacaac tacaacccca tggacgtgta cggcggcggc       300
accgccgtga ccgtgaac                                                     318
```

<210> SEQ ID NO 142
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 142

```
gccagggtgg accagacccc ccagaccatc accaaggaga ccggcgagag cctgaccatc        60
aactgcgtgc tgagggacag caactgcgcc ctgagcaacc tgtactggta caggaagaag       120
agcggcagca ggaacgagga gagcatcagc aagggcggca ggtacgtgga gaccgtgaac       180
agcggcagca agagcttcag cctgaagatc aacgacctga ccgtggagga cagcggcacc       240
tacaggtgca aggtgttcgg catgaggacc cactgccagt gggtgatcta caggatcacc       300
gacgtgtacg gcggcggcac cgccgtgacc gtgaac                                 336
```

<210> SEQ ID NO 143
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 143

```
gccagggtgg accagacccc ccagaccatc accaaggaga ccggcgagag cctgaccatc        60
aactgcgtgc tgagggacag caactgcgac ctgagcagga cctactggta caggaagaag       120
cagggcagca ccaacgagga gagcatcagc aagggcggca ggtacgtgga gaccgtgaac       180
agcggcagca agagcttcag cctgaggatc aacgacctga ccgtggagga cagcggcacc       240
tacaggtgca acgtggccct gtaccacttc accggctgca gcagggtgca ggacgtgtac       300
ggcggcggca ccgtggtgac cgtgaac                                           327
```

<210> SEQ ID NO 144

```
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 144
gccagggtgg accagacccc ccagaccatc accaaggaga ccggcgagag cctgaccatc    60
aactgcgtgc tgagggacag caactgcgac ctgagcagga cctactggta caggaagaag   120
agcggcagca ccaacgagga gagcatcagc aagggcggca ggtacgtgga gaccgtgaac   180
agcggcagca agagcttcag cctgaggatc aacgacctgg tggtggagga cagcggcacc   240
tacaggtgca acgtggccgt gttcaccagg tgccacaacc agcaggacgt gtacggcggc   300
ggcaccgccg tgaccgtgaa c                                             321

<210> SEQ ID NO 145
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 145
gccagggtgg accagacccc ccagaccatc accaaggaga ccggcgagag cctgaccatc    60
aactgcgtgc tgagggacag caactgcgac ctgagcagga cctactggta caggaagaag   120
agcggcagca ccaacgagga gagcatcagc aagggcggca ggtacgtgga gaccgtgaac   180
agcggcagca agagcttcag cctgaggatc aacgacctga ccgtggagga cagcggcacc   240
tacaggtgca acgtgacctg gctggactgc caccagtgcg cgccagcga cgtgtacggc   300 ggcggcaccg tggtgaccgt gaac                                          324

<210> SEQ ID NO 146
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 146
gccagggtgg accagacccc ccagaccatc accaaggaga ccggcgagag cctgaccatc    60
aactgcgtgc tgagggacag caactgcgac ctgagcagga cctactggta caggaagaag   120
agcggcagca ccaacgagga gagcatcagc aagggcggca ggtacgtgga gaccgtgaac   180
agcggcagca agagcttcag cctgaggatc aacgacctgg tggtggagga cagcggcacc   240
tacaggtgca acgtgcacag cgtgagctgc atccagaggc tggacgtgta cggcggcggc   300
accgtggtga ccgtgaac                                                 318

<210> SEQ ID NO 147
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 147

```
gccagggtgg accagacccc ccagaccatc accaaggaga ccggcgagag cctgaccatc    60
aactgcgtgc tgagggacag caactgcgcc ctgagcagca ccctgtggta caggaccaag   120
agcggcagca ggaacgagga gagcatcagc aagggcggca ggtacgtgga gaccgtgaac   180
agcggcagca agagcttcag cctgaggatc aacgacctga ccgtgaagga cagcggcacc   240
tacaggtgca acgtgcagca gggcgtggtg gccacctgca ccagcaagag gtgcgacgtg   300
tacggcggcg gcaccgccgt gaccgtgaac                                    330
```

<210> SEQ ID NO 148
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 148

```
gccagggtgg accagacccc ccagaccatc accaaggaga ccggcgagag cctgaccatc    60
aactgcgtgc tgagggacaa caactgcgcc ctgagcagca ccctgtggta caggaccaag   120
agcggcagca ggaacgagga gagcatcagc aagggcggca ggtacgtgga gaccgtgaac   180
agcggcagca agagcttcag cctgaggatc aacgacctga ccgtggagga cagcggcacc   240
tacaggtgca aggtgtggca ggacagcctg agccagccct gcgagagcgg ctgcctggac   300
gtgtacggcg gcggcaccgc cgtgaccgtg aac                                333
```

<210> SEQ ID NO 149
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 149

```
gccagggtgg accagacccc ccagaccatc accaaggaga ccggcgagag cctgaccatc    60
aactgcgtgc tgagggacag caactgcgcc ctgagcagca ccctgtggta caggaccaag   120
agcggcagca ggaacgagga gagcatcagc aagggcggca ggtacgtgga gaccgtgaac   180
agcggcagca agagcttcag cctgaagatc aacgacctga ccgtggagga cagcggcacc   240
tacaggtgca acgtgcaggg catggtgtac gacggcagca gcttctggtg gtgcgacgtg   300
tacggcgaca gcaccgccgt gaccgtgaac                                    330
```

<210> SEQ ID NO 150
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 150

```
gccagggtgg accagacccc ccagaccatc accaaggaga ccggcgagag cctgaccatc    60
aactgcgtgc tgagggacag caactgcgcc ctgagcagca ccctgtggta caggaccaag   120
agcggcagca ggaacgagga gagcatcagc aagggcggca ggtacgtgga gaccgtgaac   180
agcggcagca agagcttcag cctgaggatc aacgacctga ccgtggagga cagcggcacc   240
```

```
tacaggtgca acgtgcagtt cagctacaac tgcaacttct ggaaggacgt gtacggcggc    300
ggcaccgacg tgaccgtgaa c                                              321

<210> SEQ ID NO 151
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 151
gccagggtgg accagacccc ccagaccatc accaaggaga ccggcgagag cctgaccatc     60
aactgcgtgc tgagggacag caactgcgcc ctgagcagca ccctgtggta caggaccaag    120
agcggcagca ggaacgagga gagcatcagc aagggcggca ggtacgtgga gaccgtgaac    180
agcggcagca agagcttcag cctgaagatc aacgacctga ccgtggagga cagcggcacc    240
tacaggtgca aggtgtgcag gcagtgctgc gtggccacct gcgacgacct gagcctgctg    300
tgcgacgtgt acggcgacgg caccgccgtg accgtgaac                            339

<210> SEQ ID NO 152
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 152
gccagggtgg accagacccc caggagcgtg accaaggaga ccggcgagag cctgaccatc     60
aactgcgtgc tgagggacgc cagctacgcc ctgggcagca cctgctggta caggaagaag    120
agcggcagca ccaacgagga gagcatcagc aagggcggca ggtacgtgga gaccgtgaac    180
agcggcagca agagcttcag cctgaggatc aacgacctga ccgtggagga cggcggcacc    240
tacaggtgcg gcgtgtgcga gatgcagctg atcgccgtgg acagctgcga ccacaccctg    300
gacgacggcc tgtgcggcgg cgtgtacgcc gcctgcggcg acggcaccgc cgtgaccgtg    360
aac                                                                   363

<210> SEQ ID NO 153
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 153
gccagggtgg accagacccc caggagcgtg accaaggaga ccggcgagag cctgaccatc     60
aactgcgtgc tgagggacgc cagctacgcc ctgggcagca cctgctggta caggaagaag    120
agcggcagca ccaacgagga gagcatcagc aagggcggca ggtacgtgga gaccgtgaac    180
agcggcagca agagcttcag cctgaggatc aacgacctga ccgtggagga cggcggcacc    240
tacaggtgcg gcgtgtacgg cggcacccac cagggcctgt gcggctgcga ctggcagctg    300
aggttcagcc tgtgcggcga cggcagggcc gcctgcggcg acggcaccgc cgtgaccgtg    360
aac                                                                   363
```

<210> SEQ ID NO 154
<211> LENGTH: 381
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 154

```
gccagggtgg accagacccc caggagcgtg accaaggaga ccggcgagag cctgaccatc      60
aactgcgtgc tgagggacgc cagctacgcc ctgggcagca cctgctggta caggaagaag     120
agcggcagca ccaacgagga gagcatcagc aagggcggca ggtacgtgga gaccgtgaac     180
agcggcagca agagcttcag cctgaggatc aacgacctga ccgtggagga cggcggcacc     240
tacaggtgcg gcgtgtgcca gtgctggagc gccaacgtgt gggtggactg cgacatgacc     300
agcaccagca tcaggatgag ggacggcagc aggagcaacg ccagggccgc ctgcggcgac     360
ggcaccgccg tgaccgtgaa c                                                381
```

<210> SEQ ID NO 155
<211> LENGTH: 381
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 155

```
gccagggtgg accagacccc caggagcgtg accaaggaga ccggcgagag cctgaccatc      60
aactgcgtgc tgagggacgc cagctacgcc ctgggcagca cctgctggta caggaagaag     120
agcggcagca ccaacgagga gagcatcagc aagggcggca ggtacgtgga gaccgtgaac     180
agcggcagca agagcttcag cctgaggatc aacgacctga ccgtggagga cggcggcacc     240
tacaggtgcg gcgtgtgcga gagcagcttc tgcagcctgc cctacgactg cgacagcagc     300
agcgccggca gcgtgatcca gcccttcggc cacatcgtga gcctggccgc ctgcggcgac     360
ggcaccgccg tgaccgtgaa c                                                381
```

<210> SEQ ID NO 156
<211> LENGTH: 327
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 156

```
gccagggtgg accagacccc caggagcgtg accaaggaga ccggcgagag cctgaccatc      60
aactgcgtgc tgagggacgc cagctacgcc ctgggcagca cctgctggta caggaagaag     120
agcggcagca ccaacgagga gagcatcagc aagggcggca ggtacgtgga gaccgtgaac     180
agcggcagca agagcttcag cctgaggatc aacgacctga ccgtggagga cggcggcacc     240
tacaggtgcg gcgtgtgcag cgactacggc ctgcagacca ccggccagca ggccgcctgc     300
ggcgacggca ccgccgtgac cgtgaac                                          327
```

<210> SEQ ID NO 157
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 157
gccagggtgg accagacccc caggagcgtg accaaggaga ccggcgagag cctgaccatc    60
aactgcgtgc tgagggacgc cagctacgcc ctgggcagca cctgctggta caggaagaag    120
agcggcagca ccaacgagga gagcatcagc aagggcggga ggtacgtgga gaccgtgaac    180
agcggcagca agagcttcag cctgaggatc aacgacctga ccgtggagga cggcggcacc    240
tacaggtgcg cgccgccat ccagggcttc tgggccggca ggtgcgacaa cctgcccggc    300
aagtgcgtga tgcaggtgag caacgccgcc gcctgcggcg acggcaccgc cgtgaccgtg    360
aac                                                                 363

<210> SEQ ID NO 158
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 158
gccagggtgg accagacccc caggagcgtg accaaggaga ccggcgagag cctgaccatc    60
aactgcgtgc tgagggacgc cagctacgag ctgggcagca cctgctggta caggaagaag    120
agcggcagca ccaacgagga gagcatcagc aagggcggga ggtacgtgga gaccgtgaac    180
agcggcagca agagcttcag cctgaggatc aacgacctga ccgtggagga cggcggcacc    240
tacaggtgcg cgccagcct gcagtgcggc aactgcgagc tgtgcgacag ggagcagctg    300
cagtgcggcg gccagagggg ccagctggcc gcctgcggcg acggcaccgc cgtgaccgtg    360
aac                                                                 363

<210> SEQ ID NO 159
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 159
gccagggtgg accagacccc caggagcgtg accaaggaga ccggcgagag cctgaccatc    60
aactgcgtgc tgagggacgc cagctacgag ctgggcagca cctgctggta caggaagaag    120
agcggcagca ccaacgagga gagcatcagc aagggcggga ggtacgtgga gaccgtgaac    180
agcggcagca agagcttcag cctgaggatc aacgacctga ccgtggagga cggcggcacc    240
tacaggtgcg cgtgatcag ccagtacaag agctacaccc tgtggtgcga cgccctgtac    300
aggagcctgg gctgcgagtg cgccagggcc gcctgcggcg acggcaccgc cgtgaccgtg    360
aac                                                                 363

<210> SEQ ID NO 160
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 160

```
gccagggtgg accagacccc caggagcgtg accaaggaga ccggcgagag cctgaccatc    60
aactgcgtgc tgagggacgc cagctacgcc ctgggcagca cctgctggta caggaagaag   120
agcggcagca ccaacgagga gagcatcagc aagggcggga ggtacgtgga gaccgtgaac   180
agcggcagca agagcttcag cctgaggatc aacgacctga ccgtggagga cggcggcacc   240
tacaggtgcg gcgtgatgaa caacgtgagc cagacctggg tgaggtgcga cagccaggtg   300
atgagccagc agtgcgtgca gcagagcgcc gcctgcggcg acggcaccgc cgtgaccgtg   360
aac                                                                 363
```

<210> SEQ ID NO 161
<211> LENGTH: 327
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 161

```
gccagggtgg accagacccc caggagcgtg accaaggaga ccggcgagag cctgaccatc    60
aactgcgtgc tgagggacgc cagctacgcc ctgggcagca cctgctggta caggaagaag   120
agcggcagca ccaacgagga gagcatcagc aagggcggga ggtacgtgga gaccgtgaac   180
agcggcagca agagcttcag cctgaggatc aacgacctga ccgtggagga cagcggcacc   240
tacaggtgca acgtgatcca gtacctgtac ctgggcagct acttcgcctg cgacgtgtac   300
ggcggcggca ccgtggtgac cgtgaac                                       327
```

<210> SEQ ID NO 162
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 162

```
Ala Arg Val Asp Gln Thr Pro Gln Thr Ile Thr Lys Glu Thr Gly Glu
1               5                   10                  15
Ser Leu Thr Ile Asn Cys Val Leu Arg Asp Asn Asn Cys Ala Leu Ser
            20                  25                  30
Ser Thr Leu Trp Tyr Arg Thr Lys Ser Gly Ser Arg Asn Glu Glu Ser
        35                  40                  45
Ile Ser Lys Gly Gly Arg Tyr Val Glu Thr Val Asn Ser Gly Ser Lys
    50                  55                  60
Ser Phe Ser Leu Arg Ile Asn Asp Leu Thr Val Glu Asp Ser Gly Thr
65                  70                  75                  80
Tyr Arg Cys Asn Val Gln Ser Trp Pro Pro Gly Asn Gly Trp Trp Cys
                85                  90                  95
Asp Val Tyr Gly Asp Gly Thr Ala Val Thr Val Asn Ala
            100                 105
```

<210> SEQ ID NO 163
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 163

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Asp Leu Ser
            20                  25                  30

Arg Thr Tyr Trp Tyr Arg Lys Lys Ser Gly Ser Thr Asn Glu Glu Asn
        35                  40                  45

Ile Ser Lys Gly Gly Arg Tyr Val Glu Thr Val Asn Ser Gly Ser Lys
50                  55                  60

Ser Phe Ser Leu Arg Ile Asn Asp Leu Thr Val Glu Asp Ser Gly Thr
65                  70                  75                  80

Tyr Arg Cys Asn Val Gln Ser Met Tyr Val Gly Tyr Gly Trp Ser Leu
                85                  90                  95

Asp Val Tyr Gly Gly Gly Thr Val Val Thr Val Asn Ala
            100                 105

<210> SEQ ID NO 164
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Asn
        35                  40                  45

Ile Ser Lys Gly Gly Arg Tyr Val Glu Thr Val Asn Ser Gly Ser Lys
50                  55                  60

Ser Phe Ser Leu Arg Ile Asn Asp Leu Thr Val Glu Asp Ser Gly Thr
65                  70                  75                  80

Tyr Arg Cys Asn Val Gln Tyr Pro Ser Tyr Asn Asn Tyr Phe Trp
                85                  90                  95

Cys Asp Val Tyr Gly Asp Gly Thr Ala Val Thr Val Asn Ala
            100                 105                 110

<210> SEQ ID NO 165
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Asn Ser Tyr Trp Tyr Arg Lys Lys Ser Gly Ser Thr Asn Glu Glu Ser
        35                  40                  45

Ile Ser Leu Gly Gly Arg Tyr Val Glu Thr Val Asn Ser Gly Ser Lys
50                  55                  60

Ser Phe Ser Leu Arg Ile Asn Asp Leu Thr Val Glu Asp Ser Gly Thr
65                  70                  75                  80

Tyr Arg Cys Asn Val Gly Phe Thr His Pro Gln Ile Cys Asp Leu Thr
                85                  90                  95

Gln Asp Val Tyr Gly Gly Gly Thr Val Val Thr Val Asn Ala
            100                 105                 110

<210> SEQ ID NO 166
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
                20                  25                  30

Ser Thr Tyr Trp Tyr Arg Lys Lys Ser Gly Ser Thr Asn Glu Glu Asn
            35                  40                  45

Ile Ser Lys Gly Gly Arg Tyr Val Glu Thr Val Asn Ser Gly Ser Lys
50                  55                  60

Ser Phe Ser Leu Arg Ile Asn Asp Leu Thr Val Glu Asp Ser Gly Thr
65                  70                  75                  80

Tyr Arg Cys Asn Val Gln Pro His Cys Gly Tyr His Trp Leu Asp Val
                85                  90                  95

Tyr Gly Asp Gly Thr Ala Val Thr Val Asn Ala
            100                 105

<210> SEQ ID NO 167
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Ala Arg Val Asp Gln Thr Pro Gln Thr Ile Thr Lys Glu Thr Gly Glu
1               5                   10                  15

Ser Leu Thr Ile Asn Cys Val Leu Arg Asp Asn Asn Cys Ala Leu Ser
                20                  25                  30

Ser Thr Leu Trp Tyr Arg Lys Lys Ser Gly Ser Thr Asn Glu Glu Asn
            35                  40                  45

Ile Ser Lys Gly Gly Arg Tyr Val Glu Thr Val Asn Ser Gly Ser Lys
50                  55                  60

Ser Phe Ser Leu Arg Ile Asn Asp Leu Thr Val Glu Asp Ser Gly Thr
65                  70                  75                  80

Tyr Arg Cys Lys Val Leu His Ser Gln Pro Gln Asp Gly Cys Tyr Phe
                85                  90                  95

Ser Gln Ala Val Asp Val Tyr Gly Asp Gly Thr Ala Val Thr Val Asn
            100                 105                 110

Ala

<210> SEQ ID NO 168
<211> LENGTH: 110
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 168

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Arg Lys Lys Ser Gly Ser Thr Asn Glu Glu Ser
        35                  40                  45

Ile Ser Leu Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Met Gln Phe Pro Gly Pro Asp Asn Ser Thr Trp
                85                  90                  95

Trp Asp Val Tyr Gly Gly Gly Thr Val Val Thr Val Asn Ala
                100                 105                 110

<210> SEQ ID NO 169
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Glu Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Val Val Glu Asp Ser Gly Thr
65                  70                  75                  80

Tyr Arg Cys Asn Val Gln Gln Phe Pro Ser Ser Asn Gly Arg Tyr
                85                  90                  95

Trp Cys Asp Val Tyr Gly Gly Gly Thr Ala Val Thr Val Asn Ala
                100                 105                 110

<210> SEQ ID NO 170
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Asn
        35                  40                  45

```
Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Gln Phe Leu Gly Phe Thr Asn Ser Gly Gly Tyr
                 85                  90                  95

Trp Cys Asp Val Tyr Gly Gly Gly Thr Ala Val Thr Val Asn Ala
            100                 105                 110

<210> SEQ ID NO 171
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Ala Arg Val Asp Gln Thr Pro Gln Thr Ile Thr Lys Glu Thr Gly Glu
 1                   5                  10                  15

Ser Leu Thr Ile Asn Cys Val Leu Arg Asp Ser Asn Cys Ala Leu Pro
                 20                  25                  30

Ser Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Leu Asn Trp Phe Ala Tyr Glu Cys Gln Arg Gln
                 85                  90                  95

Asp Val Tyr Gly Gly Gly Thr Ala Val Thr Val Asn Ala
            100                 105

<210> SEQ ID NO 172
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Ala Arg Val Asp Gln Thr Pro Gln Thr Ile Thr Lys Glu Thr Gly Glu
 1                   5                  10                  15

Ser Leu Thr Ile Asn Cys Val Leu Arg Asp Ser Asn Cys Ala Leu Pro
                 20                  25                  30

Ser Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Val Val Glu Asp Ser Gly Thr
 65                  70                  75                  80

Tyr Arg Cys Lys Val Met Asn Tyr Phe Ser Tyr Thr Cys Gln Trp Val
                 85                  90                  95

Gly Asp Asp Asp Val Tyr Gly Asp Gly Thr Ala Val Thr Val Asn Ala
            100                 105                 110

<210> SEQ ID NO 173
```

```
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Gln Glu Asn
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Lys Trp Gly Ser Val Ser Asn Gly Trp Leu Thr
                85                  90                  95

Asp Val Tyr Gly Asp Gly Thr Val Val Thr Val Asn Ala
            100                 105

<210> SEQ ID NO 174
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Ala Arg Val Asp Gln Thr Pro Gln Thr Ile Thr Lys Gln Thr Gly Glu
1               5                   10                  15

Ser Leu Thr Ile Asn Cys Val Leu Arg Asp Ser Asn Cys Ala Leu Ser
            20                  25                  30

Ser Thr Leu Trp Tyr Arg Thr Lys Ser Gly Ser Arg Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Lys Ile Asn Asp Leu Thr Val Glu Asp Ser Gly Thr
65                  70                  75                  80

Tyr Arg Cys Asn Val Asn Tyr Arg Cys Cys Gly Leu Gln Asp Val Tyr
                85                  90                  95

Gly Gly Gly Thr Ala Val Thr Val Asn Ala
            100                 105

<210> SEQ ID NO 175
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Glu Leu Ser
            20                  25                  30
```

```
Ser Thr Tyr Trp Tyr Arg Lys Lys Ser Gly Ser Thr Asn Glu Ala Arg
        35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Gln Arg Met Tyr Cys Ala Met Ala Asn Asp Val
                 85                  90                  95

Tyr Gly Gly Gly Thr Val Val Thr Val Asn Ala
                100                 105
```

```
<210> SEQ ID NO 176
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Ala Arg Val Asp Gln Thr Pro Gln Thr Ile Thr Lys Glu Thr Gly Glu
 1                5                  10                  15

Ser Leu Thr Ile Asn Cys Val Leu Arg Asp Ser Asn Cys Ala Leu Pro
                 20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Lys Asp Ser Gly Thr
 65                  70                  75                  80

Tyr Arg Cys Asn Val Phe Gly Val Gln Asn Cys Asn Asp Gly Leu Met
                 85                  90                  95

Trp Ser Asp Val Tyr Gly Asp Gly Thr Ala Val Thr Val Asn Ala
                100                 105                 110
```

```
<210> SEQ ID NO 177
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Ala Arg Val Asp Gln Thr Pro Gln Thr Ile Thr Lys Glu Thr Gly Glu
 1                5                  10                  15

Ser Leu Thr Ile Asn Cys Val Leu Arg Asp Ser Asn Cys Ala Leu Ser
                 20                  25                  30

Asn Ser Tyr Trp Tyr Arg Lys Lys Ser Gly Ser Thr Asn Glu Glu Asn
        35                  40                  45

Ile Ser Lys Gly Gly Arg Tyr Val Glu Thr Val Asn Ser Gly Ser Lys
 50                  55                  60

Ser Phe Ser Leu Lys Ile Asn Asp Leu Thr Val Glu Asp Ser Gly Thr
 65                  70                  75                  80

Tyr Arg Cys Asn Val Gly Tyr Phe Met Gly Cys His Pro Gln Gly Asp
                 85                  90                  95

Val Tyr Gly Asp Gly Thr Ala Val Thr Val Asn Ala
                100                 105
```

<210> SEQ ID NO 178
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Trp Val Ser Gln Val Cys Asn Tyr Asp Ala Gly
                85                  90                  95

Ser Tyr Asp Val Tyr Gly Gly Gly Thr Val Val Thr Val Asn Ala
            100                 105                 110

<210> SEQ ID NO 179
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Ala Arg Val Asp Gln Thr Pro Gln Thr Ile Thr Lys Glu Thr Gly Glu
1               5                   10                  15

Ser Leu Thr Ile Asn Cys Val Leu Arg Asp Asn Asn Cys Ala Leu Ser
            20                  25                  30

Ser Thr Tyr Trp Tyr Arg Lys Lys Ser Asp Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Gln His Phe Asn Asn Trp Trp Cys Asp Val
                85                  90                  95

Tyr Gly Gly Gly Thr Val Val Thr Val Asn Ala
            100                 105

<210> SEQ ID NO 180
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Ala Arg Val Asp Gln Thr Pro Gln Thr Ile Thr Lys Glu Thr Gly Glu
1               5                   10                  15

```
Ser Leu Thr Ile Asn Cys Val Leu Arg Asp Ser Asn Cys Ala Leu Ser
            20                  25                  30

Asn Ser Tyr Trp Tyr Arg Lys Lys Ser Gly Ser Thr Asn Glu Glu Ser
        35                  40                  45

Ile Ser Leu Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Gln Val His Pro Gln Ala Ala Cys Gly Gln His
                85                  90                  95

Leu Asp Val Tyr Gly Gly Gly Thr Ala Val Thr Val Asn Ala
            100                 105                 110

<210> SEQ ID NO 181
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Ala Arg Val Asp Gln Thr Pro Gln Thr Ile Thr Lys Glu Thr Gly Glu
 1               5                  10                  15

Ser Leu Thr Ile Asn Cys Val Leu Arg Asp Asn Cys Ala Leu Ser
            20                  25                  30

Thr Thr Tyr Trp Tyr Arg Lys Lys Ser Gly Ser Thr Asn Glu Glu Asn
        35                  40                  45

Ile Ser Lys Gly Gly Arg Tyr Val Glu Thr Val Asn Ser Gly Ser Lys
 50                  55                  60

Ser Phe Ser Leu Lys Ile Asn Asp Leu Thr Val Glu Asp Ser Gly Thr
 65                  70                  75                  80

Tyr Arg Cys Asn Val Pro Val Leu Ala Gln Gln Ile Cys Gln Pro Leu
                85                  90                  95

Asp Val Tyr Gly Asp Ser Thr Ala Val Thr Val Asn Ala
            100                 105

<210> SEQ ID NO 182
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Ala Arg Val Asp Gln Thr Pro Gln Thr Ile Thr Lys Glu Thr Gly Glu
 1               5                  10                  15

Ser Leu Thr Ile Asn Cys Val Leu Arg Asp Ser Asn Cys Ala Leu Ser
            20                  25                  30

Asn Ser Tyr Trp Tyr Arg Lys Lys Ser Gly Ser Thr Asn Glu Glu Ser
        35                  40                  45

Ile Ser Leu Gly Gly Arg Tyr Val Glu Thr Val Asn Ser Gly Ser Lys
 50                  55                  60

Ser Phe Ser Leu Lys Ile Asn Asp Leu Thr Val Glu Asp Ser Gly Thr
 65                  70                  75                  80

Tyr Arg Cys Asn Val Gln Cys Tyr Glu Glu Cys Cys Asn Arg Arg Tyr
                85                  90                  95
```

Asp Val Tyr Gly Gly Gly Thr Ala Val Thr Val Asn Ala
            100                 105

<210> SEQ ID NO 183
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Asn Ser Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Phe Val Gln Gly Ser Gly Arg Gly Gly Leu Asp
                85                  90                  95

Val Tyr Gly Gly Gly Thr Ala Val Thr Val Asn Ala
            100                 105

<210> SEQ ID NO 184
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Ala Arg Val Asp Gln Thr Pro Gln Thr Ile Thr Lys Glu Thr Gly Glu
1               5                   10                  15

Ser Leu Thr Ile Asn Cys Val Leu Arg Asp Asn Asn Cys Ala Leu Ser
            20                  25                  30

Thr Thr Tyr Trp Tyr Arg Lys Lys Ser Asp Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Gln Gln Ile Gly Asn Asn Trp Trp Cys Asp Val
                85                  90                  95

Tyr Gly Gly Gly Thr Ala Val Thr Val Asn Ala
            100                 105

<210> SEQ ID NO 185
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Asp Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Val Gln Trp Pro Gly Val Tyr Asn Asp Phe Trp
                85                  90                  95

Cys Asp Val Tyr Gly Gly Gly Thr Ala Val Thr Val Asn Ala
            100                 105                 110

<210> SEQ ID NO 186
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Asn
        35                  40                  45

Ile Ser Lys Gly Gly Arg Tyr Val Glu Thr Val Asn Ser Gly Ser Lys
    50                  55                  60

Ser Phe Ser Leu Lys Ile Asn Asp Leu Thr Val Glu Asp Ser Gly Thr
65                  70                  75                  80

Tyr Arg Cys Asn Val Arg Asp Val Gln Ala Cys Gly Asn Asp Trp Val
                85                  90                  95

Trp Leu Asp Val Tyr Gly Gly Gly Thr Val Val Thr Val Asn Ala
            100                 105                 110

<210> SEQ ID NO 187
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

```
Ser Phe Ser Leu Arg Ile Asn Asp Leu Thr Val Lys Asp Ser Gly Thr
 65                  70                  75                  80

Tyr Arg Cys Lys Val Ser Val Asp Thr Pro Asp Cys Trp Gln Cys Cys
                 85                  90                  95

Asp Trp Pro Leu Pro Asp Val Tyr Gly Asp Gly Thr Ala Val Thr Val
                100                 105                 110

Asn Ala

<210> SEQ ID NO 188
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Ala Arg Val Asp Gln Thr Pro Gln Thr Ile Thr Lys Glu Thr Gly Glu
  1               5                  10                  15

Ser Leu Thr Ile Asn Cys Val Leu Arg Asp Ser Asn Cys Ala Leu Pro
                 20                  25                  30

Ser Thr Tyr Trp Tyr Arg Lys Lys Ser Gly Ser Thr Asn Glu Glu Ser
             35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Lys Asp Ser Gly Thr
 65                  70                  75                  80

Tyr Arg Cys Asn Val Cys Val Ser Phe Gln Glu Ser Gly Asp Thr Gln
                 85                  90                  95

Arg Asp Val Tyr Gly Asp Gly Thr Ala Val Thr Val Asn Ala
                100                 105                 110

<210> SEQ ID NO 189
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Ala Arg Val Asp Gln Thr Pro Gln Thr Ile Thr Lys Glu Thr Gly Glu
  1               5                  10                  15

Ser Leu Thr Ile Asn Cys Val Leu Arg Asp Ser Asn Cys Ala Leu Ser
                 20                  25                  30

Ser Thr Tyr Trp Tyr Arg Lys Lys Ser Gly Ser Thr Asn Glu Glu Ser
             35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Lys Asp Ser Gly Thr
 65                  70                  75                  80

Tyr Arg Cys Asn Val Gly Lys Gln Gly Gln Cys Asp Trp Tyr Gly Asp
                 85                  90                  95

Val Tyr Gly Gly Gly Thr Val Val Thr Val Asn Ala
                100                 105

<210> SEQ ID NO 190
<211> LENGTH: 107
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 190

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Asp Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Val Gln Ser Thr Cys Leu Arg Tyr Gly Asp Val
                85                  90                  95

Tyr Gly Gly Gly Thr Ala Val Thr Val Asn Ala
            100                 105

<210> SEQ ID NO 191
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Gln Ser Trp Pro Pro Gly Asn Gly Trp Trp Cys Asp Val
1               5                   10

<210> SEQ ID NO 192
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Gln Ser Met Tyr Val Gly Tyr Gly Trp Ser Leu Asp Val
1               5                   10

<210> SEQ ID NO 193
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Val Gln Tyr Pro Ser Tyr Asn Asn Tyr Phe Trp Cys Asp Val
1               5                   10

<210> SEQ ID NO 194
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 194

Gly Phe Thr His Pro Gln Ile Cys Asp Leu Thr Gln Asp Val
1               5                   10

<210> SEQ ID NO 195
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Gln Pro His Cys Gly Tyr His Trp Leu Asp Val
1               5                   10

<210> SEQ ID NO 196
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Leu His Ser Gln Pro Gln Asp Gly Cys Tyr Phe Ser Gln Ala Val Asp
1               5                   10                  15
Val

<210> SEQ ID NO 197
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Met Gln Phe Pro Gly Pro Asp Asn Ser Thr Trp Trp Asp Val
1               5                   10

<210> SEQ ID NO 198
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Gln Gln Phe Pro Ser Ser Ser Asn Gly Arg Tyr Trp Cys Asp Val
1               5                   10                  15

<210> SEQ ID NO 199
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Gln Phe Leu Gly Phe Thr Asn Ser Gly Gly Tyr Trp Cys Asp Val
1               5                   10                  15

<210> SEQ ID NO 200
```

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Leu Asn Trp Phe Ala Tyr Glu Cys Gln Arg Gln Asp Val
1               5                   10

<210> SEQ ID NO 201
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Asn Tyr Phe Ser Tyr Thr Cys Gln Trp Val Gly Asp Asp Asp Val
1               5                   10                  15

<210> SEQ ID NO 202
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Lys Trp Gly Ser Val Ser Asn Gly Trp Leu Thr Asp Val
1               5                   10

<210> SEQ ID NO 203
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Asn Tyr Arg Cys Cys Gly Leu Gln Asp Val
1               5                   10

<210> SEQ ID NO 204
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Gln Arg Met Tyr Cys Ala Met Ala Asn Asp Val
1               5                   10

<210> SEQ ID NO 205
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 205

Phe Gly Val Gln Asn Cys Asn Asp Gly Leu Met Trp Ser Asp Val
1               5                   10                  15

<210> SEQ ID NO 206
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Gly Tyr Phe Met Gly Cys His Pro Gln Gly Asp Val
1               5                   10

<210> SEQ ID NO 207
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Trp Val Ser Gln Val Cys Asn Tyr Asp Ala Gly Ser Tyr Asp Val
1               5                   10                  15

<210> SEQ ID NO 208
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Gln His Phe Asn Asn Asn Trp Trp Cys Asp Val
1               5                   10

<210> SEQ ID NO 209
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Gln Val His Pro Gln Ala Ala Cys Gly Gln His Leu Asp Val
1               5                   10

<210> SEQ ID NO 210
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Pro Val Leu Ala Gln Gln Ile Cys Gln Pro Leu Asp Val
1               5                   10

<210> SEQ ID NO 211
<211> LENGTH: 13

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Gln Cys Tyr Glu Glu Cys Cys Asn Arg Arg Tyr Asp Val
1               5                   10

<210> SEQ ID NO 212
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Phe Val Gln Gly Ser Gly Arg Gly Gly Leu Asp Val
1               5                   10

<210> SEQ ID NO 213
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Gln Gln Ile Gly Asn Asn Trp Trp Cys Asp Val
1               5                   10

<210> SEQ ID NO 214
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Val Gln Trp Pro Gly Val Tyr Asn Asp Phe Trp Cys Asp Val
1               5                   10

<210> SEQ ID NO 215
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Gln Ala Cys Gly Asn Asp Trp Val Trp Leu Asp Val
1               5                   10

<210> SEQ ID NO 216
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 216

Ser Val Asp Thr Pro Asp Cys Trp Gln Cys Cys Asp Trp Pro Leu Pro
1               5                   10                  15

Asp Val

<210> SEQ ID NO 217
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Cys Val Ser Phe Gln Glu Ser Gly Asp Thr Gln Arg Asp Val
1               5                   10

<210> SEQ ID NO 218
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Gly Lys Gln Gly Gln Cys Asp Trp Tyr Gly Asp Val
1               5                   10

<210> SEQ ID NO 219
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Val Gln Ser Thr Cys Leu Arg Tyr Gly Asp Val
1               5                   10

<210> SEQ ID NO 220
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 220
gccagggtgg accagacccc ccagaccatc accaaggaga ccggcgagag cctgaccatc      60
aactgcgtgc tgagggacaa caactgcgcc ctgagcagca ccctgtggta caggaccaag     120
agcggcagca ggaacgagga gagcatcagc aagggcggga ggtacgtgga gaccgtgaac     180
agcggcagca agagcttcag cctgaggatc aacgacctga ccgtggagga cagcggcacc     240
tacaggtgca acgtgcagag ctggcccccc ggcaacggct ggtggtgcga cgtgtacggc     300
gacggcaccg ccgtgaccgt gaacgcc                                         327

<210> SEQ ID NO 221
<211> LENGTH: 327
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 221
gccagggtgg accagacccc ccagaccatc accaaggaga ccggcgagag cctgaccatc    60
aactgcgtgc tgagggacag caactgcgac ctgagcagga cctactggta caggaagaag   120
agcggcagca ccaacgagga gaacatcagc aagggcggca ggtacgtgga gaccgtgaac   180
agcggcagca agagcttcag cctgaggatc aacgacctga ccgtggagga cagcggcacc   240
tacaggtgca acgtgcagag catgtacgtg ggctacggct ggagcctgga cgtgtacggc   300
ggcggcaccg tggtgaccgt gaacgcc                                       327

<210> SEQ ID NO 222
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 222
gccagggtgg accagacccc ccagaccatc accaaggaga ccggcgagag cctgaccatc    60
aactgcgtgc tgagggacag caactgcgcc ctgagcagca cctactggta caggaagaag   120
agcggcagca ccaacgagga gaacatcagc aagggcggca ggtacgtgga gaccgtgaac   180
agcggcagca agagcttcag cctgaggatc aacgacctga ccgtggagga cagcggcacc   240
tacaggtgca acgtggtgca gtacccagc tacaacaact acttctggtg cgacgtgtac   300
ggcgacggca ccgccgtgac cgtgaacgcc                                    330

<210> SEQ ID NO 223
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 223
gccagggtgg accagacccc ccagaccatc accaaggaga ccggcgagag cctgaccatc    60
aactgcgtgc tgagggacag caactgcgcc ctgagcaaca gctactggta caggaagaag   120
agcggcagca ccaacgagga gagcatcagc ctgggcggca ggtacgtgga gaccgtgaac   180
agcggcagca agagcttcag cctgaggatc aacgacctga ccgtggagga cagcggcacc   240
tacaggtgca acgtgggctt cacccacccc cagatctgcg acctgaccca ggacgtgtac   300
ggcggcggca ccgtggtgac cgtgaacgcc                                    330

<210> SEQ ID NO 224
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 224
gccagggtgg accagacccc ccagaccatc accaaggaga ccggcgagag cctgaccatc    60
aactgcgtgc tgagggacag caactgcgcc ctgagcagca cctactggta caggaagaag   120
agcggcagca ccaacgagga gaacatcagc aagggcggca ggtacgtgga gaccgtgaac   180

```
agcggcagca agagcttcag cctgaggatc aacgacctga ccgtggagga cagcggcacc    240
tacaggtgca acgtgcagcc ccactgcggc taccactggc tggacgtgta cggcgacggc    300
accgccgtga ccgtgaacgc c                                              321
```

<210> SEQ ID NO 225
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 225

```
gccagggtgg accagacccc ccagaccatc accaaggaga ccggcgagag cctgaccatc    60
aactgcgtgc tgagggacaa caactgcgcc ctgagcagca ccctgtggta caggaagaag   120
agcggcagca ccaacgagga gaacatcagc aagggcggca ggtacgtgga ccgtgaac    180 agcggcagca agagcttcag cctgaggatc aacgacctga ccgtggagga cagcggcacc   240
tacaggtgca aggtgctgca cagccagccc caggacggct gctacttcag ccaggccgtg   300
gacgtgtacg gcgacggcac cgccgtgacc gtgaacgcc                           339
```

<210> SEQ ID NO 226
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 226

```
gccagggtgg accagacccc ccagaccatc accaaggaga ccggcgagag cctgaccatc    60
aactgcgtgc tgagggacag caactgcgcc ctgcccagca cctactggta caggaagaag   120
agcggcagca ccaacgagga gagcatcagc ctgggcggca ggtacgtgga ccgtgaac    180 agcggcagca agagcttcag cctgaggatc aacgacctga ccgtggagga cagcggcacc   240
tacaggtgca acgtgatgca gttccccggc cccgacaaca gcacctggtg ggacgtgtac   300
ggcggcggca ccgtggtgac cgtgaacgcc                                    330
```

<210> SEQ ID NO 227
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 227

```
gccagggtgg accagacccc ccagaccatc accaaggaga ccggcgagag cctgaccatc    60
aactgcgtgc tgagggacag caactgcgag ctgagcagca cctactggta caggaagaag   120
agcggcagca ccaacgagga gagcatcagc aagggcggca ggtacgtgga ccgtgaac    180 agcggcagca agagcttcag cctgaggatc aacgacctgg tggtggagga cagcggcacc   240
tacaggtgca acgtgcagca gttccccagc agcagcaacg gcaggtactg gtgcgacgtg   300
tacggcggcg gcaccgccgt gaccgtgaac gcc                                333
```

<210> SEQ ID NO 228
<211> LENGTH: 333

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 228
gccagggtgg accagacccc ccagaccatc accaaggaga ccggcgagag cctgaccatc      60
aactgcgtgc tgagggacag caactgcgcc ctgagcagca cctactggta caggaagaag     120
agcggcagca ccaacgagga gaacatcagc aagggcggca ggtacgtgga ccgtgaac      180 agcggcagca agagcttcag cctgaggatc aacgacctga ccgtggagga cagcggcacc     240
tacaggtgca acgtgcagtt cctgggcttc accaacagcg cggctactg gtgcgacgtg     300 tacggcggcg gcaccgccgt gaccgtgaac gcc                                  333

<210> SEQ ID NO 229
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 229
gccagggtgg accagacccc ccagaccatc accaaggaga ccggcgagag cctgaccatc      60
aactgcgtgc tgagggacag caactgcgcc ctgcccagca cctactggta caggaagaag     120
agcggcagca ccaacgagga gagcatcagc aagggcggca ggtacgtgga ccgtgaac      180 agcggcagca agagcttcag cctgaggatc aacgacctga ccgtggagga cagcggcacc     240
tacaggtgca acgtgctgaa ctggttcgcc tacgagtgcc agaggcagga cgtgtacggc     300
ggcggcaccg ccgtgaccgt gaacgcc                                         327

<210> SEQ ID NO 230
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 230
gccagggtgg accagacccc ccagaccatc accaaggaga ccggcgagag cctgaccatc      60
aactgcgtgc tgagggacag caactgcgcc ctgcccagca cctactggta caggaagaag     120
agcggcagca ccaacgagga gagcatcagc aagggcggca ggtacgtgga ccgtgaac      180 agcggcagca agagcttcag cctgaggatc aacgacctgg tggtggagga cagcggcacc     240
tacaggtgca aggtgatgaa ctacttcagc tacacctgcc agtgggtggg cgacgacgac     300
gtgtacggcg acggcaccgc cgtgaccgtg aacgcc                               336

<210> SEQ ID NO 231
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 231

```
gccagggtgg accagacccc ccagaccatc accaaggaga ccggcgagag cctgaccatc      60
aactgcgtgc tgagggacag caactgcgcc ctgagcagca cctactggta caggaagaag     120
agcggcagca ccaaccagga gaacatcagc aagggcggca ggtacgtgga gaccgtgaac     180
agcggcagca agagcttcag cctgaggatc aacgacctga ccgtggagga cagcggcacc     240
tacaggtgca acgtgaagtg gggcagcgtg agcaacggct ggctgaccga cgtgtacggc     300
gacggcaccg tggtgaccgt gaacgcc                                          327
```

<210> SEQ ID NO 232
<211> LENGTH: 318
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 232

```
gccagggtgg accagacccc ccagaccatc accaagcaga ccggcgagag cctgaccatc      60
aactgcgtgc tgagggacag caactgcgcc ctgagcagca ccctgtggta caggaccaag     120
agcggcagca ggaacgagga gagcatcagc aagggcggca ggtacgtgga gaccgtgaac     180
agcggcagca agagcttcag cctgaagatc aacgacctga ccgtggagga cagcggcacc     240
tacaggtgca acgtgaacta caggtgctgc ggcctgcagg acgtgtacgg cggcggcacc     300
gccgtgaccg tgaacgcc                                                    318
```

<210> SEQ ID NO 233
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 233

```
gccagggtgg accagacccc ccagaccatc accaaggaga ccggcgagag cctgaccatc      60
aactgcgtgc tgagggacag caactgcgag ctgagcagca cctactggta caggaagaag     120
agcggcagca ccaacgaggc caggatcagc aagggcggca ggtacgtgga gaccgtgaac     180
agcggcagca agagcttcag cctgaggatc aacgacctga ccgtggagga cagcggcacc     240
tacaggtgca acgtgcagag gatgtactgc gccatggcca cgacgtgta cggcggcggc     300
accgtggtga ccgtgaacgc c                                                321
```

<210> SEQ ID NO 234
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 234

```
gccagggtgg accagacccc ccagaccatc accaaggaga ccggcgagag cctgaccatc      60
aactgcgtgc tgagggacag caactgcgcc ctgcccagca cctactggta caggaagaag     120
agcggcagca ccaacgagga gagcatcagc aagggcggca ggtacgtgga gaccgtgaac     180
agcggcagca agagcttcag cctgaggatc aacgacctga ccgtgaagga cagcggcacc     240
```

```
tacaggtgca acgtgttcgg cgtgcagaac tgcaacgacg gcctgatgtg gagcgacgtg      300
tacggcgacg gcaccgccgt gaccgtgaac gcc                                  333
```

<210> SEQ ID NO 235
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 235

```
gccagggtgg accagacccc ccagaccatc accaaggaga ccggcgagag cctgaccatc      60
aactgcgtgc tgagggacag caactgcgcc ctgagcaaca gctactggta caggaagaag     120
agcggcagca ccaacgagga gaacatcagc aagggcggca ggtacgtgga gaccgtgaac     180
agcggcagca agagcttcag cctgaagatc aacgacctga ccgtggagga cagcggcacc     240
tacaggtgca acgtgggcta cttcatgggc tgccaccccc agggcgacgt gtacggcgac     300
ggcaccgccg tgaccgtgaa cgcc                                            324
```

<210> SEQ ID NO 236
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 236

```
gccagggtgg accagacccc ccagaccatc accaaggaga ccggcgagag cctgaccatc      60
aactgcgtgc tgagggacag caactgcgcc ctgcccagca cctactggta caggaagaag     120
agcggcagca ccaacgagga gagcatcagc aagggcggca ggtacgtgga gaccgtgaac     180
agcggcagca agagcttcag cctgaggatc aacgacctga ccgtggagga cagcggcacc     240
tacaggtgca acgtgtgggt gagccaggtg tgcaactacg acgccggcag ctacgacgtg     300
tacggcggcg gcaccgtggt gaccgtgaac gcc                                  333
```

<210> SEQ ID NO 237
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 237

```
gccagggtgg accagacccc ccagaccatc accaaggaga ccggcgagag cctgaccatc      60
aactgcgtgc tgagggacaa caactgcgcc ctgagcagca cctactggta caggaagaag     120
agcgacagca ccaacgagga gagcatcagc aagggcggca ggtacgtgga gaccgtgaac     180
agcggcagca agagcttcag cctgaggatc aacgacctga ccgtggagga cagcggcacc     240
tacaggtgca acgtgcagca cttcaacaac aactggtggt gcgacgtgta cggcggcggc     300
accgtggtga ccgtgaacgc c                                               321
```

<210> SEQ ID NO 238
<211> LENGTH: 330
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 238
gccagggtgg accagacccc ccagaccatc accaaggaga ccggcgagag cctgaccatc      60
aactgcgtgc tgagggacag caactgcgcc ctgagcaaca gctactggta caggaagaag     120
agcggcagca ccaacgagga gagcatcagc ctgggcggca ggtacgtgga gaccgtgaac     180
agcggcagca agagcttcag cctgaggatc aacgacctga ccgtggagga cagcggcacc     240
tacaggtgca acgtgcaggt gcacccccag gccgcctgcg ccagcacct ggacgtgtac      300 ggcggcggca ccgccgtgac cgtgaacgcc                                      330

<210> SEQ ID NO 239
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 239
gccagggtgg accagacccc ccagaccatc accaaggaga ccggcgagag cctgaccatc      60
aactgcgtgc tgagggacaa caactgcgcc ctgagcacca cctactggta caggaagaag     120
agcggcagca ccaacgagga gaacatcagc aagggcggca ggtacgtgga gaccgtgaac     180
agcggcagca agagcttcag cctgaagatc aacgacctga ccgtggagga cagcggcacc     240
tacaggtgca acgtgcccgt gctggcccag cagatctgcc agcccctgga cgtgtacggc     300
gacagcaccg ccgtgaccgt gaacgcc                                         327

<210> SEQ ID NO 240
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 240
gccagggtgg accagacccc ccagaccatc accaaggaga ccggcgagag cctgaccatc      60
aactgcgtgc tgagggacag caactgcgcc ctgagcaaca gctactggta caggaagaag     120
agcggcagca ccaacgagga gagcatcagc ctgggcggca ggtacgtgga gaccgtgaac     180
agcggcagca agagcttcag cctgaagatc aacgacctga ccgtggagga cagcggcacc     240
tacaggtgca acgtgcagtg ctacgaggag tgctgcaaca ggaggtacga cgtgtacggc     300
ggcggcaccg ccgtgaccgt gaacgcc                                         327

<210> SEQ ID NO 241
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 241
gccagggtgg accagacccc ccagaccatc accaaggaga ccggcgagag cctgaccatc      60
aactgcgtgc tgagggacag caactgcgcc ctgagcaaca gctactggta caggaagaag     120
```

```
agcggcagca ccaacgagga gagcatcagc aagggcggca ggtacgtgga gaccgtgaac    180
agcggcagca agagcttcag cctgaggatc aacgacctga ccgtggagga cagcggcacc    240
tacaggtgca acgtgttcgt gcagggcagc ggcaggggcg gcctggacgt gtacggcggc    300
ggcaccgccg tgaccgtgaa cgcc                                          324
```

<210> SEQ ID NO 242
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 242

```
gccagggtgg accagacccc ccagaccatc accaaggaga ccggcgagag cctgaccatc    60
aactgcgtgc tgagggacaa caactgcgcc ctgagcacca cctactggta caggaagaag   120
agcgacagca ccaacgagga gagcatcagc aagggcggca ggtacgtgga gaccgtgaac   180
agcggcagca agagcttcag cctgaggatc aacgacctga ccgtggagga cagcggcacc   240
tacaggtgca acgtgcagca gatcggcaac aactggtggt gcgacgtgta cggcggcggc   300
accgccgtga ccgtgaacgc c                                             321
```

<210> SEQ ID NO 243
<211> LENGTH: 330
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 243

```
gccagggtgg accagacccc ccagaccatc accaaggaga ccggcgagag cctgaccatc    60
aactgcgtgc tgagggacag caactgcgcc ctgagcagca cctactggta caggaagaag   120
agcgacagca ccaacgagga gagcatcagc aagggcggca ggtacgtgga gaccgtgaac   180
agcggcagca agagcttcag cctgaggatc aacgacctga ccgtggagga cagcggcacc   240
tacaggtgca acgtggtgca gtggcccggc gtgtacaacg acttctggtg cgacgtgtac   300
ggcggcggca ccgccgtgac cgtgaacgcc                                    330
```

<210> SEQ ID NO 244
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 244

```
gccagggtgg accagacccc ccagaccatc accaaggaga ccggcgagag cctgaccatc    60
aactgcgtgc tgagggacag caactgcgcc ctgagcagca cctactggta caggaagaag   120
agcggcagca ccaacgagga gaacatcagc aagggcggca ggtacgtgga gaccgtgaac   180
agcggcagca agagcttcag cctgaagatc aacgacctga ccgtggagga cagcggcacc   240
tacaggtgca acgtgaggga cgtgcaggcc tgcggcaacg actgggtgtg gctggacgtg   300
tacggcggcg gcaccgtggt gaccgtgaac gcc                                333
```

<210> SEQ ID NO 245

<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 245

| gccagggtgg accagacccc ccagaccatc accaaggaga ccggcgagag cctgaccatc | 60 |
| aactgcgtgc tgagggacag caactgcgcc ctgcccagca cctactggta caggaagaag | 120 |
| agcggcagca ccaacgagga gagcatcagc aagggcggca ggtacgtgga ccgtgaac   | 180 |
| agcggcagca agagcttcag cctgaggatc aacgacctga ccgtgaagga cagcggcacc | 240 |
| tacaggtgca aggtgagcgt ggacaccccc gactgctggc agtgctgcga ctggcccctg | 300 |
| cccgacgtgt acggcgacgg caccgccgtg accgtgaacg cc                    | 342 |

<210> SEQ ID NO 246
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 246

| gccagggtgg accagacccc ccagaccatc accaaggaga ccggcgagag cctgaccatc | 60 |
| aactgcgtgc tgagggacag caactgcgcc ctgcccagca cctactggta caggaagaag | 120 |
| agcggcagca ccaacgagga gagcatcagc aagggcggca ggtacgtgga ccgtgaac   | 180 |
| agcggcagca agagcttcag cctgaggatc aacgacctga ccgtgaagga cagcggcacc | 240 |
| tacaggtgca acgtgtgcgt gagcttccag gagagcggcg acacccagag ggacgtgtac | 300 |
| ggcgacggca ccgccgtgac cgtgaacgcc                                  | 330 |

<210> SEQ ID NO 247
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 247

| gccagggtgg accagacccc ccagaccatc accaaggaga ccggcgagag cctgaccatc | 60 |
| aactgcgtgc tgagggacag caactgcgcc ctgagcagca cctactggta caggaagaag | 120 |
| agcggcagca ccaacgagga gagcatcagc aagggcggca ggtacgtgga ccgtgaac   | 180 |
| agcggcagca agagcttcag cctgaggatc aacgacctga ccgtgaagga cagcggcacc | 240 |
| tacaggtgca acgtgggcaa gcagggccag tgcgactggt acggcgacgt gtacggcggc | 300 |
| ggcaccgtgg tgaccgtgaa cgcc                                        | 324 |

<210> SEQ ID NO 248
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 248

```
gccagggtgg accagacccc ccagaccatc accaaggaga ccggcgagag cctgaccatc    60
aactgcgtgc tgagggacag caactgcgcc ctgagcagca cctactggta caggaagaag   120
agcgacagca ccaacgagga gagcatcagc aagggcggca ggtacgtgga gaccgtgaac   180
agcggcagca agagcttcag cctgaggatc aacgacctga ccgtggagga cagcggcacc   240
tacaggtgca acgtggtgca gagcacctgc ctgaggtacg cgacgtgta cggcggcggc   300 accgccgtga ccgtgaacgc c                                             321
```

<210> SEQ ID NO 249
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

```
Val Val Gln Tyr Pro Ser Tyr Asn Asn Tyr Phe Trp Cys Asp Val
1               5                   10                  15
```

<210> SEQ ID NO 250
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

```
Asp Lys Asp Cys Ala Leu Ser
1               5
```

<210> SEQ ID NO 251
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

```
Asp Asn Asp Cys Ala Leu Ser
1               5
```

<210> SEQ ID NO 252
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

```
Asp Asn Asp Cys Thr Leu Ser
1               5
```

<210> SEQ ID NO 253
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 253

Asp Asn Tyr Cys Pro Leu Ser
1               5

<210> SEQ ID NO 254
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Asp Arg Ala Cys Ala Leu Leu
1               5

<210> SEQ ID NO 255
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Asp Arg Asp Cys Ala Leu Ser
1               5

<210> SEQ ID NO 256
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Asp Ser Asp Cys Ala Leu Ser
1               5

<210> SEQ ID NO 257
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Asp Ser Asn Cys Ala Ala Thr
1               5

<210> SEQ ID NO 258
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 258

Asp Ser Asn Cys Pro Leu Ser
1               5

<210> SEQ ID NO 259
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Asp Ser Asn Cys Arg Leu Ser
1               5

<210> SEQ ID NO 260
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Asp Ser Val Cys Ala Leu Ser
1               5

<210> SEQ ID NO 261
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Asp Thr Ala Cys Ala Leu Asp
1               5

<210> SEQ ID NO 262
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(32)
<223> OTHER INFORMATION: This sequence may encompass 0-4 "(Gly)n(Ser)n"
      repeating units wherein n=0-4 and some positions may be
      absent
<220> FEATURE:
<223> OTHER INFORMATION: See specification as filed for detailed
      description of substitutions and preferred embodiments

<400> SEQUENCE: 262

Gly Gly Gly Gly Ser Ser Ser Ser Gly Gly Gly Gly Ser Ser Ser Ser
1               5                   10                  15

Gly Gly Gly Gly Ser Ser Ser Ser Gly Gly Gly Gly Ser Ser Ser Ser
            20                  25                  30
```

IN VIVO METHODS FOR SELECTING PEPTIDES THAT CROSS THE BLOOD BRAIN BARRIER, RELATED COMPOSITIONS AND METHODS OF USE

CROSS REFERENCE TO RELATED APPLICATION

This application a divisional application of U.S. Ser. No. 16/323,727, filed Feb. 6, 2019, which is a national stage filing under 35 U.S. § 371 of Intl. Appln. No. PCT/US2017/045592, filed Aug. 4, 2017, which claims the benefit of provisional application U.S. Ser. No. 62/415,631, filed on Nov. 1, 2016 and U.S. Ser. No. 62/371,727, filed on Aug. 6, 2016, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jul. 21, 2021, is named 9030.1601-us4_SEQ.txt and is 163 kilobytes in size.

FIELD OF THE INVENTION

The present invention relates to the fields of molecular medicine and targeted delivery of therapeutic or diagnostic agents to cells outside the vascular system and into the parenchymal tissue of organs within the body. More specifically, the present invention relates to the methods used to identify membrane receptors or transporters capable of carrying cargo specifically targeted to the parenchymal tissue of the brain and to in vivo enrichment methods for selecting peptides that are transported across the blood-brain barrier ("BBB"), or analogously, across other membrane containing organs or structures, such as liver, spleen, kidney, and tumors.

BACKGROUND OF THE INVENTION

The successful treatment of various diseases would greatly benefit from improved approaches to selectively deliver therapeutic and diagnostics agents. Several approaches to screen peptide libraries in vivo have revealed an endothelial address system that identified ligands that target specific tissues or sites of disease (Pasqualini R, Ruoslahti E, Organ targeting in vivo using phage display peptide libraries, Nature 380 (1996) 364-366). Vascular targeting based on markers expressed on endothelial cells is the basis for the success of several clinical applications. However, targeting endothelial cells is often insufficient to reach many therapeutic targets, and the ability to direct therapy to other cells within the organ/tissue may be essential for long-term efficacy. Strategies that maximize tissue penetration while minimizing trapping within vascular endothelial cells have yet to be developed.

The blood-brain barrier (BBB) is the principal interface between blood and the interstitial fluid that bathes neurons within the brain parenchyma (Abbott et al., Neurobiol Dis. 2010 January; 37(1):13-25). The BBB is formed by highly specialized endothelial cells that maintain an optimal environment for neuronal function by eliminating toxic substances and supplying the brain with nutrients and other metabolic requirements. The BBB likewise presents a formidable obstacle for the systemic delivery of many potentially important therapeutic and diagnostics agents. With the exception of small, lipophilic molecules (MW less than 500 Daltons), which can cross the BBB by transmembrane diffusion, nearly all hydrophilic small molecules, peptides, proteins, RNAs and genetic vectors that could be of therapeutic value are excluded (Pardridge, J Cereb Blood Flow Metab. 2012 November; 32(11):1959-72.). Many of the antibodies designed to treat a variety of neurodegenerative disorders including Alzheimer's disease, Parkinson's disease, Huntington's disease and frontotemporal dementia will be limited by their inability to reach the pathological target within the brain. Thus, despite tremendous progress in the discovery of potential therapeutics for CNS diseases, very few will be successfully developed without an effective means of delivery across the BBB.

Although the BBB restricts the passage of many substances, brain capillaries use membrane transport systems to deliver important nutrients and macromolecules important for normal brain function. The main route whereby large molecules, such as proteins and peptides, enter the CNS is by the receptor-mediated transcytosis (RMT) which might also be used to shuttle a wide range of therapeutics into the brain in a non-invasive manner (Jones and Shusta, Pharm Res. 2007 September; 24(9):1759-71). Circulating ligands such as transferrin, insulin and leptin interact with specific receptors concentrated on the luminal side of the brain capillary endothelial cells. Once bound to the receptor, the process of endocytosis is initiated as the receptor-ligand complexes cluster and intracellular transport vesicles detach from the membrane (Tuma and Hubbard, Physiol Rev. 2003 July; 83(3):871-932). The transport vesicles containing receptor-ligand complexes or dissociated ligands are directed away from the lysosomal compartment and trancytosed to the brain interstitial side of the endothelial cell, where they are released without disrupting the BBB.

The transferrin receptor 1 (TfR-1) endocytotic pathway for iron homeostasis has been one of the most extensively characterized systems for drug delivery across the BBB. TfR-1 mediates influx of iron-loaded transferrin from blood to brain in addition to the transcytosis of iron-depleted transferrin in the reverse direction. Transferrin itself has been used as a vehicle for brain delivery, but transferrin conjugates have to compete for the receptor with the high plasma concentration of the endogenous ligand.

Similar problems are encountered in transporting molecules, such as drug substances, across intestinal epithelium of the gut, where transcellular and paracellular routes of transport exist for water and ions but where larger molecules are transported exclusively by transporter molecules in epithelial cell plasma membranes.

Hence, it would be desirable to have new molecular tools for efficient and selective delivery of compounds such as biomolecules (e.g., therapeutics and diagnostics) across membrane systems in mammalian subject, such as into various organs, tumors or across the BBB. It would also be desirable to have new molecular tools for efficient and selective delivery of compounds, including biomolecules, across such membranes, or across cells of the gastrointestinal (GI) tract thereby increasing the oral bioavailability of certain molecules, e.g., drugs, which do not naturally cross the GI tract when delivered in oral form. Moreover, it would be advantageous to have new selective TfR-specific binding compounds, especially ones having one or more advantageous biological properties with therapeutic and/or diagnostic benefit over current anti-TfR antibodies and other regulators of iron transport systems.

SUMMARY OF THE INVENTION

The present invention addresses the needs described above by providing methods for enriching for a peptide that not only binds selectively to a membrane bound receptor or transporter protein, but which is also transported across the membrane and released into tissue internal to the membrane system with greater efficiency compared to other peptides that bind to the same membrane bound receptor or transporter protein but which are not efficiently transported across or released internal to the membrane system of choice. The methods of the invention enable the in vivo selection of peptides that are enriched from 100- to 1200-fold in brain parenchyma. At least one of the peptides identified using methods of the invention can function as a highly specific and efficient carrier of macromolecules across an endothelial barrier. Methods of the invention may be readily adapted to identify tissue-specific therapeutic or diagnostic carriers for brain and other organs systems, heart, muscle, lung, pancreas, thymus, liver, kidney, bladder, prostate, testis in addition to various tumors though out the body.

In certain embodiments, the invention provides a method of identifying a polypeptide capable of traversing a mammalian blood brain barrier (BBB) and being released into the brain.

Hence, one aspect of the invention is directed to an in vivo method to identify one or more polypeptides capable of traversing a mammalian blood-brain barrier which comprises a) delivering a plurality of polypeptides into the circulatory system of a non-human mammal, and after a time sufficient for transport; b) isolating the brain of said mammal and separating brain parenchymal tissue from capillary epithelium of the brain to obtain a parenchymal fraction; and c) detecting one or more of the polypeptides from said plurality of polypeptides in said parenchymal fraction to thereby identify at least one polypeptide capable of traversing the blood-brain barrier. In some embodiments, the method further comprises perfusing the circulatory system with a physiologically-acceptable solution in an amount and for a time sufficient to effectively reduce the circulating concentration of said plurality of polypeptides.

In further embodiments, the method of identifying includes recovering the polypeptides by performing, in addition to step c), or as an alternative to step c), a recovery step such that one or more polypeptides from the plurality in the parenchymal fraction are recovered to create an enriched pool of polypeptides capable of traversing the blood brain barrier and being released into brain parenchymal tissue. This enriched pool can be used as the plurality of polypeptides in the foregoing method, or other methods of the invention, to further nrich for one or more polypeptides capable of crossing the blood-brain barrier. The cycle of delivery and recovery can be repeated multiple times, typically from 1-5 times, to thereby enrich for and identify at least one polypeptide capable of traversing the blood-brain barrier.

In certain embodiments of the methods of the invention, the plurality of polypeptides is a library of polypeptides or a phage display library. When using phage display libraries, they have been treated to reduce endotoxin levels by at least 10-fold relative to a non-treated phage display library. In some embodiments, the plurality of polypeptides are present in a phage display library which comprises nurse shark VNAR polypeptides capable of binding to a brain receptor or transporter. In some embodiments these VNAR polypeptides are in a phage display library and the phage carrying VNAR polypeptides are isolated from the parenchymal fraction to thereby perform in vivo selection of VNAR polypeptides that penetrate the blood brain barrier.

Yet further aspects of the invention provide an isolated polypeptide identified by the foregoing methods as well as conjugates of those polypeptides. In some embodiments the conjugate comprises a heterologous agent which is a diagnostic or therapeutic agent. In other embodiments, the conjugate comprises one or more of the following agents: a small molecule, a DNA, RNA, or hybrid DNA-RNA, a traceable marker such as a fluorescent or phosphorescent molecule, a radionuclide or other radioactive agent, an antibody, single chain variable domain, immunoglobulin fragment, variant or fusion, a small molecule diagnostic or therapeutic.

In certain embodiments, the method involves exposing blood outside of the brain of a mammal to a combinatorial polypeptide library comprising at least twenty different sequences, and subsequently separating polypeptides that remain in the blood or within the BBB (e.g., brain capillary endothelium) away from polypeptides released into brain parenchymal tissue, thereby enriching for polypeptides that are transported into the brain. These steps are repeated in at least one more round, and preferably in multiple rounds, starting each round with the brain-enriched polypeptides from the previous round and re-exposing blood outside of the brain of the mammal to the previously isolated brain-enriched polypeptides, thereby performing two or more rounds of in vivo enrichment for polypeptides from the library that are transported into the brain of the mammal. In certain embodiments, a perfusion step is performed after the polypeptide library is administered to the blood and before brain parenchymal tissue is fractionated from brain capillary endothelium and blood of the mammalian subject to achieve a cleaner purification of brain transported peptides.

In certain embodiments, the combinatorial polypeptide library comprises at least twenty different sequences preselected for their ability to bind to a membrane receptor or transporter protein known or suspected to be present in a particular membrane system of choice, such as the BBB, an organ, or tumor. In such embodiments, the purified membrane receptor or transporter protein of interest and is used in a first step to select for peptides that bind to it with acceptably high affinity and/or specificity in an in vitro or ex vivo binding assay. Those pre-selected polypeptides may then be used as starting material for the in vivo enrichment methods of the invention.

In certain other embodiments, the membrane receptor or transporter protein is not known, and multiple rounds of the in vivo enrichment methods of the invention are used to enrich for peptides that are transported across the membrane, e.g., across the BBB to brain parenchymal tissue. In situations in which there is not a known receptor or transporter to use in binding assays, sequencing is performed to compare polypeptides enriched in brain parenchymal fractions to polypeptide sequences from the starting combinatorial library and/or from peptide sequences that remain in blood or in the capillary endothelium of the BBB.

Polypeptides enriched in brain parenchymal fractions in any of the above embodiments may further be formatted as fusion proteins (e.g., to an immunoglobulin Fc region) in order to quantitate and compare brain uptake after IV injection. Polypeptides enriched in brain parenchymal fractions (or smaller peptide sequences that confer transport across the selected membrane) may be used to make molecular conjugates with one or more heterologous agents to produce a bi-, tri-, or multi-functional polypeptides or vehicles that can carry heterologous agents across the blood brain barrier or other selected membrane system.

In certain embodiments of the invention, the combinatorial library is a phage library comprising at least twenty different polypeptide sequences. In certain embodiments, the phage library comprises a plurality of nurse shark VNAR-derived polypeptides comprising at least twenty different VNAR sequences. Preferably, the complexity of the library is greater than twenty sequences, e.g., is hundreds, thousands, millions or higher of unique sequences, i.e., with a complexity of at least 25, 50, 100, 1000, 5000, $1\times10^4$, $5\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$ or higher. In certain embodiments, the phage library is administered to blood outside the brain of a mammalian subject (e.g, by IV injection into a non-human mammal); perfusing outside the brain to wash away exposure to phage vectors outside of the brain; fractionating brain parenchymal tissue from brain capillary endothelium of the BBB and external blood; and isolating phage carrying VNAR polypeptides from a brain parenchymal fraction. These steps are repeated in at least one more round, and preferably in multiple rounds, starting each round with the brain-enriched phage from the previous round and re-exposing blood outside of the brain of the mammal to the previously isolated, brain-enriched VNAR carrying phage, thereby performing two or more rounds of in vivo enrichment for VNAR polypeptide sequences from the library that are transported into the brain of the mammal.

In certain embodiments, the VNAR library used in the method of the invention has been pre-selected for it binding or affinity (in vitro or ex vivo) to purified membrane receptor or transporter protein of interest. In certain embodiments, the receptor is a transferrin receptor, or TfR, such as TfR-1. Many other suitable membrane receptors and transporters may be used in performing methods according to the present invention which may be further tailored for identifying protein sequences that mediate efficient transport across different mammalian organ systems or tumors.

In certain other embodiments, the membrane receptor or transporter protein is not known and the membrane system of choice is used to find peptides that can be transported across the membrane in an ex vivo or in vivo assay membrane transport assay comprising the step of enriching for membrane transporting peptides by applying peptides external to the membrane system for a time sufficient to permit membrane transport, washing away peptides that remain external, and fractionating membrane bound peptides from peptides that have been enriched in tissue internal to the membrane system. Internalized peptides may optionally be further amplified, isolated, purified and analyzed for amino acid sequence content. In certain embodiments, the membrane receptor or transporter protein that functions in polypeptide transport will be a specific transporter (e.g, transport by transcytosis). In other embodiments, the membrane receptor or transporter protein that functions in polypeptide transport across a membrane may be a particular molecular transporter, e.g., an amino acid transporter, or a non-specific transporter.

The present invention further provides nucleic acids that encode, and polypeptides that cross the BBB and which are released in the brain, such polypeptides identified using the in vivo enrichment methods of the invention. Such polypeptides, nucleic acids and vectors encoding them, and compounds such as conjugates comprising them, as well as associated compositions, host cells and methods of making and using them, are also provided. In certain embodiments, the invention thus provides polypeptides enriched in the brain of a mammal identified using TfR-1 binding VNARs in the in vivo enrichment methods of the invention. In certain embodiments, the invention provides VNAR peptides that are transported into the brain of a mouse and which cross react with (bind to) human TfR-1. The invention further provides VNAR peptides that bind TfR-1 without substantially binding to a TfR-2. In certain embodiments, the binding of the VNAR peptides of the invention to TfR-1 does not inhibit transferrin binding to and/or its transport by TfR-1, induces endocytosis of the VNAR TfR-1 binding moiety in a TfR-1 positive cell and/or delivers molecules to the brain (or across another TfR-1 positive membrane system) in a reversibly pH dependent manner.

Still other aspects of the invention provide a VNAR polypeptides which comprises an amino acid sequence selected from any one of the sequences shown in Tables 1 or 5 or encoded by any one of the nucleic acid sequences shown in Tables 2 or 6, and which is capable of binding human and mouse TfR-1. More particularly, these VNAR polypeptides can have a CDR3 sequence selected form clones 10, 2, 1, 39; a CDR1 sequence selected form clones 10, 2, 1, 39; and/or one or more HV2 sequences selected form clones 10, 2, 1, 39.

The present invention also includes nucleic acids encoding a polypeptide or conjugate of the invention as well as vectors containing the same and host cells comprising such nucleic acids and vectors.

Yet another aspect of the invention is directed to pharmaceutical compositions that comprise the VNAR polypeptides having a CDR3 from clones 10, 2, 1 or 39, or conjugates thereof. Such compositions can be used in methods of medical treatment which comprises administering a therapeutically-effective amount of the pharmaceutical composition to deliver a diagnostic or therapeutic agent to the brain of a mammalian subject in need thereof; or in preparation of a medicament to deliver a diagnostic or therapeutic agent to the brain of a mammalian subject in need thereof.

Similarly, these VNAR polypeptides and conjugates can be used in methods of targeting delivery of a payload to brain parenchymal tissue in a mammal which comprise administering those polypeptides or conjugates to the mammal.

In some embodiments, the invention is directed to a kit for detecting or quantifying TfR-1 in a sample which comprises at least one TfR-specific binding moiety or conjugate of the invention.

In certain embodiments the invention provides for a compound for use as a diagnostic or therapeutic agent in a subject, said compound comprising a diagnostic or therapeutic agent operably linked to a TfR-specific binding moiety of any one of claims of the preceding claims, wherein the compound binds to human TfR-1 with an EC50 ranging from about 1 nM to about 800 nM and, upon binding to human TfR-1 in a cell membrane, is transcytosed to thereby deliver said diagnostic or therapeutic agent across the cell membrane. In some cases, the operable linkage dissociates after endocytosis to release the diagnostic or therapeutic agent into said cell, e.g., across a cell membrane which forms part of the blood brain barrier or the GI tract.

BRIEF DESCRIPTION OF THE DRAWINGS

FIG. 9. Effect of in vivo selection on the 20 most abundant VNAR sequences identified by panning on human TfR1 in vitro. Only a small subset of the TfR1-binding clones was further enriched after selection in mouse brain parenchyma, whereas most decreased and a few stayed the same.

FIGS. 10A and 10B. Brain penetration of VNARs to TfR1 formatted as bivalent Fc fusion proteins. Brain uptake of eight TfR1 binding VNAR-Fc fusion proteins was measured 18 hr after tail vein injection of 2 mg/kg in two separate experiments (A and B). C=Comparator VNAR to TfR1 previously isolated by internalization in vitro. After cardiac perfusion, whole brains were homogenized in 1% Triton X-100 (without capillary depletion) and the VNAR fusion protein was detected by an Fc-capture ELISA. Data represent the mean ±SD of five mice per group.

FIGS. 15A and 15B. Epitope binning by cross-competition binding to mouse and human TfR1. VNAR-Fc fusion proteins were tested for cross-blocking in a pairwise manner against mouse (A) and human TfR1 (B) immobilised on biosensors using the Octet platform. Black indicates competition for binding (signal less than half of maximum when measured against buffer), while the lack of competition and grey indicates the lack of 8D3 monoclonal antibody binding to human TfR1.

FIGS. 26A-E. Delivery of neurotensin (NT) peptide fused to a VNAR-hFc. Delivery of neurotensin (NT) peptide as described in Example 8 resulted in body temperature decrease upon parenchymal delivery using clone C VNAR as a BBB shuttle (A). Proteins were injected intravenously at 25 nmol/kg and body temperature was measured before and two hours after dosing (B). Protein levels in brain (C) and plasma (D) were measured by Fc-capture at the 2-hour time point (N=3 per group, ±SD). A time course study (E) showed the maximum reduction in body temperature occurred two hours after injection (N=3 per group, ±SD).

DETAILED DESCRIPTION OF THE INVENTION

Figure 1:
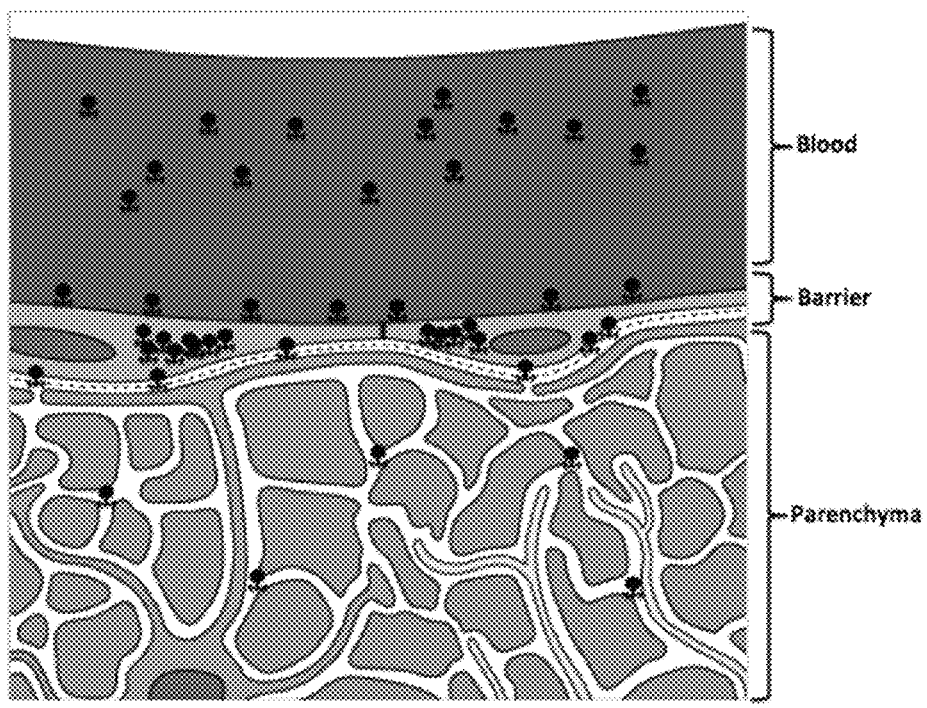
FIG. 1. Distribution of a peptide library in three different brain compartments after peripheral administration. To isolate peptides to transporters that specifically carry cargo into the brain parenchyma, the pool in the blood compartment is removed by cardiac perfusion and the pool trapped by the epithelial cell layer that forms the blood-brain barrier is removed by capillary depletion.

In order that the present invention may be more readily understood, certain terms are defined below. Additional definitions may be found within the detailed description of the invention.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to." "Including" and "including but not limited to" are used interchangeably.

The symbol "#" when used as the column header in any table depicting amino acid or nucleic acid sequences is short hand notation for "SEQ ID NO." and the number thereunder is the actual SEQ ID NO. in the Sequence Listing for the given sequence (unless indicated differently in a specific table).

The terms "patient," "subject," and "individual" may be used interchangeably and refer to either a human or a non-human animal. These terms include mammals such as humans, primates, livestock animals (e.g., bovines, porcines), companion animals (e.g., canines, felines) and rodents (e.g., mice and rats).

The term "non-human mammal" means a mammal which is not a human and includes, but is not limited to, a mouse, rat, rabbit, pig, cow, sheep, goat, dog, primate, or other non-human mammals typically used in research.

As used herein, "treating" or "treatment" and grammatical variants thereof refer to an approach for obtaining beneficial or desired clinical results. The term may refer to slowing the onset or rate of development of a condition, disorder or disease, reducing or alleviating symptoms associated with it, generating a complete or partial regression of the condition, or some combination of any of the above. For the purposes of this invention, beneficial or desired clinical results include, but are not limited to, reduction or alleviation of symptoms, diminishment of extent of disease, stabilization (i.e., not worsening) of state of disease, delay or slowing of disease progression, amelioration or palliation of the disease state, and remission (whether partial or total), whether detectable or undetectable. "Treatment" can also mean prolonging survival relative to expected survival time if not receiving treatment. A subject (e.g., a human) in need of treatment may thus be a subject already afflicted with the disease or disorder in question. The term "treatment" includes inhibition or reduction of an increase in severity of a pathological state or symptoms relative to the absence of treatment, and is not necessarily meant to imply complete cessation of the relevant disease, disorder or condition.

As used herein, the terms "preventing" and grammatical variants thereof refer to an approach for preventing the development of, or altering the pathology of, a condition, disease or disorder. Accordingly, "prevention" may refer to prophylactic or preventive measures. For the purposes of this invention, beneficial or desired clinical results include, but are not limited to, prevention or slowing of symptoms, progression or development of a disease, whether detectable or undetectable. A subject (e.g., a human) in need of prevention may thus be a subject not yet afflicted with the disease or disorder in question. The term "prevention" includes slowing the onset of disease relative to the absence of treatment, and is not necessarily meant to imply permanent prevention of the relevant disease, disorder or condition. Thus "preventing" or "prevention" of a condition may in certain contexts refer to reducing the risk of developing the condition, or preventing or delaying the development of symptoms associated with the condition.

As used herein, an "effective amount," "therapeutically-effective amount" or "effective dose" is an amount of a composition (e.g., a therapeutic composition or agent) that produces at least one desired therapeutic effect in a subject, such as preventing or treating a target condition or beneficially alleviating a symptom associated with the condition.

A physiologically-acceptable solution for use in an amount and for a time sufficient to effectively reduce a circulating concentration of the plurality of polypeptides is also referred to herein as a perfusate. The amount of perfusate and time of perfusion depends on the non-human mammal and can be readily determined by those of skill in the art. For example, with a mouse, using a volume of perfusate approximately 10× the blood volume of the mouse is effective at reducing the circulating concentration of polypetides. Likewise, any volume of perfusate that reduces the circulating concentration of the plurality of polypeptides by about 10%, 25%, 50% or more (relative to the theoretical concentration of the plurality of polypeptides) being delivered is considered effective at reducing the circulating concentration of that plurality.

As used herein, the term "TfR" or "TfR-1" refers to a mammalian transferrin receptor-1 (in context as a protein or a nucleic acid), unless the context indicates that it refers specifically to human TfR-1 (see, e.g., UniProt P02786 TFR1_Human) or mouse TfR-1.

In Vivo Methods for Selecting Polypeptides that are Transported Across Select Membrane Systems of Interest The present invention provides methods for enriching for a peptide that binds to a membrane receptor or transporter molecule external to a membrane separating or compartmentalizing a fluid or tissue, and which is transported across the membrane and released internal to the membrane system with greater efficiency than are other peptides. Such other peptides that are discarded in the enrichment methods include peptides that do not bind to, that are not transported across, or that are not released efficiently into fluid or tissue internal to the membrane system of choice.

In certain embodiments, the present invention provides a method of identifying a polypeptide capable of traversing a mammalian blood brain barrier (BBB) and being released into the brain. This is shown in the schematic of FIG. 1, illustrating the distribution of a peptide library into three different brain compartments after the library is administered peripherally to the blood by intravenous (IV) infusion. In particular, peptides localize to the blood on the outside of the brain, to the epithelial cell layer forming the BBB. Peptides that are transcytosed or transported across the BBB and released will localize to brain parenchyma.

To isolate peptides that cross the BBB (and by association, transporters that carry peptides or other cargo across the BBB into the brain or across other membrane systems to internal compartments), the pool in the blood compartment can be removed by cardiac perfusion and the pool trapped by the epithelial cell layer that forms the blood-brain barrier can be removed by capillary depletion, enriching for peptides that localize in the brain parenchymal compartment.

More specifically, several sources of non-specific contamination may be removed to improve the in vivo selection methods of the present invention. For example, in some embodiments in which the library is passaged through bacteria, such as a phage library, bacterial endotoxins are removed from the library prior to in vivo administration, as they directly disrupt and open the blood-brain barrier (Bannerman et al., Lab Invest. 1999 October; 79(10):1181-99).

Moreover, in certain embodiments, after IV (or any other mode that can deliver products to the blood, e.g., subcutaneous) administration of the library to blood but before harvesting the brain tissue, the remaining pool of peptides within the cerebral blood vessels is flushed out by cardiac perfusion. Some peptides can bind to a receptor or transporter on the luminal side of the blood-brain barrier formed by the capillary endothelial cells but never transverse the membrane. Others can be internalized but remain trapped within the cell cytoplasm, or can traverse the first membrane but are retained within the matrix without being released into the extracellular fluid of the brain parenchyma. To remove contamination associated with the barrier itself, the perfused brain is gently homogenized and the capillaries are depleted by density gradient centrifugation. Repeated rounds of in vivo phage display (or other appropriate display methods depending on the library of choice) can amplify the relatively rare peptides that are specifically transported into the brain parenchyma.

Accordingly, in certain embodiments, the method of the invention involves exposing blood outside of the brain of a mammal to a combinatorial polypeptide library comprising a multiplicity of different sequences, in most cases at least 10 or at least 20 unique sequences, up to hundreds, thousands, millions or more; and subsequently separating polypeptides that remain in the blood or within the BBB (e.g., brain capillary endothelium) away from polypeptides released into brain parenchymal tissue, thereby enriching for polypeptides that are transported into the brain. These steps are repeated in at least one more round, and preferably in multiple rounds, starting each round with the brain-enriched polypeptides from the previous round and re-exposing blood outside of the brain of the mammal to the previously isolated brain-enriched polypeptides, thereby performing one, two, three, four, five, six, seven, eight, nine, ten or more rounds of in vivo enrichment for polypeptides from the library that are transported into the brain of the mammal. In certain embodiments, a perfusion step is performed after the polypeptide library is administered to the blood and before brain parenchymal tissue is fractionated from brain capillary endothelium and blood of the mammalian subject to achieve a cleaner purification of brain transported peptides.

Figure 2:
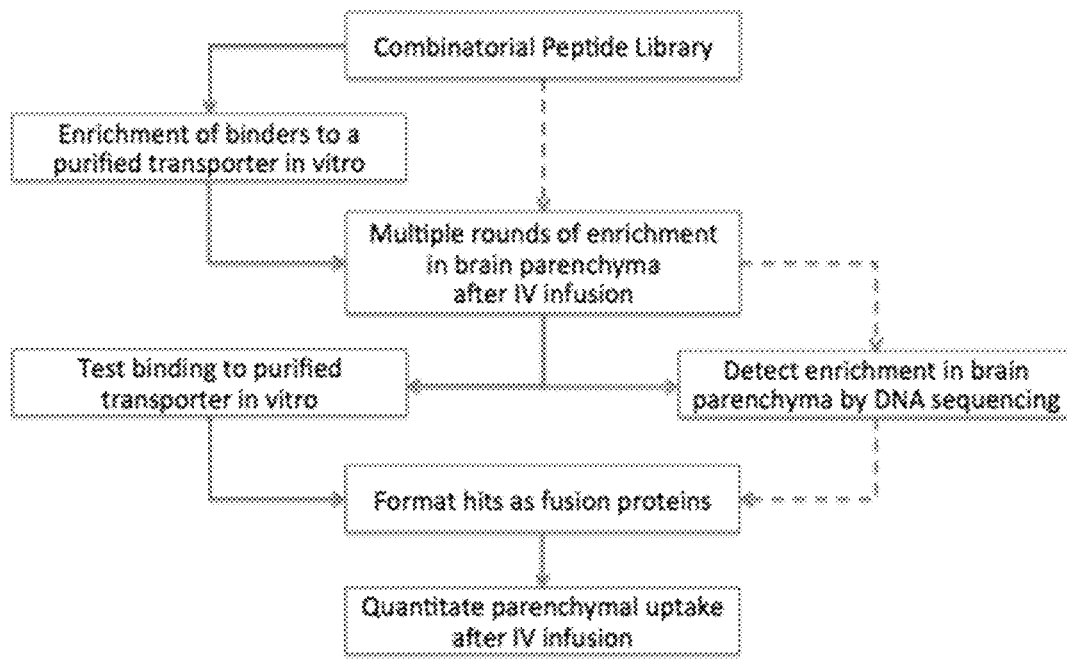
FIG. 2. In vivo selection method for identifying high efficiency peptide transporters from blood to brain parenchyma. The flow diagram outlines the method designed for identifying peptides to either known transports (solid arrows) or unknown transporters (dashed arrows) from blood into the brain parenchyma with high efficiency.

The in vivo selection methods of the invention may further be useful for identifying peptides that are productively carried across a membrane system with high efficiency, such as from blood across the BBB into the brain parenchyma, by either known or unknown membrane receptors/transporters. This is shown schematically in FIG. 2 for known transporters (solid arrows) and unknown transporters (dashed arrows).

More specifically, when applied to library-based display technology, such as phage display, where each peptide is linked to its DNA coding sequence, methods of the invention may be used for enriching the pool of binders both in vitro and in vivo. To identify the most efficient peptides to a known transporter, the library is first enriched in binders to a particular transporter in vitro. The subset of binders is then subjected to multiple rounds of enrichment in brain parenchyma after IV infusion. Enrichment is tracked by sequencing the entire pool after each round and by confirming the binding to the purified transporter in vitro. Hits are then fused to a cargo such an Fc fragment to evaluate parenchymal uptake after IV infusion.

In other embodiments, to identify the most efficiently transported peptides irrespective of the transporter system involved, the library is directly subjected to multiple round of enrichment in brain parenchyma (or other fluid or tissue internal to the membrane system selected for use). Unique hits identified by sequence analysis and are reformatted as fusion proteins to compare parenchymal uptake in vivo. Sequences showing the highest uptake are then tested for binding to a panel of known transporters. If the transport system cannot be directly identified, cell-based microarray screening strategies can be employed to uncover the target using methods available to the skilled worker.

The combinatorial library used according to methods of the invention comprises at least ten or at least twenty different sequences which preferably have been pre-selected for their ability to encode or express a peptide that binds to a membrane receptor or transporter protein known or suspected to be present in a particular membrane system of choice, such as the BBB or the GI tract. Preferably, the complexity of the library is even greater, e.g., is hundreds, thousands, millions or more unique sequences.

In such embodiments, the purified membrane receptor or transporter protein of interest and is used in a first step to select for peptides that bind to it with acceptably high affinity and/or specificity in an in vitro or ex vivo binding assay. Those pre-selected polypeptides may then be used as starting material for the in vivo enrichment methods of the invention. In such embodiments, the library used in the method of the invention has been pre-selected for it binding or affinity (in vitro or ex vivo) to purified membrane receptor or transporter protein of interest. In certain such embodiments, the receptor is a transferrin receptor, or TfR, such as TfR-1. However, it will be appreciated by the skilled artisan that many other suitable membrane receptors and transporters may be used in performing the in vitro ex vivo binding assays followed by in vivo selection methods according to the present invention. Such membrane proteins may be selected based on their particular localization to membranes associated with certain tissues or types of epithelia in the mammalian subject. One of skill in the art will know which membrane system to select in order to select for peptide sequences that may be transported across that membrane in order to deliver a heterologous molecule for diagnostic, prognostic or therapeutic benefit.

Figure 6:
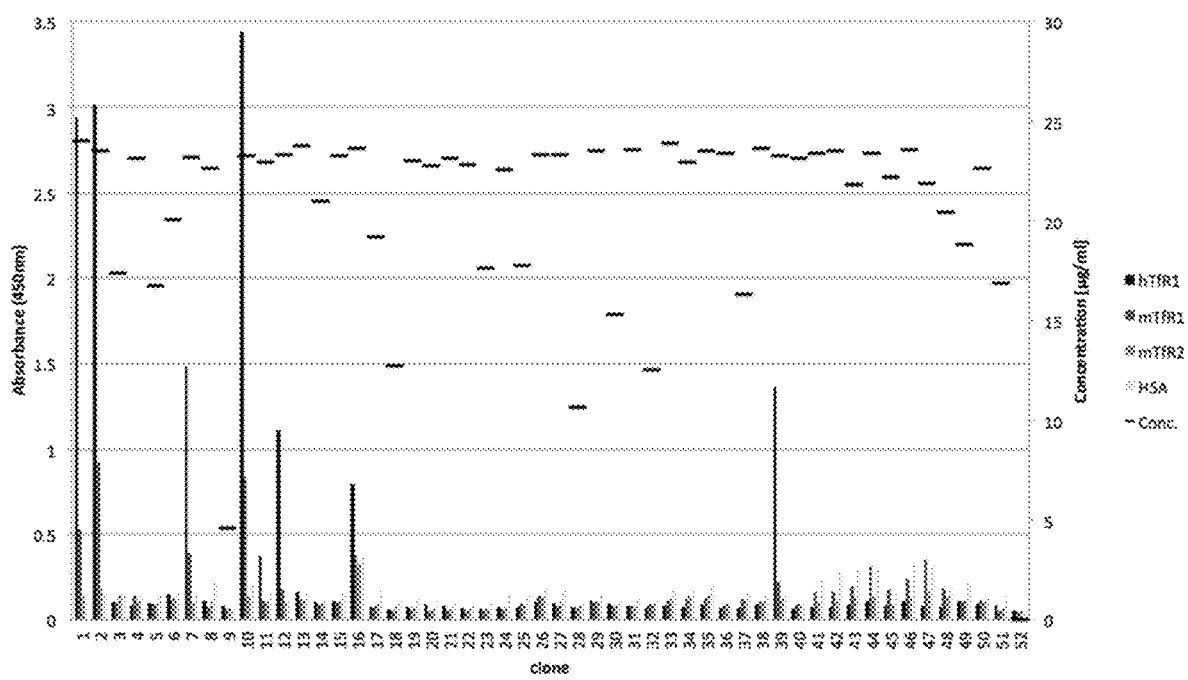
FIG. 6. Specific binding of VNAR-Fc fusion proteins to human and mouse TfR1. The VNAR-Fc fusion proteins were transiently expressed using Expi293 expression system. VNAR-Fc constructs contained signal peptide sequence in order to be secreted. Cell growth media was used directly in ELISA. HSA and mouse TfR2 were used as negative controls for unspecific binding. A clone in position 52 represents untransfected cells. Total Fc concentration was measured with capture and detection anti-Fc antibody pair using irrelevant VNAR-Fc at known concentration for standard curve.

The methods of the invention may also be used to preselect for the human form of a membrane receptor or transporter molecule in as much as the in vivo selection methods as described herein are performed in non-human animal models and produce species cross-reactive binding peptides (see e.g., Examples; FIGS. 6 and 13).

In certain other embodiments, methods of the present invention may be used in order to select transmembrane receptors or transporter proteins which have not been preselected as desirable binding targets. In such embodiments where the membrane protein is not already known, multiple rounds of the in vivo enrichment methods of the invention may be used to enrich for peptides that are transported across the membrane, such as across the BBB to brain parenchymal tissue. In situations in which there is not a known receptor or transporter to use for first round or early rounds of in vitro binding assays, sequencing is performed to compare polypeptides enriched in internal tissues (such as in brain parenchymal fractions when transport is across the BBB) to polypeptide sequences from the starting combinatorial library and/or from peptide sequences that remain in blood or in the capillary endothelium of the BBB (see e.g., FIG. 1).

Examples of receptor-mediated transport systems which can be used according to enrichment methods of the invention include but are not limited to, and identified in the following list by either the ligand or receptor (or both): transferrin, transferrin receptor-1, transferrin receptor-2, melanotransferrin, lactoferrin, apolipoprotein E receptor 2, LDL-receptor-related protein 1 and 2, receptor for advanced glycosylation end-products, immunoglobulin G, insulin, leptin, tumour necrosis factors, epidermal growth factor, heparin-binding epidermal growth factor-like growth factor (diphtheria toxin receptor), and leukaemia inhibitory factor (LIF) (see, e.g., Abbott et al., Neurobiol Dis. 2010, 37(1): 13-25).

Examples of solute carrier systems which can be used according to enrichment methods of the invention include but are not limited to: GLUT1, SGLT1, SMITHMIT/ GLUT13, CAT1, CAT3, LAT1, LAT2, SNAT2, SNAT3, SNAT 5, ASCT1, ASCT2, EAAT1, EAAT2, EAAT3, GLYT, TAUT, ENT1, ENT2, CNT1, CNT2, CNT3, MCT1, MCT2, MCT8, OAT2, OAT3, OATPB, OATP1A4, OATP1C1. OCT2, OCT3, OCTN2, PMAT, CTL1 (id.) Examples of ABC transporter systems include but are not limited to: ABCA2, ABCB1, ABCC1, ABCC2, ABCC3, ABCC4, ABCC5 and ABCG2. The identification and enrichment methods of the invention may also be applied to numerous examples of transporters for neurotransmitters and their precursors (see e.g., *Nalecz. Neurochen Res.* 2017 March; 42(3):795-809 directed to SLC families involved in blood-brain barrier transport of a variety of sugars, amino acids, neurotransmitters and precursors and organic ions).

In certain embodiments, the method further comprises identifying amino acid sequences of one or more polypeptides or fragments thereof that are transported from blood to brain parenchymal tissue and which confer transcytosis or transport activity; and optionally, making a conjugate of sequences that are necessary and/or sufficient for membrane transport with one or more heterologous agents to produce a bi-, tri-, or multi-functional polypeptide that can cross the blood brain barrier.

Polypeptides enriched in brain parenchymal fractions (or smaller peptide sequences that confer transport across the selected membrane system used in the methods of the invention) may further be formatted as fusion proteins (e.g., to an immunoglobulin Fc region) and may further be used to make molecular conjugates with one or more heterologous agents to produce a bi-, tri-, or multi-functional polypeptides or vehicles that can carry heterologous agents across the blood brain barrier or other selected membrane system.

The general methods of the invention described herein, directed to in vivo enrichment steps for identifying and isolating sequences that enhance selective or non-selective membrane transport in a mammal, have been exemplified using complex phage libraries comprising nurse shark VNAR-derived scaffolds with a high complexity of potential peptide binding moieties which can be tested for binding with selectively and with a desired affinity to mammalian membrane receptors or transport proteins. The VNAR constructs comprise a general domain structure in which a VNAR-derived CDR1 region and a CDR3 region are interspersed by a framework region FW2-3. CDR1 and CDR3 regions are also bordered by VNAR framework regions FW1 and FW4, respectively: FW1::CDR1::FW2-3::CDR3::FW4.

As exemplified herein, VNAR peptides that bind to a mouse (and cross-react with a human) transferrin receptor, TfR-1, and which have been enriched for using the in vivo enrichment methods of the invention, have identified novel TfR-1 specific binding moieties capable of being transported across the blood-brain barrier with higher efficiency than various control VNAR peptides. The present invention thus further provides VNAR-derived TfR-1 specific binding moieties, and TfR-mediated vehicles (e.g., BBB vehicles) for carrying heterologous molecules. TfR-mediated vehicles are capable of transporting one or more associated (e.g., covalently or non-covalently) heterologous molecules across the cell membrane of a TfR-positive cell by means of binding to cell surface TfR. Any non-polarized cell which expresses TfR may be used as a target for transport of a heterologous molecule using a TfR specific binding moiety of the invention. In certain embodiments, TfR expression on gut epithelial cells may advantageously be used for oral drug delivery of otherwise non-orally bioavailable drugs or compounds.

In certain embodiments, TfR expression on cells of the blood brain barrier may advantageously be used for drug or compound delivery across the blood brain barrier. In yet other embodiments, TfR antagonist compounds comprising a TfR specific binding moiety of the invention compete with or inhibit one or more bioactivities of a native TfR ligand in vitro or in vivo and may be useful for antagonizing TfR bioactivity in, e.g., cancer diagnostics and therapeutics. Nucleic acid sequences encoding one or more TfR specific binding moieties, vectors comprising nucleic acid sequences, and host cells comprising them are also provided, as are related methods for producing a TfR mediated drug delivery vehicle and a TfR antagonist compound.

TfR specific binding moieties, and vehicles and TfR antagonist compounds comprising such moieties, may be used to produce variants and derivatives, including conjugates, e.g., immunoconjugates, and multimers having multiple binding specificities built into a single molecule, such as bispecific binding molecules specific for two heterologous targets, multimers thereof, or heterospecific binding molecules specific for more than two heterologous targets. Moreover, TfR specific compounds of the invention, and variants or derivatives thereof, may be combined with other therapeutic agents in compositions for use in related therapeutic, prophylactic and diagnostic methods. Therapeutic methods are provided for treating diseases, disorders and conditions which benefit from the TfR vehicles or antagonists of the invention. In particular, compositions and methods for treating diseases, disorders and conditions of the brain and spinal cord (central nervous system) are provided, where the ability to transport heterologous molecules across the BBB may be particularly beneficial. A method for increasing the oral bioavailability of a drug by complexing or conjugating it with a TfR specific binding moiety of the invention is also provided. Methods and kits for identifying, quantifying or localizing a TfR-containing biological sample are also provided, as are methods for the targeted delivery of a payload to a TfR expressing cell using a TfR specific binding moiety-payload conjugate.

Combinatorial In Vitro and In Vivo Phage Display Selection for TfR1-Based Blood Brain Barrier Penetrating Variable New Antigen Receptor (VNAR) Domain Antibody Fragments from Nurse Shark.

Combinatorial in vitro and in vivo phage display was performed according to the Examples set forth herein in order to select for TfR1-based blood brain barrier penetrating variable new antigen receptor (VNAR) domain antibody fragments from nurse shark. As a first step, recombinant human TfR1 protein was used for in vitro phage display to raise specific VNARs that bind to TfR1 in human and cross-react with mouse TfR1 for subsequent in vivo selection steps.

A Type 2 nurse shark VNAR semi-synthetic library was previously constructed using a rationale design based on sequence analysis of 188 Type 2 VNAR sequences containing a single cysteine in their CDR3 region (see M. Diaz, et al., *Immunogenetics* 54 (2002) pp. 501-512) as described in Intl. Appln. No. PCT/US2015/038166, filed 26 Jun. 2015 (hereafter the "PCT '166 appln.") which is incorporated herein by reference in its entirety. These sequences were obtained by randomly sequencing clones in naïve VNAR libraries built from two different adult nurse sharks. Information obtained by alignment of the 188 protein sequences was used to design anew semi-synthetic library including sequence variation in both the CDR3 and the framework regions.

Selection of VNARs having particular binding specificities to TfR target proteins, isolation of monomeric VNARs, sequence analyses, next generation sequencing, species cross reactivities, phage ELISA their purification and expression in CHO cells as fusions to the N-terminus of the IgG-Fc fragment have been described previously by applicants (see Intl. Appln. No. PCT/US2015/060948, filed on Nov. 16, 2015, which is incorporated herein by reference in its entirety.)

Figure 3:
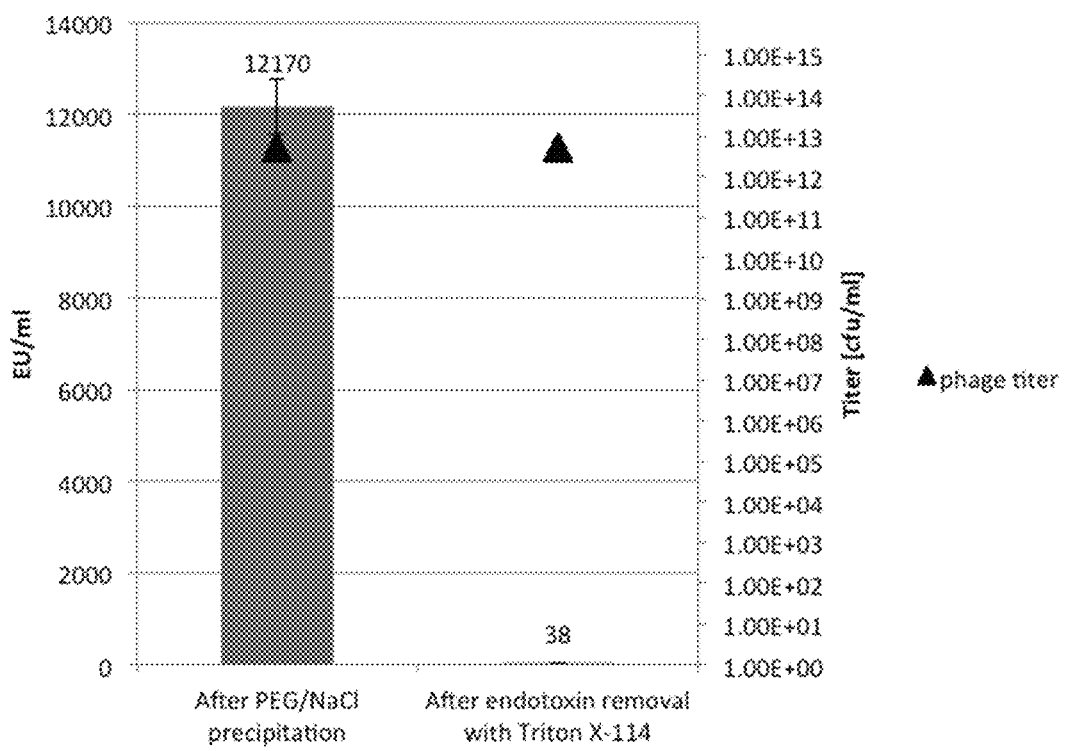
FIG. 3. Removal of endotoxin from phages display libraries used for in vivo selection of brain penetrating VNARs. Endotoxin levels were measured using LAL assay (Associates of Cape Cod Inc.) after PEG/NaCl precipitation and after endotoxin removal using Triton X-114 method (n=3, ±SD). Phage titre (▲) was determined by counting antibiotic resistant ER2738 colonies after infection with phages before and after endotoxin removal (n=3, ±SD).

In vitro phage display for TfR1 binding VNARs and in vivo selection for blood brain barrier penetrants is described in Example 1 and accompanying figures (FIGS. 1-7). Recombinant human TfR1 protein was used as targets for in vitro phage display to raise specific TfR1 binding VNARs. Two previously characterized semi-synthetic libraries, OsX-3 and OsX-4, were pre-mixed and used to perform two rounds of in vitro phage display selection (Example 1). The rescued phages from the second round of in vitro selection were PEG/NaCl precipitated and then treated to remove residual bacterial endotoxins in preparation for in vivo selection of brain penetrating phages. Preceding the in vivo selection step(s), the method was optimised for time of brain collection post phage injection and for the actual in vivo selections, the brains were extracted 1 hour after phage injections (Example 1). Three rounds of in vivo selection were performed in total. Binding to human and mouse TfR1 was monitored using phage ELISA with HSA as a negative control. Over 1000 VNAR clones in total were picked for all rounds and the percentage of binders was assessed for each round (Example 1; FIG. 3). From the phage ELISA experiments, clones that bound to both human and mouse TfR1, and that were negative for control mouse TfR2 and HSA binding, were selected and subsequently sequenced. Fifty-four VNAR sequences were retrieved, of which 51 sequences were unique. The amino acid sequences of each of the 51 unique clones are shown in Table 1 (depicting VNAR framework and CDR domain structures from N- to C-terminus, also collectively referred to as a "VNAR Domain") and corresponding nucleic acid sequences encoding these polypeptides are shown in Table 2 (depicting VNAR framework and CDR domain structures from 5'- to 3'-terminus). In Table 1, the VNAR Domain amino acid sequences are provided as SEQ ID NOS. 1-51; the CDR3 regions listed in Table 1 are provided as SEQ ID NOS. 52-102; and because so many of the above CDR1 regions have the same sequence, the unique CDR1 regions in Table 1 are provided SEQ ID Nos. as follows: DNNCALS (SEQ ID NO. 103), DSNCALS (SEQ ID NO. 104), DSNCELS (SEQ ID NO. 105), DSNCALP (SEQ ID NO. 106), DSICALS (SEQ ID NO. 107), DSNCDLS (SEQ ID NO. 108), DASYALG (SEQ ID NO. 109) and DASYELG (SEQ ID NO. 110). Additionally in Table 1, the sequences of the FW1 regions are represented by amino acids 1-25 of SEQ ID NOS. 1-51; the sequences of the FW2-3 regions are represented by amino acids 33-65 of SEQ ID NOS. 1-51; the sequences of the FW4 regions for Type II VNAR domains are represented by the last 11 amino acids of SEQ ID NOS. 1-41; and the sequences of the FW4 regions for Type I VNAR domains are represented by the last 14 amino acids of SEQ ID NOS. 42-50 and by the last 11 amino acids of SEQ ID NO. 51.

TABLE 1

Amino acid sequences of unique VNAR Domains identified by a combination of in vitro and in vivo selection that bind both human and mouse TfR1.

| # | FW1 | CDR1 | FW2-3 | CDR3 | FW4 | VNAR type | Library |
|---|---|---|---|---|---|---|---|
| 1 | ARVDQTPQTITK ETGESLTINCVLR | DNNCALS | TTYWYRKKSGSTNEENISKGGRYVETV NSGSKSFSLKINDLTVEDSGTYRCNV | RDVQACGNDWVWLDV | YGGGTVVTVNA | Type II | OsX3 |
| 2 | ARVDQTPQTITK ETGESLTINCVLR | DNNCALS | TTYWYRKKSGSTNEENISKGGRYVETV NSGSKSFSLKINDLTVEDSGTYRCNV | FGVDNGWWCDV | YGGGTVVTVNA | Type II | OsX3 |
| 3 | ARVDQTPQTITK ETGESLTINCVLR | DNNCALS | TTYWYRKKSGSTNEENISKGGRYVETV NSGSKSFSLKINDLTVEDSGTYRCNV | TGYFRSTCLWRDV | YGGGTAVTVNA | Type II | OsX3 |
| 4 | ARVDQTPQTITK ETGESLTINCVLR | DSNCALS | STYWYRKKSGSTNEENISKGGRYVETV NSGSKSFSLKINDLTVEDSGTYRCNV | QFTAALWCEAVLDV | YGGGTVVTVNA | Type II | OsX3 |
| 5 | ARVDQTPQTITK ETGESLTINCVLR | DSNCALS | STYWYRKKSGSTNEENISKGGRYVETV NSGSKSFSLKINDLTVEDSGTYRCNV | QKGQHLQCHVAVQDV | YGGGTAVTVNA | Type II | OsX3 |
| 6 | ARVDQTPQTITK ETGESLTINCVLR | DSNCALS | STYWYRKKSDSTNEESISKGGRYVETV NSGSKSFSLRINDLTVEDSGTYRCNV | QWWLRCGYFKDV | YGGGTVVTVNA | Type II | OsX3 |
| 7 | ARVDQTPQTITK ETGESLTINCVLR | DSNCELS | STYWYRKKSGSTNEARISKGGRYVETV NSGSKSFSLKINDLTVEDSGTYRCNV | LTTDSYDLGDV | YGDGTVVTVNA | Type II | OsX3 |
| 8 | ARVDQTPQTITK ETGESLTINCVLR | DSNCELS | STYWYRKKSGSTNEARISKGGRYVETV NSGSKSFSLRINDLTVEDSGTYRCNV | QYFLCHFVGDV | YGDGTAVTVNA | Type II | OsX3 |
| 9 | ARVDQTPQTITK ETGESLTINCVLR | DSNCALP | STYWYRKKSGSTNEARISKGGRYVETV NSGSKSFSLRINDLTVEDSGTIDARY | RLSASAVLYQSYVDV | YGGGTAVTVNA | Type II | OsX3 |
| 10 | ARVDQTPQTITK ETGESLTINCVLR | DSNCALS | STYWYRKKSGSTNEENISKGGRYVETV NSGSKSFSLRINDLTVEDSGTYRCNV | VQYPSYNNYFWCDV | YGDGTAVTVNA | Type II | OsX3 |
| 11 | ARVDQTPQTITK ETGESLTINCVLR | DSNCALP | STHWYRKKSGSTNEESISKGGRYVETV NSGSKSFSLRINDLTVEDSGTYRCKV | LNFFTHTCVQVQKYDV | YGGGTAVTVNA | Type II | OsX3 |
| 12 | ARVDQTPQTITK ETGESLTINCVLR | DSICALS | STHWYRKKSGSTNEESISKGGRYVETV NSGSKSFSLRINDLTVEDSGTYRCKV | VRSGVGPCWADV | YGGGTAVTVNA | Type II | OsX3 |
| 13 | ARVDQTPQTITK ETGESLTINCVLR | DSNCALP | STYRYRKKSGSTNEESISKGGRYVETV NSGSKSFSLRINDLTVEDSGTYRCKV | TMVRGRGCYQPARGQDV | YGGGTAVTVNA | Type II | OsX3 |
| 14 | ARVDQTPQTITK ETGESLTINCVLR | DSNCALP | STYWYRKKSGSTNEESISKGGRYVETV NSGSKSFSLRINDLTVEDSGTYRCKV | TFSAFEYCYVFKVQCDV | YGDGTAVTVNA | Type II | OsX3 |
| 15 | ARVDQTPQTITK ETGESLTINCVLR | DSNCALP | STYWYCKKSGSTNEESISKGGRYVETV NSGSKSFSLRINDLTVKDSGTYRCKV | HVRAQSLCCQCWYGDV | YGDGTAVTVNA | Type II | OsX3 |
| 16 | ARVDQTPQTITK ETGESLTINCVLR | DSNCALP | STYWYRKKSGSTNEESISKGGRYVETV NSGSKSFSLRINDLTVKDSGTYRCKV | DLPRYLCFSQYGRWYDV | YGDGTAVTVNA | Type II | OsX3 |
| 17 | ARVDQTPQTITK ETGESLTINCVLR | DSNCALP | STYWYRKKSGSTNEESISKGGRYVETV NSGSKSFSLRINDLTVKDSGTYRCNV | ARHWTQSCAYHRDV | YGGGTAVTVNA | Type II | OsX3 |

TABLE 1-continued

Amino acid sequences of unique VNAR Domains identified by a combination of in vitro and in vivo selection that bind both human and mouse TfR1.

| # | FW1 | CDR1 | FW2-3 | CDR3 | FW4 | VNAR type | Library |
|---|---|---|---|---|---|---|---|
| 18 | ARVDQTPQTITK ETGESLTINCVLR | DSNCALP | STYWYRKKSGSTNEESISKGGRYVETV NSGSKSFSLRINDLTVKDSGTYRCNV | QHIFQHNCYWFLYDV | YGGGTAVTVNA | Type II | OsX3 |
| 19 | ARVDQTPQTITK ETGESLTINCVLR | DSNCALP | STYWYRKKSGSTNEESISKGGRYVETV NSGSKSFSLRINDLTVEDSGTYRCNV | GWSTQYYCVLPDV | YGGGTAVTVNA | Type II | OsX3 |
| 20 | ARVDQTPQTITK ETGESLTINCVLR | DSNCALP | STYWYRKKSGSTNEESISKGGRYVETV NSGSKSFSLRINDLTVEDSGTYRCNV | YTSYCCSVADV | YGGGTAVTVNA | Type II | OsX3 |
| 21 | ARVDQTPQTITK ETGESLTINCVLR | DSNCALS | STYWYRKKSGSTNEESISKGGRYVETV NSGSKSFSLRINDLTVEDSGTYRCKV | LTSQSQGGCVRVLYSD V | YGDGTAVTVNA | Type II | OsX3 |
| 22 | ARVDQTPQTITK ETGESLTINCVLR | DSNCALS | STYWYRKKSDSTNEESISKGGRYVETV NSGSKSFSLRINDLTVEDSGTYRCKV | HSFNMDVCAEFQYSDV | YGDGTAVTVNA | Type II | OsX3 |
| 23 | ARVDQTPQTITK ETGESLTINCVLR | DSNCALS | NLYWYRKKSGSTNEESISKGGRYVETV NSGSKSFSLRINDLTVEDSGTYRCNV | INFFAMECEYQVGDV | YGDGTAVTVNA | Type II | OsX3 |
| 24 | ARVDQTPQTITK ETGESLTINCVLR | DSNCALS | NLYWYRKKSGSTNEESISKGGRYVETV NSGSKSFSLRINDLTVKDSGTYRCNV | LVSMFCQLAQDV | YGDGTAVTVNA | Type II | OsX3 |
| 25 | ARVDQTPQTITK ETGESLTINCVLR | DSNCALS | NLYWYRKKSGSTNEESISLGGRYVETV NSGSKSFSLRINDLTVEDSGTYRCNV | CLLQLAGYDSPYDV | YGGGTAVTVNA | Type II | OsX3 |
| 26 | ARVDQTPQTITK ETGESLTINCVLR | DSNCALS | NLYWYRKKSGSTNEENISKGGRYVETV NSGSKSFSLRINDLTVEDSGTYRCNV | DVTRCTQSQDV | YGGGTAVTVNA | Type II | OsX3 |
| 27 | ARVDQTPQTVTK ETGESLTINCVLR | DSNCALS | NLYWYRKKSGSTNEESISLGGRYVETV NSGSKSFSLRINDLTVEDSGTYRCNV | KHYVCMQSKDV | YGGGTVVTVNA | Type II | OsX3 |
| 28 | ARVDQTPQTITK ETGESLTINCVLR | DSNCALS | NLYWYRKKSGSTNEESISLGGRYVETV NSGSKSFSLRINDLTVKDSGTYRCNV | FSFSCQLLFDV | YGGGTAVTVNA | Type II | OsX3 |
| 29 | ARVDQTPQTITK ETGESLTINCVLR | DSNCALS | NLYWYRKKSGSTNEESISLGGRYVETV NSGSKSFSLRINDLTVEDSGTYRCKV | STSVPRHYDNCRQRRH DV | YGGGTAVTVNA | Type II | OsX3 |
| 30 | ARVDQTPQTITK ETGESLTINCVLR | DSNCALS | NLYWYRKKSGSTNEESISLGGRYVETV NSGSKSFSLRINDLTVEDSGTYRCNV | CQWLQWYGGEMEDV | YGGGTAVTVNA | Type II | OsX3 |
| 31 | ARVDQTPQTITK ETGESLTINCVLR | DSNCDLS | RTYWYRKKSGSTNEESISKGGRYVETV NSGSKSFSLKINDLTVEDSGTYRCNV | FLWNNYNPMDV | YGGGTAVTVNA | Type II | OsX3 |
| 32 | ARVDQTPQTITK ETGESLTINCVLR | DSNCALS | NLYWYRKKSGSRNEESISKGGRYVETV NSGSKSFSLKINDLTVEDSGTYRCKV | FGMRTHCQWVIYRITD V | YGGGTAVTVNA | Type II | OsX3 |
| 33 | ARVDQTPQTITK ETGESLTINCVLR | DSNCDLS | RTYWYRKKQGSTNEESISKGGRYVETV NSGSKSFSLRINDLTVEDSGTYRCNV | ALYHFTGCSRVQDV | YGGGTVVTVNA | Type II | OsX3 |
| 34 | ARVDQTPQTITK ETGESLTINCVLR | DSNCDLS | RTYWYRKKSGSTNEESISKGGRYVETV NSGSKSFSLRINDLVVEDSGTYRCNV | AVFTRCHNQQDV | YGGGTAVTVNA | Type II | OsX3 |
| 35 | ARVDQTPQTITK ETGESLTINCVLR | DSNCDLS | RTYWYRKKSGSTNEESISKGGRYVETV NSGSKSFSLRINDLTVEDSGTYRCNV | TWLDCHQCGASDV | YGGGTVVTVNA | Type II | OsX3 |
| 36 | ARVDQTPQTITK ETGESLTINCVLR | DSNCDLS | RTYWYRKKSGSTNEESISKGGRYVETV NSGSKSFSLRINDLVVEDSGTYRCNV | HSVSCIQRLDV | YGGGTVVTVNA | Type II | OsX3 |
| 37 | ARVDQTPQTITK ETGESLTINCVLR | DSNCALS | STLWYRTKSGSRNEESISKGGRYVETV NSGSKSFSLRINDLTVKDSGTYRCNV | QQGVVATCTSKRCDV | YGGGTAVTVNA | Type II | OsX3 |
| 38 | ARVDQTPQTITK ETGESLTINCVLR | DNNCALS | STLWYRTKSGSRNEESISKGGRYVETV NSGSKSFSLRINDLTVEDSGTYRCKV | WQDSLSQPCESGCLDV | YGGGTAVTVNA | Type II | OsX3 |
| 39 | ARVDQTPQTITK ETGESLTINCVLR | DSNCALS | STLWYRTKSGSRNEESISKGGRYVETV NSGSKSFSLRINDLTVEDSGTYRCNV | QGMVYDGSSFWWCDV | YGDGTAVTVNA | Type II | OsX3 |
| 40 | ARVDQTPQTITK ETGESLTINCVLR | DSNCALS | STLWYRTKSGSRNEESISKGGRYVETV NSGSKSFSLRINDLTVEDSGTYRCNV | QFSYNCNFWKDV | YGGGTDVTVNA | Type II | OsX3 |
| 41 | ARVDQTPQTITK ETGESLTINCVLR | DSNCALS | STLWYRTKSGSRNEESISKGGRYVETV NSGSKSFSLKINDLTVEDSGTYRCKVCR | QCCVATCDDLSLLCDV | YGDGTAVTVNA | Type II | OsX3 |

TABLE 1-continued

Amino acid sequences of unique VNAR Domains identified by a combination of in vitro and in vivo selection that bind both human and mouse TfR1.

| # | FW1 | CDR1 | FW2-3 | CDR3 | FW4 | VNAR type | Library |
|---|-----|------|-------|------|-----|-----------|---------|
| 42 | ARVDQTPRSVTK ETGESLTINCVLR | DASYALG | STCWYRKKSGSTNEESISKGGRYVETV NSGSKSFSLRINDLTVEDGGTYRCGV | CEMQLIAVDSCDHTLD DGLCGGV | YAACGDGTAVT VNA | Type I | OsX4 |
| 43 | ARVDQTPRSVTK ETGESLTINCVLR | DASYALG | STCWYRKKSGSTNEESISKGGRYVETV NSGSKSFSLRINDLTVEDGGTYRCGV | YGGTHQGLCGCDWQLR FSLCGDG | RAACGDGTAVT VNA | Type I | OsX4 |
| 44 | ARVDQTPRSVTK ETGESLTINCVLR | DASYALG | STCWYRKKSGSTNEESISKGGRYVETV NSGSKSFSLRINDLTVEDGGTYRCGV | CQCWSANVWVDCDMTS TSIRMRDGSRSNA | RAACGDGTAVT VNA | Type I | OsX4 |
| 45 | ARVDQTPRSVTK ETGESLTINCVLR | DASYALG | STCWYRKKSGSTNEESISKGGRYVETV NSGSKSFSLRINDLTVEDGGTYRCGV | CESSFCSLPYDCDSSS AGSVIQPFGHIVS | LAACGDGTAVT VNA | Type I | OsX4 |
| 46 | ARVDQTPRSVTK ETGESLTINCVLR | DASYALG | STCWYRKKSGSTNEESISKGGRYVETV NSGSKSFSLRINDLTVEDGGTYRCGV | CSDYGLCITTGQ | QAACGDGTAVT VNA | Type I | OsX4 |
| 47 | ARVDQTPRSVTK ETGESLTINCVLR | DASYALG | STCWYRKKSGSTNEESISKGGRYVETV NSGSKSFSLRINDLTVEDGGTYRCGA | AIQGFWAGRCDNLPGK CVMQVSN | AAACGDGTAVT VNA | Type I | OsX4 |
| 48 | ARVDQTPRSVTK ETGESLTINCVLR | DASYELG | STCWYRKKSGSTNEESISKGGRYVETV NSGSKSFSLRINDLTVEDGGTYRCGA | SLQCGNCELCDREQLQ CGGQRGQ | LAACGDGTAVT VNA | Type I | OsX4 |
| 49 | ARVDQTPRSVTK ETGESLTINCVLR | DASYELG | STCWYRKKSGSTNEESISKGGRYVETV NSGSKSFSLRINDLTVEDGGTYRCGV | ISQYKSYTLWCDALYR SLGCECA | RAACGDGTAVT VNA | Type I | OsX4 |
| 50 | ARVDQTPRSVTK ETGESLTINCVLR | DASYALG | STCWYRKKSGSTNEESISKGGRYVETV NSGSKSFSLRINDLTVEDGGTYRCGV | MNNVSQTWVRCDSQVM SQQCVQQ | SAACGDGTAVT VNA | Type I | OsX4 |
| 51 | ARVDQTPRSVTK ETGESLTINCVLR | DASYALG | STCWYRKKSGSTNEESISKGGRYVETV NSGSKSFSLRINDLTVEDSGTYRCNV | IQYLYLGSYFACDV | YGGGTVVTVNA | Type I | OsX4 |

TABLE 2

Corresponding DNA sequences of unique VNARs to TfR1 shown in Table 1 and identified by a combination of in vitro and in vivo selections.

| # | DNA sequence |
|---|---|
| 111 | GCCAGGGTGGACCAGACCCCCCAGACCATCACCAAGGAGACCGGCGAGAGCCTGACCATC AACTGCGTGCTGAGGGACAACAACTGCGCCCTGAGCACCACCTACTGGTACAGGAAGAAG AGCGGCAGCACCAACGAGGAGAACATCAGCAAGGGCGGCAGGTACGTGGAGACCGTGAAC AGCGGCAGCAAGAGCTTCAGCCTGAAGATCAACGACCTGACCGTGGAGGACAGCGGCACC TACAGGTGCAACGTGAGGGACGTGCAGGCCTGCGGCAACGACTGGGTGTGGCTGGACGTG TACGGCGGCGGCACCGTGGTGACCGTGAAC |
| 112 | GCCAGGGTGGACCAGACCCCCCAGACCATCACCAAGGAGACCGGCGAGAGCCTGACCATC AACTGCGTGCTGAGGGACAACAACTGCGCCCTGAGCACCACCTACTGGTACAGGAAGAAG AGCGGCAGCACCAACGAGGAGAACATCAGCAAGGGCGGCAGGTACGTGGAGACCGTGAAC AGCGGCAGCAAGAGCTTCAGCCTGAAGATCAACGACCTGACCGTGGAGGACAGCGGCACC TACAGGTGCAACGTGTTCGGCGTGGACAACGGCTGGTGGTGCGACGTGTACGGCGGCGGC ACCGTGGTGACCGTGAAC |
| 113 | GCCAGGGTGGACCAGACCCCCCAGACCATCACCAAGGAGACCGGCGAGAGCCTGACCATC AACTGCGTGCTGAGGGACAACAACTGCGCCCTGAGCACCACCTACTGGTACAGGAAGAAG AGCGGCAGCACCAACGAGGAGAACATCAGCAAGGGCGGCAGGTACGTGGAGACCGTGAAC AGCGGCAGCAAGAGCTTCAGCCTGAAGATCAACGACCTGACCGTGGAGGACAGCGGCACC TACAGGTGCAACGTGACCGGCTACTTCAGGAGCACCTGCCTGTGGAGGGACGTGTACGGC GGCGGCACCGCCGTGACCGTGAAC |
| 114 | GCCAGGGTGGACCAGACCCCCCAGACCATCACCAAGGAGACCGGCGAGAGCCTGACCATC AACTGCGTGCTGAGGGACAGCAACTGCGCCCTGAGCAGCACCTACTGGTACAGGAAGAAG AGCGGCAGCACCAACGAGGAGAACATCAGCAAGGGCGGCAGGTACGTGGAGACCGTGAAC AGCGGCAGCAAGAGCTTCAGCCTGAAGATCAACGACCTGACCGTGGAGGACAGCGGCACC TACAGGTGCAACGTGCAGTTCACCGCCGCCCTGTGGTGCGAGGCCGTGCTGGACGTGTAC GGCGGCGGCACCGTGGTGACCGTGAAC |
| 115 | GCCAGGGTGGACCAGACCCCCCAGACCATCACCAAGGAGACCGGCGAGAGCCTGACCATC AACTGCGTGCTGAGGGACAGCAACTGCGCCCTGAGCAGCACCTACTGGTACAGGAAGAAG AGCGGCAGCACCAACGAGGAGAACATCAGCAAGGGCGGCAGGTACGTGGAGACCGTGAAC AGCGGCAGCAAGAGCTTCAGCCTGAAGATCAACGACCTGACCGTGGAGGACAGCGGCACC |

TABLE 2-continued

Corresponding DNA sequences of unique VNARs to TfR1 shown in Table 1 and identified by a combination of in vitro and in vivo selections.

| # | DNA sequence |
|---|---|
| | TACAGGTGCAACGTGCAGAAGGGCCAGCACCTGCAGTGCCACGTGGCCGTGCAGGACGTG<br>TACGGCGGCGGCACCGCCGTGACCGTGAAC |
| 116 | GCCAGGGTGGACCAGACCCCCCAGACCATCACCAAGGAGACCGGCGAGAGCCTGACCATC<br>AACTGCGTGCTGAGGGACAGCAACTGCGCCCTGAGCAGCACCTACTGGTACAGGAAGAAG<br>AGCGACAGCACCAACGAGGAGAGCATCAGCAAGGGCGGCAGGTACGTGGAGACCGTGAAC<br>AGCGGCAGCAAGAGCTTCAGCCTGAGGATCAACGACCTGACCGTGGAGGACAGCGGCACC<br>TACAGGTGCAACGTGCAGTGGTGGCTGAGGTGCGGCTACTTCAAGGACGTGTACGGCGGC<br>GGCACCGTGGTGACCGTGAAC |
| 117 | GCCAGGGTGGACCAGACCCCCCAGACCATCACCAAGGAGACCGGCGAGAGCCTGACCATC<br>AACTGCGTGCTGAGGGACAGCAACTGCGAGCTGAGCAGCACCTACTGGTACAGGAAGAAG<br>AGCGGCAGCACCAACGAGGCCAGGATCAGCAAGGGCGGCAGGTACGTGGAGACCGTGAAC<br>AGCGGCAGCAAGAGCTTCAGCCTGAAGATCAACGACCTGACCGTGGAGGACAGCGGCACC<br>TACAGGTGCAACGTGCTGACCACCGACAGCTACGACCTGGGCGACGTGTACGGCGACGGC<br>ACCGTGGTGACCGTGAAC |
| 118 | GCCAGGGTGGACCAGACCCCCCAGACCATCACCAAGGAGACCGGCGAGAGCCTGACCATC<br>AACTGCGTGCTGAGGGACAGCAACTGCGAGCTGAGCAGCACCTACTGGTACAGGAAGAAG<br>AGCGGCAGCACCAACGAGGCCAGGATCAGCAAGGGCGGCAGGTACGTGGAGACCGTGAAC<br>AGCGGCAGCAAGAGCTTCAGCCTGAGGATCAACGACCTGACCGTGGAGGACAGCGGCACC<br>TACAGGTGCAACGTGCAGTACTTCCTGTGCCACTTCGTGGGCGACGTGTACGGCGACGGC<br>ACCGCCGTGACCGTGAAC |
| 119 | GCCAGGGTGGACCAGACCCCCCAGACCATCACCAAGGAGACCGGCGAGAGCCTGACCATC<br>AACTGCGTGCTGAGGGACAGCAACTGCGCCCTGCCCAGCACCTACTGGTACAGGAAGAAG<br>AGCGGCAGCACCAACGAGGCCAGGATCAGCAAGGGCGGCAGGTACGTGGAGACCGTGAAC<br>AGCGGCAGCAAGAGCTTCAGCCTGAGGATCAACGACCTGACCGTGGAGGACAGCGGCACC<br>ATCGACGCCAGGTACAGGCTGAGCGCCAGCGCCGTGCTGTACCAGAGCTACGTGGACGTG<br>TACGGCGGCGGCACCGCCGTGACCGTGAAC |
| 120 | GCCAGGGTGGACCAGACCCCCCAGACCATCACCAAGGAGACCGGCGAGAGCCTGACCATC<br>AACTGCGTGCTGAGGGACAGCAACTGCGCCCTGAGCAGCACCTACTGGTACAGGAAGAAG<br>AGCGGCAGCACCAACGAGGAGAACATCAGCAAGGGCGGCAGGTACGTGGAGACCGTGAAC<br>AGCGGCAGCAAGAGCTTCAGCCTGAGGATCAACGACCTGACCGTGGAGGACAGCGGCACC<br>TACAGGTGCAACGTGGTGCAGTACCCCAGCTACAACAACTACTTCTGGTGCGACGTGTAC<br>GGCGACGGCACCGCCGTGACCGTGAAC |
| 121 | GCCAGGGTGGACCAGACCCCCCAGACCATCACCAAGGAGACCGGCGAGAGCCTGACCATC<br>AACTGCGTGCTGAGGGACAGCAACTGCGCCCTGCCCAGCACCCACTGGTACAGGAAGAAG<br>AGCGGCAGCACCAACGAGGAGAGCATCAGCAAGGGCGGCAGGTACGTGGAGACCGTGAAC<br>AGCGGCAGCAAGAGCTTCAGCCTGAGGATCAACGACCTGACCGTGGAGGACAGCGGCACC<br>TACAGGTGCAAGGTGCTGAACTTCTTCACCCACACCTGCGTGCAGGTGCAGAAGTACGAC<br>GTGTACGGCGGCGGCACCGCCGTGACCGTGAAC |
| 122 | GCCAGGGTGGACCAGACCCCCCAGACCATCACCAAGGAGACCGGCGAGAGCCTGACCATC<br>AACTGCGTGCTGAGGGACAGCATCTGCGCCCTGAGCAGCACCCACTGGTACAGGAAGAAG<br>AGCGGCAGCACCAACGAGGAGAGCATCAGCAAGGGCGGCAGGTACGTGGAGACCGTGAAC<br>AGCGGCAGCAAGAGCTTCAGCCTGAGGATCAACGACCTGACCGTGGAGGACAGCGGCACC<br>TACAGGTGCAAGGTGGTGAGGAGCGGCGTGGGCCCCTGCTGGGCCGACGTGTACGGCGGC<br>GGCACCGCCGTGACCGTGAAC |
| 123 | GCCAGGGTGGACCAGACCCCCCAGACCATCACCAAGGAGACCGGCGAGAGCCTGACCATC<br>AACTGCGTGCTGAGGGACAGCAACTGCGCCCTGCCCAGCACCTACAGGTACAGGAAGAAG<br>AGCGGCAGCACCAACGAGGAGAGCATCAGCAAGGGCGGCAGGTACGTGGAGACCGTGAAC<br>AGCGGCAGCAAGAGCTTCAGCCTGAGGATCAACGACCTGACCGTGGAGGACAGCGGCACC<br>TACAGGTGCAAGGTGACCATGGTGAGGGGCAGGGGCTGCTACCAGCCCGCCAGGGGCCAG<br>GACGTGTACGGCGGCGGCACCGCCGTGACCGTGAAC |
| 124 | GCCAGGGTGGACCAGACCCCCCAGACCATCACCAAGGAGACCGGCGAGAGCCTGACCATC<br>AACTGCGTGCTGAGGGACAGCAACTGCGCCCTGCCCAGCACCTACTGGTACAGGAAGAAG<br>AGCGGCAGCACCAACGAGGAGAGCATCAGCAAGGGCGGCAGGTACGTGGAGACCGTGAAC<br>AGCGGCAGCAAGAGCTTCAGCCTGAGGATCAACGACCTGACCGTGGAGGACAGCGGCACC<br>TACAGGTGCAAGGTGACCTTCAGCGCCTTCGAGTACTGCTACGTGTTCAAGGTGCAGTGC<br>GACGTGTACGGCGACGGCACCGCCGTGACCGTGAAC |
| 125 | GCCAGGGTGGACCAGACCCCCCAGACCATCACCAAGGAGACCGGCGAGAGCCTGACCATC<br>AACTGCGTGCTGAGGGACAGCAACTGCGCCCTGCCCAGCACCTACTGGTACTGCAAGAAG<br>AGCGGCAGCACCAACGAGGAGAGCATCAGCAAGGGCGGCAGGTACGTGGAGACCGTGAAC<br>AGCGGCAGCAAGAGCTTCAGCCTGAGGATCAACGACCTGACCGTGAAGGACAGCGGCACC<br>TACAGGTGCAAGGTGCACGTGAGGGCCCAGAGCCTGTGCTGCCAGTGCTGGTACGGCGAC<br>GTGTACGGCGACGGCACCGCCGTGACCGTGAAC |

TABLE 2-continued

Corresponding DNA sequences of unique VNARs to TfR1 shown in Table 1 and identified by a combination of in vitro and in vivo selections.

| # | DNA sequence |
|---|---|
| 126 | GCCAGGGTGGACCAGACCCCCAGACCATCACCAAGGAGACCGGCGAGAGCCTGACCATC<br>AACTGCGTGCTGAGGGACAGCAACTGCGCCCTGCCCAGCACCTACTGGTACAGGAAGAAG<br>AGCGGCAGCACCAACGAGGAGAGCATCAGCAAGGGCGGCAGGTACGTGGAGACCGTGAAC<br>AGCGGCAGCAAGAGCTTCAGCCTGAGGATCAACGACCTGACCGTGAAGGACAGCGGCACC<br>TACAGGTGCAAGGTGGACCTGCCCAGGTACCTGTGCTTCAGCCAGTACGGCAGGTGGTAC<br>GACGTGTACGGCGACGGCACCGCCGTGACCGTGAAC |
| 127 | GCCAGGGTGGACCAGACCCCCAGACCATCACCAAGGAGACCGGCGAGAGCCTGACCATC<br>AACTGCGTGCTGAGGGACAGCAACTGCGCCCTGCCCAGCACCTACTGGTACAGGAAGAAG<br>AGCGGCAGCACCAACGAGGAGAGCATCAGCAAGGGCGGCAGGTACGTGGAGACCGTGAAC<br>AGCGGCAGCAAGAGCTTCAGCCTGAGGATCAACGACCTGACCGTGAAGGACAGCGGCACC<br>TACAGGTGCAACGTGGCCAGGCACTGGACCCAGAGCTGCGCCTACCACAGGGACGTGTAC<br>GGCGGCGGCACCGCCGTGACCGTGAAC |
| 128 | GCCAGGGTGGACCAGACCCCCAGACCATCACCAAGGAGACCGGCGAGAGCCTGACCATC<br>AACTGCGTGCTGAGGGACAGCAACTGCGCCCTGCCCAGCACCTACTGGTACAGGAAGAAG<br>AGCGGCAGCACCAACGAGGAGAGCATCAGCAAGGGCGGCAGGTACGTGGAGACCGTGAAC<br>AGCGGCAGCAAGAGCTTCAGCCTGAGGATCAACGACCTGACCGTGAAGGACAGCGGCACC<br>TACAGGTGCAACGTGCAGCACATCTTCCAGCACAACTGCTACTGGTTCCTGTACGACGTG<br>TACGGCGGCGGCACCGCCGTGACCGTGAAC |
| 129 | GCCAGGGTGGACCAGACCCCCAGACCATCACCAAGGAGACCGGCGAGAGCCTGACCATC<br>AACTGCGTGCTGAGGGACAGCAACTGCGCCCTGCCCAGCACCTACTGGTACAGGAAGAAG<br>AGCGGCAGCACCAACGAGGAGAGCATCAGCAAGGGCGGCAGGTACGTGGAGACCGTGAAC<br>AGCGGCAGCAAGAGCTTCAGCCTGAGGATCAACGACCTGACCGTGGAGGACAGCGGCACC<br>TACAGGTGCAACGTGGGCTGGAGCACCCAGTACTACTGCGTGCTGCCCGACGTGTACGGC<br>GGCGGCACCGCCGTGACCGTGAAC |
| 130 | GCCAGGGTGGACCAGACCCCCAGACCATCACCAAGGAGACCGGCGAGAGCCTGACCATC<br>AACTGCGTGCTGAGGGACAGCAACTGCGCCCTGCCCAGCACCTACTGGTACAGGAAGAAG<br>AGCGGCAGCACCAACGAGGAGAGCATCAGCAAGGGCGGCAGGTACGTGGAGACCGTGAAC<br>AGCGGCAGCAAGAGCTTCAGCCTGAGGATCAACGACCTGACCGTGGAGGACAGCGGCACC<br>TACAGGTGCAACGTGTACACCAGCTACTGCTGCAGCGTGGCCGACGTGTACGGCGGCGGC<br>ACCGCCGTGACCGTGAAC |
| 131 | GCCAGGGTGGACCAGACCCCCAGACCATCACCAAGGAGACCGGCGAGAGCCTGACCATC<br>AACTGCGTGCTGAGGGACAGCAACTGCGCCCTGAGCAGCACCTACTGGTACAGGAAGAAG<br>AGCGGCAGCACCAACGAGGAGAGCATCAGCAAGGGCGGCAGGTACGTGGAGACCGTGAAC<br>AGCGGCAGCAAGAGCTTCAGCCTGAGGATCAACGACCTGACCGTGGAGGACAGCGGCACC<br>TACAGGTGCAAGGTGCTGACCAGCCAGAGCCAGGGCGGCTGCGTGAGGGTGCTGTACAGC<br>GACGTGTACGGCGACGGCACCGCCGTGACCGTGAAC |
| 132 | GCCAGGGTGGACCAGACCCCCAGACCATCACCAAGGAGACCGGCGAGAGCCTGACCATC<br>AACTGCGTGCTGAGGGACAGCAACTGCGCCCTGAGCAGCACCTACTGGTACAGGAAGAAG<br>AGCGACAGCACCAACGAGGAGAGCATCAGCAAGGGCGGCAGGTACGTGGAGACCGTGAAC<br>AGCGGCAGCAAGAGCTTCAGCCTGAGGATCAACGACCTGACCGTGGAGGACAGCGGCACC<br>TACAGGTGCACAGCTTCAACATGGACGTGTGCGCCGAGTTCCAGTACAGCGAC<br>GTGTACGGCGACGGCACCGCCGTGACCGTGAAC |
| 133 | GCCAGGGTGGACCAGACCCCCAGACCATCACCAAGGAGACCGGCGAGAGCCTGACCATC<br>AACTGCGTGCTGAGGGACAGCAACTGCGCCCTGAGCAACCTGTACTGGTACAGGAAGAAG<br>AGCGGCAGCACCAACGAGGAGAGCATCAGCAAGGGCGGCAGGTACGTGGAGACCGTGAAC<br>AGCGGCAGCAAGAGCTTCAGCCTGAGGATCAACGACCTGACCGTGGAGGACAGCGGCACC<br>TACAGGTGCAACGTGATCAACTTCTTCGCCATGGAGTGCGAGTACCAGGTGGGCGACGTG<br>TACGGCGACGGCACCGCCGTGACCGTGAAC |
| 134 | GCCAGGGTGGACCAGACCCCCAGACCATCACCAAGGAGACCGGCGAGAGCCTGACCATC<br>AACTGCGTGCTGAGGGACAGCAACTGCGCCCTGAGCAACCTGTACTGGTACAGGAAGAAG<br>AGCGGCAGCACCAACGAGGAGAGCATCAGCAAGGGCGGCAGGTACGTGGAGACCGTGAAC<br>AGCGGCAGCAAGAGCTTCAGCCTGAGGATCAACGACCTGACCGTGAAGGACAGCGGCACC<br>TACAGGTGCAACGTGCTGGTGAGCATGTTCTGCCAGCTGGCCCAGGACGTGTACGGCGAC<br>GGCACCGCCGTGACCGTGAAC |
| 135 | GCCAGGGTGGACCAGACCCCCAGACCATCACCAAGGAGACCGGCGAGAGCCTGACCATC<br>AACTGCGTGCTGAGGGACAGCAACTGCGCCCTGAGCAACCTGTACTGGTACAGGAAGAAG<br>AGCGGCAGCACCAACGAGGAGAGCATCAGCCTGGGCGGCAGGTACGTGGAGACCGTGAAC<br>AGCGGCAGCAAGAGCTTCAGCCTGAGGATCAACGACCTGACCGTGGAGGACAGCGGCACC<br>TACAGGTGCAACGTGTGCCTGCTGCAGCTGGCCGGCTACGACAGCCCCTACGACGTGTAC<br>GGCGGCGGCACCGCCGTGACCGTGAAC |
| 136 | GCCAGGGTGGACCAGACCCCCAGACCATCACCAAGGAGACCGGCGAGAGCCTGACCATC<br>AACTGCGTGCTGAGGGACAGCAACTGCGCCCTGAGCAACCTGTACTGGTACAGGAAGAAG<br>AGCGGCAGCACCAACGAGGAGAACATCAGCAAGGGCGGCAGGTACGTGGAGACCGTGAAC |

TABLE 2-continued

Corresponding DNA sequences of unique VNARs to TfR1 shown in Table 1 and identified by a combination of in vitro and in vivo selections.

| # | DNA sequence |
|---|---|
|  | AGCGGCAGCAAGAGCTTCAGCCTGAGGATCAACGACCTGACCGTGGAGGACAGCGGCACC<br>TACAGGTGCAACGTGGACGTGACCAGGTGCACCCAGAGCCAGGACGTGTACGGCGGCGGC<br>ACCGCCGTGACCGTGAAC |
| 137 | GCCAGGGTGGACCAGACCCCCCAGACCGTGACCAAGGAGACCGGCGAGAGCCTGACCATC<br>AACTGCGTGCTGAGGGACAGCAACTGCGCCCTGAGCAACCTGTACTGGTACAGGAAGAAG<br>AGCGGCAGCACCAACGAGGAGAGCATCAGCCTGGGCGGCAGGTACGTGGAGACCGTGAAC<br>AGCGGCAGCAAGAGCTTCAGCCTGAGGATCAACGACCTGACCGTGGAGGACAGCGGCACC<br>TACAGGTGCAACGTGAAGCACTACGTGTGCATGCAGAGCAAGGACGTGTACGGCGGCGGC<br>ACCGTGGTGACCGTGAAC |
| 138 | GCCAGGGTGGACCAGACCCCCCAGACCATCACCAAGGAGACCGGCGAGAGCCTGACCATC<br>AACTGCGTGCTGAGGGACAGCAACTGCGCCCTGAGCAACCTGTACTGGTACAGGAAGAAG<br>AGCGGCAGCACCAACGAGGAGAGCATCAGCCTGGGCGGCAGGTACGTGGAGACCGTGAAC<br>AGCGGCAGCAAGAGCTTCAGCCTGAGGATCAACGACCTGACCGTGAAGGACAGCGGCACC<br>TACAGGTGCAACGTGTTCAGCTTCAGCTGCCAGCTGCTGTTCGACGTGTACGGCGGCGGC<br>ACCGCCGTGACCGTGAAC |
| 139 | GCCAGGGTGGACCAGACCCCCCAGACCATCACCAAGGAGACCGGCGAGAGCCTGACCATC<br>AACTGCGTGCTGAGGGACAGCAACTGCGCCCTGAGCAACCTGTACTGGTACAGGAAGAAG<br>AGCGGCAGCACCAACGAGGAGAGCATCAGCCTGGGCGGCAGGTACGTGGAGACCGTGAAC<br>AGCGGCAGCAAGAGCTTCAGCCTGAGGATCAACGACCTGACCGTGGAGGACAGCGGCACC<br>TACAGGTGCAAGGTGAGCACCAGCGTGCCCAGGCACTACGACAACTGCAGGCAGAGGAGG<br>CACGACGTGTACGGCGGCGGCACCGCCGTGACCGTGAAC |
| 140 | GCCAGGGTGGACCAGACCCCCCAGACCATCACCAAGGAGACCGGCGAGAGCCTGACCATC<br>AACTGCGTGCTGAGGGACAGCAACTGCGCCCTGAGCAACCTGTACTGGTACAGGAAGAAG<br>AGCGGCAGCACCAACGAGGAGAGCATCAGCCTGGGCGGCAGGTACGTGGAGACCGTGAAC<br>AGCGGCAGCAAGAGCTTCAGCCTGAGGATCAACGACCTGACCGTGGAGGACAGCGGCACC<br>TACAGGTGCAACGTGTGCCAGTGGCTGCAGTGGTACGGCGGCGAGATGGAGGACGTGTAC<br>GGCGGCGGCACCGCCGTGACCGTGAAC |
| 141 | GCCAGGGTGGACCAGACCCCCCAGACCATCACCAAGGAGACCGGCGAGAGCCTGACCATC<br>AACTGCGTGCTGAGGGACAGCAACTGCGACCTGAGCAGGACCTACTGGTACAGGAAGAAG<br>AGCGGCAGCACCAACGAGGAGAGCATCAGCAAGGGCGGCAGGTACGTGGAGACCGTGAAC<br>AGCGGCAGCAAGAGCTTCAGCCTGAAGATCAACGACCTGACCGTGGAGGACAGCGGCACC<br>TACAGGTGCAACGTGTTCCTGTGGAACAACTACAACCCCATGGACGTGTACGGCGGCGGC<br>ACCGCCGTGACCGTGAAC |
| 142 | GCCAGGGTGGACCAGACCCCCCAGACCATCACCAAGGAGACCGGCGAGAGCCTGACCATC<br>AACTGCGTGCTGAGGGACAGCAACTGCGCCCTGAGCAACCTGTACTGGTACAGGAAGAAG<br>AGCGGCAGCAGGAACGAGGAGAGCATCAGCAAGGGCGGCAGGTACGTGGAGACCGTGAAC<br>AGCGGCAGCAAGAGCTTCAGCCTGAAGATCAACGACCTGACCGTGGAGGACAGCGGCACC<br>TACAGGTGCAAGGTGTTCGGCATGAGGACCCACTGCCAGTGGGTGATCTACAGGATCACC<br>GACGTGTACGGCGGCGGCACCGCCGTGACCGTGAAC |
| 143 | GCCAGGGTGGACCAGACCCCCCAGACCATCACCAAGGAGACCGGCGAGAGCCTGACCATC<br>AACTGCGTGCTGAGGGACAGCAACTGCGACCTGAGCAGGACCTACTGGTACAGGAAGAAG<br>CAGGGCAGCACCAACGAGGAGAGCATCAGCAAGGGCGGCAGGTACGTGGAGACCGTGAAC<br>AGCGGCAGCAAGAGCTTCAGCCTGAGGATCAACGACCTGACCGTGGAGGACAGCGGCACC<br>TACAGGTGCAACGTGGCCCTGTACCACTTCACCGGCTGCAGCAGGGTGCAGGACGTGTAC<br>GGCGGCGGCACCGTGGTGACCGTGAAC |
| 144 | GCCAGGGTGGACCAGACCCCCCAGACCATCACCAAGGAGACCGGCGAGAGCCTGACCATC<br>AACTGCGTGCTGAGGGACAGCAACTGCGACCTGAGCAGGACCTACTGGTACAGGAAGAAG<br>AGCGGCAGCACCAACGAGGAGAGCATCAGCAAGGGCGGCAGGTACGTGGAGACCGTGAAC<br>AGCGGCAGCAAGAGCTTCAGCCTGAGGATCAACGACCTGGTGGTGGAGGACAGCGGCACC<br>TACAGGTGCAACGTGGCCGTGTTCACCAGGTGCCACAACCAGCAGGACGTGTACGGCGGC<br>GGCACCGCCGTGACCGTGAAC |
| 145 | GCCAGGGTGGACCAGACCCCCCAGACCATCACCAAGGAGACCGGCGAGAGCCTGACCATC<br>AACTGCGTGCTGAGGGACAGCAACTGCGACCTGAGCAGGACCTACTGGTACAGGAAGAAG<br>AGCGGCAGCACCAACGAGGAGAGCATCAGCAAGGGCGGCAGGTACGTGGAGACCGTGAAC<br>AGCGGCAGCAAGAGCTTCAGCCTGAGGATCAACGACCTGACCGTGGAGGACAGCGGCACC<br>TACAGGTGCAACGTGACCTGGCTGGACTGCCACCAGTGCGGCGCCAGCGACGTGTACGGC<br>GGCGGCGGCACCGTGGTGACCGTGAAC |
| 146 | GCCAGGGTGGACCAGACCCCCCAGACCATCACCAAGGAGACCGGCGAGAGCCTGACCATC<br>AACTGCGTGCTGAGGGACAGCAACTGCGACCTGAGCAGGACCTACTGGTACAGGAAGAAG<br>AGCGGCAGCACCAACGAGGAGAGCATCAGCAAGGGCGGCAGGTACGTGGAGACCGTGAAC<br>AGCGGCAGCAAGAGCTTCAGCCTGAGGATCAACGACCTGGTGGTGGAGGACAGCGGCACC<br>TACAGGTGCAACGTGCACAGCGTGAGCTGCATCCAGAGGCTGGACGTGTACGGCGGCGGC<br>ACCGTGGTGACCGTGAAC |

TABLE 2-continued

Corresponding DNA sequences of unique VNARs to TfR1 shown in Table 1 and identified by a combination of in vitro and in vivo selections.

| # | DNA sequence |
|---|---|
| 147 | GCCAGGGTGGACCAGACCCCCAGACCATCACCAAGGAGACCGGCGAGAGCCTGACCATC<br>AACTGCGTGCTGAGGGACAGCAACTGCGCCCTGAGCAGCACCCTGTGGTACAGGACCAAG<br>AGCGGCAGCAGGAACGAGGAGAGCATCAGCAAGGGCGGCAGGTACGTGGAGACCGTGAAC<br>AGCGGCAGCAAGAGCTTCAGCCTGAGGATCAACGACCTGACCGTGAAGGACAGCGGCACC<br>TACAGGTGCAACGTGCAGCAGGGCGTGGTGGCCACCTGCACCAGCAAGAGGTGCGACGTG<br>TACGGCGGCGGCACCGCCGTGACCGTGAAC |
| 148 | GCCAGGGTGGACCAGACCCCCAGACCATCACCAAGGAGACCGGCGAGAGCCTGACCATC<br>AACTGCGTGCTGAGGGACAACAACTGCGCCCTGAGCAGCACCCTGTGGTACAGGACCAAG<br>AGCGGCAGCAGGAACGAGGAGAGCATCAGCAAGGGCGGCAGGTACGTGGAGACCGTGAAC<br>AGCGGCAGCAAGAGCTTCAGCCTGAGGATCAACGACCTGACCGTGGAGGACAGCGGCACC<br>TACAGGTGCAAGGTGTGGCAGGACAGCCTGAGCCAGCCCTGCGAGAGCGGCTGCCTGGAC<br>GTGTACGGCGGCGGCACCGCCGTGACCGTGAAC |
| 149 | GCCAGGGTGGACCAGACCCCCAGACCATCACCAAGGAGACCGGCGAGAGCCTGACCATC<br>AACTGCGTGCTGAGGGACAGCAACTGCGCCCTGAGCAGCACCCTGTGGTACAGGACCAAG<br>AGCGGCAGCAGGAACGAGGAGAGCATCAGCAAGGGCGGCAGGTACGTGGAGACCGTGAAC<br>AGCGGCAGCAAGAGCTTCAGCCTGAAGATCAACGACCTGACCGTGGAGGACAGCGGCACC<br>TACAGGTGCAACGTGCAGGGCATGGTGTACGACGGCAGCAGCTTCTGGTGGTGCGACGTG<br>TACGGCGACAGCACCGCCGTGACCGTGAAC |
| 150 | GCCAGGGTGGACCAGACCCCCAGACCATCACCAAGGAGACCGGCGAGAGCCTGACCATC<br>AACTGCGTGCTGAGGGACAGCAACTGCGCCCTGAGCAGCACCCTGTGGTACAGGACCAAG<br>AGCGGCAGCAGGAACGAGGAGAGCATCAGCAAGGGCGGCAGGTACGTGGAGACCGTGAAC<br>AGCGGCAGCAAGAGCTTCAGCCTGAGGATCAACGACCTGACCGTGGAGGACAGCGGCACC<br>TACAGGTGCAACGTGCAGTTCAGCTACAACTGCAACTTCTGGAAGGACGTGTACGGCGGC<br>GGCACCGACGTGACCGTGAAC |
| 151 | GCCAGGGTGGACCAGACCCCCAGACCATCACCAAGGAGACCGGCGAGAGCCTGACCATC<br>AACTGCGTGCTGAGGGACAGCAACTGCGCCCTGAGCAGCACCCTGTGGTACAGGACCAAG<br>AGCGGCAGCAGGAACGAGGAGAGCATCAGCAAGGGCGGCAGGTACGTGGAGACCGTGAAC<br>AGCGGCAGCAAGAGCTTCAGCCTGAAGATCAACGACCTGACCGTGGAGGACAGCGGCACC<br>TACAGGTGCAAGGTGTGCAGGCAGTGCTGCGTGGCCACCTGCGACGACCTGAGCCTGCTG<br>TGCGACGTGTACGGCGACGGCACCGCCGTGACCGTGAAC |
| 152 | GCCAGGGTGGACCAGACCCCCAGGAGCGTGACCAAGGAGACCGGCGAGAGCCTGACCATC<br>AACTGCGTGCTGAGGGACGCCAGCTACGCCCTGGGCAGCACCTGCTGGTACAGGAAGAAG<br>AGCGGCAGCACCAACGAGGAGAGCATCAGCAAGGGCGGCAGGTACGTGGAGACCGTGAAC<br>AGCGGCAGCAAGAGCTTCAGCCTGAGGATCAACGACCTGACCGTGGAGGACGGCGGCACC<br>TACAGGTGCGGCGTGTGCGAGATGCAGCTGATCGCCGTGGACAGCTGCGACCACACCCTG<br>GACGACGGCCTGTGCGGCGGCGTGTACGCCGCCTGCGGCGACGGCACCGCCGTGACCGTG<br>AAC |
| 153 | GCCAGGGTGGACCAGACCCCCAGGAGCGTGACCAAGGAGACCGGCGAGAGCCTGACCATC<br>AACTGCGTGCTGAGGGACGCCAGCTACGCCCTGGGCAGCACCTGCTGGTACAGGAAGAAG<br>AGCGGCAGCACCAACGAGGAGAGCATCAGCAAGGGCGGCAGGTACGTGGAGACCGTGAAC<br>AGCGGCAGCAAGAGCTTCAGCCTGAGGATCAACGACCTGACCGTGGAGGACGGCGGCACC<br>TACAGGTGCGGCGTGTACGGCGGCACCCACCAGGGCCTGTGCGGCTGCGACTGGCAGCTG<br>AGGTTCAGCCTGTGCGGCGACGGCAGGGCCGCCTGCGGCGACGGCACCGCCGTGACCGTG<br>AAC |
| 154 | GCCAGGGTGGACCAGACCCCCAGGAGCGTGACCAAGGAGACCGGCGAGAGCCTGACCATC<br>AACTGCGTGCTGAGGGACGCCAGCTACGCCCTGGGCAGCACCTGCTGGTACAGGAAGAAG<br>AGCGGCAGCACCAACGAGGAGAGCATCAGCAAGGGCGGCAGGTACGTGGAGACCGTGAAC<br>AGCGGCAGCAAGAGCTTCAGCCTGAGGATCAACGACCTGACCGTGGAGGACGGCGGCACC<br>TACAGGTGCGGCGTGTGCCAGTGCTGGAGCGCCAACGTGTGGGTGGACTGCGACATGACC<br>AGCACCAGCATCAGGATGAGGGACGGCAGCAGGAGCAACGCCAGGGCCGCCTGCGGCGAC<br>GGCACCGCCGTGACCGTGAAC |
| 155 | GCCAGGGTGGACCAGACCCCCAGGAGCGTGACCAAGGAGACCGGCGAGAGCCTGACCATC<br>AACTGCGTGCTGAGGGACGCCAGCTACGCCCTGGGCAGCACCTGCTGGTACAGGAAGAAG<br>AGCGGCAGCACCAACGAGGAGAGCATCAGCAAGGGCGGCAGGTACGTGGAGACCGTGAAC<br>AGCGGCAGCAAGAGCTTCAGCCTGAGGATCAACGACCTGACCGTGGAGGACGGCGGCACC<br>TACAGGTGCGGCGTGTGCGAGAGCAGCTTCTGCAGCCTGCCCTACGACTGCGACAGCAGC<br>AGCGCCGGCAGCGTGATCCAGCCCTTCGGCCACATCGTGAGCCTGGCCGCCTGCGGCGAC<br>GGCACCGCCGTGACCGTGAAC |
| 156 | GCCAGGGTGGACCAGACCCCCAGGAGCGTGACCAAGGAGACCGGCGAGAGCCTGACCATC<br>AACTGCGTGCTGAGGGACGCCAGCTACGCCCTGGGCAGCACCTGCTGGTACAGGAAGAAG<br>AGCGGCAGCACCAACGAGGAGAGCATCAGCAAGGGCGGCAGGTACGTGGAGACCGTGAAC<br>AGCGGCAGCAAGAGCTTCAGCCTGAGGATCAACGACCTGACCGTGGAGGACGGCGGCACC<br>TACAGGTGCGGCGTGTGCAGCGACTACGGCCTGCAGACCACCGGCCAGCAGGCCGCCTGC<br>GGCGACGGCACCGCCGTGACCGTGAAC |

TABLE 2-continued

Corresponding DNA sequences of unique VNARs to TfR1 shown in Table 1 and identified by a combination of in vitro and in vivo selections.

| # | DNA sequence |
|---|---|
| 157 | GCCAGGGTGGACCAGACCCCCAGGAGCGTGACCAAGGAGACCGGCGAGAGCCTGACCATC<br>AACTGCGTGCTGAGGGACGCCAGCTACGCCCTGGGCAGCACCTGCTGGTACAGGAAGAAG<br>AGCGGCAGCACCAACGAGGAGAGCATCAGCAAGGGCCGGCAGGTACGTGGAGACCGTGAAC<br>AGCGGCAGCAAGAGCTTCAGCCTGAGGATCAACGACCTGACCGTGGAGGACGGCGGCACC<br>TACAGGTGCGGCGCCGCCATCCAGGGCTTCTGGGCCGGCAGGTGCGACAACCTGCCCGGC<br>AAGTGCGTGATGCAGGTGAGCAACGCCGCCGCCTGCGGCGACGGCACCGCCGTGACCGTG<br>AAC |
| 158 | GCCAGGGTGGACCAGACCCCCAGGAGCGTGACCAAGGAGACCGGCGAGAGCCTGACCATC<br>AACTGCGTGCTGAGGGACGCCAGCTACGAGCTGGGCAGCACCTGCTGGTACAGGAAGAAG<br>AGCGGCAGCACCAACGAGGAGAGCATCAGCAAGGGCCGGCAGGTACGTGGAGACCGTGAAC<br>AGCGGCAGCAAGAGCTTCAGCCTGAGGATCAACGACCTGACCGTGGAGGACGGCGGCACC<br>TACAGGTGCGGCGCCAGCCTGCAGTGCGGCAACTGCGAGCTGTGCGACAGGGAGCAGCTG<br>CAGTGCGGCGGCCAGAGGGGCCAGCTGGCCGCCTGCGGCGACGGCACCGCCGTGACCGTG<br>AAC |
| 159 | GCCAGGGTGGACCAGACCCCCAGGAGCGTGACCAAGGAGACCGGCGAGAGCCTGACCATC<br>AACTGCGTGCTGAGGGACGCCAGCTACGAGCTGGGCAGCACCTGCTGGTACAGGAAGAAG<br>AGCGGCAGCACCAACGAGGAGAGCATCAGCAAGGGCCGGCAGGTACGTGGAGACCGTGAAC<br>AGCGGCAGCAAGAGCTTCAGCCTGAGGATCAACGACCTGACCGTGGAGGACGGCGGCACC<br>TACAGGTGCGGCGTGATCAGCCAGTACAAGAGCTACACCCTGTGGTGCGACGCCCTGTAC<br>AGGAGCCTGGGCTGCGAGTGCGCCAGGGCCGCCTGCGGCGACGGCACCGCCGTGACCGTG<br>AAC |
| 160 | GCCAGGGTGGACCAGACCCCCAGGAGCGTGACCAAGGAGACCGGCGAGAGCCTGACCATC<br>AACTGCGTGCTGAGGGACGCCAGCTACGCCCTGGGCAGCACCTGCTGGTACAGGAAGAAG<br>AGCGGCAGCACCAACGAGGAGAGCATCAGCAAGGGCCGGCAGGTACGTGGAGACCGTGAAC<br>AGCGGCAGCAAGAGCTTCAGCCTGAGGATCAACGACCTGACCGTGGAGGACGGCGGCACC<br>TACAGGTGCGGCGTGATGAACAACGTGAGCCAGACCTGGGTGAGGTGCGACAGCCAGGTG<br>ATGAGCCAGCAGTGCGTGCAGCAGAGCGCCGCCTGCGGCGACGGCACCGCCGTGACCGTG<br>AAC |
| 161 | GCCAGGGTGGACCAGACCCCCAGGAGCGTGACCAAGGAGACCGGCGAGAGCCTGACCATC<br>AACTGCGTGCTGAGGGACGCCAGCTACGCCCTGGGCAGCACCTGCTGGTACAGGAAGAAG<br>AGCGGCAGCACCAACGAGGAGAGCATCAGCAAGGGCGGCAGGTACGTGGAGACCGTGAAC<br>AGCGGCAGCAAGAGCTTCAGCCTGAGGATCAACGACCTGACCGTGGAGGACAGCGGCACC<br>TACAGGTGCAACGTGATCCAGTACCTGTACCTGGGCAGCTACTTCGCCTGCGACGTGTAC<br>GGCGGCGGCACCGTGGTGACCGTGAAC |

Figure 7:
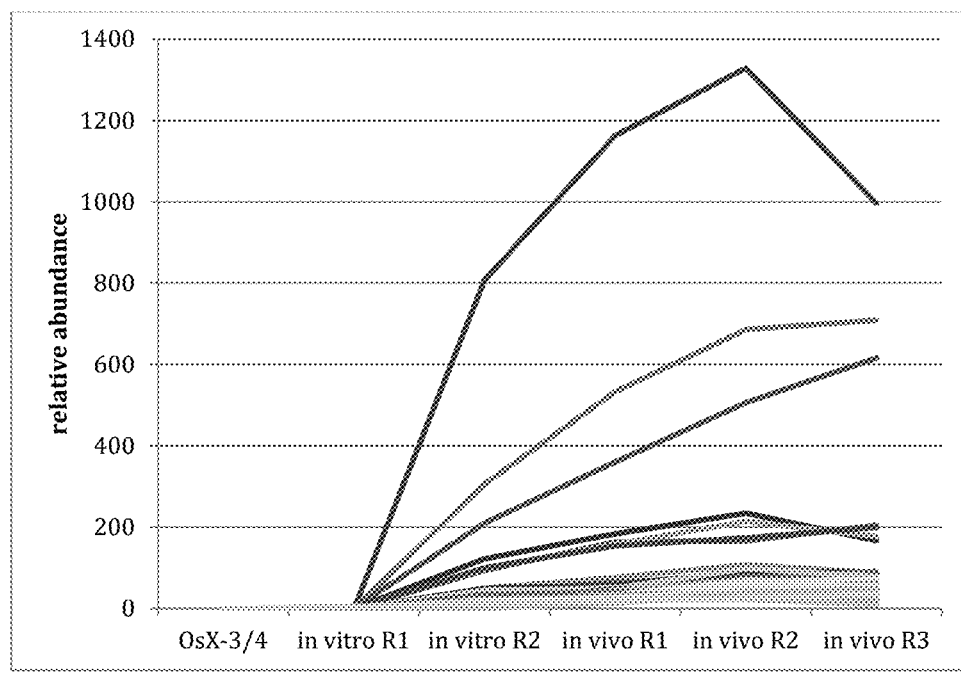
FIG. 7. Increase in relative phage abundance with sequential rounds of in vitro and in vivo selections for TfR1-mediated brain penetrants. The VNAR sequences were grouped in families with common CDR3s. The 29 most abundant families from the $3^{rd}$ in vivo round were plotted for their abundance in the previous rounds of selection. Relative abundance was calculated as per million sequences for each stage of the selection. Clone 10, identified by colony picking followed by sequencing and confirmed by phage and VNAR-Fc ELISAs as a TfR1 binder.

These fifty-one unique TfR-1 binding VNAR clones were further reformatted as bivalent VNAR-Fc by cloning the VNARs into the commercial pFUSE vector as described in Example 1. The fifty-one unique VNAR clones were expressed as Fc formats in small (1 ml) scale in 96-well plates. Media was collected and used directly for ELISA to confirm binding to mouse and human TfR1. Eight clones (clones 1, 2, 7, 10, 11, 12, 16 and 39) were selected as binders for further experiments, but clones 11, 12 and 39 were excluded because they bound only to human and not to mouse TfR1; and clone 16 which bound human TfR1 was excluded for binding non-specifically to control proteins, mouse TfR2 and HSA. (Example 1). All binding clones were of the type II VNAR class (FIG. 7).

Figure 8A:
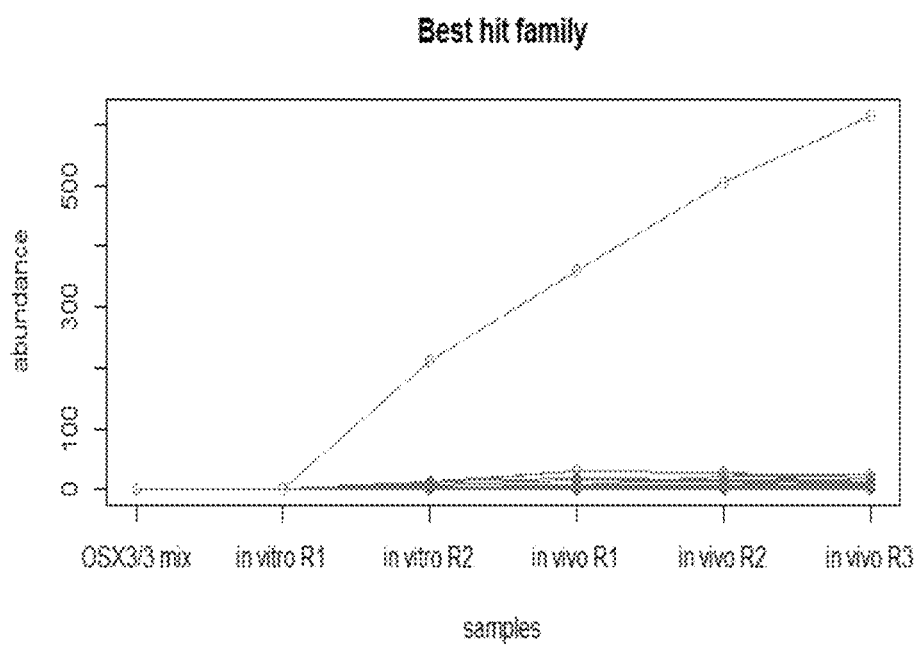
FIGS. 8A and 8B. Relative abundance of the clone 10 family. The whole clone 10 family consisted of 242 individual VNARs that shared the same CDR3 sequence. (A) The graph illustrates the dominance of an individual clone and its amplification in the subsequent rounds of selection. (B) The abundance of the remaining sequences followed the family trend.
Figure 8B:
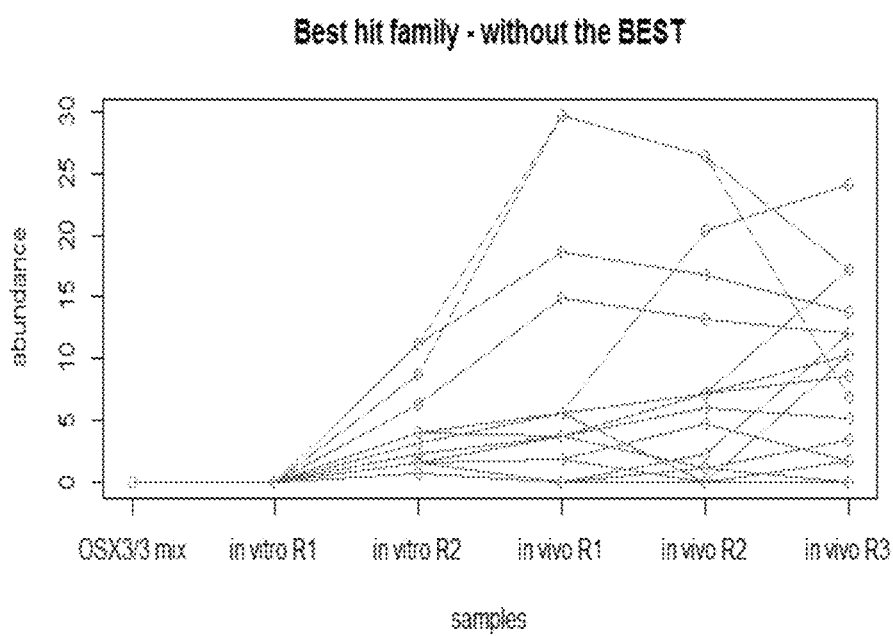

Next generation sequencing (NGS) was used to validate the above described combinatorial selection strategy for TfR1-based blood brain barrier penetrants of Example 1 (see Example 2 and accompanying FIGS. 8-11). The sequences obtained from NGS were grouped into families containing identical CDR3 sequences. Twenty-nine families that showed the highest abundance in the last round of in vivo selection were analyzed for their abundance in the previous rounds. In general, the data showed that clones selected in in vivo stage for brain penetration had been initially amplified in in vitro stage where TfR1 was used as a target protein (Example 2; FIG. 8). Interestingly, previously identified clone 10 (see FIGS. 6 and 7) was found by NGS analysis to be the third best VNAR. When the family of clone 10 was deconvoluted, 242 sequences were identified that contained minor sequence alterations but shared the same CDR3 sequence (VVQYPSYNNYFWCDV). NGS analyses as described in more detail in Example 2 suggested that binding affinity to TfR1 alone was not enough to confer brain penetration by phages, and that the applied phage display combinatorial selection strategy was generating trends expected for the selection of TfR1-dependent blood brain barrier traversing VNARs.

Figure 12:
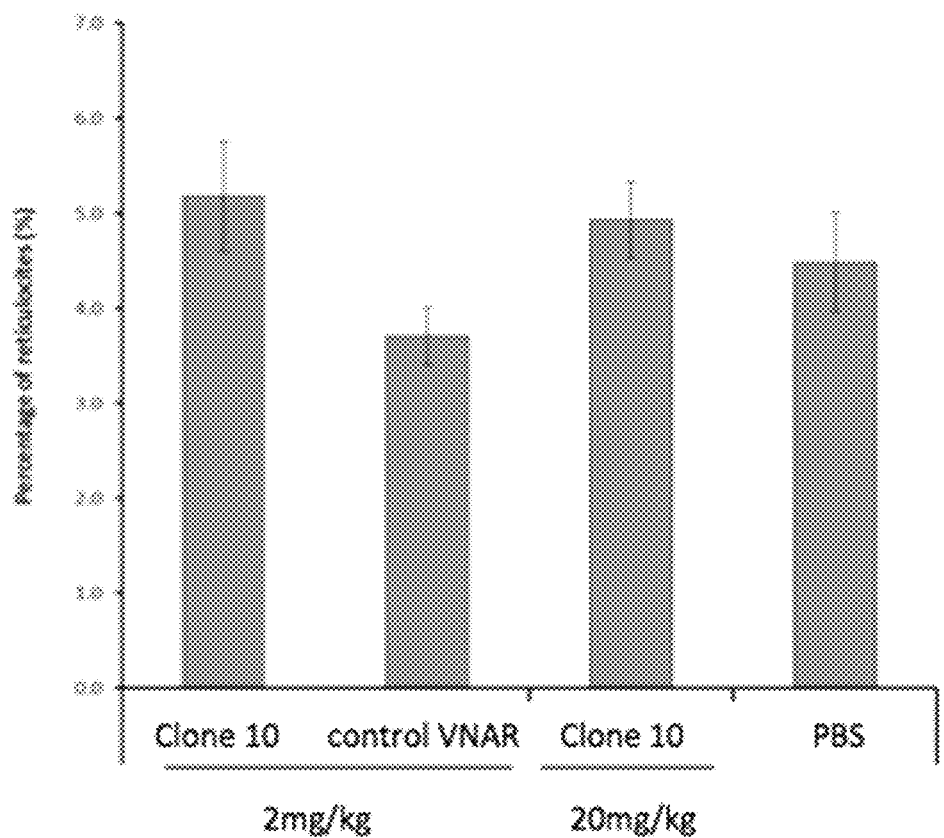
FIG. 12. Effect of clone 10 formatted as an Fc fusion protein on reticulocyte counts. Mice were injected IV with the fusion protein with the VNAR-Fc fusion protein at 2 mg/kg or 20 mg/kg and blood samples collected 18 hours later were stained with thiazole orange. The percentage of reticulocytes in the total number of red blood cells was determined by flow cytometry. Data represent the mean ±SD of five mice per group.
Figure 13A:
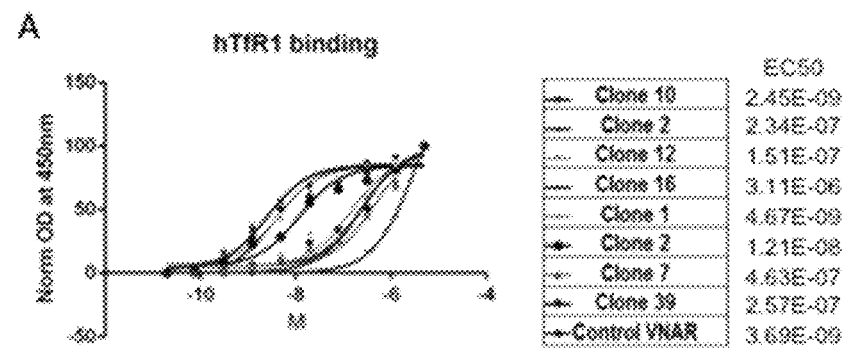
FIGS. 13A-13D. ELISA EC50 binding curves for the TfR1-binding VNAR-Fcs. ELISA plates were coated with 100 µl of 1 µg/ml of recombinant human (A) and mouse TfR1 (B), mouse TfR2 (C) or HSA (D). Purified VNAR-Fc fusion proteins were used the concentrations ranging from pM to µM and EC50 values calculated from the fitted 4-parametric binding curve.
Figure 13B:
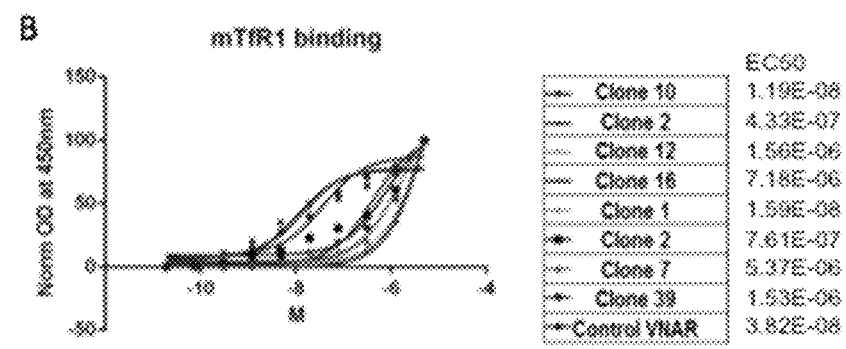
Figure 13C:
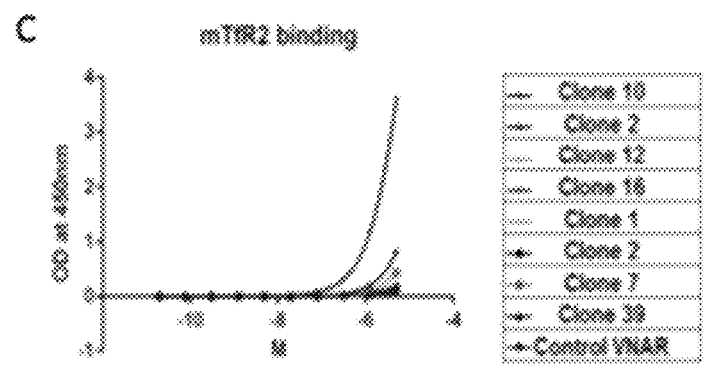
Figure 13D:
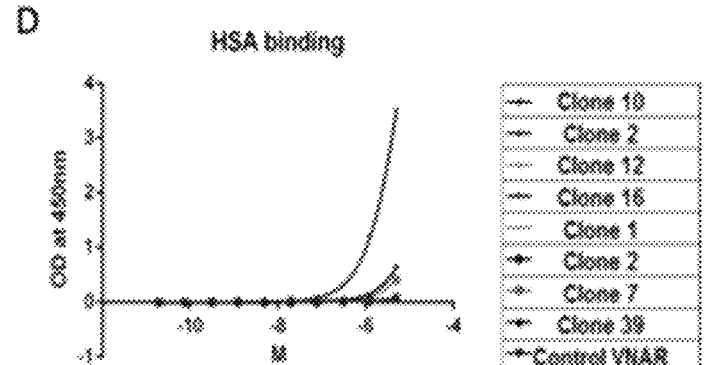

The top ten VNARs from the NGS abundance analysis were synthesised and cloned into pFUSE vector as before (Example 2; FIG. 12). All ten VNARs were of type II originating from the OsX-3 library. These VNAR-Fc formatted molecules were expressed using Expi293 expression system, purified and tested in VNAR-Fc ELISA for binding to human and mouse TfR1.

All eight clones found by colony picking and confirmed by binding to TfR1 as VNAR-Fcs were further tested in animal experiments for their blood brain barrier penetration ability (Example 3). Clone 10 showed over 10-fold higher signal than the negative control reaching 5 nM concentration in the whole brain tissue and was repeated in both experiments. Clones 2 and 39 showed a small, approximately 2-fold increase over the control.

Figure 11A:
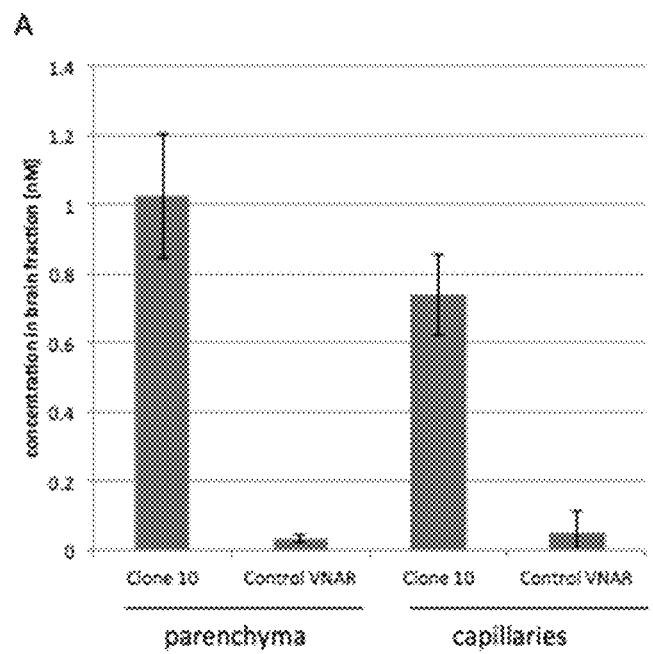
FIGS. 11A and 11B. The distribution of clone 10 as VNAR-Fc fusion in brain tissue fractions. Mice were injected IV with the fusion protein at 2 mg/kg and the brains collected 18 hr later following cardiac perfusion. Brain homogenates were fractionated by density gradient centrifugation and the capillary and parenchyma fractions were brought to the same volumes before VNAR-Fc levels (A) and alkaline phosphatase activity (B) were measured by ELISA. Data represent the mean ±SD of five mice per group.

To ensure that the selected clones were actually crossing the blood brain barrier, brain fractionations to separate capillary endothelium from parenchymal fractions were performed as during the in vivo phage selection. The brain concentration of VNAR-Fcs was measured and the parenchymal concentration of clone 10 was over 40% higher than in the capillaries (Example 3; FIG. 11). In contrast, control VNAR-Fc appeared neither to get trapped in the brain capillaries nor to be transported to brain parenchyma. Taken together, results make clear that clone 10 was successfully transported across the blood brain barrier and was not specially retained in the capillaries.

To assess the safety of clone 10, a quantitative analysis of reticulocytes in treated mice was performed (Example 3). There was no observable reduction in reticulocytes in the blood of animals injected with 25 nmol/kg of either control VNAR-Fc that binds to TfR1 but didn't penetrate blood brain barrier or of clone 10. Increasing the concentration of clone 10 by ten-fold did not affect reticulocyte count, assuring the safety of this construct for further studies.

Some TfR1 binders might present the undesirable property of competing with transferrin (Tf) for the binding site to TfR1, consequently affecting iron transport into the cells. Therefore, clones 10, 2 and 39 were further tested for whether they compete with transferrin for binding to TfR1 compared to controls (Example 3). Using two different experimental setups, none of the tested clones competed with Tf for the transferrin binding site in human TfR1.

It was previously reported that affinity might play a crucial role in TfR-1 mediated brain penetration. Advantageous penetration was observed for low affinity molecules with KD of 600 nM in comparison to their high affinity variants with KD of 20 nM (Yu, Zhang et al. 2011, Bien-Ly, Yu et al. 2014). In Example 4, the eight clones for which the binding to TfR1 as VNAR-Fc format was confirmed were analyzed for affinity to TfR-1 and for a series of other biochemical parameters to identify characteristics that could provide an advantage for BBB transport.

Further, to gain precise kinetic data, a surface plasmon resonance (SPR) technique was used for the selected clones, namely 10, 2, 1, 39 and the control VNAR with immobilised human or mouse TfR1. Clone 10 showed sub-nM KD for both mouse and human TfR1 and was the best binder, with other clones following closely with nM KDs (Example 4; Table 7). Association (ka), dissociation (kd) and affinity (KD) measurements were determined by single-cycle SPR technique (Biacore) of clones 10, 2, 1, 39, formatted as VNAR-Fcs (Example 4; Table 7). Kinetic data using different VNAR clones competing for the same epitope on TfR-1 were also compared at two different pHs to explore possible effects of pH sensitivity and endosomal release on TfR1-mediated BBB transport (Example 4; Table 8).

Figure 17A:
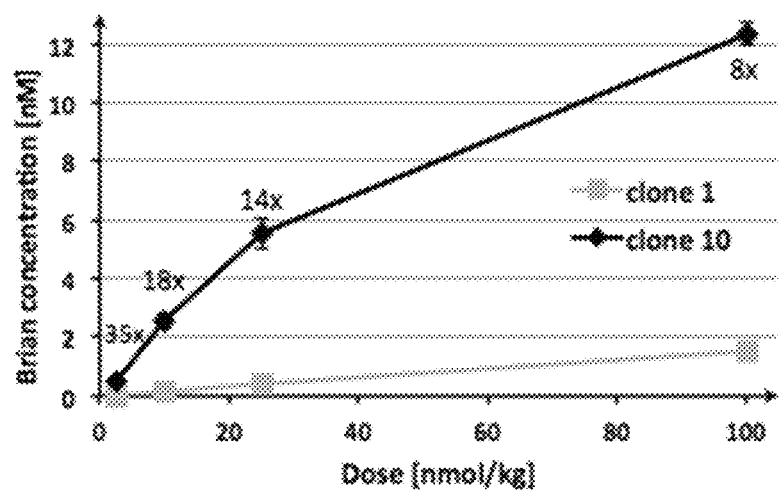
FIGS. 17A and 17B. Dose-dependent brain uptake of clone 10 as an Fc fusion protein compared to clone 1. Mice were sacrificed 18 hours after tail vein injection of either clone 10 (black) or clone 1 (grey) at doses ranging from 2-100 nmol/kg (~0.2-8 mg/kg). Brains were harvested following cardiac perfusion and homogenised in 1% Triton X-100. VNAR-hFc concentrations were determined in whole brain extracts (A) and plasma (B) using a sandwich ELISA to detect human Fc (mean ±SD, N=5).
Figure 17B:
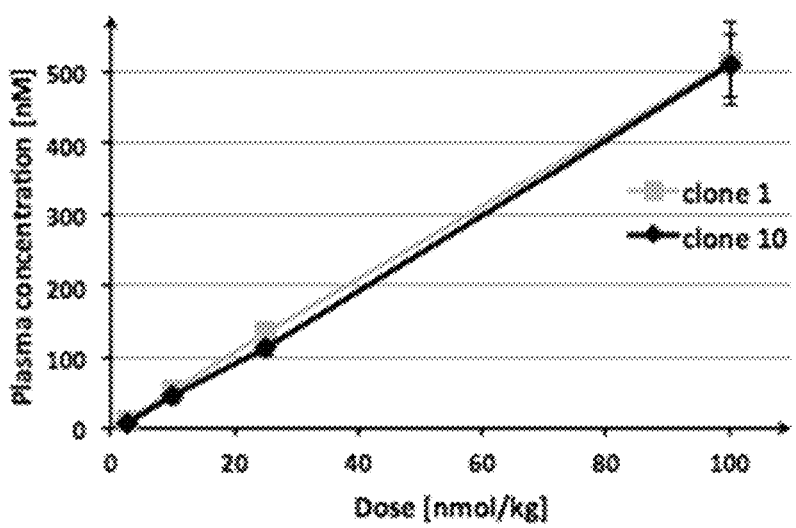

Dose response curves were generated by IV injection into mice of four increasing doses of one of two different VNAR-Fc fusion proteins (Clones 1-Fc and 10-Fc) and measuring brain uptake 18 hours later (Example 5). As shown in FIG. 17, the brain uptake of clone 10 in this Fc format was dramatically higher than that of clone 1, while plasma levels of each fusion were nearly identical at each dose. The kinetics of brain update of Clone 10-Fc appeared to have at least two phases (FIG. 17A). Brain levels of Clone 10-Fc continued to escalate with increasing doses and based on kinetics appeared at higher doses to be due to a combination of active, receptor-mediated transport and passive, and non-specific transport, which is apparent at higher doses of the comparator clone, Clone 1-Fc.

Figure 18:
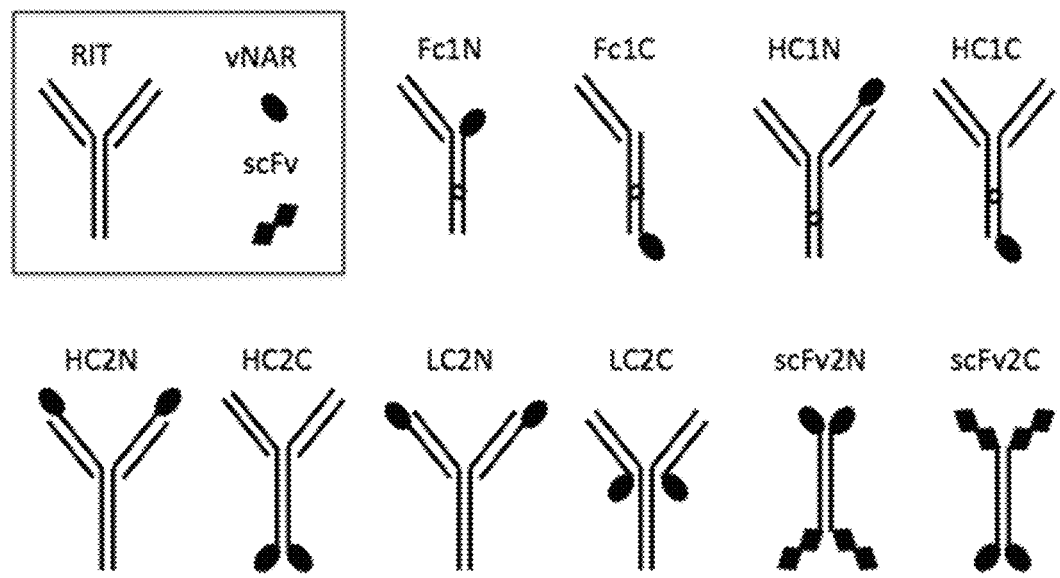
FIG. 18. Rituximab-clone 10 bispecific fusion proteins. Asymmetric antibodies with a monovalent vNAR (top row) were generated with knob-into-holes technology (Ridgeway et al., Protein Engineering vol. 9 no. 7 pp. 617-621, 1996). A series of bivalent vNAR fusions (bottom row) were produced with linkages to either the N- or C-terminus of the heavy chains (HC) or light chains (LC) of rituximab (RIT). Two additional versions were produced with the single chain variable fragment (scFv) of rituximab. The panel of bispecific antibodies were purified from CHO cell supernatants after transient transfection.
Figure 19:
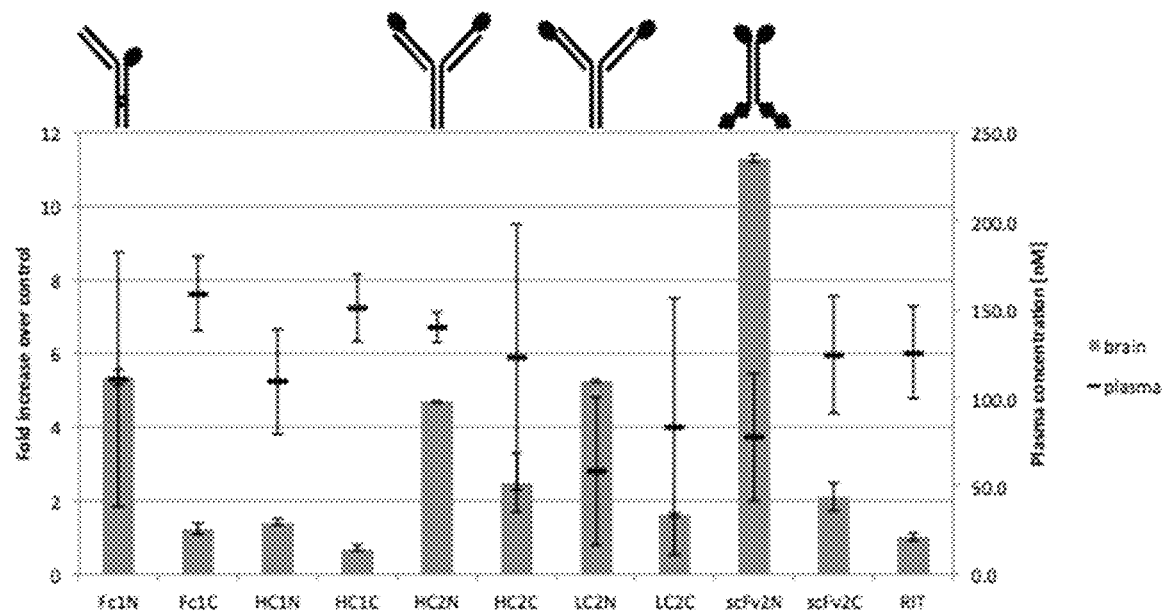
FIG. 19. Brain uptake of rituximab-clone 10 fusion proteins. Mice were sacrificed 18 hours after tail vein injection of the bispecific antibody at 25 nmol/kg (equivalent to 4 mg/kg of rituximab). Brains were harvested following cardiac perfusion and homogenised in 1% Triton X-100. VNAR-hFc concentrations were determined in whole brain extracts (grey bars) and plasma (black dash) using a sandwich ELISA to detect human Fc (mean ±SD, N=5). Brain uptake is presented as fold-increase over naked rituximab (RIT).

Clone 10-Fc was next tested for its ability, when conjugated to a therapeutic antibody, to transport that antibody across the BBB in vivo, as described in Example 5. Briefly, the clone 10-Fc was fused to an anti-CD20 antibody (rituximab) in different configurations in order to create ten different bispecific molecules, including monovalent and bivalent versions as N- or C-terminal fusions (FIG. 18). Each bispecific format was injected into mice and uptake in perfused brains measured 18 hours later using in vivo selection methods described herein. Dramatic differences in brain uptake were observed between various conjugates in these bispecific formats and those differences could not be accounted for by stability alone, as measured by plasma levels in injected mice of the same conjugates. In these experiments, two N-terminal fusions (Fc1N; monovalent and scFv2N; bivalent) showed the best brain uptake, showing an increase of greater than 11-fold compared to unmodified rituximab (FIG. 19).

Figure 20:
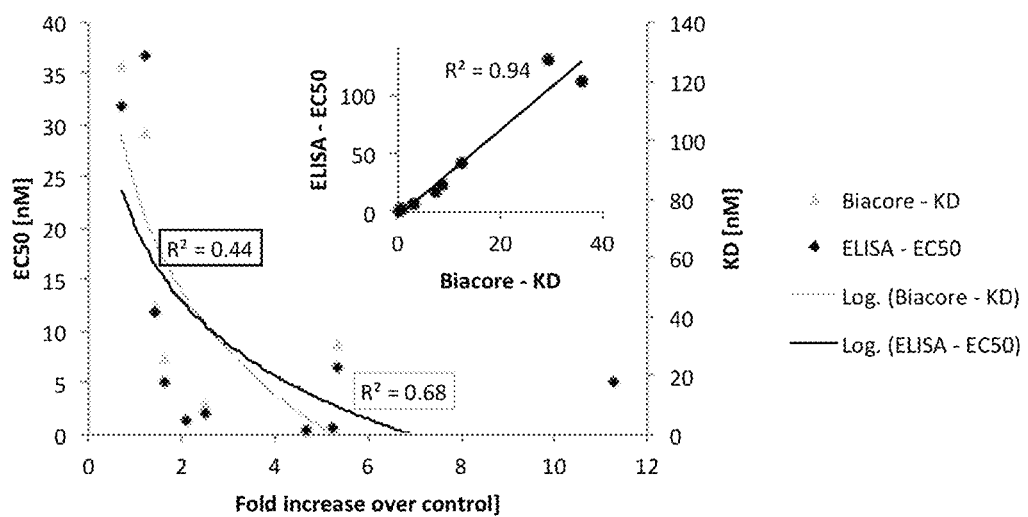
FIG. 20. Correlation of brain uptake of the clone 10-rituximab fusions with binding affinity to mouse TfR1. The KD values were measured using Biacore (Table 9) and EC50 values were obtained by ELISA (Table 10). The brain penetration expressed as fold-increase over naked rituximab was plotted against KD and EC50 values.

Binding affinities and EC50s values for mouse and human TfR1 binding for the various Clone-10-rituximab formats were measured (Example 5; Tables 9 and 10; FIG. 20.) The data showed no linear and relatively poor logarithmic correlation between affinity to mouse TfR1 and brain uptake. In these experiments, the VNAR clone with the highest brain uptake had sub-nanomolar binding affinity. This stands in contrast to a previous report showing an inverse correlation between TfR binding affinity and brain uptake for a bispecific antibody to TfR/BACE1 (Yu et al., Sci Transl Med. 2011 May 25; 3(84):84ra44). The benefit of a high affinity BBB carrier is that biological levels can be achieved at lower doses, with fewer side effects and lower costs than when using a low affinity therapeutic antibody that requires high doses for receptor mediated transport. The reason for this difference between the two TfR carriers is not yet clear, but may be related to the unique epitope and binding mode of the VNAR relative to IgG.

Figure 21:
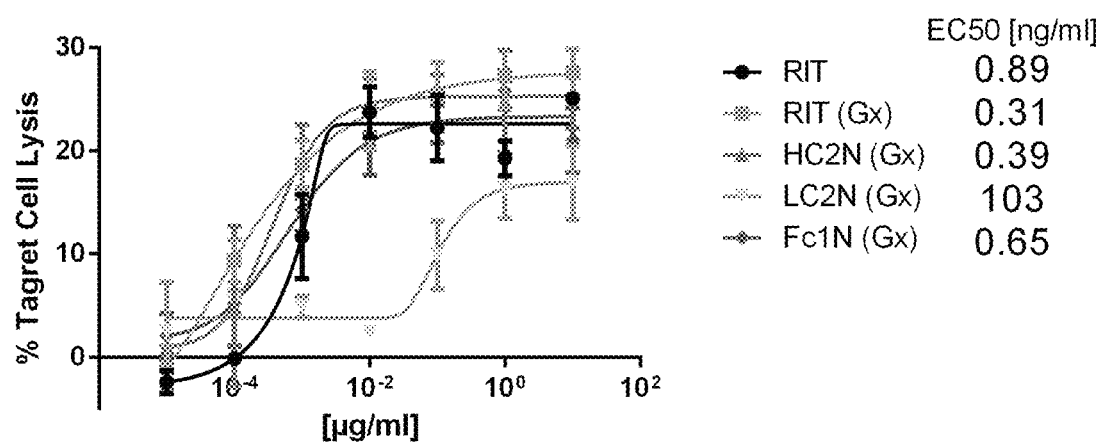
FIG. 21. Antibody-dependent cell-mediated cytotoxicity (ADCC) activity of selected rituximab-clone 10 formats. Fusion proteins were purified from GlymaxX (ProBioGen) engineered CHO cells with minimal fucose content (Gx) to increase ADCC and reduce CDC activities. CD20 expressing Raji cells were used as target cells and NK92-CD16a cells as effector cells.
Figure 22:
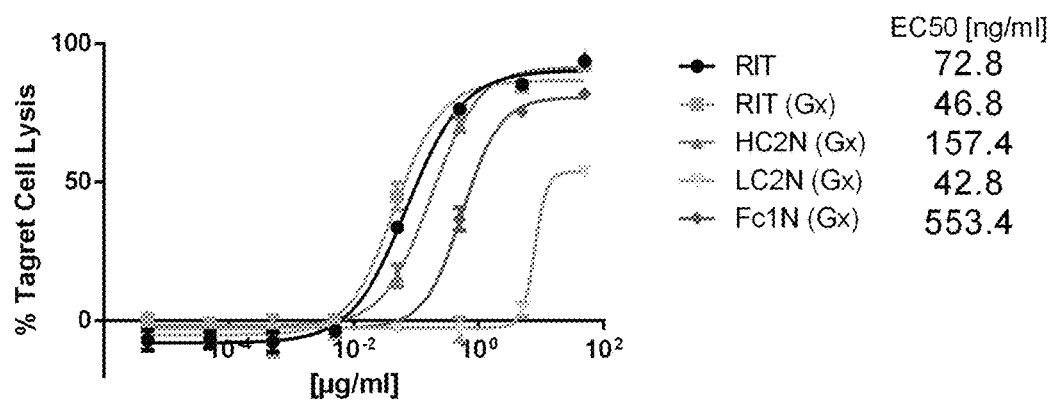
FIG. 22. Complement dependent cytotoxicity (CDC) activity of selected rituximab-clone 10 formats. Low-fucose fusion proteins (Gx) were purified from GlymaxX engineered CHO cells and CD20 expressing Raji cells were used as the target cells.

Rituximab-clone 10 fusion proteins were produced in an expressor cell line defective in fucose biosynthesis to increase ADCC activity. Various brain penetrant fusion protein formats were tested for ADCC and CDC activities (Example 5; FIGS. 21 and 22).

Figure 23A:
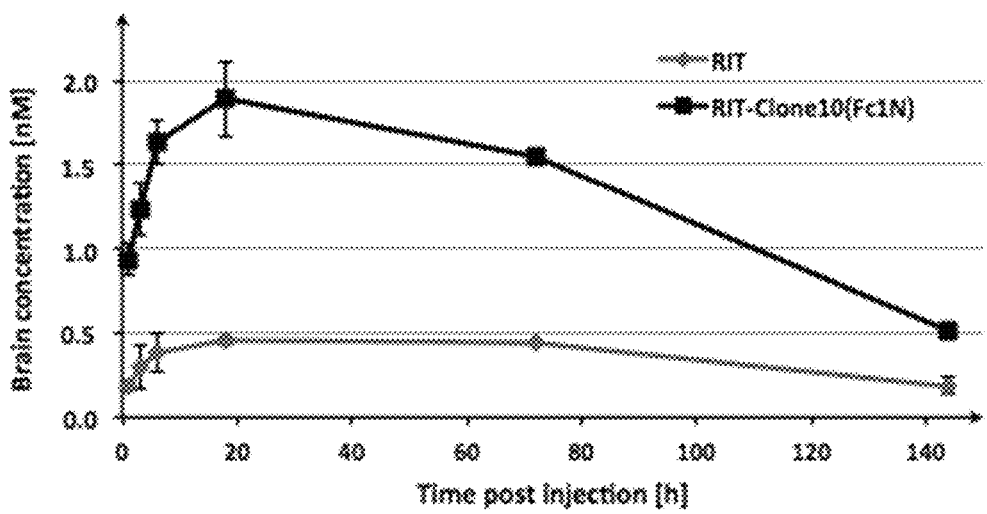
FIGS. 23A and 23B. Time-dependent brain uptake of the rituximab-clone 10 bispecific antibody in the Fc1N format. Mice were sacrificed at different times points after tail vein injection of rituximab fused to clone 10 in the Fc1N format (solid line) compared to naked rituximab (dashed line) at 25 nmol/kg (~4 mg/kg). Brains were harvested following cardiac perfusion and homogenised in 1% Triton X-100. VNAR-hFc concentrations were determined in whole brain extracts (A) and plasma (B) using a sandwich ELISA to detect human Fc (mean ±SD, N=5).
Figure 23B:
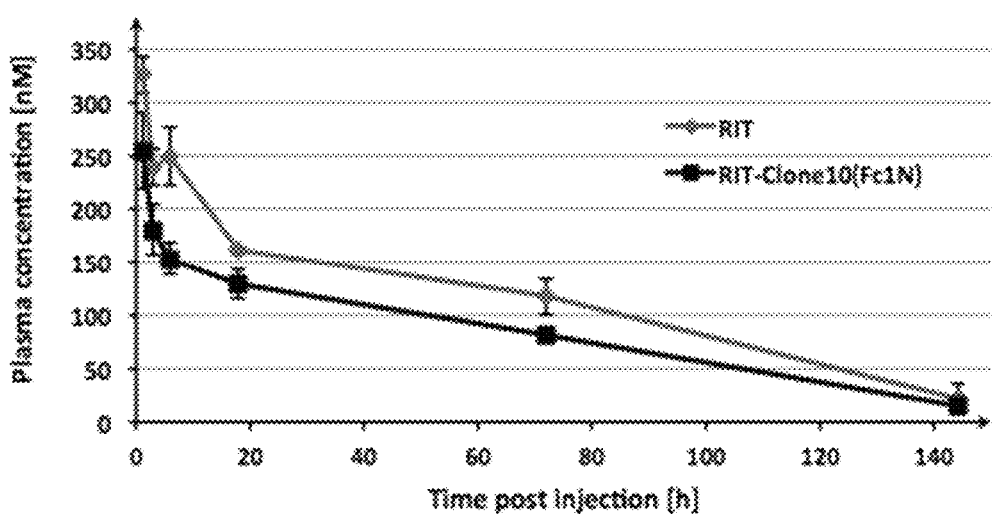

The duration of brain exposure of a rituximab(Gx)-clone 10 bispecific fusion protein in the Fc1N format was determined after being administered by tail vein injection and brain and plasma levels were monitored over a 6-day period (Example 5; FIG. 23).

To test whether the Clone 10 VNAR can carry large molecules other than monoclonal antibodies into the brain, a prototype VNAR-Fc-enzyme fusion was constructed (Example 5). Alpha-L-iduronidase (IDUA) is an enzyme found in lysosomes that is responsible for the degradation of glycosaminoglycans. A deficiency in the IDUA leads to the progressive accumulation of dermatan and heparan sulfate causing severe metabolic disturbances and early death. Although patients have been successfully treated with enzyme replacement therapy, it is not expected to treat or prevent neurological deterioration due to poor BBB penetration. IDUA can be delivered to the CSF by intrathecal lumbar injection and may improve symptoms but this route of administration carries a significant risk of adverse events (Munoz-Rojas et al., Am J Med Genet A. 2008 Oct. 1; 146A(19):2538-44; Dickson et al., Mol Genet Metab. 2015 September-October; 116(1-2):69-74).

To evaluate whether VNARs could carry IUDA into the brain, clone 1 and clone 10 VNARs were engineered as VNAR-Fc-IDUA fusion proteins and produced in CHO cells. VNAR-Fc-IDUA fusions bound mouse TfR1 with the same potency (EC50) as the VNAR-Fc as measured by ELISA (Example 5; Table 11) and IDUA fusion proteins retained the full activity of the recombinant enzyme (FIG.

24). Brain and plasma concentrations of IDUA fused to either clone 1 or clone 10 at 20 nmol/kg (5 mg/kg) was measured 18 hours after IV injection (FIG. 25B). Relative to the plasma concentration, the levels of clone 10 were higher than clone 1, although the levels of the IDUA fused to clone 10-Fc are much lower than clone 10-IgG fusions. IDUA-VNAR-Fc fusion protein were detectable in brain 18 hr later suggests that brain uptake may be biological relevant given the very short half-life (~2 hr) in mice after IV injection (Garcia et al., Mol Genet Metab. 2007 June; 91(2):183-90).

Polypeptide Sequences and Compounds Comprising a TfR Specific VNAR

Provided are polypeptides identified using the in vitro in vivo selection steps of the methods of the present invention, and nucleic acid sequences encoding them, TfR-specific binding moieties, e.g., a polypeptide comprising a TfR-binding VNAR; and TfR-mediated drug vehicles that can carry heterologous molecules across the membrane of a TfR-positive cell, such as across the BBB into the brain. Isolated TfR-binding VNARs identified by performing the methods of the invention are also provided. In certain embodiments, the TfR-specific binding moiety is specific for a non-human mammalian TfR. In certain embodiments, the TfR-binding moiety is specific for human TfR. In certain embodiments, the TfR-specific binding moiety is a component of a BBB vehicle and mediates endocytosis of an associated heterologous molecule across a cell membrane, and in particular, across the BBB. In certain embodiments, the TfR-specific binding moiety is itself or is a component of a TfR antagonist compound which blocks the interaction between TfR, such as hTfR, and one or more of its ligands in vivo. In certain embodiments, the TfR-specific binding moiety mediates endocytosis without blocking receptor ligand binding.

Hence, in accordance with the invention, certain embodiments of TfR-specific binding moieties comprise a VNAR scaffold represented by the formula, from N to C terminus, FW1-CDR1-FW2-HV2-FW2'-HV4-FW3-CDR3-FW4, wherein the CDR 1 region comprises or consists essentially of a peptide having an amino acid sequence as shown in Table 1 (of formula: $D-X_2-X_3-X_4-X_5-X_6-X_7$) and further, wherein the CDR3 region comprises or consists essentially of a peptide having an amino acid sequence from any of the CDR3 regions of Tables 1 or 5; and wherein the moiety is specific for human TfR-1. In some embodiments, the TfR-specific binding moiety has an EC50 for human Tfr-1 ranging from about 0.1 nM to about 10 µM and more preferably ranging from about 1 nM to about 800 nM. In some embodiments, the TfR-specific binding moiety does not substantially bind to human TfR 2. In some embodiments, the TfR-specific binding moiety is capable of cross reacting with mouse TfR-1. In some embodiments, binding of the TfR-specific binding moiety to TfR-1 does not inhibit transferrin binding to and/or transport by TfR-1. In some embodiments, binding of the TfR-specific binding moiety to TfR-1 induces endocytosis of said moiety in a TfR-positive cell. In some embodiments, binding of the TfR-specific binding moiety to TfR-1 is reversibly pH dependent.

As used herein, a "VNAR scaffold" has the general structure, from N to C terminus, given by the formula FW1-CDR1-FW2-HV2-FW2'-HV4-FW3-CDR3-FW4, wherein the FWs are framework regions, CDRs are complementarity determining regions and HVs are hypervariable regions that form the variable domain of a shark IgNAR ("VNAR"). VNAR scaffolds of the invention where the FW1, FW2, FW2', FW3 and FW4 regions have naturally occurring VNAR sequences or altered VNAR sequences with amino acid substitutions, insertions or deletions (typically, but not limited to, no more than 1-10 amino acids a changes) provided that such changes maintain the overall primary and tertiary structure of the VNAR. Those of skill in the art can identify and ascertain the effect of such alterations. In addition, the FW1, FW2, FW2', FW3 and FW4 regions can have any of the sequences shown in Tables 1 or 5 for these regions under the VNAR Domain Amino Acid Sequence column.

As used herein a "VNAR domain" means a naturally-occurring VNAR, an altered VNAR (such as those described in the paragraph above), a variable domain of a camelid antibody (known as a VHH) or the variable domain of any single chain antibody, whether such domains are naturally occurring, selected or engineered.

The VNARs, the VNAR scaffolds and the VNAR domains of the invention can optionally have a His-Tag (or other convenient tag for purification purposes). In some cases, such tags are removable.

In certain aspects of the embodiments with TfR-specific binding moieties comprising a VNAR scaffold, the CDR1 region, which in naturally-occurring VNARs is a conserved seven amino acid residue stretch, comprises or consists essentially of a peptide selected from DASYALG, DKDCALS, DNDCALS, DNDCTLS DNNCALS, DNYCPLS, DRACALL, DRDCALS, DSDCALS, DSNCAAT, DSNCALS, DSNCALP, DSNCDLS, DSNCPLS, DSNCRLS, DSICALS, DSVCALS or DTACALD (Table 1) or any other CDR1 shown in Tables 1 or 5.

The CDR3 region in naturally-occurring VNARs is of heterogeneous size, ranging from about 7 to about 32 amino acid residues in length. In synthetic VNAR libraries exemplifying the present invention, CDR3 regions of 11 to 18 residues were constructed. In certain embodiments, the TfR-specific binding moiety of the invention comprises a CDR3 region selected from a peptide consisting essentially of or comprising an amino acid sequence of any one of the CDR3 sequences shown in Table 1 (as well as those shown in Table 5).

In certain embodiments, the framework region interspersed between CDR1 and CDR3 comprises any one of the FW2-3 amino acid sequences shown in Tables 1 or 5. The FW2-3 region in naturally-occurring VNARs is 53 amino acids in length, with insertions and deletions rarely observed. The FW2-3 region comprises hypervariable regions HV2 and HV4 (see B. J. Fennell et al., *J Mol Biol.* 400 (2010) pp. 155-170) which display some sequence variability and hence which can be suitable regions in which amino acid residues may be modified to create a variant of the TfR specific binding moiety of the invention.

As shown by the sequences in Table 1, The VNAR scaffold consists of amino acid residues (aa) 1-25 of the framework 1 (FW1) region; aa 26-32 of the complimentary determining region 1 (CDR1); aa 33-43 of FW2; aa 44-52 of the hypervariable 2 region (HV2); aa 53-85 of FW3; aa 61-65 of HV4; the CDR3 region (of variable length) and FW4 (11 residues starting at XGXG).

In any one of the individual embodiments described above, the TfR-specific binding moiety may further comprise one or more of the FW1, FW2-3 or FW4 amino acid sequences shown in Tables 1 or 5, in any functional combination. The present invention further provides a TfR-specific binding moiety comprising one of the cloned VNAR peptide sequences shown in Tables 1 or 5, that is, in some embodiments a TfR-specific binding moiety of the invention comprises or consists essentially of an amino acid sequence of any one of SEQ. ID NOS. 1-51 (i.e., the VNAR Domain Amino Acid Sequence of any one of the clones of Table 1).

In certain other embodiments of the invention, the present invention further provides a TfR-specific binding moiety comprising a CDR1 region comprising any one of the CDR1 peptide sequences shown in Tables 1 or 5 in combination with a CDR3 region comprising any one of the CDR3 peptides shown in Tables 1 or 5. These CDR regions are separated by a framework region (see, e.g., exemplary framework regions separating CDR1 and CDR3 regions as shown in Table 1), each considered to be an independent embodiment of the invention.

Further, in accordance with the invention, certain embodiments of TfR-specific binding moieties are directed to isolated TfR-specific binding moieties which comprise a VNAR domain capable of specifically binding to human TfR-1 without substantially interfering with transferrin binding to and/or transport by said human TfR-1. In some embodiments, such antibodies bind to the apical domain of human TfR-1. In some embodiments, such antibodies bind to the apical domain of human TfR-1 to at least one epitope within amino acids 215 to 380 of human TfR-1. The epitopes may be continuous or discontinuous epitopes.

For some embodiments in the immediately foregoing paragraph, the TfR-specific binding moiety does not substantially bind to human TfR-2. For some embodiments in the immediately foregoing paragraph, the TfR-specific binding moiety has an EC50 for human Tfr-1 ranging from about 0.1 nM to about 10 µM, and preferably ranging from about 1 nM to about 800 nM. For some embodiments in the immediately foregoing paragraph, the TfR-specific binding moiety is capable of cross reacting with mouse TfR-1. For some embodiments in the immediately foregoing paragraph, binding of the TfR-specific binding moiety to TfR-1 does not inhibit transferrin binding to and/or transport by TfR-1. For some embodiments in the immediately foregoing paragraph, binding of the TfR-specific binding moiety to TfR-1 induces endocytosis of said moiety in a TfR-positive cell. For some embodiments in the immediately foregoing paragraph, binding of the TfR-specific binding moiety to TfR-1 is reversibly pH dependent. In yet further embodiments, the TfR-specific binding moiety may have any or all such activity combinations.

Another aspect of the invention is directed to variants of TfR-specific binding moieties of the invention. Such variants differ by 1 to 10 amino acid residues from a recited amino acid sequence and/or retains human TfR-1-binding activity of at least half of the activity of the corresponding non-variant binding moiety. Those of skill in the art can readily identify and characterize variants of the invention using methods known in the art.

In yet another aspect of the invention, any of the TfR-specific binding moieties can form all or part of the variable domain of a single variable domain antibody, a bi- or tri-functional VNAR, a conventional antibody, or any fragment or fusion protein of said antibody as well as variable domains with antibody-like backbones.

Examples of single variable domain antibodies include, but are not limited to, a shark or other cartilaginous fish antibodies, camelid antibodies and nanobodies. Examples conventional antibodies include, but are not limited to, immunoglobins having both heavy and light chains, such as IgM's, IgA's, IgG's, IgE's, single chain Fv's, Fab fragments, or any fragment or fusion protein of such antibodies or fragments.

Non-limiting examples of antibody-like backbones that may be used according to the invention include monospecific and bispecific such as multimerizing scFv fragments (diabodies, triabodies, tetrabodies), disulfide stabilized antibody variable (Fv) fragments, disulfide stabilized antigen-binding (Fab) fragments consisting of the $V_L$, $V_H$, $C_L$ and $C_H1$ domains, bivalent F(ab')2 fragments, Fd fragments consisting of the heavy chain and $C_H1$ domains, dimeric $C_H2$ domain fragments ($C_H2D$), Fc antigen binding domains (Fcabs), single chain Fv-$C_H3$ minibodies, bispecific minibodies, isolated complementary determining region 3 (CDR3) fragments, constrained FR3-CDR3-FR4 polypeptides, SMIP domains, and any genetically manipulated counterparts of the foregoing that retain TfR-1 binding function (see e.g., Weiner L, Cell 148: 1081-4 (2012); Ahmad Z et al., Clin Dev Immunol 2012: 980250 (2012) for reviews).

Therefore, in one aspect, the invention provides a TfR-selective compound comprising or consisting essentially of a VNAR derived TfR-specific binding moiety which binds selectively to a TfR polypeptide, preferably to human TfR (see e.g., UniProt P02786 TFR1_Human) or to a TfR, e.g., human TfR epitope-containing polypeptide.

In certain embodiments, a TfR specific binding moiety of the invention binds to a transferrin receptor (TfR) on the membrane of a mammalian cell and TfR specific binding mediates transport of the TfR specific binding moiety and at least one associated heterologous molecule across the cell membrane. Any TfR-positive cell or cell type (i.e., one with the transferrin receptor localized at the cell membrane) may thus be used to target delivery of heterologous molecules across its membrane by association (e.g., a complex or conjugate) with a TfR specific binding moiety of the invention. As described in more detail below, heterologous molecules may be selected from an enormously wide variety of agents, limited only by the target cell requiring a cell surface TfR which can internalize upon binding.

In certain embodiments of the invention, the cell membrane is part of the blood brain barrier (BBB) and TfR-mediated transport across the BBB of a heterologous molecule may be accomplished. In certain other embodiments of the invention, the cell membrane is part of the GI tract and TfR-mediated transport of a heterologous molecule may be accomplished, enabling oral drug delivery routes, especially advantageous for previously non-orally bioavailable drugs or molecules for therapeutics and/or diagnostics.

Associated heterologous molecules which may be used in conjunction with any one of the above embodiments may comprise, e.g., one or more biologically active molecules and/or imaging agents. Exemplary biologically active molecules which may be transported into a TfR-positive cell in association with a TfR-specific binding moiety of the invention include, e.g., toxins for targeted TfR-positive cell death (useful e.g., in certain hyperproliferative diseases or disorders such as cancers or aberrant proliferative conditions). Other exemplary biologically active molecules which may be transported in association with a TfR specific binding moiety include, e.g., polypeptides, such as an antibody or antibody fragment; a therapeutic peptide such as a hormone, cytokine, growth factor, enzyme, antigen or antigenic peptide, transcription factor, or any functional domain thereof. Other exemplary biologically active molecules which may be transported into a TfR-positive cell in association with a TfR specific binding moiety include, e.g., nucleic acid molecules, such as an oligonucleotide (e.g., single, double or more stranded RNA and/or DNA molecules, and analogs and derivatives thereof); small regulatory RNA such as shRNA, miRNA, siRNA and the like; and a plasmid or fragment thereof.

Exemplary polypeptides which may be therapeutically beneficial when administered as a heterologous molecule for TfR-mediated transport across the BBB or other TfR-containing cell membrane include but are not limited to: a brain derived neurotrophic factor (BDNF), a bone morphogenic protein (e.g., BMP-1 through BMP-7, BMP8a, BMP8b, BMP10 and BMP15), a ciliary neurotrophic factor (CNF), an epidermal growth factor (EGF), erythropoietin, a fibroblast growth factor (FGF), a glial derived neurotrophic factor (GDNF), a heptocyte growth factor, an interleukin (e.g., IL-1, IL-4, IL-6, IL-10, IL-12, IL-13, IL-15, IL-17), a nerve growth factor (NGF), a neurotrophin (e.g., NT-3 and NT-4/5), a neurturin, a neuregulin, a platelet derived growth factor (PDGF), a transforming growth factor (e.g., TGF-alpha and TGF-beta), apolipoprotein F (ApoE), a vasoactive intestinal peptide, artemin, persephin, netrin, neurotensin, GM-GSF, cardiotrophin-1, stem cell factor, midkine, pleiotrophin, a saposin, a semaporin, leukemia inhibitory factor, and the like.

Exemplary therapeutic antibodies or fragments that may be transported across the BBB or other TfR-containing cell membrane as a heterologous biologically active molecule of the invention include but are not limited to: antibodies for neurodegeneration including anti-Abeta, anti-Tau, anti-alpha-synuclein anti-Trem2, anti-C9orf7 dipeptides, anti-TDP-43, anti-prion protein C, anti-huntingtin, anti-nogo A, anti-TRAIL (tumor necrosis factor-related apoptosis-inducing ligand); antibodies for neuro-oncology including anti-HER2, anti-EGF, anti-PDGF, anti-PD1/PDL1, anti-CTLA-4, anti-IDO, anti-LAG-3, anti-CD20, anti-CD19, anti-CD40, anti-OX40, anti-TIM3, anti-toll-like receptors; antibodies for neuroinflammation including anti-TNF, anti-CD138, anti-IL-21, anti-IL-22; antibodies to viral diseases of the brain including anti-West Nile virus, anti-Zika, anti-HIV, anti-CMV anti-HSV and the like.

Exemplary enzymes that may be transported across the BBB or other TfR-containing cell membrane as a heterologous biologically active molecule of the invention include but are not limited to: alpha-L-iduronidase, iduronate-2-sulfatase, N-acetyl-galactosamine-6-sulfatase, arylsulfatase B, acid alpha-glucosidase, tripeptidyl-peptidase 1, acid sphingomyelinase glucocerebrosidase and heparan sulfamidase Also included as exemplary biologically active molecules are small molecules comprising chemical moieties (such as a therapeutic small molecule drugs); carbohydrates; polysaccharides; lipids; glycolipids and the like. Exemplary embodiments of such small molecule therapeutic agents include certain cancer drugs, such as daunorubicin, doxorubicin, and other cytotoxic chemical agents including microtubule inhibitors, topoisomerase inhibitors, platins, alkylating agents, and anti-metabolites all of which may beneficially be administered across the BBB at lower overall systemic doses than by IV administration. Other small molecule therapeutic agents may include corticosteroids, NSAIDs, COX-2 inhibitors, small molecule immunomodulators, non-steroidal immunosuppressants, 5-amino salicylic acid, DMARDs, hydroxychloroquine sulfate, and penicillamine. 1-D-ribofuranosyl-1,2,4-triazole-3 carboxamide, 9-2-hydroxy-ethoxy methylguanine, adamantanamine, 5-iodo-2'-deoxyuridine, trifluorothymidine, interferon, adenine arabinoside, protease inhibitors, thymidine kinase inhibitors, sugar or glycoprotein synthesis inhibitors, structural protein synthesis inhibitors, attachment and adsorption inhibitors, and nucleoside analogues such as acyclovir, penciclovir, valacyclovir, and ganciclovir, among others. Small molecule therapeutic agents which may be used according to the invention also include bevacizumab, cisplatin, irinotecan, methotrexate, temozolomide, taxol and zoledronate. Certain anti-inflammatory agents may be useful biologically active molecules. Fluoxetine, for example, reportedly inhibits MMP-2, MMP-9 and MMP-12 expression associated with blood-brain barrier disruption and inflammatory reactions after spinal cord injury, which may be used according to the invention to protect blood-brain barrier and to inhibit deleterious inflammatory responses in spinal cord injury and central nervous system disease. Other non-limiting examples of therapeutic antibodies which may be beneficially transported across the BBB include anti-CD133, anti-CD137, anti-CD27, anti-VEGF, anti-EGRFvIII, anti-IL-15 and anti-IL13R.

Exemplary embodiments of an imaging agent as an associated heterologous molecule include agents that comprise at least one of a metal such as a paramagnetic metal, a radionuclide such as a radioisotope, a fluorochrome or fluorophor, an energy emitting particle, a detectable dye, and an enzyme substrate.

Further examples of biologically active molecules include small molecules, including therapeutic agents, in particular those with low blood-brain barrier permeability. Some examples of these therapeutic agents include cancer drugs, such as daunorubicin, doxorubicin, and toxic chemicals which, because of the lower dosage that can be administered by this method, can now be more safely administered. For example, a therapeutic agent can include bevacizumab, irinotecan, zoledronate, temozolomide, taxol, methotrexate, and cisplatin.

In another embodiment, the therapeutic agent can include a broad-spectrum antibiotic (e.g., cefotaxime, ceftriaxone, ampicillin and vancomycin); an antiviral agent (e.g., acyclovir); acetazolamide; carbamazepine; clonazepam; clorazepate dipotassium; diazepam; divalproex sodium; ethosuximide; felbamate; fosphenytoin sodium; gabapentin; lamotrigine; levetiracetam; lorazepam; oxcarbazepine; phenobarbital; phenytoin; phenytoin sodium; pregabalin; primidone; tiagabine hydrochloride; topiramate; trimethadione; valproic acid; zonisamide; copaxone; tysabri; novantrone; donezepil HCL; rivastigmine; galantamine; memantine; levodopa; carbidopa; parlodel, permax, requip, mirapex; Symmetrel; artane; cogentin; eldepryl; and deprenyl. Antiviral compounds are also beneficial therapeutic agents that can be delivered using a TfR-specific binding moiety of the invention, especially for cases in which the virus uses TfR transport as its route of entry into infected cells.

Numerous other examples of biologically active molecules may be used in association with a TfR-specific binding moiety of the invention, appropriate selection of which will be apparent to the skilled artisan depending on the condition, disease or disorder to be treated.

Yet other examples of a biologically active molecule which may be used according to the present invention is an antigenic peptide. Antigenic peptides may provide immunological protection when imported by cells involved in an immune response. Other examples include immunosuppressive peptides (e.g., peptides that block autoreactive T cells, such peptides being known in the art).

An imaging agent, as used herein, may be any chemical substance which may be used to provide a signal or contrast in imaging. A signal enhancing domain may be an organic molecule, metal ion, salt or chelate, a particle (e.g., iron particle), or a labeled peptide, protein, glycoprotein, polymer or liposome. For example, an imaging agent may include one or more of a radionuclide, a paramagnetic metal, a fluorochrome, a dye, and an enzyme substrate.

For x-ray imaging, the imaging agent may comprise iodinated organic molecules or chelates of heavy metal ions of atomic numbers 57 to 83. In certain embodiments, the imaging agent is $I^{125}$ labeled IgG (see, e.g., M. Sovak, ed., "Radiocontrast Agents," Springer-Verlag, pp. 23-125 (1984).

For ultrasound imaging, an imaging agent may comprise gas-filled bubbles or particles or metal chelates where the metal ions have atomic numbers 21-29, 42, 44 or 57-83. See e.g., Tyler et al., Ultrasonic Imaging, 3, pp. 323-29 (1981) and D. P. Swanson, "Enhancement Agents for Ultrasound: Fundamentals," Pharmaceuticals in Medical Imaging, pp. 682-87. (1990) for other suitable compounds.

For nuclear radiopharmaceutical imaging or radiotherapy, an imaging agent may comprise a radioactive molecule. In certain embodiments, chelates of Tc, Re, Co, Cu, Au, Ag, Pb, Bi, In and Ga may be used. In certain embodiments, chelates of Tc-99m may be used. See e.g., Rayudu GVS, Radiotracers for Medical Applications, I, pp. 201 and D. P. Swanson et al., ed., Pharmaceuticals in Medical Imaging, pp. 279-644 (1990) for other suitable compounds.

For ultraviolet/visible/infrared light imaging, an imaging agent may comprise any organic or inorganic dye or any metal chelate.

For MRI, an imaging agent may comprise a metal-ligand complex of a paramagnetic form of a metal ion with atomic numbers 21-29, 42, 44, or 57-83. In certain embodiments, the paramagnetic metal is selected from: Cr(III), Cu(II), Dy(III), Er(III) and Eu(III), Fe(III), Gd(III), Ho(III), Mn(II and III), Tb(III). A variety of chelating ligands useful as MRI agents are well known in the art.

In sum, the invention includes TfR-specific conjugate comprising a TfR-specific binding moiety of the invention operably linked to a heterologous molecule which differs in biological activity from said moiety. Such operable linkages can be a covalent or non-covalent linkage and the heterologous molecule can be a growth factor, cytokine, lymphokine, cell surface antigen or an antibody or antibody fragment which binds to any of the foregoing; a chimeric antigen receptor; a cytotoxic small molecule; a biochemical pathway agonist or antagonist; a therapeutic agent or drug; a diagnostic agent such as a fluorescent molecule or other molecular marker; or a nucleic acid molecule with targeting or other regulatory properties (e.g., silencers) or which encodes a regulatory molecule for a cell.

For the avoidance of doubt, a TfR-selective binding compound includes TfR-specific binding moieties alone, as part of antibodies (or fragments thereof as described herein), as part of conjugates or encoded in viral or other vectors.

Monitoring TfR Binding and Cell Internalization

TfR-binding activity (also referred to herein as "TfR bioactivity") may be determined by one or more assays described in the Examples herein, or by any other suitable method in the art, including well-known immunoassays, such as for example the ELISAs or variations thereon described in the Examples. Any other binding assay which directly or indirectly measures the binding of the TfR-specific binding moiety to a cell surface TfR, or alternatively, which measures the ability of a TfR-specific binding moiety, conjugate or compound comprising such a moiety of the invention to compete for binding to TfR in the presence of a different TfR binding compound (such as an anti-TfR antibody) such as by a competitive inhibition assay, may be used. Preferably, a selected assay measures the effect of a TfR-specific binding moiety or compound comprising such a moiety on its ability to transport a heterologous molecule or biomolecule across the membrane of a TfR-positive cell.

In certain embodiments, the TfR-positive cell is one which transports a heterologous molecule across the blood brain barrier (BBB). In certain embodiments, the TfR-positive cell is one which transports a heterologous molecule across cells of the gastrointestinal tract. In certain embodiments, binding of the TfR binding moiety to TfR is measured by monitoring internalization of the TfR binding moiety into TfR-positive cells or cell type. In vivo assays of TfR bioactivity include, but are not limited to those described in the Examples herein.

Other test systems to assess TfR binding and functional activity include, for example: Surface plasmon resonance to determine affinity and off-rates; using radiolabeled or fluorescent tagged molecule or GFP fusion proteins in in vitro or in vivo animal studies including binding and internalization in tumor cell lines, immortalized endothelial cell lines or primary cells expressing TfR; in vitro transcytosis in capillary endothelial cells and cells lines; and permeability assay using Caco-2 and MDCK epithelial cell lines; in situ perfusion models and immunohistochemical or immunofluorescent staining of tissue sections; optical or PET animal imaging; standard PK and tissue distribution assays; and measuring one or more biological effects of a heterologous molecule (drug cargo or payload) in normal animals or disease animal models.

According to another embodiment, a TfR-specific binding moiety, conjugate or compound of the invention binds to human TfR in a standard ELISA or other similar assay with an EC50 of 300 nM or less, 100 nM or less, 10 nM or less, or 1 nM or less. Thus, a TfR selective binding compound of the invention binds to TfR, e.g., hTfR, in a standard ELISA or other similar assay with an EC50 in a range of 0.1 nM to 300 nM, 0.5 nM to 300 nM, 1 nM to 300 nM, 10 nM to 300 nM, 50 nM to 300 nM, 100 nM to 300 nM, 0.1 nM to 100 nM, 0.5 nM to 100 nM, 1 nM to 100 nM, 5 nM to 100 nM, 10 nM to 100 nM, 0.1 nM to 50 nM, 0.5 nM to 50 nM, 1 nM to 50 nM, 5 nM to 50 nM, 10 nM to 50 nM. It should be noted that strong selective binding may subsequently hinder transport across the membrane and/or release of the TfR-specific binding moiety and heterologous molecule(s) inside the TfR-positive cell. Hence, it should not be assumed that the tightest binding moieties are always ideal. One of skill in the art will be able to select an appropriate level of binding for desired transport and release of the therapeutic or diagnostic use envisioned. For example, in certain embodiments of the invention, the TfR-specific binding moiety binds to human TfR-1 with an EC50 in a range of about 0.1 nM to about 10 μM, or in a preferred embodiment, in a range of about 1 nM to about 800 nM.

In certain embodiments, the TfR compound of the invention binds to hTfR with a 5-fold, 10-fold, 20-fold, 50-fold, 100-fold, 500-fold or more higher affinity compared to its binding affinity to a cross reactive ligand. In some embodiments, a TfR selective binding compound of the invention is specific to human TfR but also binds to or cross-reacts with one or more other mammalian TfRs, e.g., with mouse TfR (UniProtKB/Swiss-Prot: P02786 TFR1).

Therapeutic versions of compounds with TfR-specific binding moieties of the invention include other molecular configurations, e.g., a VNAR monomer (i.e., a TfR-binding moiety) fused to stabilizing heterologous peptide regions, e.g., the Fc domain of an IgG or other immunoglobulin molecule, which may be expressed and then further purified as multimers, such as covalent dimmers, allowing the activity of certain such therapeutic molecules to have even greater potency, preferably by at least 2-10 fold higher potencies and different binding affinities to TfR-1. Any of the antibody or antibody-like structures contemplated by the invention can be used as therapeutics TfR bioactivity may also or alternatively be measured by TfR binding affinity, using any of a number of assays known in the art, such as a surface plasmon resonance assay (Example 5). According to another embodiment, a TfR-selective binding compound of the invention binds to human TfR in an affinity assay such as by surface plasmon resonance assay with a binding affinity of 300 nM or less, and preferably 100 nM or less, 10 nM or less, 1 nM or less or 100 pM or less. Thus, a TfR antagonist compound of the invention binds to TfR, e.g., hTfR, with an affinity constant ($K_A$) in a range of 0.1 nM to 500 nM, 0.5 nM to 500 nM, or 1 nM to 500 nM, 0.1 nM to 250 nM, 0.5 nM to 250 nM, or 1 nM to 250 nM as measured, e.g., by surface plasmon resonance such as in a BIACore assay. In certain embodiments, a compound of the invention binds to TfR, e.g., hTfR, with an affinity constant in a range of 0.1 nM to 100 nM, 0.1 nM to 50 nM, or 0.1 nM to 10 nM, 0.5 nM to 100 nM, 0.5 nM to 50 nM, or 0.5 nM to 10 nM, or 1 nM to 100 nM, 1 nM to 50 nM or 1 nM to 10 nM, as measured, e.g., by surface plasmon resonance such as in a BIACore assay.

Pharmaceutically acceptable salts or solvates of any of the TfR-specific binding compounds of the invention are likewise within the scope of the present invention. As used herein, the term "pharmaceutically acceptable salt" refers to a salt that is not harmful to a patient or subject to which the salt in question is administered. It may be a salt chosen, e.g., among acid addition salts and basic salts. Examples of acid addition salts include chloride salts, citrate salts and acetate salts. Examples of basic salts include salts wherein the cation is selected from alkali metal cations, such as sodium or potassium ions, alkaline earth metal cations, such as calcium or magnesium ions, as well as substituted ammonium ions, such as ions of the type N(R1)(R2)(R3)(R4)+, wherein R1, R2, R3 and R4 independently will typically designate hydrogen, optionally substituted $C_{1-6}$-alkyl groups or optionally substituted $C_{2-6}$-alkenyl groups. Examples of relevant $C_{1-6}$-alkyl groups include methyl, ethyl, 1-propyl and 2-propyl groups. Examples of $C_{2-6}$-alkenyl groups of possible relevance include ethenyl, 1-propenyl and 2-propenyl. Other examples of pharmaceutically acceptable salts are described in "Remington's Pharmaceutical Sciences", 17th edition, Alfonso R. Gennaro (Ed.), Mark Publishing Company, Easton, Pa., USA, 1985 (and more recent editions thereof), in the "Encyclopaedia of Pharmaceutical Technology", 3rd edition, James Swarbrick (Ed.), Informa Healthcare USA (Inc.), NY, USA, 2007, and in J. Pharm. Sci. 66: 2 (1977).

The term "solvate" in the context of the present invention refers to a complex of defined stoichiometry formed between a solute (in casu, a peptide compound or pharmaceutically acceptable salt thereof according to the invention) and a solvent. The solvent in this connection may, for example, be water, ethanol or another pharmaceutically acceptable, typically small-molecular organic species, such as, but not limited to, acetic acid or lactic acid. When the solvent in question is water, such a solvate is normally referred to as a hydrate.

In each of the sequences described above, and in each sequence described herein, a C-terminal "—OH" moiety may be substituted for a C-terminal "—NH$_2$" moiety, and vice-versa.

Each of the specific compounds of the invention (e.g., TfR binding moieties, TfR antagonist peptides and compounds), and pharmaceutically acceptable salts and solvates thereof, constitutes an individual embodiment of the invention.

Derivatives, Variants, Conjugates

The invention further provides variants of a TfR-specific binding moiety of the invention, wherein the variant differs from the recited amino acid sequence by up to 1, 2, 3, 4, 5, 6, 7, 8, 9, 10 or more amino acid residues (but by no more than that which retains 85%, 90%, 95%, 99% or more amino acid sequence identity) and/or retains TfR bioactivity. TfR bioactivity can be measured, for example, by TfR binding affinity, using any of a number of assays know in the art. In certain embodiments, a compound of the invention binds to TfR-1, e.g., hTfR-1, with an affinity constant in a range of 0.1 nM to 500 nM, 0.5 nM to 500 nM, or 1 nM to 500 nM, 0.1 nM to 250 nM, 0.5 nM to 250 nM, or 1 nM to 250 nM as measured, e.g., by surface plasmon resonance such as in a BIACore assay. In certain embodiments, a compound of the invention binds to TfR-1, e.g., hTfR-1, with an affinity constant in a range of 0.1 nM to 100 nM, 0.1 nM to 50 nM, or 0.1 nM to 10 nM, 0.5 nM to 100 nM, 0.5 nM to 50 nM, or 0.5 nM to 10 nM, or 1 nM to 100 nM, 1 nM to 50 nM or 1 nM to 10 nM, as measured, e.g., by surface plasmon resonance such as in a BIACore assay. It will be understood by one of skill in the art that amino acid residues outside of the conserved FW, CDR1 and CDR3 motifs are in general regions in which amino acid modifications may be tolerated more readily without deleteriously depleting TfR binding activity. And it will also be understood by one of skill in the art that in certain embodiments, the binding affinity to TfR is less important than the ability of the binding moiety to transport a heterologous molecule across the membrane of a TfR-positive cell, and to release a molecular cargo or a so called drug or molecular payload within the cell.

A biologically active fragment of any of the foregoing sequences which retains TfR bioactivity is also encompassed by the present invention. Thus, in further aspects, the invention further comprises compounds having an amino acid sequence that is truncated (shortened), from the N- or C-terminus, relative to the full length sequence of compounds of the invention. In some embodiments, the truncated compounds are truncated by up to 1, 2, 3, 4, 5, 6, 7, 8, 9, 10, 11, 12, 13, 14, 15, 16, 17, 18, 19, 20, 21, 22, 23, 24, 25 or more amino acid residues, counting from the C-terminus of a compound of the invention as disclosed above. Amino acid residue outside of the conserved VNAR framework motifs are regions in which amino acid modifications may be better tolerated without deleteriously depleting TfR binding activity.

In some embodiments, the compounds of the invention may have at least 40%, e.g., at least 45%, 50%, 55%, 60%, 65%, 70%, 75%, 80%, 85%, 90%, 95%, 96%, 97%, 98%, or 99%, 99.5%, or 99.9% amino acid sequence identity to one of the TfR selective binding compounds disclosed herein, as long as the compound retains a TfR biological activity (as measured by TfR binding affinity, EC50 or IC50) within a range described herein.

Thus in certain, TfR specific binding compounds of the invention may comprise the amino acid sequence of any one of the compounds shown in Tables 1 or 5 (see below), or a functional variant thereof that has at least about 70%, 75%, 80%, 85%, 90%, 95%, 97%, 98%, 99% or 99.5% sequence identity to any one of the compounds in Tables 1 or 5. A functional variant of a polypeptide of the invention may inhibit at least one TfR bioactivity by any one of the assays disclosed herein by at least 50%, 55%, 60%, 65%, 70%, 75%, 80%, 85%, 90%, 95%, 97%, 98%, 99%, 99.5%, or 100%. In some embodiments, a TfR selective binding compound of the invention may comprise one or more amino acid substitutions, e.g., conservative amino acid substitutions, and retain TfR binding activity of at least 50%, 55%, 60%, 65%, 70%, 75%, 80%, 85%, 90%, 95%, 97%, 98%, 99%, 99.5%, or 100% compared to the binding by an unmodified TfR selective binding compound of the invention, and/or compared to binding of any other available anti-TfR antibody, such as anti-human TfR monoclonal antibody belimumab.

Throughout the present specification, unless naturally occurring amino acids are referred to by their full name (e.g. alanine, arginine, etc.), they are designated by their conventional three-letter or single-letter abbreviations (e.g. Ala or A for alanine, Arg or R for arginine, etc.). Unless otherwise indicated, reference is made to the L-isomeric forms of the amino acids in question. Where appropriate, the D-isomeric form of an amino acid is indicated in the conventional manner by the prefix "D" before the conventional three-letter code (e.g. DAsp, DPhe). Non-traditional amino acid residues and analogs are also included within the scope of the present invention (e.g., homoserine, norleucine, norvaline, ornithine and the like; and methods for making them are well known in the art.

In certain embodiments, the invention further provides a TfR specific binding moiety or TfR selective binding compound comprising said binding moiety, in which there are one or more conservative amino acid substitutions introduced into the polypeptide sequence. As used herein, the term "conservative substitution" denotes that one or more amino acids are replaced by another, biologically similar amino acid residue. Examples include substitution of amino acid residues with similar characteristics, e. g. small amino acids, acidic amino acids, polar amino acids, basic amino acids, hydrophobic amino acids and aromatic amino acids. See, for example, the table below. An example of a conservative substitution with a residue normally not found in endogenous, mammalian peptides and proteins is the conservative substitution of Arg or Lys with, for example, ornithine, canavanine, aminoethylcysteine or another basic amino acid. For further information concerning phenotypically silent substitutions in peptides and proteins, see, e.g., Bowie et al., *Science* 247, 1306-1310, 1990. In the scheme below are conservative substitutions of amino acids grouped by physicochemical properties. I: neutral, hydrophilic, II: acids and amides, III: basic, IV: hydrophobic, V: aromatic, bulky amino acids.

| I | II | III | IV | V |
|---|----|-----|----|----|
| A | N | H | M | F |
| S | D | R | L | Y |
| T | E | K | I | W |
| P | Q |   | V |   |
| G |   |   | C |   |

In some embodiments, a polypeptide of the invention may comprise functional fragments or variants of a TfR-specific binding moiety of the invention that have, at most, 20, 15, 10, 9, 8, 7, 6, 5, 4, 3, 2, or 1 amino acid substitutions compared to a polypeptide sequence recited herein, as long as it retains measurable biological activity alone or as a component of a TfR-selective binding compound. A polypeptide of the invention may further be with or without a signal sequence. In certain embodiments, the retained activity is at least 50% that of the TfR binding moiety according to Tables 1 or 5.

In some embodiments, a polypeptide of the invention shares at least 85%, 90%, 95%, 96%, 97%, 98%, 99% or more amino acid sequence identity to any one of the amino acid sequences of FW1, FW2-3, FW4, CDR1 or CDR3 of Tables 1 or 5, as long as it retains measurable biological activity alone or as a component of a TfR selective binding compound. In certain embodiments, the retained activity is at least 50% that of the TfR binding moiety according to Tables 1 or 5.

TfR specific VNAR comprising compounds of the invention may optionally be conjugated (e.g., using linkers such as chemical linkers and/or linker peptides which are not usually associated with the domains being associated) to one or more additional agents which may include therapeutic and/or diagnostic agents. Such agents include but are not limited to chemotherapeutics such as cytostatic drugs, cytotoxins, radioisotopes, chelators, enzymes, nucleases, nucleic acids such as DNA, RNA or mixed nucleic acid oligonucleotides, including siRNAs, shRNAs, microRNAs, aptamers and the like; immunomodulators such as therapeutic antibodies, antibody and antibody-like fragments, inflammatory and anti-inflammatory cytokines, anti-inflammatory agents, radiotherapeutics, photoactive agents, diagnostic markers and the like. In certain embodiments, the pharmaceutically active moieties of the invention comprise at least one scFv molecule that is operably linked via a linker peptide to the C-terminus and/or N-terminus of an Fc region.

In certain embodiments, a compound of the invention comprising a TfR-specific binding moiety is multispecific, i.e., has at least one binding site that binds to a first molecule or epitope of a molecule (e.g., human TfR-1) and one or more other binding sites that bind to at least one heterologous molecule or to an epitope of either TfR-1 or another molecule. Multispecific binding molecules of the invention may comprise at least two binding sites, three binding sites, four binding sites or more. In certain embodiments, at least two binding site of a multispecific binding molecule of the invention are capable of transporting a linked molecule across the BBB.

The invention thus further provides methods of making derivatives of TfR specific VNARs of the invention using biochemical engineering techniques well known to those of skill in the art. Such derivatives include, inter alia, multivalent or multispecific molecules comprising a TfR-specific binding moiety, including immunoconjugates. A large body of art is available relating to how to make and use antibody drug conjugates. Such knowledge and skill in the art may be adapted for use with the TfR specific binding moieties and TfR selective binding compounds of the invention. See, e.g., WO2007/140371; WO2006/068867 specific to TfR; methods relating to making and/or using different ligand conjugates may be applied. In certain embodiments, the TfR selective binding moieties and TfR selective binding compounds of the present invention include covalently modified and conjugated polypeptides forms of the polypeptides (e.g., immunoadhesins, radiolabeled or fluorescently labeled compounds, and the like). Methods for peptide conjugation and for labeling polypeptides and conjugating molecules are well known in the art.

Nucleic Acid Sequences that Encode a TfR Selective Binding Moiety or TfR Antagonist Compound In one aspect, the invention provides an isolated nucleic acid which encodes a TfR specific binding moiety or compound of the invention, or a fragment or derivative thereof, including but not limited to nucleic acid sequences shown in Tables 2 and 6. The nucleic acid may include, e.g., nucleic acid sequence encoding a polypeptide at least 50%, 55%, 60%, 65%, 70%, 75%, 80%, 85%, 90%, 95%, 99% or more, identical to a polypeptide comprising one of the amino acid sequences of Tables 1 or 5. The invention also provides an isolated nucleic acid molecule comprising a sequence that hybridizes under stringent conditions to a nucleic acid sequence which encodes a TfR specific binding moiety or compound of the invention, or a fragment or derivative thereof, or the antisense or complement of any such sequence.

In another aspect, the invention provides an isolated nucleic acid molecule encoding a fusion protein comprising at least two segments, wherein one of the segments comprises a polypeptide or fragment thereof having CDR 1, CDR3 or framework amino acid sequences shown in Tables 1 or 5, and variants thereof according to the invention. In certain embodiments, a second segment comprises a heterologous signal polypeptide, a heterologous binding moiety, an immunoglobulin fragment such as a Fc domain, or a detectable marker.

One aspect of the invention provides isolated nucleic acid molecules that encode TfR specific binding moiety proteins or biologically active portions thereof. Also included are nucleic acid fragments sufficient for use as hybridization probes to identify TfR binding moiety encoding nucleic acids and fragments for use as polymerase chain reaction (PCR) primers for the amplification or mutation of TfR specific binding moiety encoding nucleic acid molecules.

As used herein, the term "nucleic acid molecule" is intended to include DNA molecules, RNA molecules (e.g., mRNA, shRNA, siRNA, microRNA), analogs of the DNA or RNA generated using nucleotide analogs, and derivatives, fragments and homologs thereof. The nucleic acid molecules of the invention may be single-, double-, or triple-stranded. A nucleic acid molecule of the present invention, e.g., a nucleic acid molecule encoding any one of the amino acid sequences disclosed in Tables 1 or 5 (see e.g., Tables 2 and 6), or a complement of any of these nucleotide sequences, may be isolated using sequence information provided herein and well known molecular biological techniques (e.g., as described in Sambrook et al., Eds., MOLECULAR CLONING: A LABORATORY MANUAL 2ND ED., Cold Spring Harbor Laboratory Press, Cold Spring Harbor, N.Y., 1989; and Ausubel, et al., Eds., CURRENT PROTOCOLS IN MOLECULAR BIOLOGY, John Wiley & Sons, New York, N.Y., 1993).

A nucleic acid molecule of the invention may be amplified using any form of nucleic acid template and appropriate oligonucleotide primers according to standard PCR amplification techniques. Amplified nucleic acid may be cloned into an appropriate vector and characterized, e.g., by restriction analysis or DNA sequencing. Furthermore, oligonucleotides corresponding to nucleotide sequences that encode a TfR selective binding moiety or compound of the invention may be prepared by standard synthetic techniques, e.g., using an automated DNA synthesizer.

The term "oligonucleotide" as used herein refers to a series of covalently linked nucleotide (or nucleoside residues, including ribonucleoside or deoxyribonucleoside residues) wherein the oligonucleotide has a sufficient number of nucleotide bases to be used in a PCR reaction. Oligonucleotides comprise portions of a nucleic acid sequence having at least about 10 nucleotides and as many as 50 nucleotides, preferably about 15 nucleotides to 30 nucleotides. Oligonucleotides may be chemically synthesized and may be used as probes. A short oligonucleotide sequence may be used to amplify, confirm, or reveal the presence of an identical, similar or complementary DNA or RNA in a particular cell or tissue.

Derivatives or analogs of the nucleic acid molecules (or proteins) of the invention include, inter alia, nucleic acid (or polypeptide) molecules having regions that are substantially homologous to the nucleic acid molecules or proteins of the invention, e.g., by at least about 45%, 50%, 70%, 80%, 95%, 98%, or even 99% identity (with a preferred identity of 80-99%) over a nucleic acid or amino acid sequence of the same size or when compared to an aligned sequence in which the alignment is done by a computer homology program known in the art. A percent identity for any candidate nucleic acid or polypeptide relative to a reference nucleic acid or polypeptide may be determined by aligning a reference sequence to one or more test sequences using, for example, the computer program ClustalW (version 1.83, default parameters), which enable nucleic acid or polypeptide sequence alignments across their entire lengths (global alignment) or across a specified length. The number of identical matches in such a ClustalW alignment is divided by the length of the reference sequence and multiplied by 100.

Also included are nucleic acid molecules capable of hybridizing to the complement of a sequence encoding the proteins of the invention under stringent or moderately stringent conditions. See e.g. Ausubel, et al., CURRENT PROTOCOLS IN MOLECULAR BIOLOGY, John Wiley & Sons, New York, N.Y., 1993, and below. An exemplary program is the GAP program (Wisconsin Sequence Analysis Package, Version 8 for UNIX, Genetics Computer Group, University Research Park, Madison, Wis.) using the default settings, which uses the algorithm of Smith and Waterman (1981) Adv. Appl. Math. 2:482489). Derivatives and analogs may be full length or other than full length, if the derivative or analog contains a modified nucleic acid or amino acid, as described below.

Stringent conditions are known to those skilled in the art and may be found in CURRENT PROTOCOLS IN MOLECULAR BIOLOGY, John Wiley & Sons, N.Y. (1989), 6.3.1-6.3.6. In certain embodiments, stringent conditions typically permit sequences at least about 65%, 70%, 75%, 85%, 90%, 95%, 98%, or 99% homologous to each other to remain hybridized to each other. A non-limiting example of stringent hybridization conditions is hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C. This hybridization is followed by one or more washes in 0.2×SSC, 0.01% BSA at 50° C. The term "stringent hybridization conditions" as used herein refers to conditions under which a nucleic acid probe, primer or oligonucleotide will hybridize to its target sequence, but only negligibly or not at all to other nucleic acid sequences. Stringent conditions are sequence- and length-dependent, and depend on % (percent)-identity (or %-mismatch) over a certain length of nucleotide residues. Longer sequences hybridize specifically at higher temperatures than shorter sequences. Generally, stringent conditions are selected to be about 5° C. lower than the thermal melting point (Tm) for the specific sequence at a defined ionic strength and pH. Stringent conditions may also be achieved with the addition of destabilizing agents, such as formamide.

Methods of Producing TfR Specific VNAR Binding Moieties and Compounds Comprising Them The compounds of the invention may be manufactured by standard synthetic methods, by use of recombinant expression systems, or by any other suitable method. Thus, the compounds may be synthesized in a number of ways, including, e.g., methods comprising: (1) synthesizing a polypeptide or polypeptide component of a TfR specific binding compound using standard solid-phase or liquid-phase methodology, either stepwise or by fragment assembly, and isolating and purifying the final peptide compound product; (2) expressing a nucleic acid construct that encodes a polypeptide or polypeptide component of a TfR specific binding compound in a host cell and recovering the expression product from the host cell or host cell culture; or (3) cell-free in vitro expression of a nucleic acid construct encoding a polypeptide or polypeptide component of a TfR specific binding compound, and recovering the expression product; or by any combination of the methods of (1), (2) or (3) to obtain fragments of the peptide component, subsequently joining (e.g., ligating) the fragments to obtain the peptide component, and recovering the peptide component.

It may be preferable to synthesize a polypeptide or polypeptide component of a TfR-specific binding compound of the invention by means of solid-phase or liquid-phase peptide synthesis. Compounds of the invention may suitably be manufactured by standard synthetic methods. Thus, peptides may be synthesized by, e.g., methods comprising synthesizing the peptide by standard solid-phase or liquid-phase methodology, either stepwise or by fragment assembly, and isolating and purifying the final peptide product. In this context, reference may be made to WO1998/11125 or, inter alia, Fields, G. B. et al., "Principles and Practice of Solid-Phase Peptide Synthesis"; in: Synthetic Peptides, Gregory A. Grant (ed.), Oxford University Press (2nd edition, 2002) and the synthesis examples herein.

Accordingly, the present invention also provides methods for producing a TfR specific binding compound of the invention according to above recited methods; a nucleic acid molecule encoding part or all of a polypeptide of the invention, a vector comprising at least one nucleic acid of the invention, expression vectors comprising at least one nucleic acid of the invention capable of producing a polypeptide of the invention when introduced into a host cell, and a host cell comprising a nucleic acid molecule, vector or expression vector of the invention.

TfR specific binding compounds of the invention may be prepared using recombinant techniques well known in the art. In general, methods for producing polypeptides by culturing host cells transformed or transfected with a vector comprising the encoding nucleic acid and recovering the polypeptide from cell culture are described in, e.g., Sambrook et al., Molecular Cloning: A Laboratory Manual (New York: Cold Spring Harbor Laboratory Press, 1989); Dieffenbach et al., PCR Primer: A Laboratory Manual (Cold Spring Harbor Laboratory Press, 1995).

A nucleic acid encoding a desired polypeptide may be inserted into a replication vector for further cloning (amplification) of the DNA or for expression of the nucleic acid into RNA and protein. A multitude of cloning and expression vectors are publicly available.

Expression vectors capable of directing transient or stable expression of genes to which they are operably linked are well known in the art. The vector components generally include, but are not limited to, one or more of the following: a heterologous signal sequence or peptide, an origin of replication, one or more marker genes, an enhancer element, a promoter, and a transcription termination sequence, each of which is well known in the art. Optional regulatory control sequences, integration sequences, and useful markers that can be employed are known in the art.

Any suitable host cell may be used to produce TfR specific binding compounds of the invention. Host cells may be cells stably or transiently transfected, transformed, transduced or infected with one or more expression vectors which drive expression of a polypeptide of the invention. Suitable host cells for cloning or expressing nucleic acids of the invention include prokaryote, yeast, or higher eukaryote cells. Eukaryotic microbes such as filamentous fungi yeast, *Arabidopsis*, and other plant and animal eukaryotic host cells that may be grown in liquid culture are suitable cloning or expression hosts for vectors. Suitable host cells for the expression of glycosylated polypeptides may also be derived from multicellular organisms.

Creation and isolation of host cell lines producing a TfR-specific binding moiety, conjugate or compound of the invention can be accomplished using standard techniques known in the art. Mammalian cells are preferred host cells for expression of peptides. Particularly useful mammalian cells include, inter alia, HEK 293, NSO, DG-44, and CHO cells, but any other suitable host cell may be used according to the invention. Preferably, the TfR-specific moieties, conjugates or compounds are secreted into the medium in which the host cells are cultured, from which the TfR-specific binding moieties, conjugates or compounds may be recovered or purified.

When a polypeptide is produced in a recombinant cell other than one of human origin, it is typically free of polypeptides of human origin. In certain embodiments, it is advantageous to separate a polypeptide away from other recombinant cell components such as host cell polypeptides to obtain preparations that are of high purity or substantially homogeneous. As a first step, culture medium or cell lysates may be centrifuged to remove particulate cell debris and suitable protein purification procedures may be performed. Such procedures include, inter alia, fractionation (e.g., size separation by gel filtration or charge separation by ion-exchange column); ethanol precipitation; Protein A Sepharose columns to remove contaminants such as IgG; hydrophobic interaction chromatography; reverse phase HPLC; chromatography on silica or on cation-exchange resins such as DEAE and the like; chromatofocusing; electrophoretic separations; ammonium sulfate precipitation; gel filtration using, for example, Sephadex beads such as G-75. Any number of biochemical purification techniques may be used to increase the purity of a TfR-specific binding moiety, conjugate or compound of the invention.

Methods of Detection

In certain embodiments, the TfR specific binding compounds of the invention may be used to detect and quantify levels of TfR, or cells that express TfR. This can be achieved, for example, by contacting a test sample (such as an in vitro sample) and a control sample with a TfR specific binding moiety of the invention, or a compound comprising it, under conditions which permit formation of a complex between the compound and TfR, or between TfR and an anti-TfR antibody, or both. Any bound TfR complexes are detected and/or quantified in TfR specific VNAR containing samples and control samples.

Accordingly, the invention further provides methods for detecting the presence of TfR or TfR antibodies in a sample, or measuring the amount of either of the foregoing, comprising contacting the sample, and preferably a control sample, with a TfR-binding compound of the invention under conditions that permit complex formation between the TfR binding moiety of the compound and TfR, e.g., human TfR. Formation or inhibition of formation of a TfR-binding compound/TfR complex is then detected and/or quantified. A variety of tests can be designed based on features of binding or competition for binding. For example, the presence of TfR in a test sample may be detected directly, or may be detected and quantified based on the ability to compete for binding of TfR by a TfR-binding moiety, conjugate or compound. In general, the difference in complex formation between a test sample and a control sample is indicative of a binding interaction.

Methods of Treatment Using TfR Binding Moieties and Compositions

The present invention provides a TfR binding moiety or TfR specific binding compound for use, alone or in combination with one or more additional therapeutic agents in a pharmaceutical composition, for treatment or prophylaxis of conditions, diseases and disorders responsive to modulation (such as inhibiting or blocking) of the interaction between TfR and its in vivo ligands.

In certain embodiments, a TfR specific binding moiety or a conjugate or drug delivery vehicle comprising such a binding moiety is administered in combination with at least one additional agent that mediates blood-brain barrier transport, such as an agent comprising a receptor binding domain of an apolipoprotein such as a receptor binding domain of ApoA, ApoB, ApoC, ApoD, ApoE, ApoE2, ApoE3 or ApoE4, and any combination thereof. Any one of a number of other molecules which mediate transport of heterologous molecules across the blood brain barrier may be used in combination with the TfR specific binding moiety comprising agents of the invention, including, e.g., IgG, YY (PYY), neuropeptide Y (NPY), corticotropin releasing factor (CRF) and urocortin. Certain viral glycoproteins (e.g., rabies virus glycoprotein (RVG) peptide) and antibodies and antibody fragments may also be used in this regard.

Combination therapies may include co-administration of agents or alternate administrations which result in a combination therapy within the patient based on duration of the therapeutic agent(s) or their biological effects in the patient.

In certain embodiments, a therapeutic agent transported across the BBB in association with a TfR-specific binding moiety of the invention is effective in treating a brain or CNS disease, condition, injury or disorder, such as, for example, neurodegenerative diseases, neuronal injury, stroke, genetic disorders, psychiatric disorders, developmental disorders, inflammation, infection or damage, and brain cancers, spinal cord injury (SCI) and traumatic brain injury (TBI). In certain embodiments, a brain disorder is selected from epilepsy, meningitis, encephalitis including HIV Encephalitis, progressive multifocal leukoencephalopathy, neuromyelitis optica, multiple sclerosis, late-stage neurological trypanosomiasis, amyotrophic lateral sclerosis (ALS), progressive bulbar palsy (PBP), primary lateral sclerosis (PLS), progressive muscular atrophy (PMA), Alzheimer's disease, Parkinson's disease, Huntington's disease, De Vivo disease, and any type of tumor, cancer or hyperproliferative disease in the brain or CNS.

In certain embodiments, a therapeutic agent transported across a hTfR1-containing membrane in association with a TfR-specific binding moiety of the invention is effective in treating a condition, disease or disorder associated with the GI tract or one which will otherwise benefit from drug delivery across an epithelial membrane of the gut mediated by hTfR1 transport.

The invention in certain embodiments provides methods of treatment or prevention of a TfR associated disorder, the method comprising the step of administering to a subject (e.g., a patient) in need thereof a therapeutically effective amount of the TfR specific binding compound or pharmaceutical composition comprising a TfR binding compound of the invention, as described herein. As used herein, an "effective amount," a "therapeutically effective amount" or an "effective dose" is an amount of a composition (e.g., a therapeutic composition or agent) that produces at least one desired therapeutic effect in a subject, such as preventing or treating a target condition or beneficially alleviating a symptom associated with the condition.

The most desirable therapeutically effective amount is an amount that will produce a desired efficacy of a particular treatment selected by one of skill in the art for a given subject in need thereof. This amount will vary depending upon a variety of factors understood by the skilled worker, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. See, e.g., Remington: The Science and Practice of Pharmacy 21st Ed., Univ. of Sciences in Philadelphia (USIP), Lippincott Williams & Wilkins, Philadelphia, Pa., 2005.

Additionally, for some embodiments specificity for TfR1 is an important feature for a BBB carrier because off target binding to TfR2 could have undesirable safety and/or PK consequences. The expression of TFR2 is restricted to hepatocytes and erythroid precursors (Silvestri et al., Front Pharmacol. 2014 May 7; 5:93). Interference with transferrin binding to TfR2, which is a component of the erythropoietin receptor complex, could disrupt normal erythropoiesis (Forejtniková et al., Blood. 2010 Dec. 9; 116(24):5357-67). Additionally, high levels of TfR2 expressed in the liver may be responsible for the rapid clearance and short half life of some cross-reacting TfR antibodies (Boado et al., Biotechnol Bioeng. 2009 Mar. 1; 102(4):1251-8). VNAR antibodies to TfR1 are highly specific and exhibit the same long half-life as IgG.

Pharmaceutical Compositions

The present invention further provides pharmaceutical compositions comprising a TfR-specific binding moiety of the invention or compound, or a pharmaceutically acceptable salt or solvate thereof, according to the invention, together with a pharmaceutically acceptable carrier, excipient or vehicle.

Accordingly, the present invention further provides a pharmaceutical composition comprising a TfR-specific binding moiety of the invention or compound comprising a TfR-specific binding moiety, as well as variant and derivative compounds comprising a TfR-specific binding moiety of the invention. Certain embodiments of the pharmaceutical compositions of the invention are described in further detail below.

The present invention also provides pharmaceutical compositions comprising a TfR-specific binding moiety or a TfR-specific binding compound for use in treating, ameliorating or preventing one or more diseases, conditions, disorders or symptoms relating to B cells and immunoglobulin production, as described in further detail below. Each such disease, condition, disorder or symptom is envisioned to be a separate embodiment with respect to uses of a pharmaceutical composition according to the invention.

Formulations, Administration and Dosing

TfR specific binding compounds of the present invention, or salts thereof, may be formulated as pharmaceutical compositions prepared for storage or administration, which typically comprise a therapeutically effective amount of a compound of the invention, or a salt thereof, in a pharmaceutically acceptable carrier.

The therapeutically effective amount of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy, and may depend on such factors as weight, diet, concurrent medication and other factors, well known to those skilled in the medical arts. The dosage sizes and dosing regimen most appropriate for human use may be guided by the results obtained by the present invention, and may be confirmed in properly designed clinical trials.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the skilled person. The term "pharmaceutically acceptable carrier" includes any of the standard pharmaceutical carriers. Pharmaceutically acceptable carriers for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at slightly acidic or physiological pH may be used. pH buffering agents may be phosphate, citrate, acetate, tris/hydroxymethyl)aminomethane (TRIS), N-Tris(hydroxymethyl)methyl-3-aminopropanesulphonic acid (TAPS), ammonium bicarbonate, diethanolamine, histidine, which is a preferred buffer, arginine, lysine, or acetate or mixtures thereof. The term further encompasses any agents listed in the US Pharmacopeia for use in animals, including humans.

The term "pharmaceutically acceptable salt" refers to the salt of the compounds. Salts include pharmaceutically acceptable salts such as acid addition salts and basic salts. Examples of acid addition salts include hydrochloride salts, citrate salts and acetate salts. Examples of basic salts include salts where the cation is selected from alkali metals, such as sodium and potassium, alkaline earth metals such as calcium, and ammonium ions $^+N(R^3)_3(R^4)$, where $R^3$ and $R^4$ independently designate optionally substituted $C_{1-6}$-alkyl, optionally substituted $C_{2-6}$-alkenyl, optionally substituted aryl, or optionally substituted heteroaryl. Other examples of pharmaceutically acceptable salts are described in "Remington's Pharmaceutical Sciences", 17th edition. Ed. Alfonso R. Gennaro (Ed.), Mark Publishing Company, Easton, Pa., U.S.A., 1985 and more recent editions, and in the Encyclopaedia of Pharmaceutical Technology.

"Treatment" is an approach for obtaining beneficial or desired clinical results. For the purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" is an intervention performed with the intention of preventing the development or altering the pathology of a disorder. Accordingly, "treatment" refers to both therapeutic treatment and prophylactic or preventative measures in certain embodiments. Those in need of treatment include those already with the disorder as well as those in which the disorder is to be prevented. By treatment is meant inhibiting or reducing an increase in pathology or symptoms when compared to the absence of treatment, and is not necessarily meant to imply complete cessation of the relevant condition.

The pharmaceutical compositions can be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms. It may be provided in single dose injectable form, for example in the form of a pen. Compositions may be formulated for any suitable route and means of administration.

Pharmaceutically acceptable carriers or diluents include those used in formulations suitable for oral, rectal, nasal or parenteral (including subcutaneous, intramuscular, intravenous, intradermal, and transdermal) administration. The formulations may conveniently be presented in unit dosage form and may be prepared by any of the methods well known in the art of pharmacy. Subcutaneous or transdermal modes of administration may be particularly suitable for the compounds described herein.

An acceptable route of administration may refer to any administration pathway known in the art, including but not limited to aerosol, enteral, nasal, ophthalmic, oral, parenteral, rectal, vaginal, or transdermal (e.g., topical administration of a cream, gel or ointment, or by means of a transdermal patch). "Parenteral administration" is typically associated with injection at or in communication with the intended site of action, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal administration.

In another aspect, the present invention provides a composition, e.g., a pharmaceutical composition, comprising one or a combination of different TfR specific binding compounds of the invention, or a VNAR sequence containing, TfR specific binding region thereof, or an ester, salt or amide of any of the foregoing, and at least one pharmaceutically acceptable carrier. Such compositions may include one or more different BAFF specific binding moieties or compounds in combination to produce an immunoconjugate or multi-specific molecule comprising at least one TfR specific binding moiety. For example, a pharmaceutical composition of the invention may comprise a combination of TfR specific binding moieties which bind to different epitopes of TfR or which otherwise have complementary biological activities.

Pharmaceutical compositions of the invention may be administered alone or in combination with one or more other therapeutic or diagnostic agents. A combination therapy may include a TfR specific binding compound of the present invention combined with at least one other therapeutic agent selected based on the particular patient, disease or condition to be treated. Examples of other such agents include, inter alia, a cytotoxic, anti-cancer or chemotherapeutic agent, an anti-inflammatory or anti-proliferative agent, an antimicrobial or antiviral agent, growth factors, cytokines, an analgesic, a therapeutically active small molecule or polypeptide, a single chain antibody, a classical antibody or fragment thereof, or a nucleic acid molecule which modulates one or more signaling pathways, and similar modulating therapeutics which may complement or otherwise be beneficial in a therapeutic or prophylactic treatment regimen.

As used herein, "pharmaceutically acceptable carrier" includes any and all physiologically acceptable, i.e., compatible, solvents, dispersion media, coatings, antimicrobial agents, isotonic and absorption delaying agents, and the like. In certain embodiments, the carrier is suitable for intravenous, intramuscular, subcutaneous, parenteral, spinal or epidermal administration (e.g., by injection or infusion). Depending on selected route of administration, the TfR specific binding moiety comprising compound or component may be coated in a material or materials intended to protect the compound from the action of acids and other natural inactivating conditions to which the active TfR binding moiety may encounter when administered to a subject by a particular route of administration.

As above, a compound of the invention may encompass one or more pharmaceutically acceptable salts. As used herein a "pharmaceutically acceptable salt" retains qualitatively a desired biological activity of the parent compound without imparting any undesired effects relative to the compound. Examples of pharmaceutically acceptable salts include acid addition salts and base addition salts. Acid addition salts include salts derived from nontoxic inorganic acids, such as hydrochloric, nitric, phosphorous, phosphoric, sulfuric, hydrobromic, hydroiodic and the like, or from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include salts derived from alkaline earth metals, such as sodium, potassium, magnesium, calcium and the like, as well as from nontoxic organic amines, such as N, N'-dibenzylethylenediamine, N-methylglucamine, chloroprocaine, choline, diethanolamine, ethylenediamine, procaine and the like.

A pharmaceutical composition of the invention also optionally includes a pharmaceutically acceptable antioxidant. Exemplary pharmaceutically acceptable antioxidants are water soluble antioxidants such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propylgallate, alpha-tocopherol, and the like; and metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyloleate. Proper fluidity can be maintained, for example, by the use of coating materials, such as lecithin, by the maintenance of the required particle size in the case of dispersions, and by the use of surfactants.

TfR selective binding moieties and compositions may also contain adjuvants such as preservatives, wetting agents, emulsifying agents and dispersing agents. Prevention of presence of microorganisms may be ensured both by sterilization procedures, and by the inclusion of various antibacterial and antifungal agents, for example, paraben, chlorobutanol, phenol sorbic acid, and the like. Isotonic agents, such as sugars, sodium chloride, and the like into the compositions, may also be desirable. In addition, prolonged absorption of the injectable pharmaceutical form may be brought about by the inclusion of agents which delay absorption such as, aluminum monostearate and gelatin.

Exemplary pharmaceutically acceptable carriers include sterile aqueous solutions or dispersions and sterile powders for the extemporaneous preparation of sterile injectable solutions or dispersion. Such media and reagents for pharmaceutically active substances are known in the art. The pharmaceutical compositions of the invention may include any conventional media or agent unless any is incompatible with the active TfR specific binding compound. Supplementary active compounds may further be incorporated into the compositions.

Therapeutic compositions are typically sterile and stable under the conditions of manufacture and storage. The composition may be formulated as a solution, microemulsion, liposome, or other ordered structure suitable to high drug concentration. The carrier may be a solvent or dispersion medium containing, for example, water, alcohol such as ethanol, polyol (e.g., glycerol, propylene glycol, and liquid polyethylene glycol), or any suitable mixtures. The proper fluidity may be maintained, for example, by the use of a coating such as lecithin, by the maintenance of the required particle size in the case of dispersion and by use of surfactants according to formulation chemistry well known in the art. In certain embodiments, isotonic agents, e.g., sugars, polyalcohols such as mannitol, sorbitol, or sodium chloride may be desirable in the composition. Prolonged absorption of injectable compositions may be brought about by including in the composition an agent that delays absorption for example, monostearate salts and gelatin.

Solutions or suspensions used for intradermal or subcutaneous application typically include one or more of: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and tonicity adjusting agents such as, e.g., sodium chloride or dextrose. The pH can be adjusted with acids or bases, such as hydrochloric acid or sodium hydroxide, or buffers with citrate, phosphate, acetate and the like. Such preparations may be enclosed in ampoules, disposable syringes or multiple dose vials made of glass or plastic.

Sterile injectable solutions may be prepared by incorporating a TfR specific binding moiety (or a TfR binding compound comprising such a moiety) in the required amount in an appropriate solvent with one or a combination of ingredients described above, as required, followed by sterilization microfiltration. Dispersions may be prepared by incorporating the active compound into a sterile vehicle that contains a dispersion medium and other ingredients, such as those described above. In the case of sterile powders for the preparation of sterile injectable solutions, the methods of preparation are vacuum drying and freeze-drying (lyophilization) that yield a powder of the active ingredient in addition to any additional desired ingredient from a sterile-filtered solution thereof.

When a therapeutically effective amount of a TfR selective binding moiety or composition of the invention is administered by, e.g., intravenous, cutaneous or subcutaneous injection, the binding agent will be in the form of a pyrogen-free, parenterally acceptable aqueous solution.

Methods for preparing parenterally acceptable protein solutions, taking into consideration appropriate pH, isotonicity, stability, and the like, are within the skill in the art. A preferred pharmaceutical composition for intravenous, cutaneous, or subcutaneous injection will contain, in addition to binding agents, an isotonic vehicle such as sodium chloride injection, Ringer's injection, dextrose injection, dextrose and sodium chloride injection, lactated Ringer's injection, or other vehicle as known in the art. A pharmaceutical composition of the present invention may also contain stabilizers, preservatives, buffers, antioxidants, or other additives well known to those of skill in the art.

The amount of active ingredient which can be combined with a carrier material to produce a single dosage form will vary depending on a variety of factors, including the subject being treated, and the particular mode of administration. In general, it will be an amount of the composition that produces an appropriate therapeutic effect under the particular circumstances. Generally, out of one hundred percent, this amount will range from about 0.01 percent to about ninety-nine percent of active ingredient, from about 0.1 percent to about 70 percent, or from about 1 percent to about 30 percent of active ingredient in combination with a pharmaceutically acceptable carrier.

Dosage regimens may be adjusted to provide the optimum desired response (e.g., a therapeutic response). For example, a single bolus may be administered, several divided doses may be administered over time, or the dose may be proportionally reduced or increased as indicated by the particular circumstances of the therapeutic situation, on a case by case basis. It is especially advantageous to formulate parenteral compositions in dosage unit forms for ease of administration and uniformity of dosage when administered to the subject or patient. As used herein, a dosage unit form refers to physically discrete units suitable as unitary dosages for the subjects to be treated; each unit containing a predetermined quantity of active compound calculated to produce a desired therapeutic effect in association with the required pharmaceutical carrier. The specification for the dosage unit forms of the invention depend on the specific characteristics of the active compound and the particular therapeutic effect(s) to be achieved, taking into consideration and the treatment and sensitivity of any individual patient.

For administration of a TfR selective binding moiety or compound, the dosage range will generally be from about 0.0001 to 100 mg/kg, and more usually 0.01 to 5 mg/kg, of the host body weight. Exemplary dosages may be 0.25 mg/kg body weight, 1 mg/kg body weight, 3 mg/kg body weight, 5 mg/kg body weight or 10 mg/kg body weight or within the range of 1-10 mg/kg. An exemplary treatment regime is a once or twice daily administration, or a once or twice weekly administration, once every two weeks, once every three weeks, once every four weeks, once a month, once every two or three months or once every three to 6 months. Dosages may be selected and readjusted by the skilled health care professional as required to maximize therapeutic benefit for a particular subject, e.g., patient. TfR specific binding compounds will typically be administered on multiple occasions. Intervals between single dosages can be, for example, 2-5 days, weekly, monthly, every two or three months, every six months, or yearly. Intervals between administrations can also be irregular, based on regulating blood levels of TfR specific binding compound to the target TfR ligand in the subject or patient. In some methods, dosage is adjusted to achieve a plasma antagonist concentration of about 1-1000 µg/ml and in some methods about 25-300 µg/ml. Dosage regimens for a TfR specific binding compound of the invention include intravenous administration of 1 mg/kg body weight or 3 mg/kg body weight with the compound administered every two to four weeks for six dosages, then every three months at 3 mg/kg body weight or 1 mg/kg body weight.

In certain embodiments, two or more TfR specific binding compounds with different binding properties may be administered simultaneously or sequentially, in which case the dosage of each administered compound may be adjusted to fall within the ranges described herein.

In certain embodiments, a TfR specific binding compound of the invention may be administered as a sustained release formulation, in which case less frequent administration is required. Dosage and frequency vary depending on the half-life of the TfR specific binding compound in the subject or patient. The dosage and frequency of administration may vary depending on whether the treatment is therapeutic or prophylactic (e.g., preventative), and may be adjusted during the course of treatment. In certain prophylactic applications, a relatively low dosage is administered at relatively infrequent intervals over a relatively long period of time. Some subjects may continue to receive treatment over their lifetime. In certain therapeutic applications, a relatively high dosage at relatively short intervals is sometimes required until progression of the disease is reduced or until the patient shows partial or complete amelioration of symptoms of disease. Thereafter, the patient may be switched to a suitable prophylactic dosing regimen.

Actual dosage levels of the TfR specific binding compound alone or in combination with one or more other active ingredients in the pharmaceutical compositions of the present invention may be varied so as to obtain an amount of the active ingredient which is effective to achieve the desired therapeutic response for a particular patient, composition, and mode of administration, without causing deleterious side effects to the subject or patient. A selected dosage level will depend upon a variety of factors, such as pharmacokinetic factors, including the activity of the particular TfR specific binding compound or composition employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the subject or patient being treated, and similar factors well known in the medical arts.

Administration of a "therapeutically effective dosage" of a TfR-binding compound compound of the invention may result in a decrease in severity of disease symptoms, an increase in frequency and duration of disease symptom-free periods, or a prevention of impairment or disability due to the disease affliction.

A TfR specific binding compound or composition of the present invention may be administered via one or more routes of administration, using one or more of a variety of methods known in the art. As will be appreciated by the skilled worker, the route and/or mode of administration will vary depending upon the desired results. Routes of administration for TfR specific binding compounds or compositions of the invention include, e.g., intravenous, intramuscular, intradermal, intraperitoneal, subcutaneous, spinal or other parenteral routes of administration, for example by injection or infusion. The phrase "parenteral administration" as used herein refers to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrastemal injection and infusion.

In other embodiments, a TfR specific binding compound or composition of the invention may be administered by a non-parenteral route, such as a topical, epidermal or mucosal route of administration, for example, intranasally, orally, vaginally, rectally, sublingually or topically.

As described elsewhere herein, an active TfR specific binding compound may be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compounds or compositions of the invention may be administered with one or more of a variety of medical devices known in the art. For example, in one embodiment, a therapeutic TfR specific binding composition of the invention may be administered with a needleless hypodermic injection device. Examples of well-known implants and modules useful in the present invention are in the art, including e.g., implantable micro-infusion pumps for controlled rate delivery; devices for administering through the skin; infusion pumps for delivery at a precise infusion rate; variable flow implantable infusion devices for continuous drug delivery; and osmotic drug delivery systems. These and other such implants, delivery systems, and modules are known to those skilled in the art.

In certain embodiments, the TfR specific binding compound or composition of the invention may be formulated to ensure a desired distribution in vivo. For example, the blood-brain barrier (BBB) excludes many highly hydrophilic compounds. To target a therapeutic compound or composition of the invention to a particular in vivo location, they can be formulated, for example, in liposomes which may comprise one or more moieties that are selectively transported into specific cells or organs, thus enhancing targeted drug delivery. Exemplary targeting moieties include folate or biotin; mannosides; antibodies; surfactant protein A receptor; p120 and the like.

Kits for Detecting or Quantifying TfR in a Sample

Also within the scope of the invention are kits comprising at least one TfR specific binding moiety or TfR specific binding compound or composition of the invention, and optionally, instructions for use. Kits may be useful for quantifying TfR or TfR specific antibodies in a sample, or may be useful for detection of TfR, such as in diagnostics methods. The kit may further or alternatively comprise at least one nucleic acid encoding a TfR specific binding moiety of the invention. A kit of the invention may optionally comprise at least one additional reagent (e.g., standards, markers and the like). Kits typically include a label indicating the intended use of the contents of the kit. The kit may further comprise reagents and other tools for measuring TfR in a sample or in a subject, or for diagnosing whether a patient belongs to a group that responds to a TfR-specific binding compound which makes use of a compound, composition or related method of the invention as described herein.

Delivery Devices and Further Kits

In certain embodiments, the invention relates to a device comprising one or more TfR specific binding compounds of the invention, or pharmaceutically acceptable salts or solvates thereof, for delivery to a subject. Thus, one or more compounds of the invention or pharmaceutically acceptable salts or solvates thereof can be administered to a patient in accordance with the present invention via a variety of delivery methods, including: intravenous, subcutaneous, intramuscular or intraperitoneal injection; oral administration; transdermal administration; pulmonary or transmucosal administration; administration by implant, osmotic pump, cartridge or micro pump; or by other means recognized by a person of skill in the art.

In some embodiments, the invention relates to a kit comprising one or more peptides, or pharmaceutically acceptable salts or solvates thereof, of the invention. In other embodiments, the kit comprises one or more pharmaceutical compositions comprising one or more peptides or pharmaceutically acceptable salts or solvates thereof. In certain embodiments, the kit further comprises packaging and/or instructions for use.

While some embodiments of the invention have been described by way of illustration, it will be apparent that the invention can be put into practice with many modifications, variations and adaptations, and with the use of numerous equivalents or alternative solutions that are within the scope of persons skilled in the art, without departing from the spirit of the invention or exceeding the scope of the claims.

All publications, patents, and patent applications are herein incorporated by reference in their entirety to the same extent as if each individual publication, patent or patent application was specifically and individually indicated to be incorporated by reference in its entirety.

EXAMPLES

The following examples are directed to combinatorial in vitro and in vivo phage display selection for TfR1-based blood brain barrier penetrating variable new antigen receptor (VNAR) domain antibody fragments from nurse shark. The examples presented herein represent certain embodiments of the present invention. However, it is to be understood that these examples are for illustration purposes only and do not intend, nor should any be construed, to be wholly definitive as to conditions and scope of this invention. The examples were carried out using standard techniques, which are well known and routine to those of skill in the art, except where otherwise described in detail.

Example 1. In Vitro Phage Display for TfR1 Binding VNARs and In Vivo Selection for Blood Brain Barrier Penetrants Recombinant human TfR1 protein was used for in vitro phage display to raise specific VNARs. Two pre-mixed semi-synthetic libraries, OsX-3 and OsX-4 were used. The libraries differed in the framework as well as the length of CDR3 region. OsX-3 and OsX-4 libraries were based on type II and type I nurse shark VNAR sequences, respectively. OsX-3 had mutations introduced to the framework with CDR3 length of 11-18 residues, whereas OsX-4 contained extended CDR3 region with up to 32 residues in length. Two rounds of in vitro phage display selection with fixed 100 nM TfR1 concentration were performed with outputs of $4 \times 10^7$ cfu and $2 \times 10^7$ cfu after first and second round of selection, respectively. The rescued phages from the second round of selection were PEG/NaCl precipitated in preparation for in vivo selection of brain penetrating phages. Although PEG/NaCl precipitation was reported as an efficient method for removal of contaminating DNA and proteins from phages (Branston, Stanley et al. 2012), it was not effective in endotoxin removal. Therefore, the sample was subjected to a subsequent endotoxin removal step using Triton-X114 (Liu, Tobias et al. 1997). The endotoxin removal was crucial to ensure the validity of the in vivo selection of brain penetrating phages because it was previously reported that endotoxin-induced inflammation might increase brain permeability (Shukla, Dikshit et al. 1995, Boje 1996, de Vries, Blom-Roosemalen et al. 1996, Mayhan 1998). The endotoxin level in PEG/NaCl precipitated phage was monitored by LAL assay and showed to be very high >10,000 EU/ml, but was significantly reduced by Triton X-114 treatment to <40 EU/ml (FIG. 3). The titer of phage samples was measured before and after the endotoxin removal process as a function of stability of the phages. The results showed that there was no reduction in the phage titer and infectivity of ER2738 E. coli.

Figure 4:
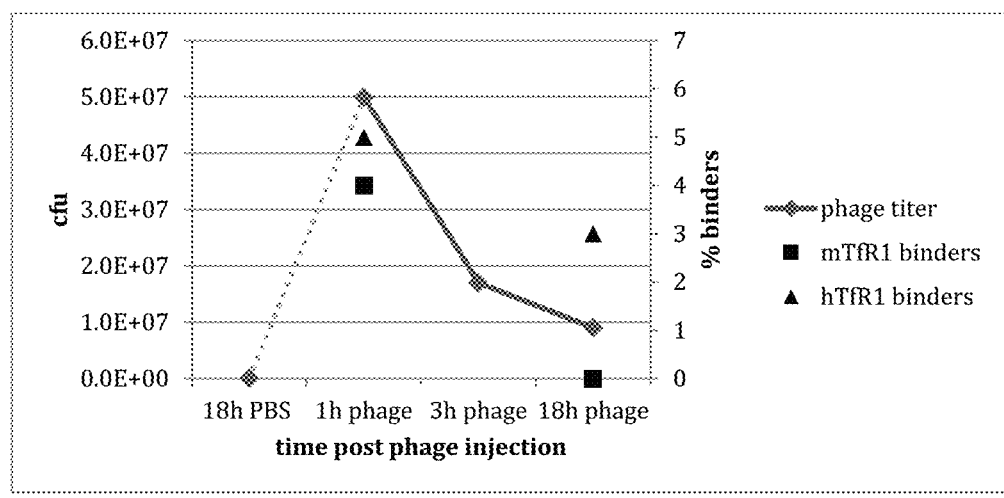
FIG. 4. Effect of time after library injection on phage titre and specific TfR1 binders isolated from brain parenchyma. An aliquot of purified and endotoxin-free phage ($5 \times 10^9$ cfu/injection) after two rounds of panning on human TfR1 was injected into each animal. The brains were extracted 1, 3 or 18 hours post phage injection and following cardiac perfusion. The brain homogenates were separated into parenchymal and capillary fractions by density gradient centrifugation. The parenchymal fraction from 1 mouse per time point was used to infect ER2738 E. coli and the antibiotic resistant colonies were counted to determine the phage output titre (cfu). Approximately 100 clones were randomly picked for 1- and 18-hour time points and binding to human (▲) and mouse (■) TfR1 was assessed by phage ELISA. PBS injection was used as a negative control. A clone was defined as a binder if its signal exceeded four times the background signal.

The in vivo selection for phage displaying VNAR fragments and able to penetrate the blood brain barrier was a novel approach, and to our knowledge only phage peptide libraries have previously been used successfully for in vivo selection of tissue and tumour-homing specific peptides (Pasqualini and Ruoslahti 1996)(Arap, Pasqualini et al. 1998). Preceding the actual selection, the method was optimised for time of brain collection post phage injection. In particular, mice were intravenously injected with purified and endotoxin-free phages, and the brains were collected at different time points 1, 3 and 18 hours post-injection. The phage titers in parenchymal fractions of extracted brains were measured and data showed that the highest level was observed 1 hour post-injection (FIG. 4). PBS injected mice showed no presence of phages. The phage titer gradually decreased with time post-injection. Phages from each time point were further used to infect E. coli cells and individual clones were randomly picked and used in phage ELISA to assess percentage of binders to human and mouse TfR1. Approximately 100 clones were picked for each 1 hour and 18 hour time points. A higher percentage of TfR1 binders was observed at 1 hour post-injection than at 18 hour post-injection and was consistent for both human and mouse TfR1 (FIG. 4). All TfR1 binders were negative for human serum albumin (HSA) binding. Consequently, for the actual in vivo selections, the brains were extracted 1 hour after phage injections.

Figure 5:
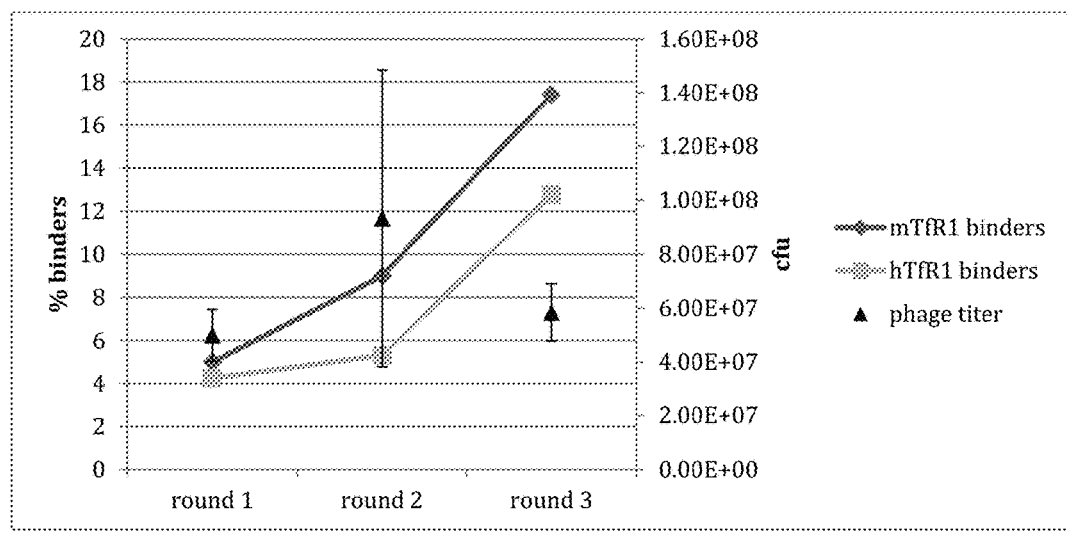
FIG. 5. Percentage of TfR1 binders increased relative to phage titre after multiple rounds of in vivo selection. Phage titre (cfu) was assessed in parenchymal fraction after each round by counting antibiotic resistant colonies (n=3, ±SD). Binding to human (▲) and mouse (■) TfR1 was assessed by phage ELISA. A clone was defined as a binder if its signal exceeded four times the background signal.

Three rounds of in vivo selection were performed in total. Binding to human and mouse TfR1 was monitored using phage ELISA with HSA as a negative control. Over 1000 VNAR clones in total were picked for all rounds and the percentage of binders was assessed for each round (FIG. 5). The percentage of human and mouse TfR1 binders was observed to increase from approximately 5% in round 1 to 13% and 17% in round 3 for human and mouse TfR1, respectively. The phage titer in each round did not change significantly and was in the range of $5 \times 10^7 - 1 \times 10^8$ (FIG. 5).

Phage ELISA was performed not only to assess a number of binders to TfR1 but also to estimate a relative binding strength of the clones defined as binders (four times over the background signal) to the target proteins. It was observed that although the number of binders was increasing in subsequent rounds of selection (FIG. 5), the relative binding assessed as absorbance in phage ELISA was decreasing (FIG. 7). To verify the relative binding data, the experiment was performed at the same time for all clones from all rounds of selection with the same development time allowed for ELISA.

From the phage ELISA experiment, clones that bound to both human and mouse TfR1, and which were negative for mouse TfR2 and HSA binding, were selected and subsequently sequenced. Fifty-four VNAR sequences were retrieved and only two clones were found to be repeated giving a total of 51 unique clones (Tables 1 and 2). Approximately 20% and 80% of them were represented by type I and type II VNARs, respectively These 51 unique clones were further reformatted as bivalent VNAR-Fc by cloning the VNARs into the commercial pFUSE vector (pFUSE-hIgGle3-Fc2). The Fc region of the protein contained CH2 and CH3 domains with the hinge that served as a flexible spacer between the two parts of the Fc-fusion protein. N-termini of the construct contained the IL2 signal sequence to allow secretion. A HEK Expi293 expression system was used to transiently express the proteins. Fifty-one VNAR clones were expressed as Fc formats in small (1 ml) scale in 96-well plates. Media was collected and used directly for ELISA in order to confirm binding to mouse and human TfR1. The expression level was relatively the same amongst different clones with an average concentration of approximately at 21 µg/ml (FIG. 7). Eight clones (1, 2, 7, 10, 11, 12, 16 and 39) were selected as binders for further experiments, but clones 11, 12 and 39 only bound to human and not mouse TfR1. This however might have been a result of lower sensitivity observed for mouse versus human TfR1 ELISA assay. Clone 16 bound to human TfR1 but was shown also to bind non-specifically to control proteins, mouse TfR2 and HSA. All binding clones were of the type II VNAR class (FIG. 7). Only 15% of clones identified to bind as phage retained binding activity in the VNAR-Fc format, although this may have resulted from the higher sensitivity of phage ELISA compared with VNAR-Fc ELISA. This speculation can be partially confirmed by the observation that the best binders in VNAR-Fc ELISA were also performing well in the phage ELISA. Consequently, the correlation analysis of phage and VNAR-Fc ELISA results produced R squared values in the range of >0.4-0.7 and significant p-values (Table 3).

TABLE 3

Pearson correlation analysis of phage and VNAR-Fc ELISA results. P values and R squared values were provided for each human and mouse TfR1

| Pearson correlation | R squared | phage ELISA | | Fc ELISA | |
|---|---|---|---|---|---|
| | | hTfR1 | mTfR1 | hTfR1 | mTfR1 |
| phage ELISA | hTfR1 | | 0.7 | 0.5 | 0.4 |
| | mTfR1 | | | 0.7 | 0.6 |
| VNAR-Fc ELISA | hTfR1 | | | | 0.8 |
| | mTfR1 | | | | |

| Pearson correlation | P value | phage ELISA | | Fc ELISA | |
|---|---|---|---|---|---|
| | | hTfR1 | mTfR1 | hTfR1 | mTfR1 |
| phage ELISA | hTfR1 | | 3E-14 | 9E-09 | 2E-06 |
| | mTfR1 | | | 4E-14 | 1E-12 |
| VNAR-Fc ELISA | hTfR1 | | | | 8E-19 |
| | mTfR1 | | | | |

Example 2. NGS Analysis and Validation of Combinatorial Selection Strategy for TfR1-Based Blood Brain Barrier Penetrants Next generation sequencing (NGS) was used to validate the selection strategy. By sequencing the phage outputs from each round of selection as well as of the starting library, we were able to gain insight into the process of selection and to assess its validity. NGS produced approximately 670,000 to 1,400,000 sequences depending on the sample (Table 4). Unique sequences were gradually reduced with each of the in vitro and in vivo rounds, from approximately 90% to <80%. The reduction of diversity of slightly more than 10% was lower than expected and wasn't confirming the selection process. However, when the abundance of individual clones was tracked, the validity of the selection process became more apparent.

TABLE 4

Quality and complexity analysis of next generation sequencing reads.

|  | OSX3/4 mix | In vitro R1 | In vitro R2 | In vivo R1 | In vivo R2 | In vivo R3 |
|---|---|---|---|---|---|---|
| Total | 819607 | 882241 | 1395033 | 613760 | 947768 | 669022 |
| Total pairs | 728654 | 788468 | 1251675 | 538231 | 835335 | 581122 |
| Total pairs (%) | 88.9 | 89.4 | 89.7 | 87.7 | 88.1 | 86.9 |
| Unique DNAs | 647693 | 718691 | 1046306 | 456986 | 652053 | 452510 |
| Unique DNAs (%) | 88.9 | 91.2 | 83.6 | 84.9 | 78.1 | 77.9 |
| VNARs (%) | 73.2 | 81.7 | 81.2 | 73.3 | 71.1 | 69.2 |
| VNARs no STOP (%) | 96.5 | 97.5 | 97 | 92.3 | 90.7 | 87.4 |

Total represents a number of sequences obtained by NGS, while total pairs is the number of identical sequences obtained by a pair of sequencing primers, also presented as a percentage of the total. Unique DNAs is a number of identified unique sequences, also presented as a percentage of the total pairs. VNARs is a percentage of sequences that retain VNAR germline characteristics in the total pairs group and VNARs no STOP is a percentage of VNAR sequences without stop codons.

The sequences obtained from NGS were grouped into families containing identical CDR3 sequences. The twenty-nine families that showed the highest abundance in the last round of in vivo selection are shown by amino acid sequence in Table 5 and by nucleic acid sequence in Table 6, below. In Table 5, the VNAR Domain amino acid sequences are provided as SEQ ID NOS. 162-190 and the CDR3 regions listed in Table 5 are provided as SEQ ID NOS. 191-219. The CDR1 regions are all repeated from Table 1 and not provided with new SEQ ID NOS. Additionally in Table 5, the sequences of the FW1 regions are represented by amino acids 1-25 of SEQ ID NOS. 162-190; the sequences of the FW2-3 regions are represented by amino acids 33-65 of SEQ ID NOS. 162-190; and the sequences of the FW4 regions are represented by the last 11 amino acids of SEQ ID NOS. 162-190. The VNAR domain having SEQ ID NO. 164 is also interchangeabley referred to herein as clone 10 or as clone C.

TABLE 5

Amino acid sequences of the 29 most abundant VNAR families identified by NGS after the 3$^{rd}$ in vivo round selection.

| # | FW1 | CDR1 | FW2-3 | CDR3 | FW4 | VNAR type | Library |
|---|---|---|---|---|---|---|---|
| 162 | ARVDQTPQTITK ETGESLTINCVLR | DNNCALS | STLWYRTKSGSRNEESISK GGRYVETVNSGSKSFSLRI NDLTVEDSGTYRCNV | QSWPPGNGWWCDV | YGDGTAVTVNA | Type II | OsX-3 |
| 163 | ARVDQTPQTITK ETGESLTINCVLR | DSNCDLS | RTYWYRKKSGSTNEENIS KGGRYVETVNSGSKSFSLR INDLTVEDSGTYRCNV | QSMYGYGWSLDV | YGGGTVVTVNA | Type II | OsX-3 |
| 164 C (10) | ARVDQTPQTITK ETGESLTINCVLR | DSNCALS | STYWYRKKSGSTNEENISK GGRYVETVNSGSKSFSLRI NDLTVEDSGTYRCNV | VQYPSYNNYFWCDV | YGDGTAVTVNA | Type II | OsX-3 |

TABLE 5-continued

Amino acid sequences of the 29 most abundant VNAR families identified by NGS after the 3rd in vivo round selection.

| # | FW1 | CDR1 | FW2-3 | CDR3 | FW4 | VNAR type | Library |
|---|---|---|---|---|---|---|---|
| 165 | ARVDQTPQTITK ETGESLTINCVLR | DSNCALS | NSYWYRKKSGSTNEESISL GGRYVETVNSGSKSFSLRI NDLTVEDSGTYRCNV | GFTHPQICDLTQDV | YGGGTVVTVNA | Type II | OsX-3 |
| 166 | ARVDQTPQTITK ETGESLTINCVLR | DSNCALS | STYWYRKKSGSTNEENISK GGRYVETVNSGSKSFSLRI NDLTVEDSGTYRCNV | QPHCGYHWLDV | YGDGTAVTVNA | Type II | OsX-3 |
| 167 | ARVDQTPQTITK ETGESLTINCVLR | DNNCALS | STLWYRKKSGSTNEENISK GGRYVETVNSGSKSFSLRI NDLTVEDSGTYRCKV | LHSQPQDGCYFSQAVD V | YGDGTAVTVNA | Type II | OsX-3 |
| 168 | ARVDQTPQTITK ETGESLTINCVLR | DSNCALP | STYWYRKKSGSTNEESISL GGRYVETVNSGSKSFSLRI NDLTVEDSGTYRCNV | MQFPGPDNSTWWDV | YGGGTVVTVNA | Type II | OsX-3 |
| 169 | ARVDQTPQTITK ETGESLTINCVLR | DSNCELS | STYWYRKKSGSTNEESISK GGRYVETVNSGSKSFSLRI NDLVVEDSGTYRCNV | QQFPSSSNGRYWCDV | YGGGTAVTVNA | Type II | OsX-3 |
| 170 | ARVDQTPQTITK ETGESLTINCVLR | DSNCALS | STYWYRKKSGSTNEENISK GGRYVETVNSGSKSFSLRI NDLTVEDSGTYRCNV | QFLGFTNSGGYWCDV | YGGGTAVTVNA | Type II | OsX-3 |
| 171 | ARVDQTPQTITK ETGESLTINCVLR | DSNCALP | STYWYRKKSGSTNEESISK GGRYVETVNSGSKSFSLRI NDLTVEDSGTYRCNV | LNWFAYECQRQDV | YGGGTAVTVNA | Type II | OsX-3 |
| 172 | ARVDQTPQTITK ETGESLTINCVLR | DSNCALP | STYWYRKKSGSTNEESISK GGRYVETVNSGSKSFSLRI NDLVVEDSGTYRCKVM | NYFSYTCQWVGDDDV | YGDGTAVTVNA | Type II | OsX-3 |
| 173 | ARVDQTPQTITK ETGESLTINCVLR | DSNCALS | STYWYRKKSGSTNQENIS KGGRYVETVNSGSKSFSLR INDLTVEDSGTYRCNV | KWGSVSNGWLTDV | YGGGTVVTVNA | Type II | OsX-3 |
| 174 | ARVDQTPQTITK QTGESLTINCVLR | DSNCALS | STLWYRTKSGSRNEESISK GGRYVETVNSGSKSFSLKI NDLTVEDSGTYRCNV | NYRCCGLQDV | YGGGTAVTVNA | Type II | OsX-3 |
| 175 | ARVDQTPQTITK ETGESLTINCVLR | DSNCELS | STYWYRKKSGSTNEARISK GGRYVETVNSGSKSFSLRI NDLTVEDSGTYRCNV | QRMYCAMANDV | YGGGTVVTVNA | Type II | OsX-3 |
| 176 | ARVDQTPQTITK ETGESLTINCVLR | DSNCALP | STYWYRKKSGSTNEESISK GGRYVETVNSGSKSFSLRI NDLTVKDSGTYRCNV | FGVQNCNDGLMWSDV | YGDGTAVTVNA | Type II | OsX-3 |
| 177 | ARVDQTPQTITK ETGESLTINCVLR | DSNCALS | NSYWYRKKSGSTNEENIS KGGRYVETVNSGSKSFSLK INDLTVEDSGTYRCNV | GYFMGCHPQGDV | YGDGTAVTVNA | Type II | OsX-3 |
| 178 | ARVDQTPQTITK ETGESLTINCVLR | DSNCALP | STYWYRKKSGSTNEESISK GGRYVETVNSGSKSFSLRI NDLTVEDSGTYRCNV | WVSQVCNYDAGSYDV | YGGGTVVTVNA | Type II | OsX-3 |
| 179 | ARVDQTPQTITK ETGESLTINCVLR | DNNCALS | STYWYRKKSDSTNEESISK GGRYVETVNSGSKSFSLRI NDLTVEDSGTYRCNV | QHFNNNWWCDV | YGGGTVVTVNA | Type II | OsX-3 |
| 180 | ARVDQTPQTITK ETGESLTINCVLR | DSNCALS | NSYWYRKKSGSTNEESISL GGRYVETVNSGSKSFSLRI NDLTVEDSGTYRCNV | QVHPQAACGQHLDV | YGGGTAVTVNA | Type II | OsX-3 |
| 181 | ARVDQTPQTITK ETGESLTINCVLR | DNNCALS | TTYWYRKKSGSTNEENISK GGRYVETVNSGSKSFSLKI NDLTVEDSGTYRCNV | PVLAQQICQPLDV | YGDSTAVTVNA | Type II | OsX-3 |
| 182 | ARVDQTPQTITK ETGESLTINCVLR | DSNCALS | NSYWYRKKSGSTNEESISL GGRYVETVNSGSKSFSLKI NDLTVEDSGTYRCNV | QCYEECCNRRYDV | YGGGTAVTVNA | Type II | OsX-3 |

TABLE 5-continued

Amino acid sequences of the 29 most abundant VNAR families identified by NGS after the 3rd in vivo round selection.

| # | FW1 | CDR1 | FW2-3 | CDR3 | FW4 | VNAR type | Library |
|---|-----|------|-------|------|-----|-----------|---------|
| 183 | ARVDQTPQTITK ETGESLTINCVLR | DSNCALS | NSYWYRKKSGSTNEESISK GGRYVETVNSGSKSFSLRI NDLTVEDSGTYRCNV | FVQGSRGGLDV | YGGGTAVTVNA | Type II | OsX-3 |
| 184 | ARVDQTPQTITK ETGESLTINCVLR | DNNCALS | TTYWYRKKSDSTNEESISK GGRYVETVNSGSKSFSLRI NDLTVEDSGTYRCNV | QQIGNNWWCDV | YGGGTAVTVNA | Type II | OsX-3 |
| 185 | ARVDQTPQTITK ETGESLTINCVLR | DSNCALS | STYWYRKKSDSTNEESISK GGRYVETVNSGSKSFSLRI NDLTVEDSGTYRCNV | VQWPGVYNDFWCDV | YGGGTAVTVNA | Type II | OsX-3 |
| 186 | ARVDQTPQTITK ETGESLTINCVLR | DSNCALS | STYWYRKKSGSTNEENISK GGRYVETVNSGSKSFSLKI NDLTVEDSGTYRCNVRDV | QACGNDWVWLDV | YGGGTVVTVNA | Type II | OsX-3 |
| 187 | ARVDQTPQTITK ETGESLTINCVLR | DSNCALP | STYWYRKKSGSTNEESISK GGRYVETVNSGSKSFSLRI NDLTVKDSGTYRCKV | SVDTPDCWQCCDWPLP DV | YGDGTAVTVNA | Type II | OsX-3 |
| 188 | ARVDQTPQTITK ETGESLTINCVLR | DSNCALP | STYWYRKKSGSTNEESISK GGRYVETVNSGSKSFSLRI NDLTVKDSGTYRCNV | CVSFQESGDTQRDV | YGDGTAVTVNA | Type II | OsX-3 |
| 189 | ARVDQTPQTITK ETGESLTINCVLR | DSNCALS | STYWYRKKSGSTNEESISK GGRYVETVNSGSKSFSLRI NDLTVKDSGTYRCNV | GKQGQCDWYGDV | YGGGTVVTVNA | Type II | OsX-3 |
| 190 | ARVDQTPQTITK ETGESLTINCVLR | DSNCALS | STYWYRKKSDSTNEESISK GGRYVETVNSGSKSFSLRI NDLTVEDSGTYRCNV | VQSTCLRYGDV | YGGGTAVTVNA | Type II | OsX-3 |

TABLE 6

Corresponding DNA sequences of the 29 most abundant VNAR families identified by NGS shown in Table 4.

| # | DNA sequences |
|---|---------------|
| 220 | GCCAGGGTGGACCAGACCCCCCAGACCATCACCAAGGAGACCGGCGAGAGCCTGACCATC<br>AACTGCGTGCTGAGGGACAACAACTGCGCCCTGAGCAGCACCCTGTGGTACAGGACCAAG<br>AGCGGCAGCAGGAACGAGGAGAGCATCAGCAAGGGCGGCAGGTACGTGGAGACCGTGAAC<br>AGCGGCAGCAAGAGCTTCAGCCTGAGGATCAACGACCTGACCGTGGAGGACAGCGGCACC<br>TACAGGTGCAACGTGCAGAGCTGGCCCCCCGGCAACGGCTGGTGGTGCGACGTGTACGGC<br>GACGGCACCGCCGTGACCGTGAACGCC |
| 221 | GCCAGGGTGGACCAGACCCCCCAGACCATCACCAAGGAGACCGGCGAGAGCCTGACCATC<br>AACTGCGTGCTGAGGGACAGCAACTGCGACCTGAGCAGGACCTACTGGTACAGGAAGAAG<br>AGCGGCAGCACCAACGAGGAGAACATCAGCAAGGGCGGCAGGTACGTGGAGACCGTGAAC<br>AGCGGCAGCAAGAGCTTCAGCCTGAGGATCAACGACCTGACCGTGGAGGACAGCGGCACC<br>TACAGGTGCAACGTGCAGAGCATGTACGTGGGCTACGGCTGGAGCCTGGACGTGTACGGC<br>GGCGGCACCGTGGTGACCGTGAACGCC |
| 222 C (10) | GCCAGGGTGGACCAGACCCCCCAGACCATCACCAAGGAGACCGGCGAGAGCCTGACCATC<br>AACTGCGTGCTGAGGGACAGCAACTGCGCCCTGAGCAGCACCCTACTGGTACAGGAAGAAG<br>AGCGGCAGCACCAACGAGGAGAACATCAGCAAGGGCGGCAGGTACGTGGAGACCGTGAAC |

TABLE 6-continued

Corresponding DNA sequences of the 29 most abundant VNAR families identified by NGS shown in Table 4.

| # | DNA sequences |
|---|---|
|   | AGCGGCAGCAAGAGCTTCAGCCTGAGGATCAACGACCTGACCGTGGAGGACAGC |
|   | GGCACC |
|   | TACAGGTGCAACGTGGTGCAGTACCCCAGCTACAACAACTACTTCTGGTGCGAC |
|   | GTGTAC |
|   | GGCGACGGCACCGCCGTGACCGTGAACGCC |
| 223 | GCCAGGGTGGACCAGACCCCCCAGACCATCACCAAGGAGACCGGCGAGAGCCTG |
|   | ACCATC |
|   | AACTGCGTGCTGAGGGACAGCAACTGCGCCCTGAGCAACAGCTACTGGTACAGG |
|   | AAGAAG |
|   | AGCGGCAGCACCAACGAGGAGAGCATCAGCCTGGGCGGCAGGTACGTGGAGACC |
|   | GTGAAC |
|   | AGCGGCAGCAAGAGCTTCAGCCTGAGGATCAACGACCTGACCGTGGAGGACAGC |
|   | GGCACC |
|   | TACAGGTGCAACGTGGGCTTCACCCACCCCCAGATCTGCGACCTGACCCAGGAC |
|   | GTGTAC |
|   | GGCGGCGGCACCGTGGTGACCGTGAACGCC |
| 224 | GCCAGGGTGGACCAGACCCCCCAGACCATCACCAAGGAGACCGGCGAGAGCCTG |
|   | ACCATC |
|   | AACTGCGTGCTGAGGGACAGCAACTGCGCCCTGAGCAGCACCTACTGGTACAGG |
|   | AAGAAG |
|   | AGCGGCAGCACCAACGAGGAGAACATCAGCAAGGGCGGCAGGTACGTGGAGACC |
|   | GTGAAC |
|   | AGCGGCAGCAAGAGCTTCAGCCTGAGGATCAACGACCTGACCGTGGAGGACAGC |
|   | GGCACC |
|   | TACAGGTGCAACGTGCAGCCCCACTGCGGCTACCACTGGCTGGACGTGTACGGC |
|   | GACGGC |
|   | ACCGCCGTGACCGTGAACGCC |
| 225 | GCCAGGGTGGACCAGACCCCCCAGACCATCACCAAGGAGACCGGCGAGAGCCTG |
|   | ACCATC |
|   | AACTGCGTGCTGAGGGACAACAACTGCGCCCTGAGCAGCACCCTGTGGTACAGG |
|   | AAGAAG |
|   | AGCGGCAGCACCAACGAGGAGAACATCAGCAAGGGCGGCAGGTACGTGGAGACC |
|   | GTGAAC |
|   | AGCGGCAGCAAGAGCTTCAGCCTGAGGATCAACGACCTGACCGTGGAGGACAGC |
|   | GGCACC |
|   | TACAGGTGCAAGGTGCTGCACAGCCAGCCCCAGGACGGCTGCTACTTCAGCCAG |
|   | GCCGTG |
|   | GACGTGTACGGCGACGGCACCGCCGTGACCGTGAACGCC |
| 226 | GCCAGGGTGGACCAGACCCCCCAGACCATCACCAAGGAGACCGGCGAGAGCCTG |
|   | ACCATC |
|   | AACTGCGTGCTGAGGGACAGCAACTGCGCCCTGCCCAGCACCTACTGGTACAGG |
|   | AAGAAG |
|   | AGCGGCAGCACCAACGAGGAGAGCATCAGCCTGGGCGGCAGGTACGTGGAGACC |
|   | GTGAAC |
|   | AGCGGCAGCAAGAGCTTCAGCCTGAGGATCAACGACCTGACCGTGGAGGACAGC |
|   | GGCACC |
|   | TACAGGTGCAACGTGATGCAGTTCCCCGGCCCCGACAACAGCACCTGGTGGGAC |
|   | GTGTAC |
|   | GGCGGCGGCACCGTGGTGACCGTGAACGCC |
| 227 | GCCAGGGTGGACCAGACCCCCCAGACCATCACCAAGGAGACCGGCGAGAGCCTG |
|   | ACCATC |
|   | AACTGCGTGCTGAGGGACAGCAACTGCGAGCTGAGCAGCACCTACTGGTACAGG |
|   | AAGAAG |
|   | AGCGGCAGCACCAACGAGGAGAGCATCAGCAAGGGCGGCAGGTACGTGGAGACC |
|   | GTGAAC |
|   | AGCGGCAGCAAGAGCTTCAGCCTGAGGATCAACGACCTGGTGGTGGAGGACAGC |
|   | GGCACC |
|   | TACAGGTGCAACGTGCAGCAGTTCCCCAGCAGCAGCAACGGCAGGTACTGGTGC |
|   | GACGTG |
|   | TACGGCGGCGGCACCGCCGTGACCGTGAACGCC |
| 228 | GCCAGGGTGGACCAGACCCCCCAGACCATCACCAAGGAGACCGGCGAGAGCCTG |
|   | ACCATC |
|   | AACTGCGTGCTGAGGGACAGCAACTGCGCCCTGAGCAGCACCTACTGGTACAGG |
|   | AAGAAG |
|   | AGCGGCAGCACCAACGAGGAGAACATCAGCAAGGGCGGCAGGTACGTGGAGACC |
|   | GTGAAC |
|   | AGCGGCAGCAAGAGCTTCAGCCTGAGGATCAACGACCTGACCGTGGAGGACAGC |
|   | GGCACC |

TABLE 6-continued

Corresponding DNA sequences of the 29 most abundant VNAR families identified by NGS shown in Table 4.

| # | DNA sequences |
|---|---|
| | TACAGGTGCAACGTGCAGTTCCTGGGCTTCACCAACAGCGGCGGCTACTGGTGCGACGTG<br>TACGGCGGCGGCACCGCCGTGACCGTGAACGCC |
| 229 | GCCAGGGTGGACCAGACCCCCCAGACCATCACCAAGGAGACCGGCGAGAGCCTGACCATC<br>AACTGCGTGCTGAGGGACAGCAACTGCGCCCTGCCCAGCACCTACTGGTACAGGAAGAAG<br>AGCGGCAGCACCAACGAGGAGAGCATCAGCAAGGGCGGCAGGTACGTGGAGACCGTGAAC<br>AGCGGCAGCAAGAGCTTCAGCCTGAGGATCAACGACCTGACCGTGGAGGACAGCGGCACC<br>TACAGGTGCAACGTGCTGAACTGGTTCGCCTACGAGTGCCAGAGGCAGGACGTGTACGGC<br>GGCGGCACCGCCGTGACCGTGAACGCC |
| 230 | GCCAGGGTGGACCAGACCCCCCAGACCATCACCAAGGAGACCGGCGAGAGCCTGACCATC<br>AACTGCGTGCTGAGGGACAGCAACTGCGCCCTGCCCAGCACCTACTGGTACAGGAAGAAG<br>AGCGGCAGCACCAACGAGGAGAGCATCAGCAAGGGCGGCAGGTACGTGGAGACCGTGAAC<br>AGCGGCAGCAAGAGCTTCAGCCTGAGGATCAACGACCTGGTGGTGGAGGACAGCGGCACC<br>TACAGGTGCAAGGTGATGAACTACTTCAGCTACACCTGCCAGTGGGTGGGCGACGACGAC<br>GTGTACGGCGACGGCACCGCCGTGACCGTGAACGCC |
| 231 | GCCAGGGTGGACCAGACCCCCCAGACCATCACCAAGGAGACCGGCGAGAGCCTGACCATC<br>AACTGCGTGCTGAGGGACAGCAACTGCGCCCTGAGCAGCACCTACTGGTACAGGAAGAAG<br>AGCGGCAGCACCAACCAGGAGAACATCAGCAAGGGCGGCAGGTACGTGGAGACCGTGAAC<br>AGCGGCAGCAAGAGCTTCAGCCTGAGGATCAACGACCTGACCGTGGAGGACAGCGGCACC<br>TACAGGTGCAACGTGAAGTGGGGCAGCGTGAGCAACGGCTGGCTGACCGACGTGTACGGC<br>GACGGCACCGTGGTGACCGTGAACGCC |
| 232 | GCCAGGGTGGACCAGACCCCCCAGACCATCACCAAGCAGACCGGCGAGAGCCTGACCATC<br>AACTGCGTGCTGAGGGACAGCAACTGCGCCCTGAGCAGCACCCTGTGGTACAGGACCAAG<br>AGCGGCAGCAGGAACGAGGAGAGCATCAGCAAGGGCGGCAGGTACGTGGAGACCGTGAAC<br>AGCGGCAGCAAGAGCTTCAGCCTGAAGATCAACGACCTGACCGTGGAGGACAGCGGCACC<br>TACAGGTGCAACGTGAACTACAGGTGCTGCGGCCTGCAGGACGTGTACGGCGGCGGCACC<br>GCCGTGACCGTGAACGCC |
| 233 | GCCAGGGTGGACCAGACCCCCCAGACCATCACCAAGGAGACCGGCGAGAGCCTGACCATC<br>AACTGCGTGCTGAGGGACAGCAACTGCGAGCTGAGCAGCACCTACTGGTACAGGAAGAAG<br>AGCGGCAGCACCAACGAGGCCAGGATCAGCAAGGGCGGCAGGTACGTGGAGACCGTGAAC<br>AGCGGCAGCAAGAGCTTCAGCCTGAGGATCAACGACCTGACCGTGGAGGACAGCGGCACC<br>TACAGGTGCAACGTGCAGAGGATGTACTGCGCCATGGCCAACGACGTGTACGGCGGCGGC<br>ACCGTGGTGACCGTGAACGCC |
| 234 | GCCAGGGTGGACCAGACCCCCCAGACCATCACCAAGGAGACCGGCGAGAGCCTGACCATC<br>AACTGCGTGCTGAGGGACAGCAACTGCGCCCTGCCCAGCACCTACTGGTACAGGAAGAAG<br>AGCGGCAGCACCAACGAGGAGAGCATCAGCAAGGGCGGCAGGTACGTGGAGACCGTGAAC<br>AGCGGCAGCAAGAGCTTCAGCCTGAGGATCAACGACCTGACCGTGAAGGACAGCGGCACC<br>TACAGGTGCAACGTGTTCGGCGTGCAGAACTGCAACGACGGCCTGATGTGGAGCGACGTG |

TABLE 6-continued

Corresponding DNA sequences of the 29 most abundant VNAR families identified by NGS shown in Table 4.

| # | DNA sequences |
|---|---|
|  | TACGGCGACGGCACCGCCGTGACCGTGAACGCC |
| 235 | GCCAGGGTGGACCAGACCCCCCAGACCATCACCAAGGAGACCGGCGAGAGCCTG<br>ACCATC<br>AACTGCGTGCTGAGGGACAGCAACTGCGCCCTGAGCAACAGCTACTGGTACAGG<br>AAGAAG<br>AGCGGCAGCACCAACGAGGAGAACATCAGCAAGGGCGGCAGGTACGTGGAGACC<br>GTGAAC<br>AGCGGCAGCAAGAGCTTCAGCCTGAAGATCAACGACCTGACCGTGGAGGACAGC<br>GGCACC<br>TACAGGTGCAACGTGGGCTACTTCATGGGCTGCCACCCCCAGGGCGACGTGTAC<br>GGCGAC<br>GGCACCGCCGTGACCGTGAACGCC |
| 236 | GCCAGGGTGGACCAGACCCCCCAGACCATCACCAAGGAGACCGGCGAGAGCCTG<br>ACCATC<br>AACTGCGTGCTGAGGGACAGCAACTGCGCCCTGCCCAGCACCTACTGGTACAGG<br>AAGAAG<br>AGCGGCAGCACCAACGAGGAGAGCATCAGCAAGGGCGGCAGGTACGTGGAGACC<br>GTGAAC<br>AGCGGCAGCAAGAGCTTCAGCCTGAGGATCAACGACCTGACCGTGGAGGACAGC<br>GGCACC<br>TACAGGTGCAACGTGTGGGTGAGCCAGGTGTGCAACTACGACGCCGGCAGCTAC<br>GACGTG<br>TACGGCGGCGGCACCGTGGTGACCGTGAACGCC |
| 237 | GCCAGGGTGGACCAGACCCCCCAGACCATCACCAAGGAGACCGGCGAGAGCCTG<br>ACCATC<br>AACTGCGTGCTGAGGGACAACAACTGCGCCCTGAGCAGCACCTACTGGTACAGG<br>AAGAAG<br>AGCGACAGCACCAACGAGGAGAGCATCAGCAAGGGCGGCAGGTACGTGGAGACC<br>GTGAAC<br>AGCGGCAGCAAGAGCTTCAGCCTGAGGATCAACGACCTGACCGTGGAGGACAGC<br>GGCACC<br>TACAGGTGCAACGTGCAGCACTTCAACAACAACTGGTGGTGCGACGTGTACGGC<br>GGCGGC<br>ACCGTGGTGACCGTGAACGCC |
| 238 | GCCAGGGTGGACCAGACCCCCCAGACCATCACCAAGGAGACCGGCGAGAGCCTG<br>ACCATC<br>AACTGCGTGCTGAGGGACAGCAACTGCGCCCTGAGCAACAGCTACTGGTACAGG<br>AAGAAG<br>AGCGGCAGCACCAACGAGGAGAGCATCAGCCTGGGCGGCAGGTACGTGGAGACC<br>GTGAAC<br>AGCGGCAGCAAGAGCTTCAGCCTGAGGATCAACGACCTGACCGTGGAGGACAGC<br>GGCACC<br>TACAGGTGCAACGTGCAGGTGCACCCCCAGGCCGCCTGCGGCCAGCACCTGGAC<br>GTGTAC<br>GGCGGCGGCACCGCCGTGACCGTGAACGCC |
| 239 | GCCAGGGTGGACCAGACCCCCCAGACCATCACCAAGGAGACCGGCGAGAGCCTG<br>ACCATC<br>AACTGCGTGCTGAGGGACAACAACTGCGCCCTGAGCACCACCTACTGGTACAGG<br>AAGAAG<br>AGCGGCAGCACCAACGAGGAGAACATCAGCAAGGGCGGCAGGTACGTGGAGACC<br>GTGAAC<br>AGCGGCAGCAAGAGCTTCAGCCTGAAGATCAACGACCTGACCGTGGAGGACAGC<br>GGCACC<br>TACAGGTGCAACGTGCCCGTGCTGGCCCAGCAGATCTGCCAGCCCCTGGACGTG<br>TACGGC<br>GACAGCACCGCCGTGACCGTGAACGCC |
| 240 | GCCAGGGTGGACCAGACCCCCCAGACCATCACCAAGGAGACCGGCGAGAGCCTG<br>ACCATC<br>AACTGCGTGCTGAGGGACAGCAACTGCGCCCTGAGCAACAGCTACTGGTACAGG<br>AAGAAG<br>AGCGGCAGCACCAACGAGGAGAGCATCAGCCTGGGCGGCAGGTACGTGGAGACC<br>GTGAAC<br>AGCGGCAGCAAGAGCTTCAGCCTGAAGATCAACGACCTGACCGTGGAGGACAGC<br>GGCACC<br>TACAGGTGCAACGTGCAGTGCTACGAGGAGTGCTGCAACAGGAGGTACGACGTG<br>TACGGC<br>GGCGGCACCGCCGTGACCGTGAACGCC |

TABLE 6-continued

Corresponding DNA sequences of the 29 most abundant VNAR families identified by NGS shown in Table 4.

| # | DNA sequences |
|---|---|
| 241 | GCCAGGGTGGACCAGACCCCCCAGACCATCACCAAGGAGACCGGCGAGAGCCTG<br>ACCATC<br>AACTGCGTGCTGAGGGACAGCAACTGCGCCCTGAGCAACAGCTACTGGTACAGG<br>AAGAAG<br>AGCGGCAGCACCAACGAGGAGAGCATCAGCAAGGGCGGCAGGTACGTGGAGACC<br>GTGAAC<br>AGCGGCAGCAAGAGCTTCAGCCTGAGGATCAACGACCTGACCGTGGAGGACAGC<br>GGCACC<br>TACAGGTGCAACGTGTTCGTGCAGGGCAGCGGCAGGGGCGGCCTGGACGTGTAC<br>GGCGGC<br>GGCACCGCCGTGACCGTGAACGCC |
| 242 | GCCAGGGTGGACCAGACCCCCCAGACCATCACCAAGGAGACCGGCGAGAGCCTG<br>ACCATC<br>AACTGCGTGCTGAGGGACAACAACTGCGCCCTGAGCACCACCTACTGGTACAGG<br>AAGAAG<br>AGCGACAGCACCAACGAGGAGAGCATCAGCAAGGGCGGCAGGTACGTGGAGACC<br>GTGAAC<br>AGCGGCAGCAAGAGCTTCAGCCTGAGGATCAACGACCTGACCGTGGAGGACAGC<br>GGCACC<br>TACAGGTGCAACGTGCAGCAGATCGGCAACAACTGGTGGTGCGACGTGTACGGC<br>GGCGGC<br>ACCGCCGTGACCGTGAACGCC |
| 243 | GCCAGGGTGGACCAGACCCCCCAGACCATCACCAAGGAGACCGGCGAGAGCCTG<br>ACCATC<br>AACTGCGTGCTGAGGGACAGCAACTGCGCCCTGAGCAGCACCTACTGGTACAGG<br>AAGAAG<br>AGCGACAGCACCAACGAGGAGAGCATCAGCAAGGGCGGCAGGTACGTGGAGACC<br>GTGAAC<br>AGCGGCAGCAAGAGCTTCAGCCTGAGGATCAACGACCTGACCGTGGAGGACAGC<br>GGCACC<br>TACAGGTGCAACGTGGTGCAGTGGCCCGGCGTGTACAACGACTTCTGGTGCGAC<br>GTGTAC<br>GGCGGCGGCACCGCCGTGACCGTGAACGCC |
| 244 | GCCAGGGTGGACCAGACCCCCCAGACCATCACCAAGGAGACCGGCGAGAGCCTG<br>ACCATC<br>AACTGCGTGCTGAGGGACAGCAACTGCGCCCTGAGCAGCACCTACTGGTACAGG<br>AAGAAG<br>AGCGGCAGCACCAACGAGGAGAACATCAGCAAGGGCGGCAGGTACGTGGAGACC<br>GTGAAC<br>AGCGGCAGCAAGAGCTTCAGCCTGAAGATCAACGACCTGACCGTGGAGGACAGC<br>GGCACC<br>TACAGGTGCAACGTGAGGGACGTGCAGGCCTGCGGCAACGACTGGGTGTGGCTG<br>GACGTG<br>TACGGCGGCGGCACCGTGGTGACCGTGAACGCC |
| 245 | GCCAGGGTGGACCAGACCCCCCAGACCATCACCAAGGAGACCGGCGAGAGCCTG<br>ACCATC<br>AACTGCGTGCTGAGGGACAGCAACTGCGCCCTGCCCAGCACCTACTGGTACAGG<br>AAGAAG<br>AGCGGCAGCACCAACGAGGAGAGCATCAGCAAGGGCGGCAGGTACGTGGAGACC<br>GTGAAC<br>AGCGGCAGCAAGAGCTTCAGCCTGAGGATCAACGACCTGACCGTGAAGGACAGC<br>GGCACC<br>TACAGGTGCAAGGTGAGCGTGGACACCCCCGACTGCTGGCAGTGCTGCGACTGG<br>CCCCTG<br>CCCGACGTGTACGGCGACGGCACCGCCGTGACCGTGAACGCC |
| 246 | GCCAGGGTGGACCAGACCCCCCAGACCATCACCAAGGAGACCGGCGAGAGCCTG<br>ACCATC<br>AACTGCGTGCTGAGGGACAGCAACTGCGCCCTGCCCAGCACCTACTGGTACAGG<br>AAGAAG<br>AGCGGCAGCACCAACGAGGAGAGCATCAGCAAGGGCGGCAGGTACGTGGAGACC<br>GTGAAC<br>AGCGGCAGCAAGAGCTTCAGCCTGAGGATCAACGACCTGACCGTGAAGGACAGC<br>GGCACC<br>TACAGGTGCAACGTGTGCGTGAGCTTCCAGGAGAGCGGCGACACCCAGAGGGAC<br>GTGTAC<br>GGCGACGGCACCGCCGTGACCGTGAACGCC |
| 247 | GCCAGGGTGGACCAGACCCCCCAGACCATCACCAAGGAGACCGGCGAGAGCCTG<br>ACCATC |

TABLE 6-continued

Corresponding DNA sequences of the 29 most abundant VNAR
families identified by NGS shown in Table 4.

| # | DNA sequences |
|---|---|
|  | AACTGCGTGCTGAGGGACAGCAACTGCGCCCTGAGCAGCACCTACTGGTACAGG<br>AAGAAG<br>AGCGGCAGCACCAACGAGGAGAGCATCAGCAAGGGCGGCAGGTACGTGGAGACC<br>GTGAAC<br>AGCGGCAGCAAGAGCTTCAGCCTGAGGATCAACGACCTGACCGTGAAGGACAGC<br>GGCACC<br>TACAGGTGCAACGTGGGCAAGCAGGGCCAGTGCGACTGGTACGGCGACGTGTAC<br>GGCGGC<br>GGCACCGTGGTGACCGTGAACGCC |
| 248 | GCCAGGGTGGACCAGACCCCCCAGACCATCACCAAGGAGACCGGCGAGAGCCTG<br>ACCATC<br>AACTGCGTGCTGAGGGACAGCAACTGCGCCCTGAGCAGCACCTACTGGTACAGG<br>AAGAAG<br>AGCGACAGCACCAACGAGGAGAGCATCAGCAAGGGCGGCAGGTACGTGGAGACC<br>GTGAAC<br>AGCGGCAGCAAGAGCTTCAGCCTGAGGATCAACGACCTGACCGTGGAGGACAGC<br>GGCACC<br>TACAGGTGCAACGTGGTGCAGAGCACCTGCCTGAGGTACGGCGACGTGTACGGC<br>GGCGGC<br>ACCGCCGTGACCGTGAACGCC |

The high abundance sequences shown in Tables 4 and 5 were back tracked for their abundance in the previous rounds. In general, the data showed that clones selected in in vivo stage for brain penetration had been initially amplified in an in vitro stage where TfR1 was used as a target protein for phage display (FIG. 8). Interestingly, previously identified clone 10 (see FIGS. 6 and 7) was found by NGS analysis to be the third best VNAR. When the family of clone 10 was deconvoluted, we identified 242 sequences that contained minor sequence alterations but shared the same CDR3 (VVQYPSYNNYFWCDV; SEQ ID NO. 249). One sequence was dominant and was responsible for driving the abundance trend but other sequences generally were following the same trend (FIG. 9). To further validate the selection strategy, we looked at clones ungrouped by CDR3 raw sequencing data and this time selected the twenty most abundant sequences after only the in vitro stage. These were then tracked for the abundance in the subsequent rounds of in vivo selection for brain penetration (FIG. 10). Interestingly, a majority of the clones that showed amplification in the in vitro stage had a decreasing trend in the in vivo stage. These results suggested that binding affinity to TfR1 alone was not enough to confer brain penetration by phages. When we looked at the twenty most abundant sequences in the starting library, we identified some clones that were overrepresented. This overrepresentation was, however, reduced in both the in vitro selection stage and also in the in vivo stage (FIG. 11). Put together, NGS analysis showed that the applied phage display combinatorial selection strategy was generating trends expected for the selection of TfR1-dependent, blood brain barrier traversing VNARs.

NGS data show that the most abundant phage clones in round 3 of the in vivo selection were also being amplified in the in vitro stage, suggesting binding to human TfR1 that was used as target for phage display (see FIG. 8). However, only clone 10 which was identified by colony picking followed by phage and VNAR-Fc ELISAs as a TfR1 binder was also found by the NGS abundance analysis. The results consequently may suggest that these phage clones were penetrating blood brain barrier utilising other than TfR1 as vehicle. In order to verify these speculations, the top ten VNARs from the NGS abundance analyses were synthesised and cloned into a pFUSE vector, as before (FIG. 12). All ten VNARs were of type II and were originating from the OsX-3 library. These VNAR-Fc formatted molecules were expressed using Expi293 expression system, purified and tested at equal (100 nM) concentrations in a VNAR-Fc ELISA for binding to human and mouse TfR1.

Example 3. Assessment of Blood Brain Barrier Penetration by Selected VNAR-Fc Formatted Constructs All eight clones that were found by colony picking and then confirmed by binding to TfR1 as VNAR-Fcs were further tested in animal experiments for their blood brain barrier penetration ability. Five animals per group were used. Mice were intravenously injected with 25 nmol/kg (approximately 2 mg/kg) of purified VNAR-Fc constructs and the brains were collected 18 hours post injection. The whole brains were homogenised in 1% Triton X-100 and used for ELISA with anti-Fc capture and detection antibody. Standard curves were prepared individually for each of the molecules to assure accuracy of the calculated concentrations. In total, two separate experiments were performed to cover all eight constructs. Control VNAR-Fc that binds at nM concentration to TfR1 but lacks a blood brain penetration property was used as negative control. Clone 10 showed over 10-fold higher signal than the negative control reaching 5 nM concentration in the whole brain tissue and was repeated in both experiments. Clones 2 and 39 showed a small, approximately 2-fold increase over the control (FIG. 13).

Figure 11B:
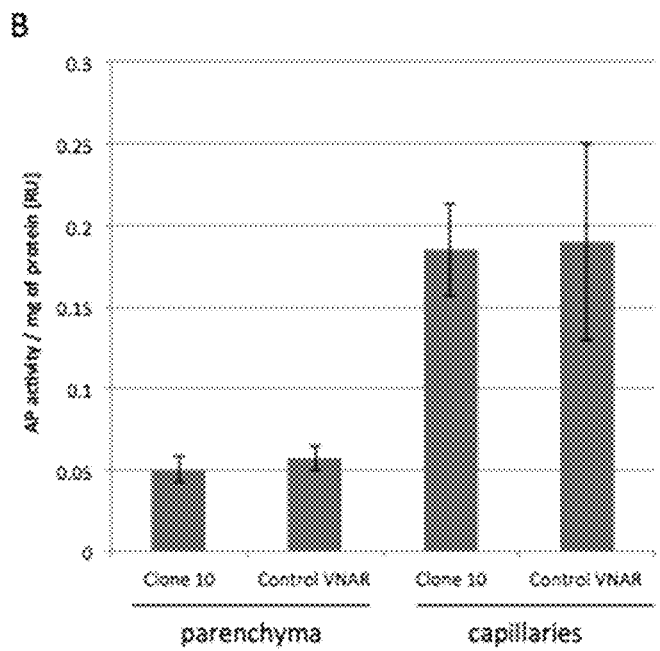

The measurement of VNAR-Fc concentration levels in the whole brain does not necessarily proving blood brain barrier penetration because, as reported previously, some TfR1 binders might be retained in the capillaries rather than traversing into the parenchyma (Moos and Morgan 2001, Yu, Zhang et al. 2011, Alata, Paris-Robidas et al. 2014). In order to ensure the blood brain barrier crossing, the brain fractionation for capillary endothelium and parenchymal fractions were performed as it was done during the in vivo phage selection. The experiment was performed with five animals per group and intravenous injection of 25 nmol/kg (approximately 2 mg/kg) of VNAR-Fc constructs. The brains were collected 18 hours post injection. Fractionation for capillary and parenchymal fractions was performed followed by assessment of alkaline phosphatase (AP) activity that has epithelial cell localisation (Williams, Gillis et al. 1980). Although there was some cross-fractional contamination, the fractionation method resulted in a 4-fold increase in AP activity in capillaries versus parenchyma (FIG. 11B). Taken together, these results make clear that clone 10 was successfully transported through the blood brain barrier and not restricted to the capillaries.

It has been previously reported that TfR1 based blood brain barrier transporters can have safety liabilities, namely acute clinical signs as well as decreasing circulating reticulocytes that have high expression of TfR1. These toxic effects were resulting from the Fc portion of the molecule used and were triggering ADCC and CDC mediated immune responses which were ameliorated after Fc effector functions were eliminated (Couch, Yu et al. 2013). In order to reduce immune system recruitment and adverse reactions, the Fc portion of the hIgG1e3 construct that was used was engineered to contain numerus mutations (E233P/L234V/L235A/$\Delta$G236+A327G/A330S/P331S) and greatly reduced ADCC and CDC (Armour, Clark et al. 1999, Shields, Namenuk et al. 2001). To assess the safety of clone 10, the quantitative analysis of reticulocytes in mice injected with 25 nmol/kg and 250 nmol/kg (approximately 2 mg/kg and 20 mg/kg) was performed. Five mice per group were used and blood was collected 18 hours post injection. Blood sample were stained with Thiazole Orange in order to differentiate reticulocytes from mature red cells, analysed using flow cytometry and the data were presented as the percentage of reticulocytes in the total number of red cells. There was no observable reduction in reticulocytes in the blood of animals injected with 25 nmol/kg of either control VNAR-Fc that binds to TfR1 but didn't penetrate blood brain barrier or of clone 10 (FIG. 12). Increasing the concentration of clone 10 by ten-fold did not affect reticulocyte count, assuring the safety of the used construct.

Example 4. Affinity Assessment of VNAR-Fc Constructs

It was previously reported that affinity might play a crucial role in TfR1 mediated brain penetration. Advantageous penetration was observed for low affinity molecules with KD of 600 nM in comparison to their high affinity variants with KD of 20 nM (Yu, Zhang et al. 2011, Bien-Ly, Yu et al. 2014). Affinity estimation and unspecific binding was initially assessed using ELISA for human and mouse TfR1. The EC50 values for human and mouse TfR1 were at the range of 1E-9M-1E-6M and 1E-8M-1E-6M, respectively (FIG. 13). Control VNAR that was previously found to bind to TfR1 at known nM KD was used as a control and confirmed the accuracy of the assay in terms of affinity estimation. Clone 10 and clone 1 as well as the control VNAR showed the highest affinity at 1E-9M and 1E-8M for human and mouse TfR1, respectively. Except for clone 16, there was no cross-reactivity with mouse TfR2 and no binding to control protein, HSA.

To gain precise kinetic data, surface plasmon resonance (SPR) technique was used for the selected clones, namely 10, 2, 1, 39 and the control VNAR. Single cycle kinetic SPR method was used with immobilised human or mouse TfR1 and used to assess binding kinetics of clones 1, 2, 10 and 39 formatted as VNAR-Fcs. A VNAR of known nM binding to TfR1 was used as an internal control. VNAR-Fc constructs were injected in five sequentially increasing concentrations reaching a maximum at the concentration of 250 nM. Clone 10 was the highest affinity binder with a KD of 400 pM for mouse and 500 pM for human TfR1, with other clones following with low nM KDs (Table 7).

Binding kinetics of selected VNAR-Fcs to mouse TfR1 at pH 7.2 and pH 6.0 was measured by SPR (Octet). Mouse TfR1 (10 µg/ml) was immobilised on anti-His biosensors and the binding kinetics of VNAR-Fcs and 8D3 antibody (10 nM) was measured at pH 7.2 and pH 6.0 in phosphate buffered saline (PBS) (Table 8).

TABLE 7

Binding kinetics of selected VNAR-Fcs to mouse and human TfR1.

| | human TfR1 | | | mouse TfR1 | | |
|---|---|---|---|---|---|---|
| | ka (1/Ms) | kd (1/s) | KD (M) | ka (1/Ms) | kd (1/s) | KD (M) |
| Clone 1 | 6.60E+04 | 1.23E−04 | 1.87E−09 | 7.47E+04 | 2.50E−04 | 3.34E−09 |
| Clone 2 | 1.90E+05 | 4.45E−04 | 2.34E−09 | 1.95E+05 | 5.01E−04 | 2.56E−09 |
| Clone 10 | 3.06E+05 | 1.60E−04 | 5.23E−10 | 2.85E+05 | 1.16E−04 | 4.08E−10 |
| Clone 39 | 9.47E+04 | 6.84E−04 | 7.22E−09 | 1.61E+05 | 2.94E−03 | 1.83E−08 |
| F02 | 1.13E+05 | 1.10E−04 | 9.69E−10 | 1.09E+05 | 1.60E−04 | 1.46E−09 |

TABLE 8

Binding kinetics of selected VNAR-Fcs to mouse TfR1 at pH 7.2 and pH 6.

| Sample ID | pH | ka (1/Ms) | kd (1/s) | KD (M) |
|---|---|---|---|---|
| Clone 1 | 7.20 | 8.04E+05 | 2.92E−04 | 3.63E−10 |
| | 6.00 | 6.66E+05 | 3.60E−04 | 5.41E−10 |
| Clone 10 | 7.20 | 6.30E+05 | 4.43E−05 | 7.03E−11 |
| | 6.00 | 7.15E+05 | 3.00E−04 | 4.19E−10 |
| 8D3 | 7.20 | 5.91E+05 | 1.31E−04 | 2.21E−10 |
| | 6.00 | 5.11E+05 | 1.26E−04 | 2.47E−10 |
| F02 | 7.20 | 3.35E+05 | 9.86E−05 | 2.94E−10 |
| | 6.00 | 4.26E+05 | 1.47E−04 | 3.44E−10 |

Figure 14A:
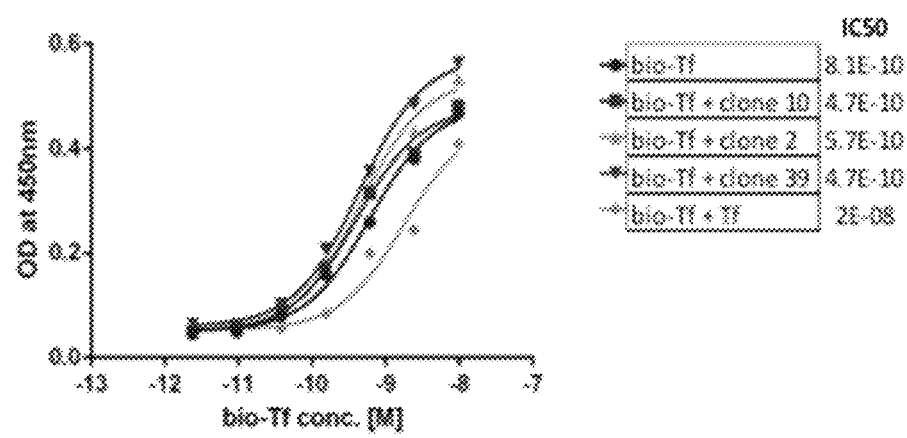
FIGS. 14A and 14B. Competition assay between VNAR-Fcs and Tf for binding to human TfR1. ELISA plates were coated with 100 µl of 5 µg/ml of recombinant human TfR1. Plates were then pre-incubated with biotinylated transferrin (Tf) at the concentration ranging from pM to µM before VNAR-Fc proteins or Tf were added at 2.44 nM concentration. Streptavidin was used to detect biotinylated Tf (A) and anti-human Fc antibody was used to detect VNAR-Fcs (B) and 4-parametric logistic curve was used to fit the data.
Figure 14B:
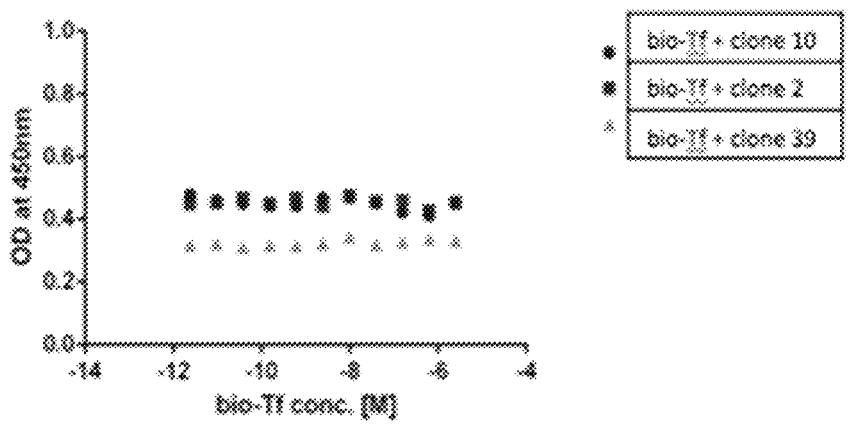

Some TfR1 binders might present the undesirable property of competing with transferrin (Tf) for the binding site to TfR1 consequently affecting ion transport into the cells. Therefore, clones 10, 2 and 39 were further tested for whether they compete with transferrin for binding to TfR1. Biotinylated-Tf was added with increasing concentrations while the VNAR-Fc concentration was held constant. None of the tested clones competed with Tf for the binding site in human TfR1 (FIG. 14A). Non-biotinylated Tf was used as a positive control to compete with biotinylated Tf and (unlike the tested VNAR-Fc constructs) it reduced EC50 from 8.1E-10M to 2E-8M. Under the same conditions, the binding of Tf to TfR1 did not affect the binding of the VNAR-Fcs at another site on the receptor (FIG. 14B).

Figures 15A, 15B:
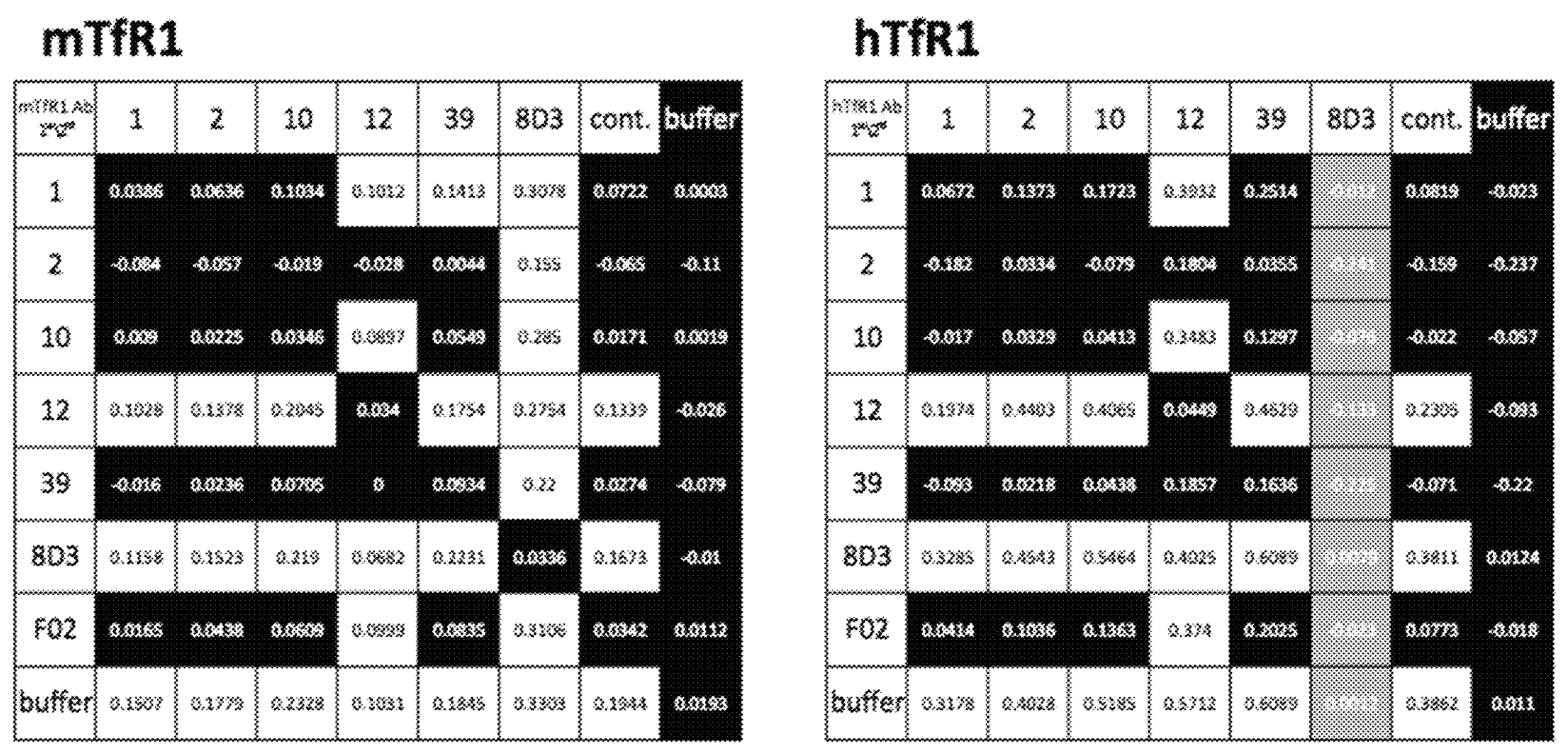

Example 5: Additional Assessments of VNAR-Fc Constructs Identified Using In Vivo Phage Display Selection Methods A series of biochemical parameters was examined to further characterize the panel VNAR to TfR1 obtained from in vivo phage display selections. Epitope binning experiments were performed to assess whether the VNARs could compete against each other for binding to either the mouse or human TfR1. A VNAR identified from an earlier in vitro selection campaign, which had been epitope mapped by chemical crosslinking and mass spectrometry (cited $1^{st}$ provisional), was used for comparison along with the mouse-specific 8D3 monoclonal antibody to TfR (Lee, Engelhardt et al. 2000). Epitope binning showed that clones 1, 2, 10 and 39 shared a similar epitope on human and mouse TfR1, whereas clone 12 had a unique binding epitope (FIG. 15). 8D3 also bound to a unique epitope on mouse TfR1 and did not bind human TfR1. Surprisingly, clone 10 also competed for the same or an overlapping epitope on TfR1 as clone F02, which binds to a highly conserved alpha-helix in the apical domain of the receptor. Because each VNAR binds via a unique CDR3 region with a different structural topography, steric interactions could be important efficient transcytosis.

Additional biophysical features were investigated to identify other characteristics that could provide an advantage for BBB transport. It has been previously reported that low affinity binding (~600 nm) was required for the transport of a monoclonal antibody from the capillary endothelium into the brain (Yu et al., Sci Transl Med. 2011 May 25; 3(84): 84ra44). On the contrary, all of the VNARs identified by in vivo phage display were tight binders, as shown by low nM to pM binding affinities (Table 7) and clone 10, which had the highest brain uptake and was transported to the brain parenchyma (FIG. 10), had the highest affinity binding to TfR1 (~500 pM). These data indicate that the properties required for BBB transport of the monoclonal antibody described by Yu et al., which bind to a mouse-specific epitope, are distinctly different from those required for BBB transport of clone 10.

It has also been suggested that pH sensitivity might play a role in TfR1 mediated blood-brain barrier antibody transport. Using an in vitro model system (Sade et al., PLoS One. 2014 Apr. 30; 9(4):e96340), an antibody with reduced affinity at pH 5.5 showed significant transcytosis, while two other pH-independent antibodies of comparable affinities at pH 7.4 were associated with vesicles targeted for degradation. To assess the role of pH-dependence in VNAR binding, the affinity of three VNAR clones competing for the same epitope (clones 1, 10 and F02) in addition to the 8D3 antibody was compared at pH 7.2 and pH 6.0. The kinetic data showed no or very little change in association rate for the tested VNARs under the two pH conditions for the antibodies tested (Table 8). As the dissociation rates at pH 6.0 were all very similar, it is unlikely that endosomal release at low pH explains the enhanced brain uptake of clone 10. Rather, the major difference between clone 10 and the other antibodies was its higher affinity and dissociation rate at pH 7.2.

Figure 16A:
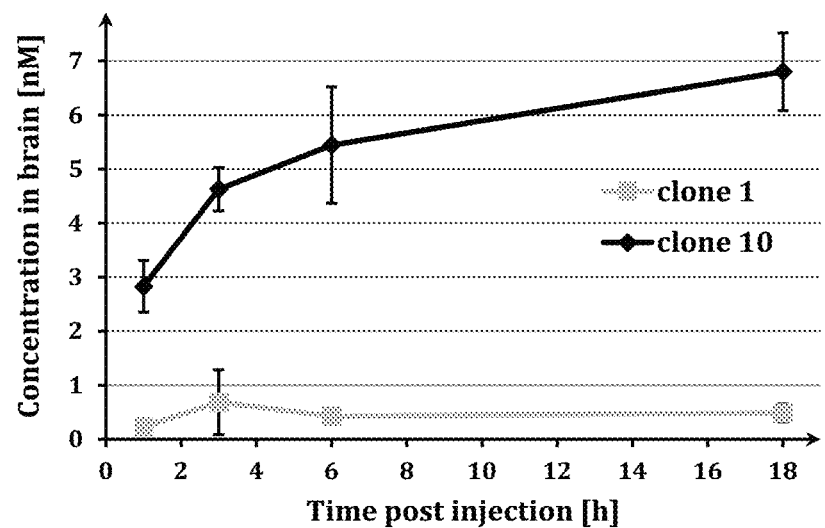
FIGS. 16A and 16B. Time-dependent brain uptake of clone 10 as an Fc fusion protein compared to clone 1. Mice were sacrificed at different times points after tail vein injection of either clone 10 (black) or clone 1 (grey) at 25 nmol/kg (~2 mg/kg). Brains were harvested following cardiac perfusion and homogenised in 1% Triton X-100. VNAR-hFc concentrations were determined in whole brain extracts (A) and plasma (B) using a sandwich ELISA to detect human Fc (mean ±SD, N=5).
Figure 16B:
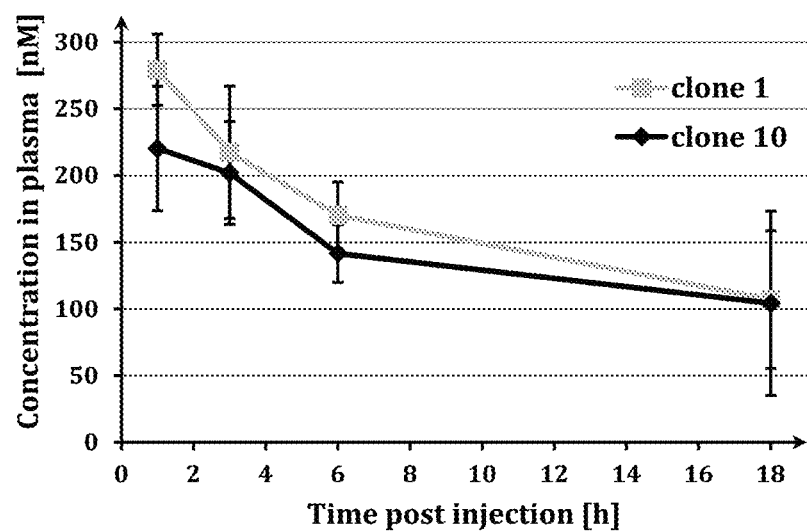

The pharmacokinetic activity of clone 10 formatted as a bivalent VNAR-Fc fusion protein was evaluated in mice. Brain and plasma concentrations were measured a 4 time points over an 18-hr period after a single IV injection of 25 nmol/kg (~2 mg/kg). Brain uptake of clone 10-Fc was rapid and significantly higher than clone 1-Fc at 1-hr after injection and it continued to rise over an 18-hr time course reaching a concentration of 7 nM in the brain homogenate (FIG. 16). The effective concentration of the antibody would be approximately 8-times higher in the brain extracellular fluid, which constitutes only about 12-15% of the brain homogenate (Wolak & Thorne, Mol. Pharmaceutics 2013, 10, 1492-1504).

To evaluate the dose-response, mice were injected IV with four different doses of the same two VNAR-Fc fusion proteins ranging from 2.5 to 100 nmol/kg (~0.2 to 8 mg/kg) and brain uptake was measured 18 hours later. While the plasma levels of clone 1-Fc and clone 10-Fc fusions were nearly identical at each dose, the brain uptake of clone 10 was dramatically higher (FIG. 17) and appeared biphasic with a steeper slope at lower doses. This pattern is consistent with TfR1 receptor saturation between 10 and 25 nmol/kg (~1-2 mg/kg), as previously reported for other high affinity antibodies to the TfR (Lee et al., J Pharmacol Exp Ther. 2000 March; 292(3):1048-52). However, brain levels continue to escalate with higher doses due to a combination of active, receptor-mediated transport and passive, non-specific transport, which is apparent at higher dose of the comparator clone 1-Fc. Thus, the relative fold-increase of clone 10-Fc over clone 1-Fc progressively decreases with increasing dose due to the linear increase in passive transport of clone 1-Fc (decreases from 35-fold at the lowest dose to 8-fold at the highest dose).

Example 6: VNAR-Mediated In Vivo Transport of a Therapeutic Antibody Across the Blood Brain Barrier To test the ability of clone 10 to carry a therapeutic antibody across the BBB, it was fused to a functional antibody against CD20 (rituximab) to create ten different bispecific molecules (FIG. 18), including monovalent and bivalent versions as N- or C-terminal fusions. Each bispecific format was injected into mice at the standard test concentration of 25 nmol/kg (corresponding to 4 mg/kg of unmodified rituximab antibody) and uptake in perfused brain was measured 18 hours later. Of these, Fc1N (monovalent) and scFv2N (bivalent) molecules, both N-terminal fusions, showed the best brain uptake producing over an 11-fold increase over unmodified rituximab (FIG. 19). Two other N-terminal bispecific formats produced approximately 5-fold increase over the unmodified antibody. C-terminal fusions showed poor brain penetration with HC2C and scFv2C averaging a 2-fold increase whereas the others were similar to unmodified rituximab. Plasma levels for all of the constructs were in the range of 50-170 nM, which did not account for the dramatic difference in brain uptake between the various formats.

The binding affinity (Table 9) and EC50 (Table 10) values for mouse and human TfR1 were determined for the various clone 10-rituximab formats, as shown below.

TABLE 9

Single-cycle SPR analysis (Biacore) of binding kinetics of rituximab-clone 10 in different formats to mouse and human TfR1.

| Clone 10-Rituximab | human TfR1 | | | mouse TfR1 | | |
|---|---|---|---|---|---|---|
| | ka (1/Ms) | kd (1/s) | KD (M) | ka (1/Ms) | kd (1/s) | KD (M) |
| Fc1N | 2.3E+04 | 1.6E−04 | 6.9E−09 | 4.2E+04 | 3.7E−04 | 8.8E−09 |
| Fc1C | 7.3E+03 | 3.2E−04 | 4.4E−08 | 9.2E+04 | 2.7E−03 | 2.9E−08 |
| HC1N | 3.4E+04 | 3.4E−04 | 1.0E−08 | 7.5E+04 | 9.4E−04 | 1.3E−08 |
| HC1C | 1.1E+04 | 4.9E−04 | 4.5E−08 | 6.6E+04 | 2.4E−03 | 3.6E−08 |
| HC2N | 3.1E+05 | 2.5E−04 | 8.2E−10 | 3.7E+05 | 1.3E−04 | 3.5E−10 |
| HC2C | 4.3E+04 | 2.0E−04 | 4.6E−09 | 4.8E+04 | 1.4E−04 | 3.0E−09 |
| LC2N | 2.9E+05 | 4.0E−04 | 1.4E−09 | 2.4E+05 | 1.8E−04 | 7.2E−10 |
| LC2C | 2.5E+04 | 2.4E−04 | 9.5E−09 | 2.9E+04 | 2.1E−04 | 7.4E−09 |

TABLE 10

Binding EC50s to mouse TfR1 of rituximab-clone 10 formats as determined by ELISA.

| Rituximab-clone 10 formats | mouse TfR1 EC50 [M] |
|---|---|
| Fc1N | 2.28E−08 |
| Fc1C | 1.288E−07 |
| HC1N | 4.13E−08 |
| HC1C | 1.111E−07 |
| HC2N | 1.46E−09 |
| HC2C | 7.21E−09 |
| LC2N | 2.07E−09 |
| LC2C | 1.79E−08 |
| scFv2N | 1.75E−08 |
| scFv2C | 5.06E−09 |

EC50 values showed a close linear correlation with KD values obtained by Biacore (FIG. 20, inset). The bispecific formats had a relatively high affinity for the TfR1 receptor by either measure, with KDs ranging from 350 pM to 45 nM and the EC50s ranging from 1.5 to 130 nM. The monovalent versions had lower affinities than the bivalent versions and the close correlation between binding to the mouse and human receptors was retained for all the rituximab bispecific formats. The poor performance of the C-terminal fusion does not appear to be related to affinity for the receptor in vitro, which does not rule out steric interference with receptor binding in the capillary endothelium in vivo.

KD and EC50 values were also plotted against the brain uptake as fold-increase over naked rituximab (FIG. 20). The data showed no linear and relatively poor logarithmic correlation between affinity to mouse TfR1 and brain uptake. This stands in contrast to a previous report showing an inverse correlation between TfR binding and brain uptake for a bispecific antibody to TfR/BACE1 (Yu et al., Sci Transl Med. 2011 May 25; 3(84):84ra44). Low affinity TfR binding (~600 nM) was associated with the highest brain uptake whereas we found that VNAR with the highest brain uptake had sub-nanomolar binding affinity. The benefit of a high affinity BBB carrier is that biological levels can be achieved at lower doses, few side effects and lower cost than a low affinity antibody, which requires higher doses for receptor mediated transport. The reason for this difference between the two TfR carriers is not yet clear, but may be related to the unique epitope and binding mode of the VNAR relative to IgG.

Rituximab targets the CD20 antigen expressed on the surface of pre-B and mature B-lymphocytes and can lyse cells by both complement-dependent cytotoxicity (CDC) and antibody-dependent, cell-mediated cytotoxicity (ADCC) pathways. However, afucosylated anti-CD20 antibodies were shown to have greater ADCC and B-cell depletion than rituximab (Gasdaska et al., Mol Immunol. 2012 March; 50(3):134-41), particularly in the brain (Abdelwahed et al., Invest Ophthalmol Vis Sci. 2013 May 1; 54(5):3657-65). Therefore, the rituximab-clone 10 fusion proteins were produced in an expressor cell line defective in fucose biosynthesis to increase ADCC. Brain-penetrant formats were tested for ADCC and CDC using CD20 expressing Raji cells. Low-fucose rituximab (Gx) showed a 3-fold increased ADCC compared to rituximab (FIG. 21) and two of the three formats tested (HC2N-Gx and Fc1N-Gx) retained ADCC whereas the LC2N format lost this activity. In the CDC assay, the activity of rituximab-Gx and LC2N format bispecific were similar to unmodified rituximab whereas the activity of the HC2N and Fc1N formats was much reduced (FIG. 22). The higher ADCC and B-cell depletion suggest a potential improvement in efficacy, while lower CDC may mitigate infusion toxicity as previously reported (Gasdaska et al., Mol Immunol. 2012 March; 50(3):134-41).

To further explore the duration of brain exposure of a rituximab(Gx)-clone 10 bispecific, a single dose was 25 nmol/kg dose of the Fc1N format (equivalent to 4 mg/kg IgG) was administered by tail vein injection and brain and plasma levels were monitored over a 6-day period (FIG. 23). The plasma levels fell rapidly during the initial biodistribution phase and then flattened during the elimination phase with a terminal half-life of approximately four days. Brain uptake was rapid and peaked at approximately 24 hours after injection and had a half-life of approximately five days in the brain. Preliminary PK measures will assist with multiple dosing schedules for animal efficacy studies. However, the brain exposure would be considerably greater in humans as the serum half-life of IgG is about 20 days.

Figure 25A:
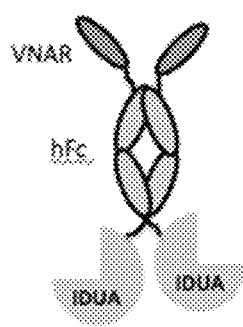
FIGS. 25A and 25B. Brain uptake of iduronidase (IDUA) fused to a VNAR-hFc. Clone 1 and clone 10 VNAR-Fcs fused to IDUA were purified from CHO cells (A, schematic). Mice were sacrificed 18 hours after tail vein injection of IDUA fused to either clone 1 or clone 10 at 20 nmol/kg (5 mg/kg). Brains were harvested following cardiac perfusion and homogenised in 1% Triton X-100. VNAR-hFc concentrations were determined in whole brain extracts (B, top) and plasma (B, bottom) by a sandwich ELISA to detect human Fc (mean ±SD, N=4).
Figure 25B:
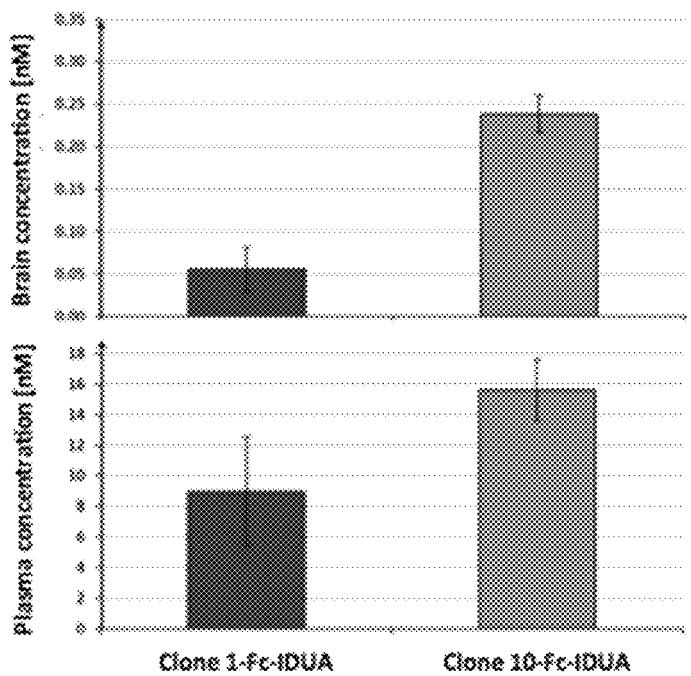

To test whether the clone 10 is capable of carrying different large molecules other than monoclonal antibodies into the brain, a prototype VNAR-Fc-enzyme fusion was constructed (FIG. 25A). Alpha-L-iduronidase (IDUA) is an enzyme found in lysosomes that is responsible for the degradation of glycosaminogly cans. A deficiency in the IDUA leads to the progressive accumulation of dermatan and heparan sulfate causing severe metabolic disturbances and early death. Although patients have been successfully treated with enzyme replacement therapy, it is not expected to treat or prevent neurological deterioration due to poor BBB penetration. IDUA can be delivered to the CSF by intrathecal lumbar injection and may improve symptoms but this route of administration carries a significant risk of adverse events (Munoz-Rojas et al., Am J Med Genet A. 2008 Oct. 1; 146A(19):2538-44; Dickson et al., Mol Genet Metab, 2015 September-October; 116(1-2):69-74).

Figure 24:
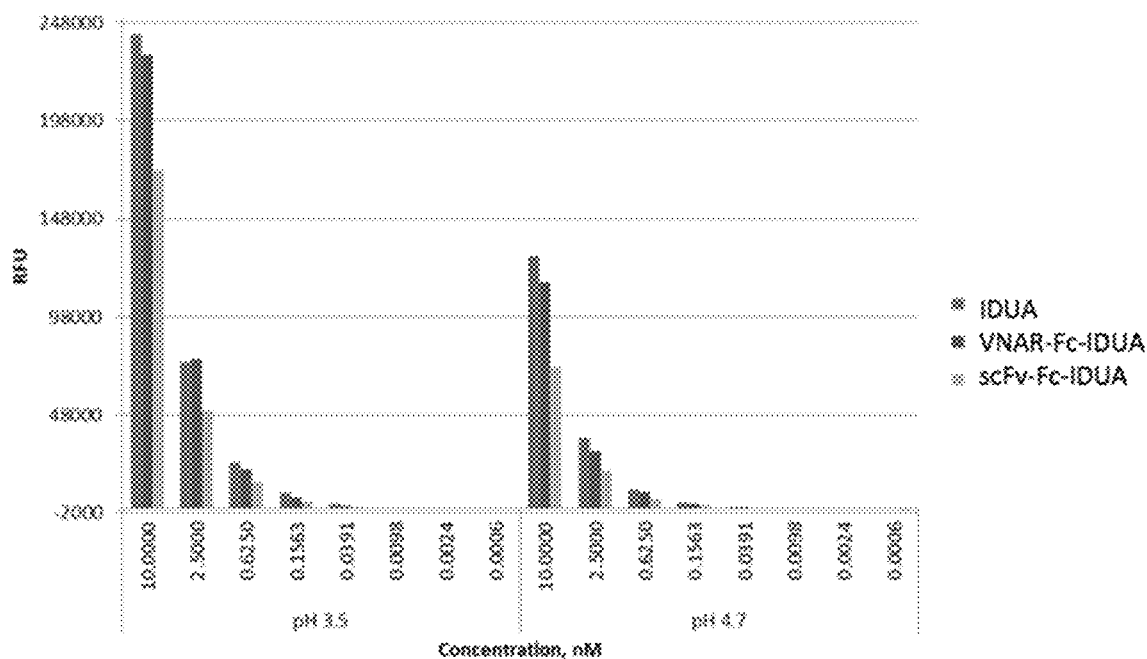
FIG. 24. Enzymatic activity of recombinant IDUA, VNAR-Fc-IDUA fusion, and anti-TfR(scFv)-IDUA fusion. Recombinant IDUA, VNAR-Fc-IDUA fusion, and anti-TfR (scFv)-IDUA fusion were expressed in expi 293F cells, purified by affinity chromatography and tested for enzymatic activity. Various concentrations of the proteins were incubated in the buffers of pH 3.5 or 4.7 with 4-methylumbelliferyl-alpha-L-iduronide for 60 min. After neutralization of the reaction mixture, the fluorescence of released 4-methylumbelliferone was measured at λex=365 nm and λem=445 nm.

To evaluate whether VNARs could carry IUDA into the brain, the clone 1 and clone 10 were engineered as VNAR-Fc-IDUA fusion protein was produced in CHO cells. VNAR-Fc-IDUA fusions bound mouse TfR1 with the same potency (EC50) as the VNAR-Fc as measured by ELISA (Table 11) and IDUA fusion proteins retained the full activity of the recombinant enzyme (FIG. 24). Brain and plasma concentrations of IDUA fused to either clone 1 or clone 10 at 20 nmol/kg (5 mg/kg) was measured 18 hours after IV injection (FIG. 25B). Relative to the plasma concentration the levels of clone 10 were higher than clone 1, although the levels of the IDUA fused to clone 10-Fc are much lower than clone 10-IgG fusions. IDUA-VNAR-Fc fusion proteins were detectable in brain 18 hours later, which suggests that brain uptake may be biologically relevant given the very short half-life (~2 hr) in mice after IV injection (Garcia et al., Mol Genet Metab. 2007 June; 91(2):183-90).

TABLE 11

Binding EC50s to mouse TfR1 of VNAR-hFc or IDUA-VNAR-hFc formats as determined by ELISA.

| VNAR formats | mouse TfR1 EC50 [M] |
| --- | --- |
| Control 1-hFc | 4.82856E−09 |
| Clone 10-hFc | 2.95881E−09 |
| IDUA-clone 1-hFc | 7.24399E−09 |
| IDUA-clone 10-hFc | 8.32831E−09 |

Example 6: Additional Methods

Phage Display for Selection of TfR1 Binding VNARs

Two semi-synthetic libraries OsX-3 and OsX-4 have been previously described and are based on type II and type I nurse shark VNAR sequences, respectively. The libraries included framework mutations (OsX-3) as well as CDR3 randomisation (OsX-3 and OsX-4). Modified pSEX81 (Progen) plasmid was used for M13-based phage display (Hasler, Flajnik et al. 2016). Recombinant human TfR1 (Sino Biological, 11020-H07H) protein was biotinylated using Sulfo-NHS-Biotin EZ-Link kit (Thermo, 21326) and subsequently used at 100 nM concentration in two rounds of soluble phase in vitro selection (Griffiths, Williams et al. 1994). Magnetic streptavidin coupled Dynabeads (Thermo) were used for pulldown of the protein that following washes was eluted with 100 nM triethylamine, then pH adjusted and subsequently used for infection of E. coli ER2738 bacterial strain. The output titer was calculated by counting antibiotic resistant colonies and the culture was super-infected with M13KO7 helper phage in order to produce phage for subsequent rounds of selection. Two rounds of in vitro selection were performed in total.

Phage Precipitation and Endotoxin Removal

Phage was PEG/NaCl precipitated as described before (Branston, Stanley et al. 2012). In brief, super-infected ER2738 culture was grown at 30° C. overnight to produce phages and was spun down at 8000×g for 15 minutes at 4° C. The supernatant was collected and mixed at the ratio of 4-to-1 with 20% solution of PEG-6000 and 2.5M NaCl, and incubated on ice for 30 minutes following by centrifugation at 8000×g for 15 minutes at 4° C. The pellet was resuspended in 1 ml of D-PBS and spun down at 13,000 rpm for 1 minute at 4° C. The supernatant was transferred into a new tube and mixed again at the ratio of 4-to-1 with PEG/NaCl solution and incubated on ice for 15 minutes. Next, it was spun down at 13,000 rpm for 15 minutes at 4° C., the pellet was resuspended in 1 ml of D-PBS, then centrifuged again at 13,000 rpm for 1 minute at 4° C. and the supernatant was transferred to a new tube.

Endotoxin Removal from Phages

Endotoxin removal was based on a previously published protocol with modifications (Liu, Tobias et al. 1997). In brief, Triton X-114 was added to the sample to the final concentration of 1%, mixed and incubated on ice for 5 minutes. Then, the sample was incubated at 37° C. for 5 minutes following by a subsequent 5 minute centrifugation at 13,000 rpm at 37° C. The supernatant was recovered and transferred to a new tube. The procedure was repeated three times in total. Endotoxin levels were monitored using LAL assay (Associates of Cape Cod Inc.).

In Vivo Phage Selection for BBB Penetrants

Balb-C female 6-12 week old mice were subjected to intravenous tail injections with 100 μl of phage solution in D-PBS ($5 \times 10^{11}$ cfu). The animals were sacrificed at different time points, either 1, 3 or 18 hours post injection as indicated in the specific experiment. Before the brains were collected, the mice were perfused with 25 ml of D-PBS supplemented with 1 EU/ml of heparin.

Brain Fractionation and Phage Rescue

Capillary depletion from excised brains was performed as described before (Triguero, Buciak et al. 1990). In brief, each brain's weight was recorded and Dounce homogenised (14 strokes) on ice in the volume equal three times the weight of the brain in capillary depletion buffer (2.603 g HEPES, 8.24 g NaCl, 0.2982 g KCl, 0.2465 g $MgSO_4.7H_2O$, 0.1560 g $NaH_2PO_4.2H_2O$, 2.8 ml $CaCl_2.6H_2O$ (1M aq.), 1.8016 g glucose, in 1 l $H_2O$). 26% dextran (60,000-90,000 Da) solution was added in the volume equal four times the original weight of the brain and vortexed. The homogenate was centrifuged for 15 minutes at 5400×g at 4° C. 1 ml of the supernatant was added to 30 ml of E. coli ER2738 cells in 2×YT with tetracycline at 5 μg/ml that were at mid-logarithmic growth phase at OD=0.4-0.6. The bacteria were further grown at 37° C. for 2 hours while shaken at 250 rpm. The bacteria were then harvested by centrifugation at 3,000 rpm for 15 minutes and the pellet was resuspended and plated onto 2×YT bioassay agar plates containing ampicillin (100 μg/ml) and glucose (2% w/v), and incubated overnight at 30° C. The output titer was calculated by counting antibiotic resistant colonies. A new suspension culture was initiated from bioassay plate harvested bacteria and allowed to grow to mid-logarithmic phase in 2×YT media with ampicillin (100 μg/ml) and glucose (2% w/v) before being super-infected with M13KO7 helper phage. The culture was further grown for 1 h before the media was changed to 2×YT with ampicillin (100 μg/ml) and kanamycin (50 μg/ml) and subsequently grown overnight at 30° C. while shaken at 250 rpm in order to produce phage. Before the next rounds of selection, the rescued phages were PEG/NaCl precipitated and subjected to endotoxin removal as described above.

Reticulocytes Count

Mice were injected with 2 mg/kg or 20 mg/kg of the VNAR-Fc fusion protein (5 subjects/group) and blood samples collected 18 hr later. For analysis, 10 μl of blood (diluted 1:5 in PBS) was added to 1 ml of BD Retic-Count and the samples were incubated for 30-60 minutes in dark at room temperature. Samples were strained (35 μm nylon mesh) and the reticulocytes counted using Cytomics FC 500 MPL flow cytometry system with MXP software.

Small Scale (96-Well Plate) Expi293 Transfection

The transient transfection Expi293 expression system (Thermo) was used following the manufacturer's manual. In brief, 425 µl of Expi293 cells at the concentration of 2.94×10$^6$/ml were plated into a 96-well block. 0.5 µg of each DNA was mixed with Opti-MEM media (Thermo) to make a total volume of 25 µl. 1.35 µl of expifectamine was mixed with 23.65 µl Opti-MEM media and after 5 minutes added to the DNA mix; then incubated for an additional 25 minutes. The cells were grown in an incubator at 350 rpm, 37° C. with 8% CO$_2$ overnight before enhancer 1 (2.5 µl) and enhancer 2 (25 µl) were added and the cells grown for 5 more days.

VNAR-Fc ELISA

Maxisorp™ plates (Nunc, Thermo) were coated with 100 µl of 1 µg/ml of recombinant mouse TfR1 (Sino 50741-M07H-100), human TfR1 (Sino 11020-H07H-100), HSA (Sigma A3139), mouse TfR2 (ACRO Biosystems TF2-M5269) and incubated at 4° C. overnight; to measure VNAR-Fc express levels the plate was coated with 1:500 diluted anti-Fc antibody (Sigma I2136). The next day the plates were blocked with 2.5% (w/v) in PBS with 0.1% Tween20 (PBST) for 1 hour at room temperature. Transfected cells were spun down at 2000 rpm for 10 minutes and the collected supernatant was mixed with milk in PBST to a final 2.5% concentration and incubated for 30 minutes. 100 µl of blocked supernatant was transferred into coated plates and incubated for 1 hour. Then the plates were washed with PBST and incubated with anti-Fc-peroxidase antibodies (1:5000) (Sigma A0170) in 2.5% milk in PBST for 30 min. The plates were washed and developed with TMB detection solution before stopping the reaction with 1% HCl. Absorbance was measured at 450 nm. A VNAR-Fc at know concentration was used for standard curve to calculate VNAR-Fc expression level.

Competition ELISA—Variant 1

Maxisorp™ plates (Nunc, Thermo) were coated with 100 µl of hTfR1 (Sino 11020-H07H-100) at the concentration of 5 ug/ml at 4° C. overnight. Plates were washed with PBST and blocked for 1 h with 2% BSA in PBST. Plates were washed again before adding 100 µl of human biotinylated Tf at the concentration of 2.5 µM (Sigma T3915) in 0.1% BSA in PBST and subjected to a1 hour incubation at room temperature. Then 100 µl of VNAR-Fc at the concentration ranging from pM to µM was added and further incubated for 1 hour. Following washing, 100 µl of 1:5000 diluted in 0.5% BSA in PBST detection antibody anti-human Fc peroxidase-conjugated (Sigma A0170) was added and incubated for 1 hour. The plates were washed and developed with TMB detection solution before stopping the reaction with 1% HCl. Absorbance was measured at 450 nm. A VNAR-Fc at know concentration was used for standard curve to calculate VNAR-Fc expression level.

Competition ELISA—Variant 2

Maxisorp plates (Nunc, Thermo) were coated with 100 µl of hTfR1 (Sino 11020-H07H-100) at the concentration of 5 ug/ml at 4° C. overnight. Plates were washed with PBST and blocked for 1 h with 2% BSA in PBST. Washed again before adding 100 ul of human biotinylated Tf at the concentration ranging from pM to µM (Sigma T3915) in 0.1% BSA in PBST. Then incubated for 1 hour at room temperature. Subsequently 100 µl of VNAR-Fc or holo-Tf (Sigmal T4132-100MG) at the concentration of 2.44 nM was added and further incubated for 1 hour. Following washing, 100 µl of either 1:5000 or 1:20,000 diluted in 0.5% BSA in PBST detection antibody anti-human Fc peroxidase-conjugated (Sigma A0170) or streptavidin-peroxidase (Fitzgerald 65R-S104PHRP) was added and incubated for 1 hour, respectively. The plates were washed and developed with TMB detection solution before stopping the reaction with 1% HCl. Absorbance was measured at 450 nm. A VNAR-Fc at know concentration was used for standard curve to calculate VNAR-Fc expression level.

Expression and Purification of VNAR-Fc Fusion Proteins

Selected VNARs were expressed as N-terminal fusions to the human IgG1-Fc region (CH2 and CH3 domains) engineered for the reduced ADCC and CDC of pFUSE-hIgGle3-Fc2 plasmid. Briefly, cDNAs encoding the VNARs were synthesized and cloned using EcoRV and BglII restrictions site. In addition, the IgG hinge region was extended by incorporating a flexible linker sequences comprising glycine- and serine-rich residues $(GxSx)_n$, where x and n typically=0-4. The IL2 secretory signal sequence (IL2Ss) of the parent plasmid was retained.

Expi293F (Invitrogen) cells were cultured in Expi293 expression medium (Invitrogen) supplemented with penicillin (100 U/ml), streptomycin (100 □g/ml) and maintained in a humidified shaking incubator at 37° C. and 5% CO$_2$. Cells were transfected using ExpiFectamine™ 293 Transfection Kit (Invitrogen) according to the manufacturer's protocol. Cells removed from the expression medium by centrifugation 5 days post transfection. The media was filtered and loaded onto PBS equilibrated MabSelect Sure columns (GE Life Sciences). The columns were washed with 10 volumes of PBS and the recombinant protein eluted with linear gradient of 0.1M glycine, pH 2.5 and PBS. Fractions containing the proteins were pooled and buffer exchanged to PBS using Sepadex 25 desalting columns (GE Life Sciences). Protein concentrations were estimated by absorbance at $280_{nm}$. Purified proteins were stored at −80° C. and once thawed maintained at 4° C. for a period of up to 2 weeks.

Alkaline Phosphatase (AP) Activity

The activity of alkaline phosphatase was used to monitor capillary contamination of the parenchymal supernatant (Moos and Morgan J Neurochem. 2001 October; 79(1):119-29). In brief, 100 µl aliquot of the suspensions of pellets were added to a 0.9 mL of buffer [50 mM MgCl2, 5 mM CaCl2, 100 mM KCl, 5 mM p-nitrophenyl phosphate, and 100 mM Tris (pH 9.0)] and incubated for 20 minutes at 37° C. After the addition of 0.2 mL 5 mM NaOH, any insoluble material was removed by spinning for 10 minutes at 3,000 g. Absorbance was determined at 420 nm and activity converted to nM per minute per mg protein using the activity of purified alkaline phosphatase (Sigma P-7640).

Binding Kinetic and Affinity Analysis

Binding kinetics of VNAR-Fcs was determined by surface plasmon resonance (Biacore T200, GE Healthcare). CM5 chips were coated with anti-His antibodies (His Capture Kit, GE Healthcare) as recommended by the manufacturer and human or mouse his-tagged TfR1 (SinoBiological) at 10 ug/mL in HBS-EP+ (GE Healthcare) was captured at flow rate 10 ul/min (contact time 120 s). Single cycle kinetic analyses were performed by injecting VNAR-Fcs at increasing concentrations (0.98, 3.9, 15.6, 62.5 and 250 nM) in HBS-EP at flow rate 30 ul/min (contact time: 360 s; dissociation time after injecting 250 nM analyte: 1500 s). A flow cell without TfR1 captured served as a reference. Sensorgrams were fitted and kinetic constants were determined using Biacore T200 Evaluation software. Chips were regenerated in 10 mM Glycine-HCl, pH 1.5 (contact time: 120 s at flow rate 30 ul/min).

NGS Analysis

Full VNAR cDNAs were PCR amplified from phagemid DNA and the resultant products were sequenced with MiSeq System (Illumina) in the 2×250 bp pair-end configuration. The sequencing reads were processed using a combination of software for clustering and comparing nucleotide sequences including FLASH, R and in-house written scripts. VNARs whose read counts increased significantly during subsequent rounds of in vitro and in vivo selections were expressed as human-Fc fusion proteins and directly tested for their TfR1 binding and functional activity.

Example 7: Single Dose Brain Uptake Study of B2-Rituximab Bispecific Antibody

One of the clone 10-rituximab bispecific antibody formats described in Example 6 (rituximab-B2(HC2N); "rituximab-B2"), was compared to a control rituximab antibody lacking the VNAR clone 10 in experiments to look at brain uptake of a B2-rituximab bispecific antibody in vivo in primate subjects. Seven male cynomolgus macaques (ages between 3-6 years) were dosed intravenously (IV route v. saphenous) with either rituximab (3 subjects; Group 1) or rituximab-B2 (HC2N) (4 subjects; Group 2). Body weight (BW) of all subjects was taken on the day of the study (pre-sampling). All subjects were anesthetized using Ketamine, and a single bolus of drug is administered at 3 mg/kg body weight (BW) for rituximab or 3.5 mg/kg BW for rituximab-B2. Dosing was done once at Hour 0 and the duration of the study was 24 hours.

Blood and CSF Collection.

Two ml of blood were withdrawn into heparinized tubes by venipuncture (from v. *femoralis*) per animal (at Hour 24) under anesthesia (Ketamine). 100 microliters were transferred to a separate tube containing 500 microliters of 2% paraformaldehyde and plasma is isolated from the remainder. One cerebrospinal fluid (CSF) sample was taken per animal (at Hour 24) following blood collection. CSF sampling (volume of 1-2 ml) was performed under aseptic conditions on deeply-anesthetized animals (under Ketamine followed by Sod. pentobarbital).

CSF & Blood Samples.

CSF samples were immediately stored at −80° C. Plasma was isolated from blood and samples and immediately stored at −80° C.

Euthanasia.

Under a deep surgical plane of anesthesia, cardiac perfusion and exsanguination was performed.

Tissue Samples.

Brain:

Blood was cleared from the brain by perfusion. After death was confirmed, the brain was removed from the skull and cut into 4-6 coronal slabs to expose brain regions. Each slab was further dissected into right and left hemispheres and 1-2 cubic centimeters of tissue was removed from the following six brain regions: cortex, hippocampus, striatum, thalamus, cerebellum and brain stem. Left hemisphere samples were flash-frozen on dry ice and stored at −80° C. Samples were taken from contralateral positions on the right and left hemispheres, and fixed in cold 4% Paraformaldehyde.

Other Organs:

Tissue samples were collected from the following five peripheral organs: liver, lung, kidney, spleen and testis. Approximately 2×1 cubic cm samples were removed from each organ and one piece was flash frozen and the other placed in 4% Paraformaldehyde fixative.

Anaysis.

Brain, CSF and plasma levels of rituximab are measured by ELISA. B-cell counts are determined by flow cytometry.

Example 8: Brain Delivery of a Neurotensin Peptide

Neurotensin (NT) was used to test whether VNAR clone C can deliver conjugated peptide payloads to the brain parenchyma in mice. NT is not active peripherally but when injected directly into the brain, it interacts with specific receptors (NTR1 and NTS2) to induce numerous physiological changes, including hypothermia (Demeule, Beaudet et al. 2014). A change in body temperature can be easily monitored in animals after IV injection with NT-containing constructs to provide a physiological readout of parenchymal delivery.

Constructs were prepared with clone C or a control VNAR fused to the N-terminus of the human Fc fragment with NT fused to C-terminal end of the molecule (FIG. 26A) Human Fc alone with NT at C-terminus was made as an additional control. Only the clone C construct showed a physiological effect at 25 nmol/kg (~2 mg/kg) with over a 2-degree drop in body temperature 2 hours after IV injection (FIG. 26B). Neither the control VNAR, which also binds TfR1 but is transcytosed poorly, nor Fc-NT had any effect on body temperature.

To measure the amount of the NT constructs reaching the brain, mice were perfused immediately after the 2-hour body temperature measurement. Brains were removed and homogenised in lysis buffer containing 1% Triton X-100 and plasma was isolated from the blood. The amounts of the NT constructs in the brain and plasma were measured using a human Fc-capture ELISA. Clone C-Fc-NT reached approximately 5 micromolar (μM) concentration in brain at the 2-hour time point, which was 10-fold higher than that achieved by the control constructs (FIG. 26 C). Plasma concentrations were similar between the treatment groups (180-300 μM) and could not account for the difference in brain concentration (FIGS. 26C and 26D. In addition, the time course of the effect on NT on body temperature was examined in a separate experiment (FIG. 26E) and the maximum reduction occurred at approximately 2 hours after administration as previously observed (Demeule, Beaudet et al. 2014). These results demonstrate that the VNAR clone C, which binds specifically to TfR1, can carry a neuroactive peptide into the brain and achieve physiological concentrations that produce a biological response.

Methods

Protein purification—

DNA constructs were synthesised and cloned into pFUSE-hIgGle3-Fc2 vector (InvivoGen). Proteins were expressed by transient transfection in the Expi293 system (Thermo) was used following the manufacturer's protocol. After 5 days the cells were spun centrifuged at 2,000 rpm for 10 minutes and the protein was purified from the supernatant by protein A chromatography followed by size exclusion chromatography (SEC).

Animal Model—

Female BalB-C mice (6-12 weeks old) received tail vein injections with 100 μl of purified proteins at 5 μM concentration. Body temperature was measured at the indicated time-points using a rectal probe. Blood was collected 2 hours post injections followed by perfusion with 25 ml of D-PBS supplemented with 1 EU/ml of heparin. Brains were collected after perfusion and stored at −80° C. freezer.

ELISA—

Maxisorp plates (Nunc, Thermo) were coated with 100 μl of 1:500 diluted in PBS of goat anti-human Fc antibody (Sigma I2136) and incubated at 4° C. overnight. Then the plates were blocked with 2.5% (w/v) milk in PBS with 0.1% Tween20 (PBST) for 1 hour at room temperature. Before homogenisation brains were placed in lysis buffer (3:1 v/w ratio) containing 1% Triton X-100 in PBS supplemented with cOmplete™ Protease Inhibitor Cocktail (Roche). Brains were homogenised with a TissueRuptor (Qiagen) at medium speed for 10 seconds and lysed for 30 min on ice. Lysates were centrifuged at 17,000×g for 20 min and the supernatant was blocked in 2.5% milk in PBST overnight at 4° C. Blocked brain lysates (100 μl) were added to the blocked plates and incubated for 1 hour at room temperature. Plates were washed and goat anti-human Fc antibodies, coupled to HRP (Sigma #A0170) were added for 1 hour. The plates were washed and developed using SureBlue, TMB substrate solution (KPL, Inc. #52-00-03). The reaction was stopped with 1% HCl and the OD was measured at 450 nm. Standard curves were prepared individually for each of the compounds to assure accuracy.

REFERENCES

Alata, W., S. Paris-Robidas, V. Emond, F. Bourasset and F. Calon (2014). "Brain uptake of a fluorescent vector targeting the transferrin receptor: a novel application of in situ brain perfusion." *Mol Pharm* 11(1): 243-253.

Arap, W., R. Pasqualini and E. Ruoslahti (1998). "Cancer treatment by targeted drug delivery to tumor vasculature in a mouse model." *Science* 279(5349): 377-380.

Armour, K. L., M. R. Clark, A. G. Hadley and L. M. Williamson (1999). "Recombinant human IgG molecules lacking Fcgamma receptor I binding and monocyte triggering activities." *Eur J Immunol* 29(8): 2613-2624.

Bien-Ly, N., Y. J. Yu, D. Bumbaca, J. Elstrott, C. A. Boswell, Y. Zhang, W. Luk, Y. Lu, M. S. Dennis, R. M. Weimer, I. Chung and R. J. Watts (2014). "Transferrin receptor (TfR) trafficking determines brain uptake of TfR antibody affinity variants." *J Exp Med* 211(2): 233-244.

Boje, K. M. (1996). "Inhibition of nitric oxide synthase attenuates blood-brain barrier disruption during experimental meningitis." *Brain Res* 720(1-2): 75-83.

Branston, S., E. Stanley, E. Keshavarz-Moore and J. Ward (2012). "Precipitation of filamentous bacteriophages for their selective recovery in primary purification." *Biotechnol Prog* 28(1): 129-136.

Couch, J. A., Y. J. Yu, Y. Zhang, J. M. Tarrant, R. N. Fuji, W. J. Meilandt, H. Solanoy, R. K. Tong, K. Hoyte, W. Luk, Y. Lu, K. Gadkar, S. Prabhu, B. A. Ordonia, Q. Nguyen, Y. Lin, Z. Lin, M. Balazs, K. Scearce-Levie, J. A. Ernst, M. S. Dennis and R. J. Watts (2013). "Addressing safety liabilities of TfR bispecific antibodies that cross the blood-brain barrier." *Sci Transl Med* 5(183): 183ra157, 181-112.

Demeule, M., N. Beaudet, A. Regina, E. Besserer-Offroy, A. Murza, P. Tetreault, K. Belleville, C. Che, A. Larocque, C. Thiot, R. Beliveau, J. M. Longpre, E. Marsault, R. Leduc, J. E. Lachowicz, S. L. Gonias, J. P. Castaigne and P. Sarret (2014). "Conjugation of a brain-penetrant peptide with neurotensin provides antinociceptive properties." *J Clin Invest* 124(3): 1199-1213.

de Vries, H. E., M. C. Blom-Roosemalen, A. G. de Boer, T. J. van Berkel, D. D. Breimer and J. Kuiper (1996). "Effect of endotoxin on permeability of bovine cerebral endothelial cell layers in vitro." *J Pharmacol Exp Ther* 277(3): 1418-1423.

Griffiths, A. D., S. C. Williams, O. Hartley, I. M. Tomlinson, P. Waterhouse, W. L. Crosby, R. E. Kontermann, P. T. Jones, N. M. Low, T. J. Allison and et al. (1994). "Isolation of high affinity human antibodies directly from large synthetic repertoires." *EMBO J* 13(14): 3245-3260.

Hasler, J., M. F. Flajnik, G. Williams, F. S. Walsh and J. L. Rutkowski (2016). "VNAR single-domain antibodies specific for BAFF inhibit B cell development by molecular mimicry." *Mol Immunol* 75: 28-37.

Liu, S., R. Tobias, S. McClure, G. Styba, Q. Shi and G. Jackowski (1997). "Removal of endotoxin from recombinant protein preparations." *Clin Biochem* 30(6): 455-463.

Mayhan, W. G. (1998). "Effect of lipopolysaccharide on the permeability and reactivity of the cerebral microcirculation: role of inducible nitric oxide synthase." *Brain Res* 792(2): 353-357.

Moos, T. and E. H. Morgan (2001). "Restricted transport of anti-transferrin receptor antibody (OX26) through the blood-brain barrier in the rat." *J Neurochem* 79(1): 119-129.

Pasqualini, R. and E. Ruoslahti (1996). "Organ targeting in vivo using phage display peptide libraries." *Nature* 380 (6572): 364-366.

Shields, R. L., A. K. Namenuk, K. Hong, Y. G. Meng, J. Rae, J. Briggs, D. Xie, J. Lai, A. Stadlen, B. Li, J. A. Fox and L. G. Presta (2001). "High resolution mapping of the binding site on human IgG1 for Fc gamma RI, Fc gamma RII, Fc gamma RIII, and FcRn and design of IgG1 variants with improved binding to the Fc gamma R." *J Biol Chem* 276(9): 6591-6604.

Shukla, A., M. Dikshit and R. C. Srimal (1995). "Nitric oxide modulates blood-brain barrier permeability during infections with an inactivated bacterium." *Neuroreport* 6(12): 1629-1632.

Triguero, D., J. Buciak and W. M. Pardridge (1990). "Capillary depletion method for quantification of blood-brain barrier transport of circulating peptides and plasma proteins." *J Neurochem* 54(6): 1882-1888.

Williams, S. K., J. F. Gillis, M. A. Matthews†, R. C. Wagnert and M. W. Bitensky (1980). "Isolation and Characterization of Brain Endothelial Cells: Morphology and Enzyme Activity." *Journal of Neurochemistry* 35(2): 374-381.

Yu, Y. J., Y. Zhang, M. Kenrick, K. Hoyte, W. Luk, Y. Lu, J. Atwal, J. M. Elliott, S. Prabhu, R. J. Watts and M. S. Dennis (2011). "Boosting brain uptake of a therapeutic antibody by reducing its affinity for a transcytosis target." *Sci Transl Med* 3(84): 84ra44.

We claim:

1. A nucleic acid encoding a type II VNAR polypeptide which comprises a VNAR scaffold represented by the formula, from N to C terminus,

FW1-CDR1-FW2-HV2-FW2'-HV4-FW3-CDR3-FW4, wherein the CDR1 sequence comprises or consists essentially of a peptide having an amino acid sequence of one of SEQ ID NOS. 103-108, wherein the CDR3 sequence comprises or consists essentially of a peptide having an amino acid sequence of one of SEQ ID NOS. 52-92, 191-219, and 249 and wherein said polypeptide is capable of binding human TfR-1.

2. The nucleic acid of claim 1, wherein said VNAR scaffold has a CDR1 sequence selected from SEQ ID NO. 103, 104 or 105.

3. The nucleic acid of claim 1, wherein said VNAR scaffold has a CDR3 sequence selected from one of SEQ ID NOS. 52, 53, 61, 90 or 198.

4. The nucleic acid of claim 1, wherein said VNAR scaffold comprises any one of SEQ ID NOS. 1, 2, 7, 10, 11, 12, 39 or 169.

5. The nucleic acid of claim 4, wherein said VNAR scaffold comprises SEQ ID NO. 10.

6. The nucleic acid of claim 4, wherein said VNAR scaffold comprises SEQ ID NO. 169.

7. The nucleic acid of any one of claim 1, 5 or 6, wherein said polypeptide comprises a fusion protein of said VNAR scaffold operably linked to a proteinaceous heterologous diagnostic or therapeutic agent.

8. The nucleic acid of claim 7, wherein said diagnostic or therapeutic agent is selected from the group consisting of an antibody, an Fc fragment, a single chain variable domain or any other immunoglobulin fragment.

9. An expression vector comprising a nucleic acid of claim 1.

10. An expression vector comprising a nucleic acid of claim 7.

11. A host cell comprising a vector of claim 9.

12. A host cell comprising a nucleic acid of claim 7.

* * * * *